(12) United States Patent
Marsault et al.

(10) Patent No.: US 12,358,948 B2
(45) Date of Patent: Jul. 15, 2025

(54) NEUROTENSINERGIC AGONISTS AND METHODS OF USING SAME PREVENTING OR TREATING PAIN

(71) Applicant: SOCPRA SCIENCES SANTÉ ET HUMAINES S.E.C., Sherbrooke (CA)

(72) Inventors: Éric Marsault, Sherbrooke (CA); Michael Desgagne, Sherbrooke (CA); Marc Sousbie, Grenoble (FR); Philippe Sarret, Sherbrooke (CA); Magali Chartier, Sherbrooke (CA); Jean-Michel Longpre, Magog (CA)

(73) Assignee: SOCPRA SCIENCES SANTÉ ET HUMAINES S.E.C., Quebec (CA)

( * ) Notice: Subject to any disclaimer, the term of this patent is extended or adjusted under 35 U.S.C. 154(b) by 0 days.

(21) Appl. No.: 17/310,506

(22) PCT Filed: Feb. 10, 2020

(86) PCT No.: PCT/CA2020/050176
§ 371 (c)(1),
(2) Date: Aug. 6, 2021

(87) PCT Pub. No.: WO2020/160685
PCT Pub. Date: Aug. 13, 2020

(65) Prior Publication Data
US 2022/0168383 A1 Jun. 2, 2022

Related U.S. Application Data

(60) Provisional application No. 62/803,041, filed on Feb. 8, 2019.

(51) Int. Cl.
C07K 7/06 (2006.01)
A61P 25/04 (2006.01)

(52) U.S. Cl.
CPC ............... *C07K 7/06* (2013.01); *A61P 25/04* (2018.01)

(58) Field of Classification Search
None
See application file for complete search history.

(56) References Cited

U.S. PATENT DOCUMENTS

| 4,412,988 | A | * | 11/1983 | Gasc | ............ | C07K 7/06 514/17.7 |
| 4,439,359 | A | | 3/1984 | Holly | | |
| 8,440,851 | B2 | | 5/2013 | Marsault | | |
| 2018/0362582 | A1 | * | 12/2018 | Marsault | ............ | A61P 29/00 |

FOREIGN PATENT DOCUMENTS

| CN | 103333227 B | 10/2015 |
| EP | 2118080 B1 | 8/2016 |

OTHER PUBLICATIONS

Munekata et al. "Epitope mapping in the protein of hepatitis B-virus," Peptide Chemistry (1990), Volume Date 1989, 27th, 281-4, Abstract only CAS Accession No. 1990:476023 (Year: 1990).*
Cas Registry No. 83228-12-0, Database Registry, [online], 1984, Retrieved from STN.
CN103333227, Oct. 7, 2015, English translation.
Notification of reasons for refusal JP 2021-545970, Japanese Patent Office, Nov. 14, 2023.
Notification of reasons for refusal JP 2021-545970, Japanese Patent Office, Nov. 14, 2023, English translation.
Notice of eligibility for grant SG11202108026U, Intellectual Property Office of Singapore, Mar. 27, 2024.
Liehr S., et al., «Synthesis and Biological Activity of Cyclic Peptide Inhibitors of Ribonucleotide Reductase», Organic Letters, 1999, vol. 1, No. 8, pp. 1201-1204.
Misicka A., et al., «Design of Cyclic Deltorphins and Dermenkephalins with a Disulfide Bridge Leads to Analogues with High Selectivity for delta-Opioid Receptors», Journal of Medicinal Chemistry, 1994, 37, pp. 141-145.
Roussy G., et al., «Evidence for a role of NTS2 receptors in the modulation of tonic pain sensitivity», Molecular Pain, 2009, Jul. 6, 2009.
Sousbie M., et al., «In Search of the Optimal Macrocyclization Site for Neurotensin», ACS Medicinal Chemistry Letters, 2018, 9, pp. 227-232.
Sousbie M., et al. «Structural Optimization and Characterization of Potent Analgesic Macrocyclic Analogues of Neurotensin (8-13)», Journal of Medicinal Chemistry, 2018, 61, pp. 7103-7115.
Extended European Search Report, EP 20752246.7, Oct. 26, 2022.
Invitation to Respond to Written Opinion and Written Opinion S535564331, Intellectual Property Office of Singapore, May 3, 2023.

(Continued)

*Primary Examiner* — Christina Bradley
(74) *Attorney, Agent, or Firm* — Lavery, de Billy, L.L.P; Julie Gauvreau

(57) ABSTRACT

The present disclosure provides a macrocyclic compound of formula (I) (I), compositions and kits comprising this compound and their use for preventing or treating pain without inducing hypothermia, hypotension or ileum relaxation.

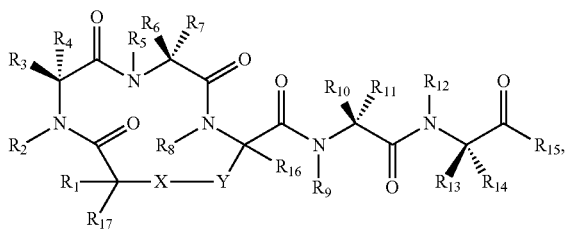

12 Claims, 24 Drawing Sheets
Specification includes a Sequence Listing.

(56) References Cited

OTHER PUBLICATIONS

International Preliminary Report on Patentability, PCT/CA2020/050176, Priority date Feb. 8, 2019.
International Search Report And Written Opinion, PCT/CA2020/050176, Priority date Feb. 8, 2019.
First Office Action and Search Report, State Intellectual Property Office of the People's Republic of China, 202080027426.X, 200032, Sep. 22, 2023 (English translation).

* cited by examiner

SEQUENCE LISTING

<160> NUMBER OF SEQ ID NOS: 170

<210> SEQ ID NO 1
<211> LENGTH: 6
<212> TYPE: PRT
<213> ORGANISM: homo sapiens

<400> SEQUENCE: 1

Arg Arg Pro Tyr Ile Leu
1               5

<210> SEQ ID NO 2
<211> LENGTH: 13
<212> TYPE: PRT
<213> ORGANISM: homo sapiens

<400> SEQUENCE: 2

Glu Leu Tyr Glu Asn Lys Pro Arg Arg Pro Tyr Ile Leu
1               5                   10

<210> SEQ ID NO 3
<211> LENGTH: 6
<212> TYPE: PRT
<213> ORGANISM: Artificial sequence
<220> FEATURE:
<223> OTHER INFORMATION: synthetic construct
<220> FEATURE:
<221> NAME/KEY: misc_feature
<222> LOCATION: (1)..(6)
<223> OTHER INFORMATION: Xaa can be any naturally occurring amino acid

<400> SEQUENCE: 3

Xaa Xaa Xaa Xaa Xaa Xaa
1               5

<210> SEQ ID NO 4
<211> LENGTH: 6
<212> TYPE: PRT
<213> ORGANISM: Artificial sequence
<220> FEATURE:
<223> OTHER INFORMATION: synthetic construct
<220> FEATURE:
<221> NAME/KEY: misc_feature
<222> LOCATION: (1)..(5)
<223> OTHER INFORMATION: Xaa can be any naturally occurring amino acid

```
<400> SEQUENCE: 4

Xaa Xaa Xaa Xaa Xaa Leu
1               5

<210> SEQ ID NO 5
<211> LENGTH: 6
<212> TYPE: PRT
<213> ORGANISM: Artificial sequence
<220> FEATURE:
<223> OTHER INFORMATION: synthetic construct
<220> FEATURE:
<221> NAME/KEY: misc_feature
<222> LOCATION: (1)..(4)
<223> OTHER INFORMATION: Xaa can be any naturally occurring amino acid
<220> FEATURE:
<221> NAME/KEY: misc_feature
<222> LOCATION: (6)..(6)
<223> OTHER INFORMATION: Xaa can be any naturally occurring amino acid

<400> SEQUENCE: 5

Xaa Xaa Xaa Xaa Tyr Xaa
1               5

<210> SEQ ID NO 6
<211> LENGTH: 6
<212> TYPE: PRT
<213> ORGANISM: Artificial sequence
<220> FEATURE:
<223> OTHER INFORMATION: synthetic construct
<220> FEATURE:
<221> NAME/KEY: misc_feature
<222> LOCATION: (1)..(3)
<223> OTHER INFORMATION: Xaa can be any naturally occurring amino acid
<220> FEATURE:
<221> NAME/KEY: misc_feature
<222> LOCATION: (5)..(6)
<223> OTHER INFORMATION: Xaa can be any naturally occurring amino acid

<400> SEQUENCE: 6

Xaa Xaa Xaa Gly Xaa Xaa
1               5

<210> SEQ ID NO 7
<211> LENGTH: 6
<212> TYPE: PRT
<213> ORGANISM: Artificial sequence
<220> FEATURE:
<223> OTHER INFORMATION: synthetic construct
<220> FEATURE:
<221> NAME/KEY: misc_feature
<222> LOCATION: (1)..(2)
<223> OTHER INFORMATION: Xaa can be any naturally occurring amino acid
<220> FEATURE:
<221> NAME/KEY: misc_feature
<222> LOCATION: (4)..(6)
<223> OTHER INFORMATION: Xaa can be any naturally occurring amino acid

<400> SEQUENCE: 7

Xaa Xaa Lys Xaa Xaa Xaa
1               5

<210> SEQ ID NO 8
<211> LENGTH: 6
<212> TYPE: PRT
<213> ORGANISM: Artificial sequence
<220> FEATURE:
<223> OTHER INFORMATION: synthetic construct
<220> FEATURE:
<221> NAME/KEY: misc_feature
<222> LOCATION: (1)..(1)
<223> OTHER INFORMATION: Xaa can be any naturally occurring amino acid
```

```
<220> FEATURE:
<221> NAME/KEY: misc_feature
<222> LOCATION: (3)..(6)
<223> OTHER INFORMATION: Xaa can be any naturally occurring amino acid

<400> SEQUENCE: 8

Xaa Lys Xaa Xaa Xaa Xaa
1               5

<210> SEQ ID NO 9
<211> LENGTH: 6
<212> TYPE: PRT
<213> ORGANISM: Artificial sequence
<220> FEATURE:
<223> OTHER INFORMATION: synthetic construct
<220> FEATURE:
<221> NAME/KEY: misc_feature
<222> LOCATION: (2)..(6)
<223> OTHER INFORMATION: Xaa can be any naturally occurring amino acid

<400> SEQUENCE: 9

Gly Xaa Xaa Xaa Xaa Xaa
1               5

<210> SEQ ID NO 10
<211> LENGTH: 6
<212> TYPE: PRT
<213> ORGANISM: Artificial sequence
<220> FEATURE:
<223> OTHER INFORMATION: synthetic construct
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (4)..(4)
<223> OTHER INFORMATION: Xaa can be any naturally occurring amino acid

<400> SEQUENCE: 10

Xaa Lys Lys Xaa Tyr Leu
1               5

<210> SEQ ID NO 11
<211> LENGTH: 6
<212> TYPE: PRT
<213> ORGANISM: Artificial sequence
<220> FEATURE:
<223> OTHER INFORMATION: synthetic construct
<220> FEATURE:
<221> NAME/KEY: misc_feature
<222> LOCATION: (1)..(2)
<223> OTHER INFORMATION: Xaa can be any naturally occurring amino acid
<220> FEATURE:
<221> NAME/KEY: misc_feature
<222> LOCATION: (4)..(4)
<223> OTHER INFORMATION: Xaa can be any naturally occurring amino acid

<400> SEQUENCE: 11

Xaa Xaa Lys Xaa Tyr Leu
1               5

<210> SEQ ID NO 12
<211> LENGTH: 6
<212> TYPE: PRT
<213> ORGANISM: Artificial sequence
<220> FEATURE:
<223> OTHER INFORMATION: synthetic construct
<220> FEATURE:
<221> NAME/KEY: misc_feature
<222> LOCATION: (1)..(1)
```

```
<223> OTHER INFORMATION: Xaa can be any naturally occurring amino acid
<220> FEATURE:
<221> NAME/KEY: misc_feature
<222> LOCATION: (3)..(4)
<223> OTHER INFORMATION: Xaa can be any naturally occurring amino acid

<400> SEQUENCE: 12

Xaa Lys Xaa Xaa Tyr Leu
1               5

<210> SEQ ID NO 13
<211> LENGTH: 6
<212> TYPE: PRT
<213> ORGANISM: Artificial sequence
<220> FEATURE:
<223> OTHER INFORMATION: synthetic construct
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (4)..(5)
<223> OTHER INFORMATION: Xaa can be any naturally occurring amino acid

<400> SEQUENCE: 13

Xaa Lys Lys Xaa Xaa Leu
1               5

<210> SEQ ID NO 14
<211> LENGTH: 6
<212> TYPE: PRT
<213> ORGANISM: Artificial sequence
<220> FEATURE:
<223> OTHER INFORMATION: synthetic construct
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (4)..(4)
<223> OTHER INFORMATION: Xaa can be any naturally occurring amino acid
<220> FEATURE:
<221> NAME/KEY: misc_feature
<222> LOCATION: (6)..(6)
<223> OTHER INFORMATION: Xaa can be any naturally occurring amino acid

<400> SEQUENCE: 14

Xaa Lys Lys Xaa Tyr Xaa
1               5

<210> SEQ ID NO 15
<211> LENGTH: 6
<212> TYPE: PRT
<213> ORGANISM: Artificial sequence
<220> FEATURE:
<223> OTHER INFORMATION: synthetic construct

<400> SEQUENCE: 15

Gly Lys Lys Gly Tyr Leu
1               5

<210> SEQ ID NO 16
<211> LENGTH: 6
<212> TYPE: PRT
<213> ORGANISM: Artificial sequence
<220> FEATURE:
<223> OTHER INFORMATION: synthetic construct
<220> FEATURE:
<221> NAME/KEY: misc_feature
```

```
<222> LOCATION: (1)..(1)
<223> OTHER INFORMATION: Xaa can be any naturally occurring amino acid

<400> SEQUENCE: 16

Xaa Lys Lys Gly Tyr Leu
1               5

<210> SEQ ID NO 17
<211> LENGTH: 6
<212> TYPE: PRT
<213> ORGANISM: Artificial sequence
<220> FEATURE:
<223> OTHER INFORMATION: synthetic construct
<220> FEATURE:
<221> NAME/KEY: misc_feature
<222> LOCATION: (2)..(2)
<223> OTHER INFORMATION: Xaa can be any naturally occurring amino acid

<400> SEQUENCE: 17

Gly Xaa Lys Gly Tyr Leu
1               5

<210> SEQ ID NO 18
<211> LENGTH: 6
<212> TYPE: PRT
<213> ORGANISM: Artificial sequence
<220> FEATURE:
<223> OTHER INFORMATION: synthetic construct
<220> FEATURE:
<221> NAME/KEY: misc_feature
<222> LOCATION: (3)..(3)
<223> OTHER INFORMATION: Xaa can be any naturally occurring amino acid

<400> SEQUENCE: 18

Gly Lys Xaa Gly Tyr Leu
1               5

<210> SEQ ID NO 19
<211> LENGTH: 6
<212> TYPE: PRT
<213> ORGANISM: Artificial sequence
<220> FEATURE:
<223> OTHER INFORMATION: synthetic construct
<220> FEATURE:
<221> NAME/KEY: misc_feature
<222> LOCATION: (4)..(4)
<223> OTHER INFORMATION: Xaa can be any naturally occurring amino acid

<400> SEQUENCE: 19

Gly Lys Lys Xaa Tyr Leu
1               5

<210> SEQ ID NO 20
<211> LENGTH: 6
<212> TYPE: PRT
<213> ORGANISM: Artificial sequence
<220> FEATURE:
<223> OTHER INFORMATION: synthetic construct
<220> FEATURE:
<221> NAME/KEY: misc_feature
<222> LOCATION: (5)..(5)
<223> OTHER INFORMATION: Xaa can be any naturally occurring amino acid

<400> SEQUENCE: 20

Gly Lys Lys Gly Xaa Leu
1               5

<210> SEQ ID NO 21
<211> LENGTH: 6
```

```
<212> TYPE: PRT
<213> ORGANISM: Artificial sequence
<220> FEATURE:
<223> OTHER INFORMATION: synthetic construct
<220> FEATURE:
<221> NAME/KEY: misc_feature
<222> LOCATION: (6)..(6)
<223> OTHER INFORMATION: Xaa can be any naturally occurring amino acid

<400> SEQUENCE: 21

Gly Lys Lys Gly Tyr Xaa
1               5

<210> SEQ ID NO 22
<211> LENGTH: 6
<212> TYPE: PRT
<213> ORGANISM: Artificial sequence
<220> FEATURE:
<223> OTHER INFORMATION: synthetic construct
<220> FEATURE:
<221> NAME/KEY: site
<222> LOCATION: (1)..(1)
<223> OTHER INFORMATION: allylglycine
<220> FEATURE:
<221> NAME/KEY: site
<222> LOCATION: (4)..(4)
<223> OTHER INFORMATION: allylglycine

<400> SEQUENCE: 22

Gly Lys Lys Gly Tyr Leu
1               5

<210> SEQ ID NO 23
<211> LENGTH: 6
<212> TYPE: PRT
<213> ORGANISM: Artificial sequence
<220> FEATURE:
<223> OTHER INFORMATION: synthetic construct
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: site
<222> LOCATION: (4)..(4)
<223> OTHER INFORMATION: allylglycine

<400> SEQUENCE: 23

Xaa Lys Lys Gly Tyr Leu
1               5

<210> SEQ ID NO 24
<211> LENGTH: 6
<212> TYPE: PRT
<213> ORGANISM: Artificial sequence
<220> FEATURE:
<223> OTHER INFORMATION: synthetic construct
<220> FEATURE:
<221> NAME/KEY: site
<222> LOCATION: (1)..(1)
<223> OTHER INFORMATION: allylglycine
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: site
<222> LOCATION: (4)..(4)
<223> OTHER INFORMATION: allylglycine

<400> SEQUENCE: 24

Gly Xaa Lys Gly Tyr Leu
```

<210> SEQ ID NO 25
<211> LENGTH: 6
<212> TYPE: PRT
<213> ORGANISM: Artificial sequence
<220> FEATURE:
<223> OTHER INFORMATION: synthetic construct
<220> FEATURE:
<221> NAME/KEY: site
<222> LOCATION: (1)..(1)
<223> OTHER INFORMATION: allylglycine
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: site
<222> LOCATION: (4)..(4)
<223> OTHER INFORMATION: allylglycine

<400> SEQUENCE: 25

Gly Lys Xaa Gly Tyr Leu
1               5

<210> SEQ ID NO 26
<211> LENGTH: 6
<212> TYPE: PRT
<213> ORGANISM: Artificial sequence
<220> FEATURE:
<223> OTHER INFORMATION: synthetic construct
<220> FEATURE:
<221> NAME/KEY: site
<222> LOCATION: (1)..(1)
<223> OTHER INFORMATION: allylglycine
<220> FEATURE:
<221> NAME/KEY: misc_feature
<222> LOCATION: (4)..(4)
<223> OTHER INFORMATION: Xaa can be any naturally occurring amino acid

<400> SEQUENCE: 26

Gly Lys Lys Xaa Tyr Leu
1               5

<210> SEQ ID NO 27
<211> LENGTH: 6
<212> TYPE: PRT
<213> ORGANISM: Artificial sequence
<220> FEATURE:
<223> OTHER INFORMATION: synthetic construct
<220> FEATURE:
<221> NAME/KEY: site
<222> LOCATION: (1)..(1)
<223> OTHER INFORMATION: allylglycine
<220> FEATURE:
<221> NAME/KEY: site
<222> LOCATION: (4)..(4)
<223> OTHER INFORMATION: allylglycine
<220> FEATURE:
<221> NAME/KEY: misc_feature
<222> LOCATION: (5)..(5)
<223> OTHER INFORMATION: Xaa can be any naturally occurring amino acid

<400> SEQUENCE: 27

Gly Lys Lys Gly Xaa Leu
1               5

<210> SEQ ID NO 28
<211> LENGTH: 6
<212> TYPE: PRT
<213> ORGANISM: Artificial sequence
<220> FEATURE:

```
<223> OTHER INFORMATION: synthetic construct
<220> FEATURE:
<221> NAME/KEY: site
<222> LOCATION: (1)..(1)
<223> OTHER INFORMATION: allylglycine
<220> FEATURE:
<221> NAME/KEY: site
<222> LOCATION: (4)..(4)
<223> OTHER INFORMATION: allylglycine
<220> FEATURE:
<221> NAME/KEY: misc_feature
<222> LOCATION: (6)..(6)
<223> OTHER INFORMATION: Xaa can be any naturally occurring amino acid

<400> SEQUENCE: 28

Gly Lys Lys Gly Tyr Xaa
1               5

<210> SEQ ID NO 29
<211> LENGTH: 7
<212> TYPE: PRT
<213> ORGANISM: Artificial sequence
<220> FEATURE:
<223> OTHER INFORMATION: synthetic construct
<220> FEATURE:
<221> NAME/KEY: site
<222> LOCATION: (1)..(1)
<223> OTHER INFORMATION: allylglycine
<220> FEATURE:
<221> NAME/KEY: site
<222> LOCATION: (4)..(4)
<223> OTHER INFORMATION: allylglycine

<400> SEQUENCE: 29

Gly Lys Lys Gly Tyr Leu Ile
1               5

<210> SEQ ID NO 30
<211> LENGTH: 6
<212> TYPE: PRT
<213> ORGANISM: Artificial sequence
<220> FEATURE:
<223> OTHER INFORMATION: synthetic construct
<220> FEATURE:
<221> NAME/KEY: site
<222> LOCATION: (1)..(1)
<223> OTHER INFORMATION: allylglycine
<220> FEATURE:
<221> NAME/KEY: site
<222> LOCATION: (4)..(4)
<223> OTHER INFORMATION: allylglycine

<400> SEQUENCE: 30

Gly Lys Lys Gly Tyr Ile
1               5

<210> SEQ ID NO 31
<211> LENGTH: 6
<212> TYPE: PRT
<213> ORGANISM: Artificial sequence
<220> FEATURE:
<223> OTHER INFORMATION: synthetic construct
<220> FEATURE:
<221> NAME/KEY: site
<222> LOCATION: (1)..(1)
<223> OTHER INFORMATION: allylglycine
<220> FEATURE:
<221> NAME/KEY: site
<222> LOCATION: (4)..(4)
<223> OTHER INFORMATION: allylglycine
<220> FEATURE:
<221> NAME/KEY: site
<222> LOCATION: (5)..(5)
```

```
<223> OTHER INFORMATION: O-acetyl tyrosine

<400> SEQUENCE: 31

Gly Lys Lys Gly Tyr Leu
1               5

<210> SEQ ID NO 32
<211> LENGTH: 6
<212> TYPE: PRT
<213> ORGANISM: Artificial sequence
<220> FEATURE:
<223> OTHER INFORMATION: synthetic construct
<220> FEATURE:
<221> NAME/KEY: site
<222> LOCATION: (1)..(1)
<223> OTHER INFORMATION: allylglycine
<220> FEATURE:
<221> NAME/KEY: site
<222> LOCATION: (4)..(4)
<223> OTHER INFORMATION: allylglycine

<400> SEQUENCE: 32

Gly Lys Lys Gly Trp Leu
1               5

<210> SEQ ID NO 33
<211> LENGTH: 6
<212> TYPE: PRT
<213> ORGANISM: Artificial sequence
<220> FEATURE:
<223> OTHER INFORMATION: synthetic construct
<220> FEATURE:
<221> NAME/KEY: site
<222> LOCATION: (1)..(1)
<223> OTHER INFORMATION: allylglycine
<220> FEATURE:
<221> NAME/KEY: site
<222> LOCATION: (4)..(4)
<223> OTHER INFORMATION: allylglycine

<400> SEQUENCE: 33

Gly Lys Lys Gly Lys Leu
1               5

<210> SEQ ID NO 34
<211> LENGTH: 6
<212> TYPE: PRT
<213> ORGANISM: Artificial sequence
<220> FEATURE:
<223> OTHER INFORMATION: synthetic construct
<220> FEATURE:
<221> NAME/KEY: site
<222> LOCATION: (1)..(1)
<223> OTHER INFORMATION: allylglycine
<220> FEATURE:
<221> NAME/KEY: site
<222> LOCATION: (4)..(4)
<223> OTHER INFORMATION: allylglycine
<220> FEATURE:
<221> NAME/KEY: site
<222> LOCATION: (5)..(5)
<223> OTHER INFORMATION: D-amino acid

<400> SEQUENCE: 34

Gly Lys Lys Gly Tyr Leu
1               5

<210> SEQ ID NO 35
<211> LENGTH: 6
<212> TYPE: PRT
<213> ORGANISM: Artificial sequence
```

```
<220> FEATURE:
<223> OTHER INFORMATION: synthetic construct
<220> FEATURE:
<221> NAME/KEY: site
<222> LOCATION: (1)..(1)
<223> OTHER INFORMATION: allylglycine
<220> FEATURE:
<221> NAME/KEY: site
<222> LOCATION: (4)..(4)
<223> OTHER INFORMATION: allylglycine
<220> FEATURE:
<221> NAME/KEY: site
<222> LOCATION: (5)..(5)
<223> OTHER INFORMATION: Tert-Leucine

<400> SEQUENCE: 35

Gly Lys Lys Gly Tyr Leu
1               5

<210> SEQ ID NO 36
<211> LENGTH: 6
<212> TYPE: PRT
<213> ORGANISM: Artificial sequence
<220> FEATURE:
<223> OTHER INFORMATION: synthetic construct
<220> FEATURE:
<221> NAME/KEY: site
<222> LOCATION: (1)..(1)
<223> OTHER INFORMATION: allylglycine
<220> FEATURE:
<221> NAME/KEY: site
<222> LOCATION: (4)..(4)
<223> OTHER INFORMATION: allylglycine
<220> FEATURE:
<221> NAME/KEY: site
<222> LOCATION: (6)..(6)
<223> OTHER INFORMATION: norleucine

<400> SEQUENCE: 36

Gly Lys Lys Gly Tyr Xaa
1               5

<210> SEQ ID NO 37
<211> LENGTH: 6
<212> TYPE: PRT
<213> ORGANISM: Artificial sequence
<220> FEATURE:
<223> OTHER INFORMATION: synthetic construct
<220> FEATURE:
<221> NAME/KEY: site
<222> LOCATION: (1)..(1)
<223> OTHER INFORMATION: allylglycine
<220> FEATURE:
<221> NAME/KEY: site
<222> LOCATION: (4)..(4)
<223> OTHER INFORMATION: allylglycine
<220> FEATURE:
<221> NAME/KEY: site
<222> LOCATION: (6)..(6)
<223> OTHER INFORMATION: norvaline

<400> SEQUENCE: 37

Gly Lys Lys Gly Tyr Xaa
1               5

<210> SEQ ID NO 38
<211> LENGTH: 6
<212> TYPE: PRT
<213> ORGANISM: Artificial sequence
<220> FEATURE:
<223> OTHER INFORMATION: synthetic construct
<220> FEATURE:
<221> NAME/KEY: site
```

```
<222> LOCATION: (1)..(1)
<223> OTHER INFORMATION: allylglycine
<220> FEATURE:
<221> NAME/KEY: site
<222> LOCATION: (4)..(4)
<223> OTHER INFORMATION: allylglycine
<220> FEATURE:
<221> NAME/KEY: site
<222> LOCATION: (6)..(6)
<223> OTHER INFORMATION: cyclohexylglycine

<400> SEQUENCE: 38

Gly Lys Lys Gly Tyr Gly
1               5

<210> SEQ ID NO 39
<211> LENGTH: 6
<212> TYPE: PRT
<213> ORGANISM: Artificial sequence
<220> FEATURE:
<223> OTHER INFORMATION: synthetic construct
<220> FEATURE:
<221> NAME/KEY: site
<222> LOCATION: (1)..(1)
<223> OTHER INFORMATION: allylglycine
<220> FEATURE:
<221> NAME/KEY: site
<222> LOCATION: (4)..(4)
<223> OTHER INFORMATION: allylglycine
<220> FEATURE:
<221> NAME/KEY: site
<222> LOCATION: (6)..(6)
<223> OTHER INFORMATION: cyclohexylalanine

<400> SEQUENCE: 39

Gly Lys Lys Gly Tyr Ala
1               5

<210> SEQ ID NO 40
<211> LENGTH: 6
<212> TYPE: PRT
<213> ORGANISM: Artificial sequence
<220> FEATURE:
<223> OTHER INFORMATION: synthetic construct
<220> FEATURE:
<221> NAME/KEY: site
<222> LOCATION: (1)..(1)
<223> OTHER INFORMATION: allylglycine
<220> FEATURE:
<221> NAME/KEY: site
<222> LOCATION: (4)..(4)
<223> OTHER INFORMATION: allylglycine

<400> SEQUENCE: 40

Gly Lys Lys Gly Tyr Phe
1               5

<210> SEQ ID NO 41
<211> LENGTH: 6
<212> TYPE: PRT
<213> ORGANISM: Artificial sequence
<220> FEATURE:
<223> OTHER INFORMATION: synthetic construct
<220> FEATURE:
<221> NAME/KEY: site
<222> LOCATION: (1)..(1)
<223> OTHER INFORMATION: allylglycine
<220> FEATURE:
<221> NAME/KEY: site
<222> LOCATION: (4)..(4)
<223> OTHER INFORMATION: allylglycine

<400> SEQUENCE: 41
```

Gly Lys Lys Gly Tyr Val
1               5

<210> SEQ ID NO 42
<211> LENGTH: 6
<212> TYPE: PRT
<213> ORGANISM: Artificial sequence
<220> FEATURE:
<223> OTHER INFORMATION: synthetic construct
<220> FEATURE:
<221> NAME/KEY: site
<222> LOCATION: (1)..(1)
<223> OTHER INFORMATION: allylglycine
<220> FEATURE:
<221> NAME/KEY: site
<222> LOCATION: (4)..(4)
<223> OTHER INFORMATION: allylglycine
<220> FEATURE:
<221> NAME/KEY: site
<222> LOCATION: (6)..(6)
<223> OTHER INFORMATION: D-amino acid

<400> SEQUENCE: 42

Gly Lys Lys Gly Tyr Leu
1               5

<210> SEQ ID NO 43
<211> LENGTH: 6
<212> TYPE: PRT
<213> ORGANISM: Artificial sequence
<220> FEATURE:
<223> OTHER INFORMATION: synthetic construct
<220> FEATURE:
<221> NAME/KEY: site
<222> LOCATION: (1)..(1)
<223> OTHER INFORMATION: allylglycine
<220> FEATURE:
<221> NAME/KEY: site
<222> LOCATION: (4)..(4)
<223> OTHER INFORMATION: allylglycine
<220> FEATURE:
<221> NAME/KEY: site
<222> LOCATION: (5)..(5)
<223> OTHER INFORMATION: meta-tyrosine

<400> SEQUENCE: 43

Gly Lys Lys Gly Tyr Leu
1               5

<210> SEQ ID NO 44
<211> LENGTH: 6
<212> TYPE: PRT
<213> ORGANISM: Artificial sequence
<220> FEATURE:
<223> OTHER INFORMATION: synthetic construct
<220> FEATURE:
<221> NAME/KEY: site
<222> LOCATION: (1)..(1)
<223> OTHER INFORMATION: allylglycine
<220> FEATURE:
<221> NAME/KEY: site
<222> LOCATION: (4)..(4)
<223> OTHER INFORMATION: D-allylglycine

<400> SEQUENCE: 44

Gly Lys Lys Gly Tyr Leu
1               5

<210> SEQ ID NO 45
<211> LENGTH: 6
<212> TYPE: PRT

```
<213> ORGANISM: Artificial sequence
<220> FEATURE:
<223> OTHER INFORMATION: synthetic construct
<220> FEATURE:
<221> NAME/KEY: site
<222> LOCATION: (1)..(1)
<223> OTHER INFORMATION: D allylglycine
<220> FEATURE:
<221> NAME/KEY: site
<222> LOCATION: (1)..(1)
<223> OTHER INFORMATION: D-allylglycine
<220> FEATURE:
<221> NAME/KEY: site
<222> LOCATION: (4)..(4)
<223> OTHER INFORMATION: allylglycine

<400> SEQUENCE: 45

Gly Lys Lys Gly Tyr Leu
1               5

<210> SEQ ID NO 46
<211> LENGTH: 6
<212> TYPE: PRT
<213> ORGANISM: Artificial sequence
<220> FEATURE:
<223> OTHER INFORMATION: synthetic construct
<220> FEATURE:
<221> NAME/KEY: site
<222> LOCATION: (1)..(1)
<223> OTHER INFORMATION: D-allylglycine
<220> FEATURE:
<221> NAME/KEY: site
<222> LOCATION: (4)..(4)
<223> OTHER INFORMATION: D-allylglycine

<400> SEQUENCE: 46

Gly Lys Lys Gly Tyr Leu
1               5

<210> SEQ ID NO 47
<211> LENGTH: 6
<212> TYPE: PRT
<213> ORGANISM: Artificial sequence
<220> FEATURE:
<223> OTHER INFORMATION: synthetic construct
<220> FEATURE:
<221> NAME/KEY: site
<222> LOCATION: (1)..(1)
<223> OTHER INFORMATION: allylglycine
<220> FEATURE:
<221> NAME/KEY: site
<222> LOCATION: (4)..(4)
<223> OTHER INFORMATION: allylglycine
<220> FEATURE:
<221> NAME/KEY: site
<222> LOCATION: (5)..(5)
<223> OTHER INFORMATION: D-amino acid

<400> SEQUENCE: 47

Gly Lys Lys Gly Trp Leu
1               5

<210> SEQ ID NO 48
<211> LENGTH: 6
<212> TYPE: PRT
<213> ORGANISM: Artificial sequence
<220> FEATURE:
<223> OTHER INFORMATION: synthetic construct
<220> FEATURE:
<221> NAME/KEY: site
<222> LOCATION: (1)..(1)
<223> OTHER INFORMATION: allylglycine
<220> FEATURE:
```

```
<221> NAME/KEY: site
<222> LOCATION: (4)..(4)
<223> OTHER INFORMATION: allylglycine
<220> FEATURE:
<221> NAME/KEY: site
<222> LOCATION: (6)..(6)
<223> OTHER INFORMATION: D-amino acid

<400> SEQUENCE: 48

Gly Lys Lys Gly Tyr Leu
1               5

<210> SEQ ID NO 49
<211> LENGTH: 6
<212> TYPE: PRT
<213> ORGANISM: Artificial sequence
<220> FEATURE:
<223> OTHER INFORMATION: synthetic construct
<220> FEATURE:
<221> NAME/KEY: site
<222> LOCATION: (1)..(1)
<223> OTHER INFORMATION: allylglycine
<220> FEATURE:
<221> NAME/KEY: site
<222> LOCATION: (4)..(4)
<223> OTHER INFORMATION: allylglycine
<220> FEATURE:
<221> NAME/KEY: site
<222> LOCATION: (5)..(5)
<223> OTHER INFORMATION: N-methyl-tyrosine

<400> SEQUENCE: 49

Gly Lys Lys Gly Tyr Leu
1               5

<210> SEQ ID NO 50
<211> LENGTH: 6
<212> TYPE: PRT
<213> ORGANISM: Artificial sequence
<220> FEATURE:
<223> OTHER INFORMATION: synthetic construct
<220> FEATURE:
<221> NAME/KEY: site
<222> LOCATION: (1)..(1)
<223> OTHER INFORMATION: allylglycine
<220> FEATURE:
<221> NAME/KEY: site
<222> LOCATION: (4)..(4)
<223> OTHER INFORMATION: allylglycine
<220> FEATURE:
<221> NAME/KEY: site
<222> LOCATION: (5)..(5)
<223> OTHER INFORMATION: N-methyl-tyrosine

<400> SEQUENCE: 50

Gly Lys Lys Gly Tyr Leu
1               5

<210> SEQ ID NO 51
<211> LENGTH: 6
<212> TYPE: PRT
<213> ORGANISM: Artificial sequence
<220> FEATURE:
<223> OTHER INFORMATION: synthetic construct
<220> FEATURE:
<221> NAME/KEY: site
<222> LOCATION: (1)..(1)
<223> OTHER INFORMATION: ethylglycine
<220> FEATURE:
<221> NAME/KEY: site
<222> LOCATION: (4)..(4)
<223> OTHER INFORMATION: ethylglycine
```

```
<400> SEQUENCE: 51

Gly Lys Lys Gly Tyr Leu
1               5

<210> SEQ ID NO 52
<211> LENGTH: 6
<212> TYPE: PRT
<213> ORGANISM: Artificial sequence
<220> FEATURE:
<223> OTHER INFORMATION: synthetic construct
<220> FEATURE:
<221> NAME/KEY: site
<222> LOCATION: (1)..(1)
<223> OTHER INFORMATION: allylglycine
<220> FEATURE:
<221> NAME/KEY: site
<222> LOCATION: (4)..(4)
<223> OTHER INFORMATION: allylglycine
<220> FEATURE:
<221> NAME/KEY: site
<222> LOCATION: (5)..(5)
<223> OTHER INFORMATION: D-amino acid

<400> SEQUENCE: 52

Gly Lys Lys Gly Lys Leu
1               5

<210> SEQ ID NO 53
<211> LENGTH: 6
<212> TYPE: PRT
<213> ORGANISM: Artificial sequence
<220> FEATURE:
<223> OTHER INFORMATION: synthetic construct
<220> FEATURE:
<221> NAME/KEY: site
<222> LOCATION: (1)..(1)
<223> OTHER INFORMATION: allylglycine
<220> FEATURE:
<221> NAME/KEY: site
<222> LOCATION: (4)..(4)
<223> OTHER INFORMATION: allylglycine
<220> FEATURE:
<221> NAME/KEY: site
<222> LOCATION: (6)..(6)
<223> OTHER INFORMATION: neopentylglycine

<400> SEQUENCE: 53

Gly Lys Lys Gly Tyr Gly
1               5

<210> SEQ ID NO 54
<211> LENGTH: 6
<212> TYPE: PRT
<213> ORGANISM: Artificial sequence
<220> FEATURE:
<223> OTHER INFORMATION: synthetic construct
<220> FEATURE:
<221> NAME/KEY: site
<222> LOCATION: (1)..(1)
<223> OTHER INFORMATION: allylglycine
<220> FEATURE:
<221> NAME/KEY: site
<222> LOCATION: (3)..(3)
<223> OTHER INFORMATION: ornithine
<220> FEATURE:
<221> NAME/KEY: site
<222> LOCATION: (4)..(4)
<223> OTHER INFORMATION: allylglycine

<400> SEQUENCE: 54

Gly Lys Xaa Gly Tyr Leu
1               5
```

```
<210> SEQ ID NO 55
<211> LENGTH: 6
<212> TYPE: PRT
<213> ORGANISM: Artificial sequence
<220> FEATURE:
<223> OTHER INFORMATION: synthetic construct
<220> FEATURE:
<221> NAME/KEY: site
<222> LOCATION: (1)..(1)
<223> OTHER INFORMATION: allylglycine
<220> FEATURE:
<221> NAME/KEY: site
<222> LOCATION: (3)..(3)
<223> OTHER INFORMATION: 2,4diaminobutyric acid
<220> FEATURE:
<221> NAME/KEY: site
<222> LOCATION: (4)..(4)
<223> OTHER INFORMATION: allylglycine

<400> SEQUENCE: 55

Gly Lys Xaa Gly Tyr Leu
1               5

<210> SEQ ID NO 56
<211> LENGTH: 6
<212> TYPE: PRT
<213> ORGANISM: Artificial sequence
<220> FEATURE:
<223> OTHER INFORMATION: synthetic construct
<220> FEATURE:
<221> NAME/KEY: site
<222> LOCATION: (1)..(1)
<223> OTHER INFORMATION: allylglycine
<220> FEATURE:
<221> NAME/KEY: site
<222> LOCATION: (3)..(3)
<223> OTHER INFORMATION: 2,3 diaminopropionic acid
<220> FEATURE:
<221> NAME/KEY: site
<222> LOCATION: (4)..(4)
<223> OTHER INFORMATION: allylglycine

<400> SEQUENCE: 56

Gly Lys Xaa Gly Tyr Leu
1               5

<210> SEQ ID NO 57
<211> LENGTH: 6
<212> TYPE: PRT
<213> ORGANISM: Artificial sequence
<220> FEATURE:
<223> OTHER INFORMATION: synthetic construct
<220> FEATURE:
<221> NAME/KEY: site
<222> LOCATION: (1)..(1)
<223> OTHER INFORMATION: allylglycine
<220> FEATURE:
<221> NAME/KEY: site
<222> LOCATION: (3)..(3)
<223> OTHER INFORMATION: D-amino acid
<220> FEATURE:
<221> NAME/KEY: site
<222> LOCATION: (4)..(4)
<223> OTHER INFORMATION: allylglycine

<400> SEQUENCE: 57

Gly Lys Lys Gly Tyr Leu
1               5

<210> SEQ ID NO 58
<211> LENGTH: 6
```

```
<212> TYPE: PRT
<213> ORGANISM: Artificial sequence
<220> FEATURE:
<223> OTHER INFORMATION: synthetic construct
<220> FEATURE:
<221> NAME/KEY: site
<222> LOCATION: (1)..(1)
<223> OTHER INFORMATION: allylglycine
<220> FEATURE:
<221> NAME/KEY: site
<222> LOCATION: (4)..(4)
<223> OTHER INFORMATION: allylglycine

<400> SEQUENCE: 58

Gly Lys His Gly Tyr Leu
1               5

<210> SEQ ID NO 59
<211> LENGTH: 6
<212> TYPE: PRT
<213> ORGANISM: Artificial sequence
<220> FEATURE:
<223> OTHER INFORMATION: synthetic construct
<220> FEATURE:
<221> NAME/KEY: site
<222> LOCATION: (1)..(1)
<223> OTHER INFORMATION: allylglycine
<220> FEATURE:
<221> NAME/KEY: site
<222> LOCATION: (3)..(3)
<223> OTHER INFORMATION: norleucine
<220> FEATURE:
<221> NAME/KEY: site
<222> LOCATION: (4)..(4)
<223> OTHER INFORMATION: allylglycine

<400> SEQUENCE: 59

Gly Lys Xaa Gly Tyr Leu
1               5

<210> SEQ ID NO 60
<211> LENGTH: 6
<212> TYPE: PRT
<213> ORGANISM: Artificial sequence
<220> FEATURE:
<223> OTHER INFORMATION: synthetic construct
<220> FEATURE:
<221> NAME/KEY: site
<222> LOCATION: (1)..(1)
<223> OTHER INFORMATION: allylglycine
<220> FEATURE:
<221> NAME/KEY: site
<222> LOCATION: (3)..(3)
<223> OTHER INFORMATION: norvaline
<220> FEATURE:
<221> NAME/KEY: site
<222> LOCATION: (4)..(4)
<223> OTHER INFORMATION: allylglycine

<400> SEQUENCE: 60

Gly Lys Xaa Gly Tyr Leu
1               5

<210> SEQ ID NO 61
<211> LENGTH: 6
<212> TYPE: PRT
<213> ORGANISM: Artificial sequence
<220> FEATURE:
<223> OTHER INFORMATION: synthetic construct
<220> FEATURE:
<221> NAME/KEY: site
<222> LOCATION: (1)..(1)
<223> OTHER INFORMATION: allylglycine
```

```
<220> FEATURE:
<221> NAME/KEY: site
<222> LOCATION: (4)..(4)
<223> OTHER INFORMATION: allylglycine

<400> SEQUENCE: 61

Gly Lys Gly Gly Tyr Leu
1               5

<210> SEQ ID NO 62
<211> LENGTH: 6
<212> TYPE: PRT
<213> ORGANISM: Artificial sequence
<220> FEATURE:
<223> OTHER INFORMATION: synthetic construct
<220> FEATURE:
<221> NAME/KEY: site
<222> LOCATION: (1)..(1)
<223> OTHER INFORMATION: pentenoyl lysine
<220> FEATURE:
<221> NAME/KEY: site
<222> LOCATION: (3)..(3)
<223> OTHER INFORMATION: allylglycine

<400> SEQUENCE: 62

Lys Lys Lys Gly Tyr Leu
1               5

<210> SEQ ID NO 63
<211> LENGTH: 6
<212> TYPE: PRT
<213> ORGANISM: Artificial sequence
<220> FEATURE:
<223> OTHER INFORMATION: synthetic construct
<220> FEATURE:
<221> NAME/KEY: site
<222> LOCATION: (1)..(1)
<223> OTHER INFORMATION: allylglycine
<220> FEATURE:
<221> NAME/KEY: site
<222> LOCATION: (4)..(4)
<223> OTHER INFORMATION: allylglycine

<400> SEQUENCE: 63

Gly Lys Glu Gly Tyr Leu
1               5

<210> SEQ ID NO 64
<211> LENGTH: 6
<212> TYPE: PRT
<213> ORGANISM: Artificial sequence
<220> FEATURE:
<223> OTHER INFORMATION: synthetic construct
<220> FEATURE:
<221> NAME/KEY: site
<222> LOCATION: (1)..(1)
<223> OTHER INFORMATION: allylglycine
<220> FEATURE:
<221> NAME/KEY: site
<222> LOCATION: (4)..(4)
<223> OTHER INFORMATION: allylglycine
<220> FEATURE:
<221> NAME/KEY: site
<222> LOCATION: (6)..(6)
<223> OTHER INFORMATION: O-methyl tyrosine

<400> SEQUENCE: 64

Gly Lys Lys Gly Tyr Tyr
1               5

<210> SEQ ID NO 65
```

```
<211> LENGTH: 6
<212> TYPE: PRT
<213> ORGANISM: Artificial sequence
<220> FEATURE:
<223> OTHER INFORMATION: synthetic construct
<220> FEATURE:
<221> NAME/KEY: site
<222> LOCATION: (1)..(1)
<223> OTHER INFORMATION: allylglycine
<220> FEATURE:
<221> NAME/KEY: site
<222> LOCATION: (4)..(4)
<223> OTHER INFORMATION: allylglycine
<220> FEATURE:
<221> NAME/KEY: site
<222> LOCATION: (6)..(6)
<223> OTHER INFORMATION: 2,4,5-trifluorophenylalanine

<400> SEQUENCE: 65

Gly Lys Lys Gly Tyr Phe
1               5

<210> SEQ ID NO 66
<211> LENGTH: 6
<212> TYPE: PRT
<213> ORGANISM: Artificial sequence
<220> FEATURE:
<223> OTHER INFORMATION: synthetic construct
<220> FEATURE:
<221> NAME/KEY: site
<222> LOCATION: (1)..(1)
<223> OTHER INFORMATION: allylglycine
<220> FEATURE:
<221> NAME/KEY: site
<222> LOCATION: (4)..(4)
<223> OTHER INFORMATION: allylglycine
<220> FEATURE:
<221> NAME/KEY: site
<222> LOCATION: (6)..(6)
<223> OTHER INFORMATION: homocyclohexyl alanine

<400> SEQUENCE: 66

Gly Lys Lys Gly Tyr Ala
1               5

<210> SEQ ID NO 67
<211> LENGTH: 6
<212> TYPE: PRT
<213> ORGANISM: Artificial sequence
<220> FEATURE:
<223> OTHER INFORMATION: synthetic construct
<220> FEATURE:
<221> NAME/KEY: site
<222> LOCATION: (1)..(1)
<223> OTHER INFORMATION: allylglycine
<220> FEATURE:
<221> NAME/KEY: site
<222> LOCATION: (4)..(4)
<223> OTHER INFORMATION: allylglycine
<220> FEATURE:
<221> NAME/KEY: site
<222> LOCATION: (6)..(6)
<223> OTHER INFORMATION: cyclopropyl alanine

<400> SEQUENCE: 67

Gly Lys Lys Gly Tyr Ala
1               5

<210> SEQ ID NO 68
<211> LENGTH: 6
<212> TYPE: PRT
<213> ORGANISM: Artificial sequence
<220> FEATURE:
```

```
<223> OTHER INFORMATION: synthetic construct
<220> FEATURE:
<221> NAME/KEY: site
<222> LOCATION: (1)..(1)
<223> OTHER INFORMATION: allylglycine
<220> FEATURE:
<221> NAME/KEY: site
<222> LOCATION: (4)..(4)
<223> OTHER INFORMATION: allylglycine
<220> FEATURE:
<221> NAME/KEY: site
<222> LOCATION: (6)..(6)
<223> OTHER INFORMATION: cyclobutyl alanine

<400> SEQUENCE: 68

Gly Lys Lys Gly Tyr Ala
1               5

<210> SEQ ID NO 69
<211> LENGTH: 6
<212> TYPE: PRT
<213> ORGANISM: Artificial sequence
<220> FEATURE:
<223> OTHER INFORMATION: synthetic construct
<220> FEATURE:
<221> NAME/KEY: site
<222> LOCATION: (1)..(1)
<223> OTHER INFORMATION: allylglycine
<220> FEATURE:
<221> NAME/KEY: site
<222> LOCATION: (4)..(4)
<223> OTHER INFORMATION: allylglycine
<220> FEATURE:
<221> NAME/KEY: site
<222> LOCATION: (6)..(6)
<223> OTHER INFORMATION: cyclopentyl alanine

<400> SEQUENCE: 69

Gly Lys Lys Gly Tyr Ala
1               5

<210> SEQ ID NO 70
<211> LENGTH: 6
<212> TYPE: PRT
<213> ORGANISM: Artificial sequence
<220> FEATURE:
<223> OTHER INFORMATION: synthetic construct
<220> FEATURE:
<221> NAME/KEY: site
<222> LOCATION: (1)..(1)
<223> OTHER INFORMATION: allylglycine
<220> FEATURE:
<221> NAME/KEY: site
<222> LOCATION: (4)..(4)
<223> OTHER INFORMATION: allylglycine
<220> FEATURE:
<221> NAME/KEY: site
<222> LOCATION: (6)..(6)
<223> OTHER INFORMATION: cycloheptyl alanine

<400> SEQUENCE: 70

Gly Lys Lys Gly Tyr Ala
1               5

<210> SEQ ID NO 71
<211> LENGTH: 6
<212> TYPE: PRT
<213> ORGANISM: Artificial sequence
<220> FEATURE:
<223> OTHER INFORMATION: synthetic construct
<220> FEATURE:
<221> NAME/KEY: site
<222> LOCATION: (1)..(1)
```

-continued

```
<223> OTHER INFORMATION: allylglycine
<220> FEATURE:
<221> NAME/KEY: site
<222> LOCATION: (4)..(4)
<223> OTHER INFORMATION: allylglycine
<220> FEATURE:
<221> NAME/KEY: site
<222> LOCATION: (5)..(5)
<223> OTHER INFORMATION: N-isobutyl glycine

<400> SEQUENCE: 71

Gly Lys Lys Gly Gly Gly
1               5

<210> SEQ ID NO 72
<211> LENGTH: 6
<212> TYPE: PRT
<213> ORGANISM: Artificial sequence
<220> FEATURE:
<223> OTHER INFORMATION: synthetic construct
<220> FEATURE:
<221> NAME/KEY: site
<222> LOCATION: (1)..(1)
<223> OTHER INFORMATION: allylglycine
<220> FEATURE:
<221> NAME/KEY: site
<222> LOCATION: (4)..(4)
<223> OTHER INFORMATION: allylglycine
<220> FEATURE:
<221> NAME/KEY: site
<222> LOCATION: (5)..(5)
<223> OTHER INFORMATION: N-(4-hydroxy)benzyl glycine

<400> SEQUENCE: 72

Gly Lys Lys Gly Gly Leu
1               5

<210> SEQ ID NO 73
<211> LENGTH: 6
<212> TYPE: PRT
<213> ORGANISM: Artificial sequence
<220> FEATURE:
<223> OTHER INFORMATION: synthetic construct
<220> FEATURE:
<221> NAME/KEY: site
<222> LOCATION: (1)..(1)
<223> OTHER INFORMATION: alylglycine
<220> FEATURE:
<221> NAME/KEY: site
<222> LOCATION: (4)..(4)
<223> OTHER INFORMATION: alylglycine
<220> FEATURE:
<221> NAME/KEY: site
<222> LOCATION: (5)..(5)
<223> OTHER INFORMATION: N-(4-hydroxy)benzyl glycine
<220> FEATURE:
<221> NAME/KEY: site
<222> LOCATION: (6)..(6)
<223> OTHER INFORMATION: N-isobutyl Glycineglycine
<220> FEATURE:
<221> NAME/KEY: site
<222> LOCATION: (6)..(6)
<223> OTHER INFORMATION: N-isobutyl glycine

<400> SEQUENCE: 73

Gly Lys Lys Gly Gly Gly
1               5

<210> SEQ ID NO 74
<211> LENGTH: 6
<212> TYPE: PRT
<213> ORGANISM: Artificial sequence
<220> FEATURE:
```

```
<223> OTHER INFORMATION: synthetic construct
<220> FEATURE:
<221> NAME/KEY: site
<222> LOCATION: (1)..(1)
<223> OTHER INFORMATION: allylglycine
<220> FEATURE:
<221> NAME/KEY: site
<222> LOCATION: (3)..(3)
<223> OTHER INFORMATION: N-methyl lysine
<220> FEATURE:
<221> NAME/KEY: site
<222> LOCATION: (4)..(4)
<223> OTHER INFORMATION: allylglycine

<400> SEQUENCE: 74

Gly Lys Lys Gly Tyr Leu
1               5

<210> SEQ ID NO 75
<211> LENGTH: 6
<212> TYPE: PRT
<213> ORGANISM: Artificial sequence
<220> FEATURE:
<223> OTHER INFORMATION: synthetic construct
<220> FEATURE:
<221> NAME/KEY: site
<222> LOCATION: (1)..(1)
<223> OTHER INFORMATION: allylglycine
<220> FEATURE:
<221> NAME/KEY: site
<222> LOCATION: (2)..(2)
<223> OTHER INFORMATION: N-methyl lysine
<220> FEATURE:
<221> NAME/KEY: site
<222> LOCATION: (4)..(4)
<223> OTHER INFORMATION: allylglycine

<400> SEQUENCE: 75

Gly Lys Lys Gly Tyr Leu
1               5

<210> SEQ ID NO 76
<211> LENGTH: 6
<212> TYPE: PRT
<213> ORGANISM: Artificial sequence
<220> FEATURE:
<223> OTHER INFORMATION: synthetic construct
<220> FEATURE:
<221> NAME/KEY: site
<222> LOCATION: (1)..(1)
<223> OTHER INFORMATION: allylglycine
<220> FEATURE:
<221> NAME/KEY: site
<222> LOCATION: (2)..(3)
<223> OTHER INFORMATION: Nalpha-methyl lysine
<220> FEATURE:
<221> NAME/KEY: site
<222> LOCATION: (4)..(4)
<223> OTHER INFORMATION: allylglycine

<400> SEQUENCE: 76

Gly Lys Lys Gly Tyr Leu
1               5

<210> SEQ ID NO 77
<211> LENGTH: 6
<212> TYPE: PRT
<213> ORGANISM: Artificial sequence
<220> FEATURE:
<223> OTHER INFORMATION: synthetic construct
<220> FEATURE:
<221> NAME/KEY: site
<222> LOCATION: (1)..(1)
```

```
<223> OTHER INFORMATION: allylglycine
<220> FEATURE:
<221> NAME/KEY: site
<222> LOCATION: (4)..(4)
<223> OTHER INFORMATION: allylglycine
<220> FEATURE:
<221> NAME/KEY: site
<222> LOCATION: (5)..(5)
<223> OTHER INFORMATION: O-mehyl tyrosine

<400> SEQUENCE: 77

Gly Lys Lys Gly Tyr Leu
1               5

<210> SEQ ID NO 78
<211> LENGTH: 6
<212> TYPE: PRT
<213> ORGANISM: Artificial sequence
<220> FEATURE:
<223> OTHER INFORMATION: synthetic construct
<220> FEATURE:
<221> NAME/KEY: site
<222> LOCATION: (1)..(1)
<223> OTHER INFORMATION: allylglycine
<220> FEATURE:
<221> NAME/KEY: site
<222> LOCATION: (4)..(4)
<223> OTHER INFORMATION: allylglycine

<400> SEQUENCE: 78

Gly Lys Lys Gly Phe Leu
1               5

<210> SEQ ID NO 79
<211> LENGTH: 6
<212> TYPE: PRT
<213> ORGANISM: Artificial sequence
<220> FEATURE:
<223> OTHER INFORMATION: synthetic construct
<220> FEATURE:
<221> NAME/KEY: site
<222> LOCATION: (1)..(1)
<223> OTHER INFORMATION: allylglycine
<220> FEATURE:
<221> NAME/KEY: site
<222> LOCATION: (4)..(4)
<223> OTHER INFORMATION: allylglycine
<220> FEATURE:
<221> NAME/KEY: site
<222> LOCATION: (5)..(5)
<223> OTHER INFORMATION: 4-fluoro phenylalanine

<400> SEQUENCE: 79

Gly Lys Lys Gly Phe Leu
1               5

<210> SEQ ID NO 80
<211> LENGTH: 6
<212> TYPE: PRT
<213> ORGANISM: Artificial sequence
<220> FEATURE:
<223> OTHER INFORMATION: synthetic construct
<220> FEATURE:
<221> NAME/KEY: site
<222> LOCATION: (1)..(1)
<223> OTHER INFORMATION: allylglycine
<220> FEATURE:
<221> NAME/KEY: site
<222> LOCATION: (4)..(4)
<223> OTHER INFORMATION: allylglycine
<220> FEATURE:
<221> NAME/KEY: site
<222> LOCATION: (5)..(5)
```

```
<223> OTHER INFORMATION: 4-iodo phenylalanine

<400> SEQUENCE: 80

Gly Lys Lys Gly Phe Leu
1               5

<210> SEQ ID NO 81
<211> LENGTH: 6
<212> TYPE: PRT
<213> ORGANISM: Artificial sequence
<220> FEATURE:
<223> OTHER INFORMATION: synthetic construct
<220> FEATURE:
<221> NAME/KEY: site
<222> LOCATION: (1)..(1)
<223> OTHER INFORMATION: allylglycine
<220> FEATURE:
<221> NAME/KEY: site
<222> LOCATION: (2)..(2)
<223> OTHER INFORMATION: ornithine
<220> FEATURE:
<221> NAME/KEY: site
<222> LOCATION: (4)..(4)
<223> OTHER INFORMATION: allylglycine

<400> SEQUENCE: 81

Gly Xaa Lys Gly Tyr Leu
1               5

<210> SEQ ID NO 82
<211> LENGTH: 6
<212> TYPE: PRT
<213> ORGANISM: Artificial sequence
<220> FEATURE:
<223> OTHER INFORMATION: synthetic construct
<220> FEATURE:
<221> NAME/KEY: site
<222> LOCATION: (1)..(1)
<223> OTHER INFORMATION: allylglycine
<220> FEATURE:
<221> NAME/KEY: site
<222> LOCATION: (2)..(2)
<223> OTHER INFORMATION: 2,4 diaminobutyric acid
<220> FEATURE:
<221> NAME/KEY: site
<222> LOCATION: (4)..(4)
<223> OTHER INFORMATION: allylglycine

<400> SEQUENCE: 82

Gly Xaa Lys Gly Tyr Leu
1               5

<210> SEQ ID NO 83
<211> LENGTH: 6
<212> TYPE: PRT
<213> ORGANISM: Artificial sequence
<220> FEATURE:
<223> OTHER INFORMATION: synthetic construct
<220> FEATURE:
<221> NAME/KEY: site
<222> LOCATION: (1)..(1)
<223> OTHER INFORMATION: allylglycine
<220> FEATURE:
<221> NAME/KEY: site
<222> LOCATION: (2)..(2)
<223> OTHER INFORMATION: 2,3 diaminopropionic acid
<220> FEATURE:
<221> NAME/KEY: site
<222> LOCATION: (4)..(4)
<223> OTHER INFORMATION: allylglycine

<400> SEQUENCE: 83
```

```
Gly Xaa Lys Gly Tyr Leu
1               5

<210> SEQ ID NO 84
<211> LENGTH: 6
<212> TYPE: PRT
<213> ORGANISM: Artificial sequence
<220> FEATURE:
<223> OTHER INFORMATION: synthetic construct
<220> FEATURE:
<221> NAME/KEY: site
<222> LOCATION: (1)..(1)
<223> OTHER INFORMATION: alylglycine
<220> FEATURE:
<221> NAME/KEY: site
<222> LOCATION: (2)..(2)
<223> OTHER INFORMATION: D-amino acid
<220> FEATURE:
<221> NAME/KEY: site
<222> LOCATION: (4)..(4)
<223> OTHER INFORMATION: alylglycine

<400> SEQUENCE: 84

Gly Lys Lys Gly Tyr Leu
1               5

<210> SEQ ID NO 85
<211> LENGTH: 6
<212> TYPE: PRT
<213> ORGANISM: Artificial sequence
<220> FEATURE:
<223> OTHER INFORMATION: synthetic construct
<220> FEATURE:
<221> NAME/KEY: site
<222> LOCATION: (1)..(1)
<223> OTHER INFORMATION: allylglycine
<220> FEATURE:
<221> NAME/KEY: site
<222> LOCATION: (4)..(4)
<223> OTHER INFORMATION: allylglycine

<400> SEQUENCE: 85

Gly His Lys Gly Tyr Leu
1               5

<210> SEQ ID NO 86
<211> LENGTH: 6
<212> TYPE: PRT
<213> ORGANISM: Artificial sequence
<220> FEATURE:
<223> OTHER INFORMATION: synthetic construct
<220> FEATURE:
<221> NAME/KEY: site
<222> LOCATION: (1)..(1)
<223> OTHER INFORMATION: allylglycine
<220> FEATURE:
<221> NAME/KEY: site
<222> LOCATION: (2)..(2)
<223> OTHER INFORMATION: D-amino acid
<220> FEATURE:
<221> NAME/KEY: site
<222> LOCATION: (4)..(4)
<223> OTHER INFORMATION: allylglycine

<400> SEQUENCE: 86

Gly His Lys Gly Tyr Leu
1               5

<210> SEQ ID NO 87
<211> LENGTH: 6
<212> TYPE: PRT
<213> ORGANISM: Artificial sequence
```

```
<220> FEATURE:
<223> OTHER INFORMATION: synthetic construct
<220> FEATURE:
<221> NAME/KEY: site
<222> LOCATION: (1)..(1)
<223> OTHER INFORMATION: allylglycine
<220> FEATURE:
<221> NAME/KEY: site
<222> LOCATION: (2)..(2)
<223> OTHER INFORMATION: norleucine
<220> FEATURE:
<221> NAME/KEY: site
<222> LOCATION: (4)..(4)
<223> OTHER INFORMATION: allylglycine

<400> SEQUENCE: 87

Gly Xaa Lys Gly Tyr Leu
1               5

<210> SEQ ID NO 88
<211> LENGTH: 6
<212> TYPE: PRT
<213> ORGANISM: Artificial sequence
<220> FEATURE:
<223> OTHER INFORMATION: synthetic construct
<220> FEATURE:
<221> NAME/KEY: site
<222> LOCATION: (1)..(1)
<223> OTHER INFORMATION: allylglycine
<220> FEATURE:
<221> NAME/KEY: site
<222> LOCATION: (2)..(2)
<223> OTHER INFORMATION: norvaline
<220> FEATURE:
<221> NAME/KEY: site
<222> LOCATION: (4)..(4)
<223> OTHER INFORMATION: allylglycine

<400> SEQUENCE: 88

Gly Xaa Lys Gly Tyr Leu
1               5

<210> SEQ ID NO 89
<211> LENGTH: 6
<212> TYPE: PRT
<213> ORGANISM: Artificial sequence
<220> FEATURE:
<223> OTHER INFORMATION: synthetic construct
<220> FEATURE:
<221> NAME/KEY: site
<222> LOCATION: (1)..(1)
<223> OTHER INFORMATION: allylglycine
<220> FEATURE:
<221> NAME/KEY: site
<222> LOCATION: (4)..(4)
<223> OTHER INFORMATION: allylglycine

<400> SEQUENCE: 89

Gly Gly Lys Gly Tyr Leu
1               5

<210> SEQ ID NO 90
<211> LENGTH: 6
<212> TYPE: PRT
<213> ORGANISM: Artificial sequence
<220> FEATURE:
<223> OTHER INFORMATION: synthetic construct
<220> FEATURE:
<221> NAME/KEY: site
<222> LOCATION: (1)..(1)
<223> OTHER INFORMATION: allylglycine
<220> FEATURE:
<221> NAME/KEY: site
```

```
<222> LOCATION: (4)..(4)
<223> OTHER INFORMATION: allylglycine

<400> SEQUENCE: 90

Gly Glu Lys Gly Tyr Leu
1               5

<210> SEQ ID NO 91
<211> LENGTH: 6
<212> TYPE: PRT
<213> ORGANISM: Artificial sequence
<220> FEATURE:
<223> OTHER INFORMATION: synthetic construct
<220> FEATURE:
<221> NAME/KEY: site
<222> LOCATION: (1)..(1)
<223> OTHER INFORMATION: alpha-Me-(4-pentenyl) glycine
<220> FEATURE:
<221> NAME/KEY: site
<222> LOCATION: (4)..(4)
<223> OTHER INFORMATION: allylglycine

<400> SEQUENCE: 91

Gly Lys Lys Gly Tyr Leu
1               5

<210> SEQ ID NO 92
<211> LENGTH: 6
<212> TYPE: PRT
<213> ORGANISM: Artificial sequence
<220> FEATURE:
<223> OTHER INFORMATION: synthetic construct
<220> FEATURE:
<221> NAME/KEY: site
<222> LOCATION: (1)..(1)
<223> OTHER INFORMATION: alpha-Me-(4-pentenyl) D glycine
<220> FEATURE:
<221> NAME/KEY: site
<222> LOCATION: (4)..(4)
<223> OTHER INFORMATION: allylglycine

<400> SEQUENCE: 92

Gly Lys Lys Gly Tyr Leu
1               5

<210> SEQ ID NO 93
<211> LENGTH: 6
<212> TYPE: PRT
<213> ORGANISM: Artificial sequence
<220> FEATURE:
<223> OTHER INFORMATION: synthetic construct
<220> FEATURE:
<221> NAME/KEY: site
<222> LOCATION: (1)..(1)
<223> OTHER INFORMATION: allylglycine
<220> FEATURE:
<221> NAME/KEY: site
<222> LOCATION: (4)..(4)
<223> OTHER INFORMATION: alpha-Me-(4-pentenyl) glycine

<400> SEQUENCE: 93

Gly Lys Lys Gly Tyr Leu
1               5

<210> SEQ ID NO 94
<211> LENGTH: 6
<212> TYPE: PRT
<213> ORGANISM: Artificial sequence
<220> FEATURE:
<223> OTHER INFORMATION: synthetic construct
<220> FEATURE:
```

```
<221> NAME/KEY: site
<222> LOCATION: (1)..(1)
<223> OTHER INFORMATION: allylglycine
<220> FEATURE:
<221> NAME/KEY: site
<222> LOCATION: (4)..(4)
<223> OTHER INFORMATION: alpha-Me-(4-pentenyl) D-glycine

<400> SEQUENCE: 94

Gly Lys Lys Gly Tyr Leu
1               5

<210> SEQ ID NO 95
<211> LENGTH: 6
<212> TYPE: PRT
<213> ORGANISM: Artificial sequence
<220> FEATURE:
<223> OTHER INFORMATION: synthetic construct
<220> FEATURE:
<221> NAME/KEY: site
<222> LOCATION: (1)..(1)
<223> OTHER INFORMATION: alpha-Me-(4-pentenyl) glycine
<220> FEATURE:
<221> NAME/KEY: site
<222> LOCATION: (4)..(4)
<223> OTHER INFORMATION: alpha-Me-(4-pentenyl) glycine

<400> SEQUENCE: 95

Gly Lys Lys Gly Tyr Leu
1               5

<210> SEQ ID NO 96
<211> LENGTH: 6
<212> TYPE: PRT
<213> ORGANISM: Artificial sequence
<220> FEATURE:
<223> OTHER INFORMATION: synthetic construct
<220> FEATURE:
<221> NAME/KEY: site
<222> LOCATION: (1)..(1)
<223> OTHER INFORMATION: 2,3 diaminopropionic acid

<400> SEQUENCE: 96

Xaa Lys Lys Asp Tyr Leu
1               5

<210> SEQ ID NO 97
<211> LENGTH: 6
<212> TYPE: PRT
<213> ORGANISM: Artificial sequence
<220> FEATURE:
<223> OTHER INFORMATION: synthetic construct
<220> FEATURE:
<221> NAME/KEY: site
<222> LOCATION: (1)..(1)
<223> OTHER INFORMATION: 2,4 Diaminobutyric acid

<400> SEQUENCE: 97

Xaa Lys Lys Asp Tyr Leu
1               5

<210> SEQ ID NO 98
<211> LENGTH: 6
<212> TYPE: PRT
<213> ORGANISM: Artificial sequence
<220> FEATURE:
<223> OTHER INFORMATION: synthetic construct
<220> FEATURE:
<221> NAME/KEY: site
<222> LOCATION: (1)..(1)
<223> OTHER INFORMATION: ornithine
```

<400> SEQUENCE: 98

Xaa Lys Lys Asp Tyr Leu
1               5

<210> SEQ ID NO 99
<211> LENGTH: 6
<212> TYPE: PRT
<213> ORGANISM: Artificial sequence
<220> FEATURE:
<223> OTHER INFORMATION: synthetic construct

<400> SEQUENCE: 99

Lys Lys Lys Asp Tyr Leu
1               5

<210> SEQ ID NO 100
<211> LENGTH: 6
<212> TYPE: PRT
<213> ORGANISM: Artificial sequence
<220> FEATURE:
<223> OTHER INFORMATION: synthetic construct
<220> FEATURE:
<221> NAME/KEY: site
<222> LOCATION: (1)..(1)
<223> OTHER INFORMATION: 2,3 diaminopropionic acid

<400> SEQUENCE: 100

Xaa Lys Lys Glu Tyr Leu
1               5

<210> SEQ ID NO 101
<211> LENGTH: 6
<212> TYPE: PRT
<213> ORGANISM: Artificial sequence
<220> FEATURE:
<223> OTHER INFORMATION: synthetic construct
<220> FEATURE:
<221> NAME/KEY: site
<222> LOCATION: (1)..(1)
<223> OTHER INFORMATION: 2,4 Diaminobutyric acid

<400> SEQUENCE: 101

Xaa Lys Lys Glu Tyr Leu
1               5

<210> SEQ ID NO 102
<211> LENGTH: 6
<212> TYPE: PRT
<213> ORGANISM: Artificial sequence
<220> FEATURE:
<223> OTHER INFORMATION: synthetic construct
<220> FEATURE:
<221> NAME/KEY: site
<222> LOCATION: (1)..(1)
<223> OTHER INFORMATION: ornithine

<400> SEQUENCE: 102

Xaa Lys Lys Glu Tyr Leu
1               5

<210> SEQ ID NO 103
<211> LENGTH: 6
<212> TYPE: PRT
<213> ORGANISM: Artificial sequence
<220> FEATURE:
<223> OTHER INFORMATION: synthetic construct

<400> SEQUENCE: 103

```
Lys Lys Lys Glu Tyr Leu
1               5

<210> SEQ ID NO 104
<211> LENGTH: 6
<212> TYPE: PRT
<213> ORGANISM: Artificial sequence
<220> FEATURE:
<223> OTHER INFORMATION: synthetic construct
<220> FEATURE:
<221> NAME/KEY: site
<222> LOCATION: (4)..(4)
<223> OTHER INFORMATION: 2,3 diaminopropionic acid

<400> SEQUENCE: 104

Glu Lys Lys Xaa Tyr Leu
1               5

<210> SEQ ID NO 105
<211> LENGTH: 6
<212> TYPE: PRT
<213> ORGANISM: Artificial sequence
<220> FEATURE:
<223> OTHER INFORMATION: synthetic construct
<220> FEATURE:
<221> NAME/KEY: site
<222> LOCATION: (4)..(4)
<223> OTHER INFORMATION: 2,3 diaminopropionic acid

<400> SEQUENCE: 105

Asp Lys Lys Xaa Tyr Leu
1               5

<210> SEQ ID NO 106
<211> LENGTH: 6
<212> TYPE: PRT
<213> ORGANISM: Artificial sequence
<220> FEATURE:
<223> OTHER INFORMATION: synthetic construct
<220> FEATURE:
<221> NAME/KEY: site
<222> LOCATION: (4)..(4)
<223> OTHER INFORMATION: 2,4 diaminobutyric acid

<400> SEQUENCE: 106

Glu Lys Lys Xaa Tyr Leu
1               5

<210> SEQ ID NO 107
<211> LENGTH: 6
<212> TYPE: PRT
<213> ORGANISM: Artificial sequence
<220> FEATURE:
<223> OTHER INFORMATION: synthetic construct
<220> FEATURE:
<221> NAME/KEY: site
<222> LOCATION: (4)..(4)
<223> OTHER INFORMATION: 2,4 diaminobutyric acid

<400> SEQUENCE: 107

Asp Lys Lys Xaa Tyr Leu
1               5

<210> SEQ ID NO 108
<211> LENGTH: 6
<212> TYPE: PRT
<213> ORGANISM: Artificial sequence
<220> FEATURE:
<223> OTHER INFORMATION: synthetic construct
```

```
<220> FEATURE:
<221> NAME/KEY: site
<222> LOCATION: (4)..(4)
<223> OTHER INFORMATION: ornithine

<400> SEQUENCE: 108

Glu Lys Lys Xaa Tyr Leu
1               5

<210> SEQ ID NO 109
<211> LENGTH: 6
<212> TYPE: PRT
<213> ORGANISM: Artificial sequence
<220> FEATURE:
<223> OTHER INFORMATION: synthetic construct
<220> FEATURE:
<221> NAME/KEY: site
<222> LOCATION: (4)..(4)
<223> OTHER INFORMATION: ornithine

<400> SEQUENCE: 109

Asp Lys Lys Xaa Tyr Leu
1               5

<210> SEQ ID NO 110
<211> LENGTH: 6
<212> TYPE: PRT
<213> ORGANISM: Artificial sequence
<220> FEATURE:
<223> OTHER INFORMATION: synthetic construct

<400> SEQUENCE: 110

Glu Lys Lys Lys Tyr Leu
1               5

<210> SEQ ID NO 111
<211> LENGTH: 6
<212> TYPE: PRT
<213> ORGANISM: Artificial sequence
<220> FEATURE:
<223> OTHER INFORMATION: synthetic construct

<400> SEQUENCE: 111

Asp Lys Lys Lys Tyr Leu
1               5

<210> SEQ ID NO 112
<211> LENGTH: 6
<212> TYPE: PRT
<213> ORGANISM: Artificial sequence
<220> FEATURE:
<223> OTHER INFORMATION: synthetic construct
<220> FEATURE:
<221> NAME/KEY: site
<222> LOCATION: (1)..(1)
<223> OTHER INFORMATION: allylglycine
<220> FEATURE:
<221> NAME/KEY: site
<222> LOCATION: (4)..(4)
<223> OTHER INFORMATION: allylglycine
<220> FEATURE:
<221> NAME/KEY: site
<222> LOCATION: (5)..(5)
<223> OTHER INFORMATION: 4-tert butyl phenylalanine

<400> SEQUENCE: 112

Gly Lys Lys Gly Phe Leu
1               5
```

```
<210> SEQ ID NO 113
<211> LENGTH: 6
<212> TYPE: PRT
<213> ORGANISM: Artificial sequence
<220> FEATURE:
<223> OTHER INFORMATION: synthetic construct
<220> FEATURE:
<221> NAME/KEY: site
<222> LOCATION: (1)..(1)
<223> OTHER INFORMATION: allylglycine
<220> FEATURE:
<221> NAME/KEY: site
<222> LOCATION: (4)..(4)
<223> OTHER INFORMATION: allylglycine
<220> FEATURE:
<221> NAME/KEY: site
<222> LOCATION: (5)..(5)
<223> OTHER INFORMATION: 4-CF3 phenylalanine

<400> SEQUENCE: 113

Gly Lys Lys Gly Phe Leu
1               5

<210> SEQ ID NO 114
<211> LENGTH: 6
<212> TYPE: PRT
<213> ORGANISM: Artificial sequence
<220> FEATURE:
<223> OTHER INFORMATION: synthetic construct
<220> FEATURE:
<221> NAME/KEY: site
<222> LOCATION: (1)..(1)
<223> OTHER INFORMATION: allylglycine
<220> FEATURE:
<221> NAME/KEY: site
<222> LOCATION: (4)..(4)
<223> OTHER INFORMATION: allylglycine
<220> FEATURE:
<221> NAME/KEY: site
<222> LOCATION: (5)..(5)
<223> OTHER INFORMATION: naphtyl alanine

<400> SEQUENCE: 114

Gly Lys Lys Gly Ala Leu
1               5

<210> SEQ ID NO 115
<211> LENGTH: 6
<212> TYPE: PRT
<213> ORGANISM: Artificial sequence
<220> FEATURE:
<223> OTHER INFORMATION: synthetic construct
<220> FEATURE:
<221> NAME/KEY: site
<222> LOCATION: (1)..(1)
<223> OTHER INFORMATION: allylglycine
<220> FEATURE:
<221> NAME/KEY: site
<222> LOCATION: (4)..(4)
<223> OTHER INFORMATION: allylglycine
<220> FEATURE:
<221> NAME/KEY: site
<222> LOCATION: (5)..(5)
<223> OTHER INFORMATION: 3-chloro phenylalanine

<400> SEQUENCE: 115

Gly Lys Lys Gly Phe Leu
1               5

<210> SEQ ID NO 116
<211> LENGTH: 6
<212> TYPE: PRT
<213> ORGANISM: Artificial sequence
```

```
<220> FEATURE:
<223> OTHER INFORMATION: synthetic construct
<220> FEATURE:
<221> NAME/KEY: site
<222> LOCATION: (1)..(1)
<223> OTHER INFORMATION: allylglycine
<220> FEATURE:
<221> NAME/KEY: site
<222> LOCATION: (4)..(4)
<223> OTHER INFORMATION: allylglycine
<220> FEATURE:
<221> NAME/KEY: site
<222> LOCATION: (5)..(5)
<223> OTHER INFORMATION: 4-chloro phenylalanine

<400> SEQUENCE: 116

Gly Lys Lys Gly Phe Leu
1               5

<210> SEQ ID NO 117
<211> LENGTH: 6
<212> TYPE: PRT
<213> ORGANISM: Artificial sequence
<220> FEATURE:
<223> OTHER INFORMATION: synthetic construct
<220> FEATURE:
<221> NAME/KEY: site
<222> LOCATION: (1)..(1)
<223> OTHER INFORMATION: allylglycine
<220> FEATURE:
<221> NAME/KEY: site
<222> LOCATION: (4)..(4)
<223> OTHER INFORMATION: allylglycine
<220> FEATURE:
<221> NAME/KEY: site
<222> LOCATION: (5)..(5)
<223> OTHER INFORMATION: 3-bromo phenylalanine

<400> SEQUENCE: 117

Gly Lys Lys Gly Phe Leu
1               5

<210> SEQ ID NO 118
<211> LENGTH: 6
<212> TYPE: PRT
<213> ORGANISM: Artificial sequence
<220> FEATURE:
<223> OTHER INFORMATION: synthetic construct
<220> FEATURE:
<221> NAME/KEY: site
<222> LOCATION: (1)..(1)
<223> OTHER INFORMATION: allylglycine
<220> FEATURE:
<221> NAME/KEY: site
<222> LOCATION: (4)..(4)
<223> OTHER INFORMATION: allylglycine
<220> FEATURE:
<221> NAME/KEY: site
<222> LOCATION: (5)..(5)
<223> OTHER INFORMATION: 4-bromo phenylalanine

<400> SEQUENCE: 118

Gly Lys Lys Gly Phe Leu
1               5

<210> SEQ ID NO 119
<211> LENGTH: 6
<212> TYPE: PRT
<213> ORGANISM: Artificial sequence
<220> FEATURE:
<223> OTHER INFORMATION: synthetic construct
<220> FEATURE:
<221> NAME/KEY: site
```

```
<222> LOCATION: (1)..(1)
<223> OTHER INFORMATION: allylglycine
<220> FEATURE:
<221> NAME/KEY: site
<222> LOCATION: (4)..(4)
<223> OTHER INFORMATION: allylglycine
<220> FEATURE:
<221> NAME/KEY: site
<222> LOCATION: (5)..(5)
<223> OTHER INFORMATION: 3-iodo phenylalanine

<400> SEQUENCE: 119

Gly Lys Lys Gly Phe Leu
1               5

<210> SEQ ID NO 120
<211> LENGTH: 6
<212> TYPE: PRT
<213> ORGANISM: Artificial sequence
<220> FEATURE:
<223> OTHER INFORMATION: synthetic construct
<220> FEATURE:
<221> NAME/KEY: site
<222> LOCATION: (1)..(1)
<223> OTHER INFORMATION: allylglycine
<220> FEATURE:
<221> NAME/KEY: site
<222> LOCATION: (4)..(4)
<223> OTHER INFORMATION: allylglycine
<220> FEATURE:
<221> NAME/KEY: site
<222> LOCATION: (5)..(5)
<223> OTHER INFORMATION: 4-cyano phenylalanine

<400> SEQUENCE: 120

Gly Lys Lys Gly Phe Leu
1               5

<210> SEQ ID NO 121
<211> LENGTH: 6
<212> TYPE: PRT
<213> ORGANISM: Artificial sequence
<220> FEATURE:
<223> OTHER INFORMATION: synthetic construct
<220> FEATURE:
<221> NAME/KEY: site
<222> LOCATION: (1)..(1)
<223> OTHER INFORMATION: allylglycine
<220> FEATURE:
<221> NAME/KEY: site
<222> LOCATION: (4)..(4)
<223> OTHER INFORMATION: allylglycine
<220> FEATURE:
<221> NAME/KEY: site
<222> LOCATION: (5)..(5)
<223> OTHER INFORMATION: cyclohexyl alanine

<400> SEQUENCE: 121

Gly Lys Lys Gly Ala Leu
1               5

<210> SEQ ID NO 122
<211> LENGTH: 6
<212> TYPE: PRT
<213> ORGANISM: Artificial sequence
<220> FEATURE:
<223> OTHER INFORMATION: synthetic construct
<220> FEATURE:
<221> NAME/KEY: site
<222> LOCATION: (1)..(1)
<223> OTHER INFORMATION: allylglycine
<220> FEATURE:
<221> NAME/KEY: site
```

```
<222> LOCATION: (4)..(4)
<223> OTHER INFORMATION: allylglycine
<220> FEATURE:
<221> NAME/KEY: site
<222> LOCATION: (5)..(5)
<223> OTHER INFORMATION: 2-furyl alanine

<400> SEQUENCE: 122

Gly Lys Lys Gly Ala Leu
1               5

<210> SEQ ID NO 123
<211> LENGTH: 6
<212> TYPE: PRT
<213> ORGANISM: Artificial sequence
<220> FEATURE:
<223> OTHER INFORMATION: synthetic construct
<220> FEATURE:
<221> NAME/KEY: site
<222> LOCATION: (1)..(1)
<223> OTHER INFORMATION: allylglycine
<220> FEATURE:
<221> NAME/KEY: site
<222> LOCATION: (4)..(4)
<223> OTHER INFORMATION: allylglycine
<220> FEATURE:
<221> NAME/KEY: site
<222> LOCATION: (5)..(5)
<223> OTHER INFORMATION: 4-amino phenylalanine

<400> SEQUENCE: 123

Gly Lys Lys Gly Phe Leu
1               5

<210> SEQ ID NO 124
<211> LENGTH: 6
<212> TYPE: PRT
<213> ORGANISM: Artificial sequence
<220> FEATURE:
<223> OTHER INFORMATION: synthetic construct
<220> FEATURE:
<221> NAME/KEY: site
<222> LOCATION: (1)..(1)
<223> OTHER INFORMATION: allylglycine
<220> FEATURE:
<221> NAME/KEY: site
<222> LOCATION: (4)..(4)
<223> OTHER INFORMATION: allylglycine
<220> FEATURE:
<221> NAME/KEY: site
<222> LOCATION: (5)..(5)
<223> OTHER INFORMATION: 4-nitro phenylalanine

<400> SEQUENCE: 124

Gly Lys Lys Gly Phe Leu
1               5

<210> SEQ ID NO 125
<211> LENGTH: 6
<212> TYPE: PRT
<213> ORGANISM: Artificial sequence
<220> FEATURE:
<223> OTHER INFORMATION: synthetic construct
<220> FEATURE:
<221> NAME/KEY: site
<222> LOCATION: (1)..(1)
<223> OTHER INFORMATION: allylglycine
<220> FEATURE:
<221> NAME/KEY: site
<222> LOCATION: (4)..(4)
<223> OTHER INFORMATION: allylglycine
<220> FEATURE:
<221> NAME/KEY: site
```

```
<222> LOCATION: (5)..(5)
<223> OTHER INFORMATION: 4-methyl phenylalanine

<400> SEQUENCE: 125

Gly Lys Lys Gly Phe Leu
1               5

<210> SEQ ID NO 126
<211> LENGTH: 6
<212> TYPE: PRT
<213> ORGANISM: Artificial sequence
<220> FEATURE:
<223> OTHER INFORMATION: synthetic construct
<220> FEATURE:
<221> NAME/KEY: site
<222> LOCATION: (1)..(1)
<223> OTHER INFORMATION: allylglycine
<220> FEATURE:
<221> NAME/KEY: site
<222> LOCATION: (4)..(4)
<223> OTHER INFORMATION: allylglycine
<220> FEATURE:
<221> NAME/KEY: site
<222> LOCATION: (5)..(5)
<223> OTHER INFORMATION: 2,3,4,5,6 -pentafluoro phenylalanine

<400> SEQUENCE: 126

Gly Lys Lys Gly Phe Leu
1               5

<210> SEQ ID NO 127
<211> LENGTH: 6
<212> TYPE: PRT
<213> ORGANISM: Artificial sequence
<220> FEATURE:
<223> OTHER INFORMATION: synthetic construct
<220> FEATURE:
<221> NAME/KEY: site
<222> LOCATION: (1)..(1)
<223> OTHER INFORMATION: allylglycine
<220> FEATURE:
<221> NAME/KEY: site
<222> LOCATION: (4)..(4)
<223> OTHER INFORMATION: allylglycine
<220> FEATURE:
<221> NAME/KEY: site
<222> LOCATION: (5)..(5)
<223> OTHER INFORMATION: 4-Hydroxyphenylglycine

<400> SEQUENCE: 127

Gly Lys Lys Gly Gly Leu
1               5

<210> SEQ ID NO 128
<211> LENGTH: 6
<212> TYPE: PRT
<213> ORGANISM: Artificial sequence
<220> FEATURE:
<223> OTHER INFORMATION: synthetic construct
<220> FEATURE:
<221> NAME/KEY: site
<222> LOCATION: (1)..(1)
<223> OTHER INFORMATION: allylglycine
<220> FEATURE:
<221> NAME/KEY: site
<222> LOCATION: (4)..(4)
<223> OTHER INFORMATION: allylglycine
<220> FEATURE:
<221> NAME/KEY: site
<222> LOCATION: (5)..(5)
<223> OTHER INFORMATION: homotyrosine

<400> SEQUENCE: 128
```

```
Gly Lys Lys Gly Tyr Leu
1               5

<210> SEQ ID NO 129
<211> LENGTH: 6
<212> TYPE: PRT
<213> ORGANISM: Artificial sequence
<220> FEATURE:
<223> OTHER INFORMATION: synthetic construct
<220> FEATURE:
<221> NAME/KEY: site
<222> LOCATION: (1)..(1)
<223> OTHER INFORMATION: allylglycine
<220> FEATURE:
<221> NAME/KEY: site
<222> LOCATION: (4)..(4)
<223> OTHER INFORMATION: allylglycine
<220> FEATURE:
<221> NAME/KEY: site
<222> LOCATION: (5)..(5)
<223> OTHER INFORMATION: 4-bromo phenylalanine
<220> FEATURE:
<221> NAME/KEY: site
<222> LOCATION: (6)..(6)
<223> OTHER INFORMATION: cyclopentyl alanine

<400> SEQUENCE: 129

Gly Lys Lys Gly Phe Ala
1               5

<210> SEQ ID NO 130
<211> LENGTH: 6
<212> TYPE: PRT
<213> ORGANISM: Artificial sequence
<220> FEATURE:
<223> OTHER INFORMATION: synthetic construct
<220> FEATURE:
<221> NAME/KEY: site
<222> LOCATION: (1)..(1)
<223> OTHER INFORMATION: allylglycine
<220> FEATURE:
<221> NAME/KEY: site
<222> LOCATION: (4)..(4)
<223> OTHER INFORMATION: (S)-alpha-Methyl-(4-pentenyl) glycine
<220> FEATURE:
<221> NAME/KEY: site
<222> LOCATION: (6)..(6)
<223> OTHER INFORMATION: cyclopentylalanine

<400> SEQUENCE: 130

Gly Lys Lys Gly Tyr Ala
1               5

<210> SEQ ID NO 131
<211> LENGTH: 5
<212> TYPE: PRT
<213> ORGANISM: Artificial sequence
<220> FEATURE:
<223> OTHER INFORMATION: synthetic construct
<220> FEATURE:
<221> NAME/KEY: site
<222> LOCATION: (1)..(1)
<223> OTHER INFORMATION: lysine pentenoyl
<220> FEATURE:
<221> NAME/KEY: site
<222> LOCATION: (3)..(3)
<223> OTHER INFORMATION: allylglycine
<220> FEATURE:
<221> NAME/KEY: site
<222> LOCATION: (5)..(5)
<223> OTHER INFORMATION: cyclopentyl alanine

<400> SEQUENCE: 131
```

Lys Lys Gly Tyr Ala
1               5

<210> SEQ ID NO 132
<211> LENGTH: 6
<212> TYPE: PRT
<213> ORGANISM: Artificial sequence
<220> FEATURE:
<223> OTHER INFORMATION: synthetic construct
<220> FEATURE:
<221> NAME/KEY: site
<222> LOCATION: (1)..(1)
<223> OTHER INFORMATION: allylglycine
<220> FEATURE:
<221> NAME/KEY: site
<222> LOCATION: (4)..(4)
<223> OTHER INFORMATION: alpha-Me-(4-pentenyl) glycine
<220> FEATURE:
<221> NAME/KEY: site
<222> LOCATION: (5)..(5)
<223> OTHER INFORMATION: 4-bromo phenylalanine

<400> SEQUENCE: 132

Gly Lys Lys Gly Phe Leu
1               5

<210> SEQ ID NO 133
<211> LENGTH: 5
<212> TYPE: PRT
<213> ORGANISM: Artificial sequence
<220> FEATURE:
<223> OTHER INFORMATION: synthetic construct
<220> FEATURE:
<221> NAME/KEY: site
<222> LOCATION: (1)..(1)
<223> OTHER INFORMATION: lysine pentenoyl
<220> FEATURE:
<221> NAME/KEY: site
<222> LOCATION: (3)..(3)
<223> OTHER INFORMATION: allylglycine
<220> FEATURE:
<221> NAME/KEY: site
<222> LOCATION: (4)..(4)
<223> OTHER INFORMATION: 4-bromo phenylalanine

<400> SEQUENCE: 133

Lys Lys Gly Phe Leu
1               5

<210> SEQ ID NO 134
<211> LENGTH: 5
<212> TYPE: PRT
<213> ORGANISM: Artificial sequence
<220> FEATURE:
<223> OTHER INFORMATION: synthetic construct
<220> FEATURE:
<221> NAME/KEY: site
<222> LOCATION: (1)..(1)
<223> OTHER INFORMATION: lysine pentenoyl
<220> FEATURE:
<221> NAME/KEY: site
<222> LOCATION: (3)..(3)
<223> OTHER INFORMATION: alpha-methyl-(4-pentenyl) glycine

<400> SEQUENCE: 134

Lys Lys Gly Tyr Leu
1               5

<210> SEQ ID NO 135
<211> LENGTH: 6
<212> TYPE: PRT

```
<213> ORGANISM: Artificial sequence
<220> FEATURE:
<223> OTHER INFORMATION: synthetic construct
<220> FEATURE:
<221> NAME/KEY: site
<222> LOCATION: (1)..(1)
<223> OTHER INFORMATION: allylglycine
<220> FEATURE:
<221> NAME/KEY: site
<222> LOCATION: (4)..(4)
<223> OTHER INFORMATION: alpha-methyl-(4-pentenyl) glycine
<220> FEATURE:
<221> NAME/KEY: site
<222> LOCATION: (5)..(5)
<223> OTHER INFORMATION: 4-bromo phenylalanine
<220> FEATURE:
<221> NAME/KEY: site
<222> LOCATION: (6)..(6)
<223> OTHER INFORMATION: cyclopentyl alanine

<400> SEQUENCE: 135

Gly Lys Lys Gly Phe Ala
1               5

<210> SEQ ID NO 136
<211> LENGTH: 5
<212> TYPE: PRT
<213> ORGANISM: Artificial sequence
<220> FEATURE:
<223> OTHER INFORMATION: synthetic construct
<220> FEATURE:
<221> NAME/KEY: site
<222> LOCATION: (1)..(1)
<223> OTHER INFORMATION: lysine pentenoyl
<220> FEATURE:
<221> NAME/KEY: site
<222> LOCATION: (3)..(3)
<223> OTHER INFORMATION: allylglycine
<220> FEATURE:
<221> NAME/KEY: site
<222> LOCATION: (4)..(4)
<223> OTHER INFORMATION: 4-bromo phenylalanine
<220> FEATURE:
<221> NAME/KEY: site
<222> LOCATION: (5)..(5)
<223> OTHER INFORMATION: cyclopentyl alanine

<400> SEQUENCE: 136

Lys Lys Gly Phe Ala
1               5

<210> SEQ ID NO 137
<211> LENGTH: 5
<212> TYPE: PRT
<213> ORGANISM: Artificial sequence
<220> FEATURE:
<223> OTHER INFORMATION: synthetic construct
<220> FEATURE:
<221> NAME/KEY: site
<222> LOCATION: (1)..(1)
<223> OTHER INFORMATION: lysine pentenoyl
<220> FEATURE:
<221> NAME/KEY: site
<222> LOCATION: (3)..(3)
<223> OTHER INFORMATION: alpha-methyl-(4-pentenyl) glycine
<220> FEATURE:
<221> NAME/KEY: site
<222> LOCATION: (5)..(5)
<223> OTHER INFORMATION: cyclopentyl alanine

<400> SEQUENCE: 137

Lys Lys Gly Tyr Ala
1               5
```

```
<210> SEQ ID NO 138
<211> LENGTH: 5
<212> TYPE: PRT
<213> ORGANISM: Artificial sequence
<220> FEATURE:
<223> OTHER INFORMATION: synthetic construct
<220> FEATURE:
<221> NAME/KEY: site
<222> LOCATION: (1)..(1)
<223> OTHER INFORMATION: lysine pentenoyl
<220> FEATURE:
<221> NAME/KEY: site
<222> LOCATION: (3)..(3)
<223> OTHER INFORMATION: alpha-methyl-(4-pentenyl) glycine
<220> FEATURE:
<221> NAME/KEY: site
<222> LOCATION: (4)..(4)
<223> OTHER INFORMATION: 4-bromo phenylalanine

<400> SEQUENCE: 138

Lys Lys Gly Phe Leu
1               5

<210> SEQ ID NO 139
<211> LENGTH: 5
<212> TYPE: PRT
<213> ORGANISM: Artificial sequence
<220> FEATURE:
<223> OTHER INFORMATION: synthetic construct
<220> FEATURE:
<221> NAME/KEY: site
<222> LOCATION: (1)..(1)
<223> OTHER INFORMATION: lysine pentenoyl
<220> FEATURE:
<221> NAME/KEY: site
<222> LOCATION: (3)..(3)
<223> OTHER INFORMATION: alpha-methyl-(4-pentenyl) glycine
<220> FEATURE:
<221> NAME/KEY: site
<222> LOCATION: (4)..(4)
<223> OTHER INFORMATION: 4-bromo phenylalanine
<220> FEATURE:
<221> NAME/KEY: site
<222> LOCATION: (5)..(5)
<223> OTHER INFORMATION: cyclopentyl alanine

<400> SEQUENCE: 139

Lys Lys Gly Phe Ala
1               5

<210> SEQ ID NO 140
<211> LENGTH: 6
<212> TYPE: PRT
<213> ORGANISM: Artificial sequence
<220> FEATURE:
<223> OTHER INFORMATION: synthetic construct
<220> FEATURE:
<221> NAME/KEY: site
<222> LOCATION: (1)..(1)
<223> OTHER INFORMATION: allylglycine
<220> FEATURE:
<221> NAME/KEY: site
<222> LOCATION: (4)..(4)
<223> OTHER INFORMATION: allylglycine

<400> SEQUENCE: 140

Gly Lys Lys Gly Ala Leu
1               5

<210> SEQ ID NO 141
<211> LENGTH: 6
<212> TYPE: PRT
```

```
<213> ORGANISM: Artificial sequence
<220> FEATURE:
<223> OTHER INFORMATION: synthetic construct
<220> FEATURE:
<221> NAME/KEY: site
<222> LOCATION: (1)..(1)
<223> OTHER INFORMATION: allylglycine
<220> FEATURE:
<221> NAME/KEY: site
<222> LOCATION: (4)..(4)
<223> OTHER INFORMATION: allylglycine
<220> FEATURE:
<221> NAME/KEY: site
<222> LOCATION: (5)..(5)
<223> OTHER INFORMATION: biphenylalanine

<400> SEQUENCE: 141

Gly Lys Lys Gly Ala Leu
1               5

<210> SEQ ID NO 142
<211> LENGTH: 6
<212> TYPE: PRT
<213> ORGANISM: Artificial sequence
<220> FEATURE:
<223> OTHER INFORMATION: synthetic construct
<220> FEATURE:
<221> NAME/KEY: site
<222> LOCATION: (1)..(1)
<223> OTHER INFORMATION: allylglycine
<220> FEATURE:
<221> NAME/KEY: site
<222> LOCATION: (4)..(4)
<223> OTHER INFORMATION: allylglycine
<220> FEATURE:
<221> NAME/KEY: site
<222> LOCATION: (5)..(5)
<223> OTHER INFORMATION: diphenylalanine

<400> SEQUENCE: 142

Gly Lys Lys Gly Ala Leu
1               5

<210> SEQ ID NO 143
<211> LENGTH: 6
<212> TYPE: PRT
<213> ORGANISM: Artificial sequence
<220> FEATURE:
<223> OTHER INFORMATION: synthetic construct
<220> FEATURE:
<221> NAME/KEY: site
<222> LOCATION: (1)..(1)
<223> OTHER INFORMATION: allylglycine
<220> FEATURE:
<221> NAME/KEY: site
<222> LOCATION: (4)..(4)
<223> OTHER INFORMATION: allylglycine
<220> FEATURE:
<221> NAME/KEY: site
<222> LOCATION: (5)..(6)
<223> OTHER INFORMATION: D-amino acids

<400> SEQUENCE: 143

Gly Lys Lys Gly Tyr Leu
1               5

<210> SEQ ID NO 144
<211> LENGTH: 6
<212> TYPE: PRT
<213> ORGANISM: Artificial sequence
<220> FEATURE:
<223> OTHER INFORMATION: synthetic construct
<220> FEATURE:
```

```
<221> NAME/KEY: site
<222> LOCATION: (1)..(1)
<223> OTHER INFORMATION: allylglycine
<220> FEATURE:
<221> NAME/KEY: site
<222> LOCATION: (4)..(4)
<223> OTHER INFORMATION: allylglycine
<220> FEATURE:
<221> NAME/KEY: site
<222> LOCATION: (5)..(5)
<223> OTHER INFORMATION: cyclopentyl alanine

<400> SEQUENCE: 144

Gly Lys Lys Gly Ala Leu
1               5

<210> SEQ ID NO 145
<211> LENGTH: 6
<212> TYPE: PRT
<213> ORGANISM: Artificial sequence
<220> FEATURE:
<223> OTHER INFORMATION: synthetic construct
<220> FEATURE:
<221> NAME/KEY: site
<222> LOCATION: (1)..(1)
<223> OTHER INFORMATION: allylglycine
<220> FEATURE:
<221> NAME/KEY: site
<222> LOCATION: (4)..(4)
<223> OTHER INFORMATION: allylglycine
<220> FEATURE:
<221> NAME/KEY: site
<222> LOCATION: (5)..(5)
<223> OTHER INFORMATION: cyclobutyl alanine

<400> SEQUENCE: 145

Gly Lys Lys Gly Ala Leu
1               5

<210> SEQ ID NO 146
<211> LENGTH: 6
<212> TYPE: PRT
<213> ORGANISM: Artificial sequence
<220> FEATURE:
<223> OTHER INFORMATION: synthetic construct
<220> FEATURE:
<221> NAME/KEY: site
<222> LOCATION: (1)..(1)
<223> OTHER INFORMATION: allylglycine
<220> FEATURE:
<221> NAME/KEY: site
<222> LOCATION: (4)..(4)
<223> OTHER INFORMATION: allylglycine
<220> FEATURE:
<221> NAME/KEY: site
<222> LOCATION: (5)..(5)
<223> OTHER INFORMATION: cyclopropyl alanine

<400> SEQUENCE: 146

Gly Lys Lys Gly Ala Leu
1               5

<210> SEQ ID NO 147
<211> LENGTH: 6
<212> TYPE: PRT
<213> ORGANISM: Artificial sequence
<220> FEATURE:
<223> OTHER INFORMATION: synthetic construct
<220> FEATURE:
<221> NAME/KEY: site
<222> LOCATION: (1)..(1)
<223> OTHER INFORMATION: allylglycine
<220> FEATURE:
```

```
<221> NAME/KEY: site
<222> LOCATION: (1)..(6)
<223> OTHER INFORMATION: D-amino acids
<220> FEATURE:
<221> NAME/KEY: site
<222> LOCATION: (4)..(4)
<223> OTHER INFORMATION: allylglycine

<400> SEQUENCE: 147

Gly Lys Lys Gly Tyr Leu
1               5

<210> SEQ ID NO 148
<211> LENGTH: 6
<212> TYPE: PRT
<213> ORGANISM: Artificial sequence
<220> FEATURE:
<223> OTHER INFORMATION: synthetic construct
<220> FEATURE:
<221> NAME/KEY: site
<222> LOCATION: (1)..(1)
<223> OTHER INFORMATION: allylglycine
<220> FEATURE:
<221> NAME/KEY: site
<222> LOCATION: (3)..(3)
<223> OTHER INFORMATION: citrulline
<220> FEATURE:
<221> NAME/KEY: site
<222> LOCATION: (4)..(4)
<223> OTHER INFORMATION: allylglycine

<400> SEQUENCE: 148

Gly Lys Ala Gly Tyr Leu
1               5

<210> SEQ ID NO 149
<211> LENGTH: 6
<212> TYPE: PRT
<213> ORGANISM: Artificial sequence
<220> FEATURE:
<223> OTHER INFORMATION: synthetic construct
<220> FEATURE:
<221> NAME/KEY: site
<222> LOCATION: (1)..(1)
<223> OTHER INFORMATION: allylglycine
<220> FEATURE:
<221> NAME/KEY: site
<222> LOCATION: (2)..(2)
<223> OTHER INFORMATION: citrulline
<220> FEATURE:
<221> NAME/KEY: site
<222> LOCATION: (4)..(4)
<223> OTHER INFORMATION: allylglycine

<400> SEQUENCE: 149

Gly Ala Lys Gly Tyr Leu
1               5

<210> SEQ ID NO 150
<211> LENGTH: 6
<212> TYPE: PRT
<213> ORGANISM: Artificial sequence
<220> FEATURE:
<223> OTHER INFORMATION: synthetic construct
<220> FEATURE:
<221> NAME/KEY: site
<222> LOCATION: (1)..(1)
<223> OTHER INFORMATION: allylglycine
<220> FEATURE:
<221> NAME/KEY: site
<222> LOCATION: (2)..(3)
<223> OTHER INFORMATION: citrulline
<220> FEATURE:
```

```
<221> NAME/KEY: site
<222> LOCATION: (4)..(4)
<223> OTHER INFORMATION: allylglycine

<400> SEQUENCE: 150

Gly Ala Ala Gly Tyr Leu
1               5

<210> SEQ ID NO 151
<211> LENGTH: 6
<212> TYPE: PRT
<213> ORGANISM: Artificial sequence
<220> FEATURE:
<223> OTHER INFORMATION: synthetic construct
<220> FEATURE:
<221> NAME/KEY: site
<222> LOCATION: (1)..(1)
<223> OTHER INFORMATION: allylglycine
<220> FEATURE:
<221> NAME/KEY: site
<222> LOCATION: (3)..(3)
<223> OTHER INFORMATION: homolysine
<220> FEATURE:
<221> NAME/KEY: site
<222> LOCATION: (4)..(4)
<223> OTHER INFORMATION: allylglycine

<400> SEQUENCE: 151

Gly Lys Lys Gly Tyr Leu
1               5

<210> SEQ ID NO 152
<211> LENGTH: 6
<212> TYPE: PRT
<213> ORGANISM: Artificial sequence
<220> FEATURE:
<223> OTHER INFORMATION: synthetic construct
<220> FEATURE:
<221> NAME/KEY: site
<222> LOCATION: (1)..(1)
<223> OTHER INFORMATION: allylglycine
<220> FEATURE:
<221> NAME/KEY: site
<222> LOCATION: (2)..(2)
<223> OTHER INFORMATION: homolysine
<220> FEATURE:
<221> NAME/KEY: site
<222> LOCATION: (4)..(4)
<223> OTHER INFORMATION: allylglycine

<400> SEQUENCE: 152

Gly Lys Lys Gly Tyr Leu
1               5

<210> SEQ ID NO 153
<211> LENGTH: 6
<212> TYPE: PRT
<213> ORGANISM: Artificial sequence
<220> FEATURE:
<223> OTHER INFORMATION: synthetic construct
<220> FEATURE:
<221> NAME/KEY: site
<222> LOCATION: (1)..(1)
<223> OTHER INFORMATION: allylglycine
<220> FEATURE:
<221> NAME/KEY: site
<222> LOCATION: (2)..(3)
<223> OTHER INFORMATION: homolysine
<220> FEATURE:
<221> NAME/KEY: site
<222> LOCATION: (4)..(4)
<223> OTHER INFORMATION: allylglycine
```

```
<400> SEQUENCE: 153

Gly Lys Lys Gly Tyr Leu
1               5

<210> SEQ ID NO 154
<211> LENGTH: 6
<212> TYPE: PRT
<213> ORGANISM: Artificial sequence
<220> FEATURE:
<223> OTHER INFORMATION: synthetic construct

<400> SEQUENCE: 154

Cys Lys Lys Cys Tyr Leu
1               5

<210> SEQ ID NO 155
<211> LENGTH: 6
<212> TYPE: PRT
<213> ORGANISM: Artificial sequence
<220> FEATURE:
<223> OTHER INFORMATION: synthetic construct
<220> FEATURE:
<221> NAME/KEY: site
<222> LOCATION: (4)..(4)
<223> OTHER INFORMATION: penicillamine

<400> SEQUENCE: 155

Cys Lys Lys Cys Tyr Leu
1               5

<210> SEQ ID NO 156
<211> LENGTH: 6
<212> TYPE: PRT
<213> ORGANISM: Artificial sequence
<220> FEATURE:
<223> OTHER INFORMATION: synthetic construct
<220> FEATURE:
<221> NAME/KEY: site
<222> LOCATION: (1)..(1)
<223> OTHER INFORMATION: penicillamine

<400> SEQUENCE: 156

Cys Lys Lys Cys Tyr Leu
1               5

<210> SEQ ID NO 157
<211> LENGTH: 6
<212> TYPE: PRT
<213> ORGANISM: Artificial sequence
<220> FEATURE:
<223> OTHER INFORMATION: synthetic construct
<220> FEATURE:
<221> NAME/KEY: site
<222> LOCATION: (1)..(1)
<223> OTHER INFORMATION: penicillamine
<220> FEATURE:
<221> NAME/KEY: site
<222> LOCATION: (4)..(4)
<223> OTHER INFORMATION: penicillamine

<400> SEQUENCE: 157

Cys Lys Lys Cys Tyr Leu
1               5

<210> SEQ ID NO 158
<211> LENGTH: 7
<212> TYPE: PRT
<213> ORGANISM: Artificial sequence
<220> FEATURE:
```

-continued

```
<223> OTHER INFORMATION: synthetic construct
<220> FEATURE:
<221> NAME/KEY: site
<222> LOCATION: (2)..(2)
<223> OTHER INFORMATION: allylglycine
<220> FEATURE:
<221> NAME/KEY: site
<222> LOCATION: (5)..(5)
<223> OTHER INFORMATION: allylglycine

<400> SEQUENCE: 158

Lys Gly Lys Lys Gly Tyr Leu
1               5

<210> SEQ ID NO 159
<211> LENGTH: 6
<212> TYPE: PRT
<213> ORGANISM: Artificial sequence
<220> FEATURE:
<223> OTHER INFORMATION: synthetic construct
<220> FEATURE:
<221> NAME/KEY: site
<222> LOCATION: (1)..(1)
<223> OTHER INFORMATION: allylglycine
<220> FEATURE:
<221> NAME/KEY: site
<222> LOCATION: (4)..(4)
<223> OTHER INFORMATION: allylglycine
<220> FEATURE:
<221> NAME/KEY: site
<222> LOCATION: (5)..(5)
<223> OTHER INFORMATION: thienyl alanine

<400> SEQUENCE: 159

Gly Lys Lys Gly Ala Leu
1               5

<210> SEQ ID NO 160
<211> LENGTH: 6
<212> TYPE: PRT
<213> ORGANISM: Artificial sequence
<220> FEATURE:
<223> OTHER INFORMATION: synthetic construct
<220> FEATURE:
<221> NAME/KEY: site
<222> LOCATION: (1)..(1)
<223> OTHER INFORMATION: allylglycine
<220> FEATURE:
<221> NAME/KEY: site
<222> LOCATION: (4)..(4)
<223> OTHER INFORMATION: allylglycine
<220> FEATURE:
<221> NAME/KEY: site
<222> LOCATION: (5)..(5)
<223> OTHER INFORMATION: benzoyl phenylalanine

<400> SEQUENCE: 160

Gly Lys Lys Gly Phe Leu
1               5

<210> SEQ ID NO 161
<211> LENGTH: 6
<212> TYPE: PRT
<213> ORGANISM: Artificial sequence
<220> FEATURE:
<223> OTHER INFORMATION: synthetic construct
<220> FEATURE:
<221> NAME/KEY: site
<222> LOCATION: (1)..(1)
<223> OTHER INFORMATION: allylglycine
<220> FEATURE:
<221> NAME/KEY: site
<222> LOCATION: (4)..(4)
```

```
<223> OTHER INFORMATION: allylglycine
<220> FEATURE:
<221> NAME/KEY: site
<222> LOCATION: (5)..(5)
<223> OTHER INFORMATION: styryl alanine

<400> SEQUENCE: 161

Gly Lys Lys Gly Ala Leu
1               5

<210> SEQ ID NO 162
<211> LENGTH: 6
<212> TYPE: PRT
<213> ORGANISM: Artificial sequence
<220> FEATURE:
<223> OTHER INFORMATION: synthetic construct
<220> FEATURE:
<221> NAME/KEY: site
<222> LOCATION: (1)..(1)
<223> OTHER INFORMATION: allylglycine
<220> FEATURE:
<221> NAME/KEY: site
<222> LOCATION: (4)..(4)
<223> OTHER INFORMATION: allylglycine
<220> FEATURE:
<221> NAME/KEY: site
<222> LOCATION: (5)..(5)
<223> OTHER INFORMATION: anthryl alanine

<400> SEQUENCE: 162

Gly Lys Lys Gly Ala Leu
1               5

<210> SEQ ID NO 163
<211> LENGTH: 6
<212> TYPE: PRT
<213> ORGANISM: Artificial sequence
<220> FEATURE:
<223> OTHER INFORMATION: synthetic construct
<220> FEATURE:
<221> NAME/KEY: site
<222> LOCATION: (1)..(1)
<223> OTHER INFORMATION: allylglycine
<220> FEATURE:
<221> NAME/KEY: site
<222> LOCATION: (4)..(4)
<223> OTHER INFORMATION: allylglycine
<220> FEATURE:
<221> NAME/KEY: site
<222> LOCATION: (5)..(5)
<223> OTHER INFORMATION: Tic glycine

<400> SEQUENCE: 163

Gly Lys Lys Gly Gly Leu
1               5

<210> SEQ ID NO 164
<211> LENGTH: 6
<212> TYPE: PRT
<213> ORGANISM: Artificial sequence
<220> FEATURE:
<223> OTHER INFORMATION: synthetic construct
<220> FEATURE:
<221> NAME/KEY: site
<222> LOCATION: (1)..(1)
<223> OTHER INFORMATION: allylglycine
<220> FEATURE:
<221> NAME/KEY: site
<222> LOCATION: (4)..(4)
<223> OTHER INFORMATION: allylglycine
<220> FEATURE:
<221> NAME/KEY: site
<222> LOCATION: (5)..(5)
```

```
<223> OTHER INFORMATION: indanyl glycine

<400> SEQUENCE: 164

Gly Lys Lys Gly Gly Leu
1               5

<210> SEQ ID NO 165
<211> LENGTH: 6
<212> TYPE: PRT
<213> ORGANISM: Artificial sequence
<220> FEATURE:
<223> OTHER INFORMATION: synthetic construct
<220> FEATURE:
<221> NAME/KEY: site
<222> LOCATION: (1)..(1)
<223> OTHER INFORMATION: allylglycine
<220> FEATURE:
<221> NAME/KEY: site
<222> LOCATION: (4)..(4)
<223> OTHER INFORMATION: allylglycine
<220> FEATURE:
<221> NAME/KEY: site
<222> LOCATION: (5)..(5)
<223> OTHER INFORMATION: 2-pyridyl alanine

<400> SEQUENCE: 165

Gly Lys Lys Gly Ala Leu
1               5

<210> SEQ ID NO 166
<211> LENGTH: 6
<212> TYPE: PRT
<213> ORGANISM: Artificial sequence
<220> FEATURE:
<223> OTHER INFORMATION: synthetic construct
<220> FEATURE:
<221> NAME/KEY: site
<222> LOCATION: (1)..(1)
<223> OTHER INFORMATION: allylglycine
<220> FEATURE:
<221> NAME/KEY: site
<222> LOCATION: (4)..(4)
<223> OTHER INFORMATION: allylglycine
<220> FEATURE:
<221> NAME/KEY: site
<222> LOCATION: (5)..(5)
<223> OTHER INFORMATION: octahydroindol glycine

<400> SEQUENCE: 166

Gly Lys Lys Gly Gly Leu
1               5

<210> SEQ ID NO 167
<211> LENGTH: 6
<212> TYPE: PRT
<213> ORGANISM: Artificial sequence
<220> FEATURE:
<223> OTHER INFORMATION: synthetic construct
<220> FEATURE:
<221> NAME/KEY: site
<222> LOCATION: (1)..(1)
<223> OTHER INFORMATION: allylglycine
<220> FEATURE:
<221> NAME/KEY: site
<222> LOCATION: (4)..(4)
<223> OTHER INFORMATION: allylglycine
<220> FEATURE:
<221> NAME/KEY: site
<222> LOCATION: (5)..(5)
<223> OTHER INFORMATION: Tic D-glycine
<220> FEATURE:
<221> NAME/KEY: site
<222> LOCATION: (6)..(6)
```

```
<223> OTHER INFORMATION: D-amino acid

<400> SEQUENCE: 167

Gly Lys Lys Gly Gly Leu
1               5

<210> SEQ ID NO 168
<211> LENGTH: 6
<212> TYPE: PRT
<213> ORGANISM: Artificial sequence
<220> FEATURE:
<223> OTHER INFORMATION: synthetic construct
<220> FEATURE:
<221> NAME/KEY: site
<222> LOCATION: (1)..(1)
<223> OTHER INFORMATION: allylglycine
<220> FEATURE:
<221> NAME/KEY: site
<222> LOCATION: (4)..(4)
<223> OTHER INFORMATION: allylglycine
<220> FEATURE:
<221> NAME/KEY: site
<222> LOCATION: (5)..(5)
<223> OTHER INFORMATION: 3-benzothienyl alanine

<400> SEQUENCE: 168

Gly Lys Lys Gly Ala Leu
1               5

<210> SEQ ID NO 169
<211> LENGTH: 6
<212> TYPE: PRT
<213> ORGANISM: Artificial sequence
<220> FEATURE:
<223> OTHER INFORMATION: synthetic construct
<220> FEATURE:
<221> NAME/KEY: site
<222> LOCATION: (1)..(1)
<223> OTHER INFORMATION: allylglycine
<220> FEATURE:
<221> NAME/KEY: site
<222> LOCATION: (4)..(4)
<223> OTHER INFORMATION: allylglycine
<220> FEATURE:
<221> NAME/KEY: site
<222> LOCATION: (5)..(5)
<223> OTHER INFORMATION: 3-pyridyl alanine

<400> SEQUENCE: 169

Gly Lys Lys Gly Ala Leu
1               5

<210> SEQ ID NO 170
<211> LENGTH: 6
<212> TYPE: PRT
<213> ORGANISM: Artificial sequence
<220> FEATURE:
<223> OTHER INFORMATION: synthetic construct
<220> FEATURE:
<221> NAME/KEY: site
<222> LOCATION: (1)..(1)
<223> OTHER INFORMATION: allylglycine
<220> FEATURE:
<221> NAME/KEY: site
<222> LOCATION: (4)..(4)
<223> OTHER INFORMATION: allylglycine
```

```
<220> FEATURE:
<221> NAME/KEY: site
<222> LOCATION: (5)..(5)
<223> OTHER INFORMATION: dihydroindolyl glycine

<400> SEQUENCE: 170

Gly Lys Lys Gly Gly Leu
1               5
```

NEUROTENSINERGIC AGONISTS AND METHODS OF USING SAME PREVENTING OR TREATING PAIN

CROSS REFERENCE TO RELATED APPLICATIONS

This application is a National Entry Application of PCT application Serial No CA2020/050176* filed on Feb. 10, 2020 and published in English under PCT Article 21(2), which itself claims benefit of U.S. provisional application Ser. No. 62/803,041, filed on Feb. 8, 2019. All documents above are incorporated herein in their entirety by reference.

STATEMENT REGARDING FEDERALLY SPONSORED RESEARCH OR DEVELOPMENT

N.A.

FIELD OF THE DISCLOSURE

The present disclosure relates to neurotensinergic agonists and methods of using same of preventing or treating pain. More specifically, the present disclosure is concerned with macrocyclic compounds, preferably selective for the NTS2 receptor, and methods of using same for preventing or treating pain.

REFERENCE TO SEQUENCE LISTING

Pursuant to 37 C.F.R. 1.821(c), a sequence listing is submitted herewith as an ASCII compliant text file named Sequence Listing G14692-00068_ST25, that was created on Dec. 15, 2024 and having a size of 56 kilobytes. The content of the aforementioned file named G14692-00068_ST25 is hereby incorporated by reference in its entirety.

BACKGROUND OF THE DISCLOSURE

Pain is the most common reason for physician consultation in most developed countries. It is a major symptom in many medical conditions and can interfere with a person's quality of life and general functioning. It also creates a significant burden on society and is one of the primary reasons for absenteeism at work. Acute pain, e.g., related to injury, surgery or disease, can be severe and has significant impact on patient recovery, while chronic pain, which affects around 20% of the population, can also cause isolation, symptoms of anxiety and is frequently accompanied by depression, which can include changes in mood, appetite and sleep, thus preventing a sufferer from typical daily activities. Acute pain is usually managed effectively with pharmacological treatments, notably with the first line agents acetaminophen and nonsteroidal anti-inflammatory drugs (NSAID). Severe acute pain is typically treated with potent opioids. Management of chronic pain, however, is much more difficult. Pain medications are only effective in 20% to 70% of cases.

Drugs currently used to treat pain are not always effective (anti-inflammatory) or exhibit severe adverse effects such as development of constipation, nausea/vomiting, respiratory depression and tolerance/dependence (opioids such as morphine) in patients. Opioids are very commonly used, despite their undesirable effects, because they are very effective to alleviate pain. Opioids work by activating the Mu opioid receptor in the central nervous system. However, it is also the activation of this opioid receptor which causes undesirable effects. To date, almost all drugs that activate this receptor have the same deleterious side effects, and opioid abuse resulting from tolerance and dependence is now a widespread problem in Western countries.

Activation of both NTS1 and NTS2 receptors, which belong to the G protein-coupled receptors (GPCRs) superfamily, results in an analgesic action similar to that obtained by activating the Mu opioid receptor they do not cause the same undesirable effects. Constipation and respiratory depression peculiar to the Mu opioid receptor are not observed subsequent to activation of the neurotensin receptors.

Compounds that activate NTS1 also present adverse side effects such as hypothermia and hypotension.

There is a need for compounds with reduced Mu-associated and/or NTS1-associated adverse effects.

The present description refers to a number of documents, the content of which is herein incorporated by reference in their entirety.

SUMMARY OF THE DISCLOSURE

The instant disclosure provides new macrocyclic compound that display analgesia. It specific embodiments, they are selective NTS2 ligands and do not display hypothermia, hypotension or ileum relaxation.

There is also provided a compound of formula (I)

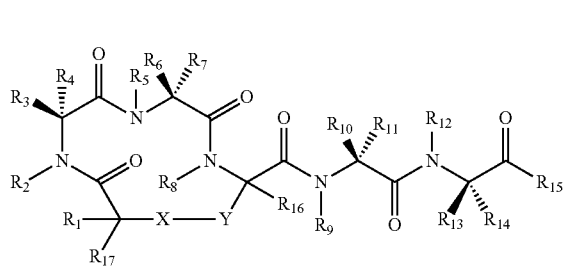

wherein:
(i) $R_1$ is H, C1-C6 alkyl, or C1-C6 aminoalkyl; and $R_{17}$ is H; or $R_{17}$ is H, C1-C6 alkyl, or C1-C6 aminoalkyl; and $R_1$ is H;
(ii) $R_3$ is H, —(CH$_2$)p-(C3-C8)heteroaryl, —(CH$_2$)p-(C3-C8)aryl, —(CH$_2$)p-(C3-C8)heterocycloalkyl, —(CH$_2$)p-(C3-C8)cycloalkyl, C1-C8 aminoalkyl, C1-C8 alkyl, or C1-C8 alkyl-C(═O)OH, wherein p is 1 to 51 to 5; and $R_4$ is H or C1-C6 alkyl; or
$R_4$ is H, —(CH$_2$)p-(C3-C8)heteroaryl, —(CH$_2$)p-(C3-C8)aryl, —(CH$_2$)p-(C3-C8)heterocycloalkyl, —(CH$_2$)p-(C3-C8)cycloalkyl, C1-C8 aminoalkyl, C1-C8 alkyl, or C1-C8 alkyl-C(═O)OH, wherein p is 1 to 5; and $R_3$ is H or C1-C6 alkyl;
(iii) $R_6$ is H, —(CH$_2$)p-(C3-C8)heteroaryl, —(CH$_2$)p-(C3-C8)aryl, —(CH$_2$)p-(C3-C8)heterocycloalkyl, —(CH$_2$)p-(C3-C8)cycloalkyl, C1-C8 aminoalkyl, C1-C8 alkyl, or C1-C8 alkyl-C(═O)OH, wherein p' is 1 to 5; and $R_7$ is H or C1-C6 alkyl; or
$R_7$ is H, —(CH$_2$)p-(C3-C8)heteroaryl, —(CH$_2$)p-(C3-C8)aryl, —(CH$_2$)p-(C3-C8)heterocycloalkyl, —(CH$_2$)p-(C3-C8)cycloalkyl, C1-C8 aminoalkyl, C1-C8 alkyl, or C1-C8 alkyl-C(═O)OH, wherein p' is 1 to 5; and $R_6$ is H or C1-C6 alkyl;
(iv) $R_{10}$ is H, —(CH$_2$)q-(C3-C8)heteroaryl, —(CH$_2$)q-(C3-C8)aryl, —(CH$_2$)q-(C3-C8)heterocycloalkyl, —(CH$_2$)q-(C3-C8) cycloalkyl, C1-C8 aminoalkyl, C1-C8 alkyl, or C1-C8 alkyl-C(═O)OH, wherein q is 1 to 5; and R$_{11}$ is H or C1-C6 alkyl; or R$_{11}$ is —(CH$_2$)q-(C3-C8)heteroaryl, —(CH$_2$)q-(C3-C8)aryl, —(CH$_2$)q-(C3-C8)heterocycloalkyl, —(CH$_2$)q-(C3-C8) cycloalkyl, C1-C8 aminoalkyl, C1-C8 alkyl, or C1-C8 alkyl-C(═O)OH, wherein q is 1 to 5; and R$_{10}$ is H or C1-C6 alkyl;

(v) R$_{13}$ is H or C1-C6 alkyl; and R$_{14}$ is H, —(CH$_2$)q'-(C3-C8)heteroaryl, —(CH$_2$)q'-(C3-C8)aryl, —(CH$_2$)q'-(C3-C8)heterocycloalkyl, —(CH$_2$)q'-(C3-C8)cycloalkyl, C1-C8 aminoalkyl, C1-C8 alkyl, or C1-C8 alkyl-C(═O)OH, wherein q' is 1 to 5; or R$_{14}$ is H or C1-C6 alkyl; and R$_{13}$ is H, —(CH$_2$)q'-(C3-C8)heteroaryl, —(CH$_2$)q'-(C3-C8)aryl, —(CH$_2$)q'-(C3-C8)heterocycloalkyl, —(CH$_2$)q'-(C3-C8)cycloalkyl, C1-C8 aminoalkyl, C1-C8 alkyl, or C1-C8 alkyl-C(═O)OH, wherein q' is 1 to 5;

(vi) R$_2$, R$_5$, R$_8$, R$_9$, and R$_{12}$ are each independently H, (C1-12)alkyl, or (C4-C14)aralkyl; or at least one of R$_2$, R$_5$, R$_8$, R$_9$, and R$_{12}$ are as follows and the other ones are:

a) R$_2$ is —(CH$_2$)p-(C3-C8)heteroaryl, —(CH$_2$)p-(C3-C8)aryl, —(CH$_2$)p-(C3-C8)heterocycloalkyl, —(CH$_2$)p-(C3-C8)cycloalkyl, C1-C8 aminoalkyl, C1-C8 alkyl, or C1-C8 alkyl-C(═O)OH, wherein p is 1 to 5, with the proviso that R$_3$ and R$_4$ are then H;

b) R$_5$ is —(CH$_2$)p-(C3-C8)heteroaryl, —(CH$_2$)p-(C3-C8)aryl, —(CH$_2$)p-(C3-C8)heterocycloalkyl, —(CH$_2$)p-(C3-C8)cycloalkyl, C1-C8 aminoalkyl, C1-C8 alkyl, or C1-C8 alkyl-C(═O)OH, wherein p' is 1 to 5, with the proviso that R$_6$ and R$_7$ are then H;

c) R$_9$ is —(CH$_2$)q-(C3-C8)heteroaryl, —(CH$_2$)q-(C3-C8)aryl, —(CH$_2$)q-(C3-C8)heterocycloalkyl, —(CH$_2$)q-(C3-C8) cycloalkyl, C1-C8 aminoalkyl, C1-C8 alkyl, or C1-C8 alkyl-C(═O)OH, wherein q is 1 to 5; and R$_{11}$ is H or C1-C6 alkyl, with the proviso that R$_{10}$ and R$_{11}$ are then H;

d) R$_{12}$ is —(CH$_2$)q'-(C3-C8)heteroaryl, —(CH$_2$)q'-(C3-C8)aryl, —(CH$_2$)q'-(C3-C8)heterocycloalkyl, —(CH$_2$)q'-(C3-C8)cycloalkyl, C1-C8 aminoalkyl, C1-C8 alkyl, or C1-C8 alkyl-C(═O)OH, wherein q' is 1 to 5, with the proviso that R$_{13}$ and R$_{14}$ are then H;

and the other ones of R$_2$, R$_5$, R$_8$, R$_9$, and R$_{12}$ are each independently H, (C1-12)alkyl, or (C4-C14)aralkyl;

(vii) R$_{15}$ is H, —OR$_{18}$ wherein R$_{18}$ is H, benzyl, (C4-C14)aralkyl or (C1-12)allyl;

(viii) R$_{16}$ is H, C3-C6 alkyl; and (x) X is —(CH$_2$)n, wherein n is 0-4; and Y is —CH═CH(CH$_2$)m-, —NR$_{13}$C(═O)(CH$_2$)m- or —C(═O)NR$_{18}$(CH$_2$)m-, wherein m is 1-4; or X and Y form together —(CH$_2$)n-aryl-(CH$_2$)m, wherein n and m are as defined above, wherein aryl is ortho, meta, or para benzene, or biaryl, substituted or not in at least one of positions 2, 3, 4, 2', 3', or 4', wherein each of the heteroaryl, aryl, heteroalkyl, alkyl, aminoalkyl, alkylC(O)OH, allyl, aralkyl are independently optionally substituted;

or a stereoisomer or a mixture thereof, or a pharmaceutically acceptable salt, ester or solvate thereof.

In another embodiment, (i) R$_1$ is H, —CH$_3$, or —NH$_2$; and R$_{17}$ is H; or R$_{17}$ is H, —NH$_2$ or —CH$_3$; and R$_1$ is H;

(ii) R$_3$ is H or —(CH$_2$)p-(C3-C8)heteroaryl, wherein p is 1 to 5; or the side chain of a lysine, ornithine, diaminobutyric acid (Dab), diaminopropionic acid (Dap), histidine, norleucine, norvaline, glycine or glutamate; and R$_4$ is H or —CH$_3$; or R$_4$ is H or —(CH$_2$)p-(C3-C8)heteroaryl, wherein p is 1 to 5; or the side chain of a lysine, ornithine, diaminobutyric acid (Dab), diaminopropionic acid (Dap), histidine, norleucine, norvaline, glycine or glutamate; and R$_3$ is H or —CH$_3$;

(iii) R$_6$ is H or a —(CH$_2$)p'-(C3-C8)heteroaryl, wherein p' is 1 to 5; or the side chain of a lysine, ornithine, diaminobutyric acid (Dab), diaminopropionic acid (Dap), histidine, norleucine, norvaline, glycine or glutamate; and R$_7$ is H or —CH$_3$; or R$_7$ is H or a —(CH$_2$)p'-(C3-C8)heteroaryl, wherein p' is 1 to 5; or the side chain of a lysine, ornithine, diaminobutyric acid (Dab), diaminopropionic acid (Dap), histidine, norleucine, norvaline, glycine or glutamate; and R$_6$ is H or —CH$_3$;

(iv) R$_{10}$ is H or —(CH$_2$)q-(C3-C8)heteroaryl, wherein q is 1 to 5; or the side chain of an alanine (cyclopentyl), alanine (furyl), phenylalanine (4-amino), phenylalanine (4-nitro), phenylalanine (4-methyl), phenylalanine (2, 3, 4, 5, 6 pentafluoro), tyrosine, tyrosine (OAc), tryptophan, lysine, m-tyrosine, tyrosine (Ome), phenylalanine, phenylalanine (4-fluoro), phenylalanine (4-iodo), phenylalanine (4-tert-butyl), phenylalanine (4-CF$_3$), alanine (naphtyl), phenylalanine (3-chloro), phenylalanine (4-chloro), phenylalanine (3-bromo), phenylalanine (4-bromo), phenylalanine (3-iodo) or phenylalanine (4-cyano); and R$_{11}$ is H or —CH$_3$; or R$_{11}$ is H or —(CH$_2$)q-(C3-C8)heteroaryl, wherein q is 1 to 5; or the side chain of a alanine (cyclopentyl), alanine (furyl), phenylalanine (4-amino), phenylalanine (4-nitro), phenylalanine (4-methyl), phenylalanine (2, 3, 4, 5, 6 pentafluoro), tyrosine, tyrosine (OAc), tryptophan, lysine, m-tyrosine, tyrosine (Ome), phenylalanine, phenylalanine (4-fluoro), phenylalanine (4-iodo), phenylalanine (4-tert-butyl), phenylalanine (4-CF$_3$), alanine (naphtyl), phenylalanine (3-chloro), phenylalanine (4-chloro), phenylalanine (3-bromo), phenylalanine (4-bromo), phenylalanine (3-iodo) or phenylalanine (4-cyano); and R$_{10}$ is H or —CH$_3$;

(v) R$_{13}$ is H or —CH$_3$; and R$_{14}$ is H, —(CH$_2$)q'-(C3-C8)heteroaryl, wherein q' is 1 to 5; or the side chain of a leucine, tert-leucine, norleucine, norvaline, valine, neopentylglycine, cyclohexylglycine, cyclohexylalanine, phenylalanine, tyrosine (Ome), 2, 4, 5,-trifluoro phenylalanine, homo cyclohexyl alanine, cyclopropyl alanine cyclobutyl alanine, cyclopentyl alanine or cycloheptyl alanine; or R$_{14}$ is H or —CH$_3$; and R$_{13}$ is H, —(CH$_2$)q'-(C3-C8)heteroaryl, wherein q' is 1 to 5; or the side chain of a leucine, tert-leucine, norleucine, norvaline, valine, neopentylglycine, cyclohexylglycine, cyclohexylalanine, phenylalanine, tyrosine (Ome), 2, 4, 5,-trifluoro phenylalanine, homo cyclohexyl alanine, cyclopropyl alanine cyclobutyl alanine, cyclopentyl alanine or cycloheptyl alanine;

(vi) R$_2$, R$_5$, R$_8$, R$_9$, and R$_{12}$ are each independently H, (C1-12)alkyl, or (C4-C14)aralkyl; or at least one of R$_2$, R$_5$, R$_8$, R$_9$, and R$_{12}$ are as follows and the other ones are:

a) R$_2$ is an —(CH$_2$)p-(C3-C8)heteroaryl, wherein p is 1 to 5; or the side chain of a lysine, ornithine, diaminobutyric acid (Dab), diaminopropionic acid (Dap), histidine, norleucine, norvaline, glycine or glutamate, with the proviso that $R_3$ and $R_4$ are then H;

b) $R_5$ is a —$(CH_2)p$-(C3-C8)heteroaryl, wherein p' is 1 to 5; or the side chain of a lysine, ornithine, diaminobutyric acid (Dab), diaminopropionic acid (Dap), histidine, norleucine, norvaline, glycine or glutamate, with the proviso that $R_6$ and $R_7$ are then H;

c) $R_9$ is —$(CH_2)q$-(C3-C8)heteroaryl, wherein q is 1 to 5; or the side chain of a alanine (cyclopentyl), alanine (furyl), phenylalanine (4-amino), phenylalanine (4-nitro), phenylalanine (4-methyl), phenylalanine (2, 3, 4, 5, 6 pentafluoro), tyrosine, tyrosine (OAc), tryptophan, lysine, m-tyrosine, tyrosine (Ome), phenylalanine, phenylalanine (4-fluoro), phenylalanine (4-iodo), phenylalanine (4-tert-butyl), phenylalanine (4-$CF_3$), alanine (naphtyl), phenylalanine (3-chloro), phenylalanine (4-chloro), phenylalanine (3-bromo), phenylalanine (4-bromo), phenylalanine (3-iodo) or phenylalanine (4-cyano), with the proviso that $R_{10}$ and $R_{11}$ are then H;

d) $R_{12}$ is —$(CH_2)q'$-(C3-C8)heteroaryl, wherein q' is 1 to 5; or the side chain of a leucine, tert-leucine, norleucine, norvaline, valine, neopentylglycine, cyclohexylglycine, cyclohexylalanine, phenylalanine, tyrosine (Ome), 2, 4, 5,-trifluoro phenylalanine, homo cyclohexyl alanine, cyclopropyl alanine cyclobutyl alanine, cyclopentyl alanine or cycloheptyl alanine, with the proviso that $R_{13}$ and $R_{14}$ are then H; and the other ones of $R_2$, $R_5$, $R_8$, $R_9$, and $R_{12}$ are each independently H, (C1-12)alkyl, or (C4-C14)aralkyl;

(vii) $R_{15}$ is H, —$OR_{18}$ wherein $R_{18}$ is H, benzyl, (C4-C14)aralkyl or (C1-12)allyl;

(viii) $R_{16}$ is H, —$CH_3$; and (x) X is —$(CH_2)n$, wherein n is 0-4; and Y is —CH=CH $(CH_2)m$-, —$NR_{18}C(=O)(CH_2)m$- or —$C(=O)NR_{18}$ (CH2)m-, wherein m is 1-4; or X and Y form together —$(CH_2)n$-aryl-$(CH_2)m$-, wherein n and m are as defined above, wherein aryl is ortho, meta, or para benzene, or biaryl, substituted or not in at least one of positions 2, 3, 4, 2', 3', or 4', or a stereoisomer or a mixture thereof, or a pharmaceutically acceptable salt, ester or solvate thereof.

Alternatively, the compound is of formula I, wherein (i) $R_1$ is H, a (C1-C5)alkyl or NHR', wherein R' is one or more amino-acid residues; and $R_{17}$ independently H or $CH_3$; or $R_{17}$ is H, a (C1-C5)alkyl or NHR', wherein R' is one or more amino-acid residues; and $R^1$ independently H or $CH_3$;

(ii) (a) $R_3$ is H, a —(C1-C5)alkyl, —(C1-C5)aminoalkyl, —(C1-C5)alkyl-C(=O)OH, —(C1-C5)alkyl-NH—C(=O)—NH2, —(C1-C5)alkyl(C3-C8)aryl, —(C1-C5)alkyl(C3-C8)heteroaryl, —(C1-C5)alkyl(C3-C8)cycloalkyl, —(C1-C5)alkyl(C3-C8)heterocycloalkyl, wherein the alkyl, aminoalkyl, aryl, heteroaryl, cycloalkyl, and heterocycloalkyl are optionally substituted by one or more substituents, wherein each substituent is independently amino, (C1-C5)alkyl, carbonyl, OH, —O-acetyl and halogen; and $R_4$ is H or (C1-C5)alkyl, wherein the alkyl, is optionally substituted by one or more substituents, wherein each substituent is as defined above; or (b) $R_4$ is H, a —(C1-C5)alkyl, —(C1-C5)aminoalkyl, —(C1-C5)alkyl-C(=O)OH, —(C1-C5)alkyl-NH—C(=O)—NH2, —(C1-C5)alkyl(C3-C8)aryl, —(C1-C5)alkyl(C3-C8)heteroaryl, —(C1-C5)alkyl(C3-C8)cycloalkyl, —(C1-C5)alkyl(C3-C8)heterocycloalkyl, wherein the alkyl, aminoalkyl, aryl, heteroaryl, cycloalkyl, and heterocycloalkyl are optionally substituted by one or more substituents, wherein each substituent is independently as defined above; and $R_3$ is H or (C1-C5)alkyl, wherein the alkyl, is optionally substituted by one or more substituents, wherein each substituent is independently as defined above;

(iii) (a) $R_6$ is H, a —(C1-C5)alkyl, —(C1-C5)aminoalkyl, —(C1-C5)alkyl-C(=O)OH, —(C1-C5)alkyl-NH—C(=O)—NH2, —(C1-C5)alkyl(C3-C8)aryl, —(C1-C5)alkyl(C3-C8)heteroaryl, —(C1-C5)alkyl(C3-C8)cycloalkyl, —(C1-C5)alkyl(C3-C8)heterocycloalkyl, wherein the alkyl, aminoalkyl, aryl, heteroaryl, cycloalkyl, and heterocycloalkyl are optionally substituted by one or more substituents, wherein each substituent is independently as defined above; and $R_7$ is H or (C1-C5)alkyl, wherein the alkyl, is optionally substituted by one or more substituents, wherein each substituent is independently as defined above; or (b) $R_7$ is H, a —(C1-C5)alkyl, —(C1-C5)aminoalkyl, —(C1-C5)alkyl-C(=O)OH, —(C1-C5)alkyl-NH—C(=O)—NH2, —(C1-C5)alkyl(C3-C8)aryl, —(C1-C5)alkyl(C3-C8)heteroaryl, —(C1-C5)alkyl(C3-C8)cycloalkyl, —(C1-C5)alkyl(C3-C8)heterocycloalkyl, wherein the alkyl, aminoalkyl, aryl, heteroaryl, cycloalkyl, and heterocycloalkyl are optionally substituted by one or more substituents, wherein each substituent is independently as defined above; and $R_6$ is H or (C1-C5)alkyl, wherein the alkyl, is optionally substituted by one or more substituents, wherein each substituent is independently as defined above;

(iv) (A) (a) $R_{10}$ is H, a —(C1-C5)alkyl, —(C1-C5)aminoalkyl, —(C1-C5)alkyl-C(=O)OH, —(C1-C5)alkyl-NH—C(=O)—NH2, —(C1-C5)alkyl(C3-C8)aryl, —(C1-C5)alkyl(C3-C8)heteroaryl, —(C1-C5)alkyl(C3-C8)cycloalkyl, —(C1-C5)alkyl(C3-C8)heterocycloalkyl, wherein the aryl, heteroaryl, cycloalkyl and heterocycloalkyl may be fused to another ring that is independently an aryl, heteroaryl, cycloalkyl and heterocycloalkyl; wherein the alkyl, aminoalkyl, aryl, heteroaryl, cycloalkyl, and heterocycloalkyl are optionally substituted by one or more substituents, wherein each substituent is independently as defined above; and R11 is H or (C1-C5)alkyl, wherein the alkyl, is optionally substituted by one or more substituents, wherein each substituent is independently as defined above; or (b) $R_{11}$ is H, a —(C1-C5)alkyl, —(C1-C5)aminoalkyl, —(C1-C5)alkyl-C(=O)OH, —(C1-C5)alkyl-NH—C(=O)—NH2, —(C1-C5)alkyl(C3-C8)aryl, —(C1-C5)alkyl(C3-C8)heteroaryl, —(C1-C5)alkyl(C3-C8)cycloalkyl, —(C1-C5)alkyl(C3-C8)heterocycloalkyl, wherein the aryl, heteroaryl, cycloalkyl and heterocycloalkyl may be fused to another ring that is independently an aryl, heteroaryl, cycloalkyl and heterocycloalkyl; wherein the alkyl, aminoalkyl, aryl, heteroaryl, cycloalkyl, and heterocycloalkyl are optionally substituted by one or more substituents, wherein each substituent is independently as defined above; and $R_{10}$ is H or (C1-C5)alkyl, wherein the alkyl, is optionally substituted by one or more substituents, wherein each substituent is independently as defined above; or (B) $R_{10}$ and $R_9$ form a ring together that is a (C3-C8)aryl, (C3-C8)heteroaryl, (C3-C8)cycloalkyl, (C3-C8)heterocycloalkyl, wherein the aryl, heteroaryl, cycloalkyl and heterocycloalkyl may be fused to another ring that is independently an (C3-C8)aryl, (C3-C8)heteroaryl, (C3-C8)cycloalkyl, and (C3-C8)heterocycloalkyl; wherein the aryl, heteroaryl, cycloalkyl, and heterocycloalkyl are optionally substituted by one or more substituents, wherein each substituent is independently as defined above; and/or (v) (a) $R_{13}$ is H, a —(C1-C5)alkyl, —(C1-C5)aminoalkyl, —(C1-C5)alkyl-C(=O)OH, —(C1-C5)alkyl-NH—C(=O)—NH2, —(C1-C5)alkyl(C3-C8)aryl, —(C1-C5)alkyl(C3-C8)heteroaryl, —(C1-C5)alkyl(C3-C8)cycloalkyl, —(C1-C5)alkyl(C3-C8)heterocycloalkyl, wherein the alkyl, aminoalkyl, aryl, heteroaryl, cycloalkyl, and heterocycloalkyl are optionally substituted by one or more substituents, wherein each substituent is independently amino, (C1-C5)alkyl, carbonyl, OH, —O-acetyl and halogen; and $R_{14}$ is H or (C1-C5)alkyl, wherein the alkyl, is optionally substituted by one or more substituents, wherein each substituent is as defined above; or (b) $R_{14}$ is H, a —(C1-C5)alkyl, —(C1-C5)aminoalkyl, —(C1-C5)alkyl-C(=O)OH, —(C1-C5)alkyl-NH—C(=O)—NH2, —(C1-C5)alkyl(C3-C8)aryl, —(C1-C5)alkyl(C3-C8)heteroaryl, —(C1-C5)alkyl(C3-C8)cycloalkyl, —(C1-C5)alkyl(C3-C8)heterocycloalkyl, wherein the alkyl, aminoalkyl, aryl, heteroaryl, cycloalkyl, and heterocycloalkyl are optionally substituted by one or more substituents, wherein each substituent is independently as defined above; and $R_{13}$ is H or (C1-C5)alkyl, wherein the alkyl, is optionally substituted by one or more substituents, wherein each substituent is independently as defined above;

and the other moieties are as defined above.

Alternatively, the compound is of formula I'

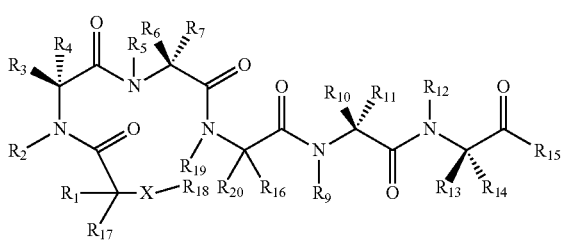

I' wherein $R_1$-$R_7$, $R_9$ to $R_{15}$, and X are as defined above, and wherein (A) $R_{18}$ and $R_{20}$ are joined together to form Y, and Y is as defined above, and $R_{19}$ is defined as R8 above; or (B) $R_{18}$ and $R_{19}$ are joined together to form Y, and Y is as defined above, and $R_{20}$ is defined as $R_8$ above, or a stereoisomer or a mixture thereof, or a pharmaceutically acceptable salt, ester or solvate thereof.

Alternatively, the compound is of formula Ia

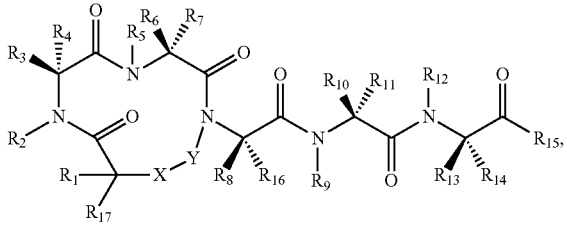

Ia wherein $R_1$-$R_7$, $R_9$ to $R_{15}$, $R_{17}$, X, Y are as defined above, and wherein $R_8$ is H, —$(CH_2)r$-(C3-C8)heteroaryl, —$(CH_2)r$-(C3-C8)aryl, —$(CH_2)r$-(C3-C8)heterocycloalkyl, —$(CH_2)r$-(C3-C8)cycloalkyl, C1-C8 aminoalkyl, C1-C8 alkyl, or C1-C8 alkyl-C(=O)OH, wherein r is 1 to 5; and $R_{16}$ is H or C1-C6 alkyl; or $R_{16}$ H, —$(CH_2)r$-(C3-C8)heteroaryl, —$(CH_2)r$-(C3-C8)aryl, —$(CH_2)r$-(C3-C8)heterocycloalkyl, —$(CH_2)r$-(C3-C8)cycloalkyl, C1-C8 aminoalkyl, C1-C8 alkyl, or C1-C8 alkyl-C(=O)OH, wherein r is 1 to 5; and $R_8$ is H or C1-C6 alkyl; or $R_8$ and $R_{16}$ form together a (C4-C6)cycloalkyl or cycloheteroalkyl.

or a stereoisomer or a mixture thereof, or a pharmaceutically acceptable salt, ester or solvate thereof.

Also provided is a composition comprising (a) the compound (e.g., of any one of formula I, I', Ia, II, III, etc.), stereoisomer, mixture, pharmaceutically acceptable salt, ester or solvate thereof defined herein; and (b) (i) at least another compound, stereoisomer, mixture, pharmaceutically acceptable salt, ester or solvate thereof defined herein; (ii) another antalgic agent; (iii) an anxiolytic agent; (iv) an antidepressant agent; (v) a pharmaceutically acceptable carrier; or (vi) a combination of at least two of (i) to (v).

Also provided is a kit for preventing or treating pain, comprising (a) the compound (e.g., of any one of formula I, I', Ia, II, III, etc.), stereoisomer, mixture, pharmaceutically acceptable salt, ester or solvate thereof defined herein; and (b) (i) at least another compound (e.g., of any one of formula I, I', Ia, II, III, etc.), stereoisomer, mixture, pharmaceutically acceptable salt, ester or solvate thereof defined herein; (ii) another antalgic agent; (iii) an anxiolytic agent; (iv) an antidepressant agent; (v) a pharmaceutically acceptable carrier; (vi) instructions to use the kit in the prevention or treatment of pain or of a symptom thereof; or (vii) a combination of at least two of (i) to (vi).

Also provided is a method of preventing or treating pain in a subject in need thereof, comprising administering to the subject an effective amount of the compound, stereoisomer, mixture, pharmaceutically acceptable salt, ester or solvate thereof defined herein; or a composition comprising the compound, stereoisomer, mixture, pharmaceutically acceptable salt, ester or solvate thereof and a pharmaceutically acceptable carrier.

Also provided are compounds as defined in in SEQ ID NOs: 1170 as modified by e.g., any of the substitutions as shown in compounds listed in Table I, compositions and kits comprising same as defined herein and methods of using these compounds as described herein.

More specifically, in accordance with the present disclosure, the following items are provided:

Item 1. A compound of formula (I)

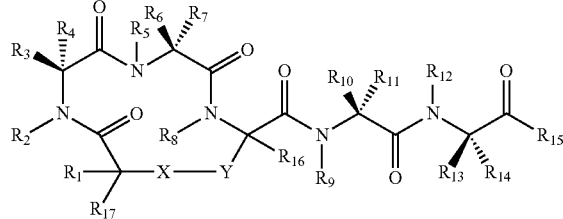

(I)

wherein:
(i) $R_1$ is H, —$CH_3$, or —$NH_2$; and $R_{17}$ is H; or $R_{17}$ is H, —$NH_2$ or —$CH_3$; and $R_1$ is H;
(ii) $R_3$ is H or —$(CH_2)$p-(C3-C8)heteroaryl, wherein p is 1 to 5; or the side chain of a lysine, ornithine, diaminobutyric acid (Dab), diaminopropionic acid (Dap), histidine, norleucine, norvaline, glycine or glutamate; and $R_4$ is H or —$CH_3$; or
$R_4$ is H or —$(CH_2)$p-(C3-C8)heteroaryl, wherein p is 1 to 5; or the side chain of a lysine, ornithine, diaminobutyric acid (Dab), diaminopropionic acid (Dap), histidine, norleucine, norvaline, glycine or glutamate; and $R_3$ is H or —$CH_3$;
(iii) $R_6$ is H or a —$(CH_2)$p'—(C3-C8)heteroaryl, wherein p' is 1 to 5; or the side chain of a lysine, ornithine, diaminobutyric acid (Dab), diaminopropionic acid (Dap), histidine, norleucine, norvaline, glycine or glutamate; and $R_7$ is H or —$CH_3$; or
$R_7$ is H or a —$(CH_2)$p'—(C3-C8)heteroaryl, wherein p' is 1 to 5; or the side chain of a lysine, ornithine, diaminobutyric acid (Dab), diaminopropionic acid (Dap), histidine, norleucine, norvaline, glycine or glutamate; and $R_6$ is H or —$CH_3$;
(iv) $R_{10}$ is H or —$(CH_2)$q-(C3-C8)heteroaryl, wherein q is 1 to 5; or the side chain of an alanine (cyclopentyl), alanine (furyl), phenylalanine (4-amino), phenylalanine (4-nitro), phenylalanine (4-methyl), phenylalanine (2, 3, 4, 5, 6 pentafluoro), tyrosine, tyrosine (OAc), tryptophan, lysine, m-tyrosine, tyrosine (Ome), phenylalanine, phenylalanine (4-fluoro), phenylalanine (4-iodo), phenylalanine (4-tert-butyl), phenylalanine (4-$CF_3$), alanine (naphtyl), phenylalanine (3-chloro), phenylalanine (4-chloro), phenylalanine (3-bromo), phenylalanine (4-bromo), phenylalanine (3-iodo) or phenylalanine (4-cyano); and $R_{11}$ is H or —$CH_3$; or
$R_{11}$ is H or —$(CH_2)$q-(C3-C8)heteroaryl, wherein q is 1 to 5; or the side chain of a alanine (cyclopentyl), alanine (furyl), phenylalanine (4-amino), phenylalanine (4-nitro), phenylalanine (4-methyl), phenylalanine (2, 3, 4, 5, 6 pentafluoro), tyrosine, tyrosine (OAc), tryptophan, lysine, m-tyrosine, tyrosine (Ome), phenylalanine, phenylalanine (4-fluoro), phenylalanine (4-iodo), phenylalanine (4-tert-butyl), phenylalanine (4-$CF_3$), alanine (naphtyl), phenylalanine (3-chloro), phenylalanine (4-chloro), phenylalanine (3-bromo), phenylalanine (4-bromo), phenylalanine (3-iodo) or phenylalanine (4-cyano); and $R_{10}$ is H or —$CH_3$;
(v) $R_{13}$ is H or —$CH_3$; and $R_{14}$ is H, —$(CH_2)$q'—(C3-C8)heteroaryl, wherein q' is 1 to 5; or the side chain of a leucine, tert-leucine, norleucine, norvaline, valine, neopentylglycine, cyclohexylglycine, cyclohexylalanine, phenylalanine, tyrosine (Ome), 2, 4, 5, -trifluoro phenylalanine, homo cyclohexyl alanine, cyclopropyl alanine cyclobutyl alanine, cyclopentyl alanine or cycloheptyl alanine; or
$R_{14}$ is H or —$CH_3$; and $R_{13}$ is H, —$(CH_2)$q'—(C3-C8) heteroaryl, wherein q' is 1 to 5; or the side chain of a leucine, tert-leucine, norleucine, norvaline, valine, neopentylglycine, cyclohexylglycine, cyclohexylalanine, phenylalanine, tyrosine (Ome), 2, 4, 5, -trifluoro phenylalanine, homo cyclohexyl alanine, cyclopropyl alanine cyclobutyl alanine, cyclopentyl alanine or cycloheptyl alanine;
(vi) $R_2$, $R_5$, $R_8$, $R_9$, and $R_{12}$ are each independently H, (C1-12)alkyl, or (C4-C14)aralkyl; or
at least one of $R_2$, $R_5$, $R_8$, $R_9$, and $R_{12}$ are as follows and the other ones are:
a) $R_2$ is an —$(CH_2)$p-(C3-C8)heteroaryl, wherein p is 1 to 5; or the side chain of a lysine, ornithine, diaminobutyric acid (Dab), diaminopropionic acid (Dap), histidine, norleucine, norvaline, glycine or glutamate, with the proviso that $R_3$ and $R_4$ are then H;
b) $R_5$ is a —$(CH_2)$p-(C3-C8)heteroaryl, wherein p' is 1 to 5; or the side chain of a lysine, ornithine, diaminobutyric acid (Dab), diaminopropionic acid (Dap), histidine, norleucine, norvaline, glycine or glutamate, with the proviso that $R_6$ and $R_7$ are then H;
c) $R_9$ is —$(CH_2)$q-(C3-C8)heteroaryl, wherein q is 1 to 5; or the side chain of a alanine (cyclopentyl), alanine (furyl), phenylalanine (4-amino), phenylalanine (4-nitro), phenylalanine (4-methyl), phenylalanine (2, 3, 4, 5, 6 pentafluoro), tyrosine, tyrosine (OAc), tryptophan, lysine, m-tyrosine, tyrosine (Ome), phenylalanine, phenylalanine (4-fluoro), phenylalanine (4-iodo), phenylalanine (4-tert-butyl), phenylalanine (4-$CF_3$), alanine (naphtyl), phenylalanine (3-chloro), phenylalanine (4-chloro), phenylalanine (3-bromo), phenylalanine (4-bromo), phenylalanine (3-iodo) or phenylalanine (4-cyano), with the proviso that $R_{10}$ and $R_{11}$ are then H;
d) $R_{12}$ is —$(CH_2)$q'—(C3-C8)heteroaryl, wherein q' is 1 to 5; or the side chain of a leucine, tert-leucine, norleucine, norvaline, valine, neopentylglycine, cyclohexylglycine, cyclohexylalanine, phenylalanine, tyrosine (Ome), 2, 4, 5,-trifluoro phenylalanine, homo cyclohexyl alanine, cyclopropyl alanine cyclobutyl alanine, cyclopentyl alanine or cycloheptyl alanine, with the proviso that $R_{13}$ and $R_{14}$ are then H;
and the other ones of $R_2$, $R_5$, $R_8$, $R_9$, and $R_{12}$ are each independently H, (C1-12)alkyl, or (C4-C14)aralkyl;
(vii) $R_{15}$ is H, —$OR_{18}$ wherein $R_{18}$ is H, benzyl, (C4-C14)aralkyl or (C1-12)allyl;
(viii) $R_{16}$ is H, —$CH_3$; and
(x) X is —$(CH_2)$n, wherein n is 0-4; and Y is —CH=CH $(CH_2)$m-, —$NR_{18}C$(=O)$(CH_2)$m- or —C(=O)$NR_{18}$ (CH2)m-, wherein m is 1-4; or
X and Y form together —$(CH_2)$n-aryl-$(CH_2)$m-, wherein n and m are as defined above, wherein aryl is ortho, meta, or para benzene, or biaryl, substituted or not in at least one of positions 2, 3, 4, 2', 3', or 4', or a stereoisomer or a mixture thereof, or a pharmaceutically acceptable salt, ester or solvate thereof.

Item 2. The compound, stereoisomer, mixture, pharmaceutically acceptable salt, ester or solvate thereof of item 1, wherein:

(a) $R_{10}$ is a substituted or unsubstituted —$(CH_2)q$-(C3-C8)aryl or —$(CH_2)q$-(C3-C8)heteroaryl; and $R_{11}$ is H or —$CH_3$;

(b) $R_{13}$ is H or —$CH_3$; and $R_{14}$ is a substituted or unsubstituted —$(CH_2)q'$—(C3-C8)cycloalkyl or —$(CH_2)q'$—(C3-C8)heterocycloalkyl;

(c) $R_1$ is H, $R_{17}$ is H, X is —$CH_2$ and Y is —CH=CH—$CH_2$—; and/or (d) $R_1$ is —$NH_2$, $R_{17}$ is H, X is —$CH_2$ and Y is —CH=CH—$CH_2$—$CH_2$—.

Item 3. The compound, stereoisomer, mixture, pharmaceutically acceptable salt, ester or solvate thereof of item 1, wherein the compound is one of the compounds of Table 1.

Item 4. The compound, stereoisomer, mixture, pharmaceutically acceptable salt, ester or solvate thereof of item 1 or 2, wherein the compound is

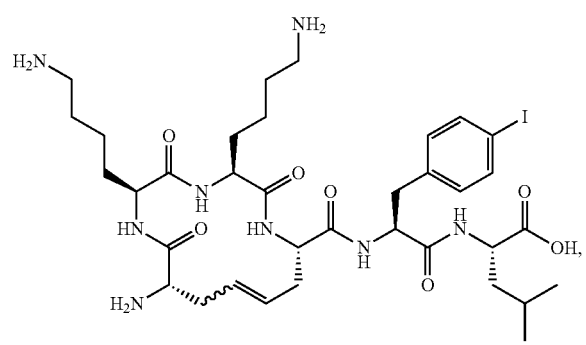

78

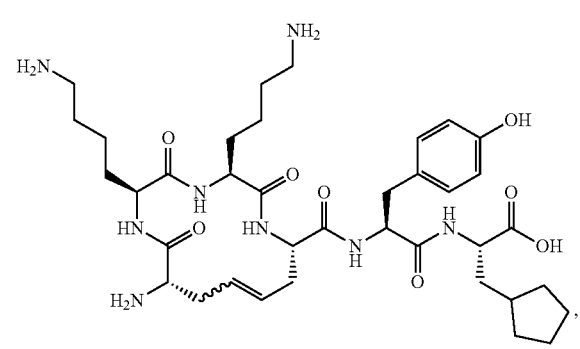

67

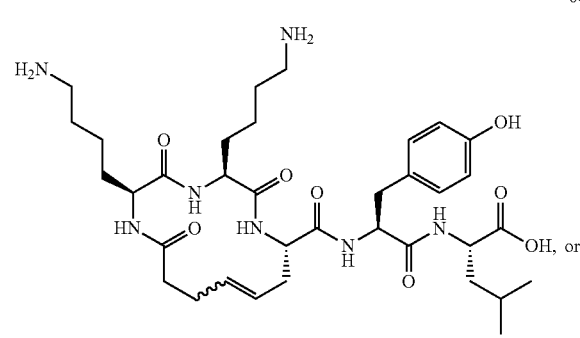

, or

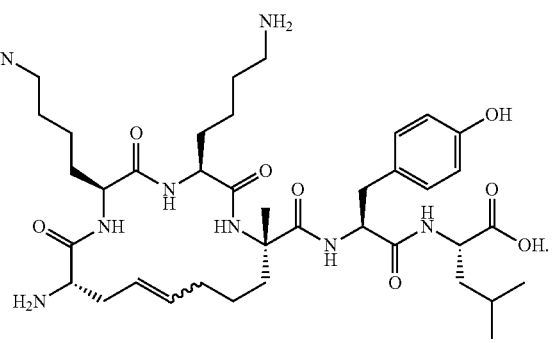

91

Item 5. A composition comprising (a) the compound, stereoisomer, mixture, pharmaceutically acceptable salt, ester or solvate thereof defined in any one of items 1 to 5; and (b) (i) at least another compound, stereoisomer, mixture, pharmaceutically acceptable salt, ester or solvate thereof defined in any one of items 1 to 5; (ii) another antalgic agent; (iii) an anxiolytic agent; (iv) an antidepressant agent; (v) a pharmaceutically acceptable carrier; or (vi) a combination of at least two of (i) to (v).

Item 6. A kit for preventing or treating pain, comprising (a) the compound, stereoisomer, mixture, pharmaceutically acceptable salt, ester or solvate thereof defined in any one of items 1 to 5; and (b) (i) at least another compound, stereoisomer, mixture, pharmaceutically acceptable salt, ester or solvate thereof defined in item 1; (ii) another antalgic agent; (iii) an anxiolytic agent; (iv) an antidepressant agent; (v) a pharmaceutically acceptable carrier; (vi) instructions to use the kit in the prevention or treatment of pain or of a symptom thereof; or (vii) a combination of at least two of (i) to (vi).

Item 7. A method of preventing or treating pain in a subject in need thereof, comprising administering to the subject an effective amount of the compound, stereoisomer, mixture, pharmaceutically acceptable salt, ester or solvate thereof defined in any one of items 1 to 5; or a composition comprising the compound, stereoisomer, mixture, pharmaceutically acceptable salt, ester or solvate thereof and a pharmaceutically acceptable carrier.

There are also provided the following items:

1. A compound of formula (I)

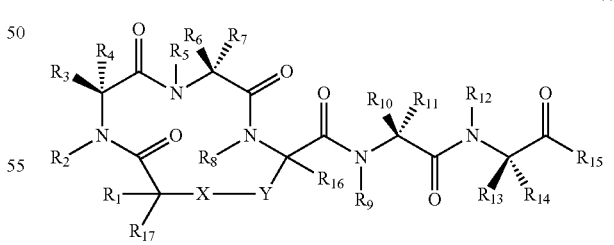

(I)

wherein:

(i) $R_1$ is H, (C3-C8)alkyl, or (C3-C8)aminoalkyl; or H, —$CH_3$, or —$NH_2$ or —NH-amino acid; and $R_{17}$ is H or $CH_3$; or $R_{17}$ is H, (C3-C8)alkyl, or (C3-C8)aminoalkyl; or H, —$NH_2$, —NHamino-acid or —$CH_3$; and $R_1$ is H or $CH_3$; (ii) $R_3$ is H or a —$(CH_2)p$-(C3-C8)alkyl, —$(CH_2)p$-(C3-C8)heteroaryl, a —$(CH_2)p$-(C3-C8)aryl, a —$(CH_2)p$-(C3-C8)cycloalkyl, or a —$(CH_2)p$-

(C3-C8)heterocycloalkyl, wherein p is 1 to 5, wherein the aryl or heteroaryl is optionally fused with one or two (C3-C8)aryl, and wherein the alkyl, heteroaryl, aryl, cycloalkyl and heterocycloalkyl is optionally substituted with one or more substituents, wherein each substituent is independently an halogen, or a (C1-C6) alkyl; or the side chain of a lysine, ornithine, diaminobutyric acid (Dab), diaminopropionic acid (Dap), citrulline, homolysine, histidine, norleucine, norvaline, glycine or glutamate; and $R_4$ is H or —$CH_3$; or $R_4$ is H or a —$(CH_2)$p-(C3-C8)alkyl, —$(CH_2)$p-(C3-C8)heteroaryl, a —$(CH_2)$p-(C3-C8)aryl, a —$(CH_2)$p-(C3-C8)cycloalkyl, or a —$(CH_2)$p-(C3-C8)heterocycloalkyl, wherein p is 1 to 5, wherein the aryl or heteroaryl is optionally fused with one or two (C3-C8)aryl; or the side chain of a lysine, ornithine, diaminobutyric acid (Dab), diaminopropionic acid (Dap), citrulline, homolysine, histidine, norleucine, norvaline, glycine or glutamate; and $R_3$ is H or —$CH_3$;

(iii) $R_6$ is H or a —$(CH_2)$p'—(C3-C8)alkyl, —$(CH_2)$p'—(C3-C8)heteroaryl, a —$(CH_2)$p'—(C3-C8)aryl, a —$(CH_2)$p'—(C3-C8)cycloalkyl, or a-$(CH_2)$p'—(C3-C8)heterocycloalkyl, wherein p' is 1 to 5, wherein the aryl or heteroaryl is optionally fused with one or two (C3-C8)aryl, and wherein the alkyl, heteroaryl, aryl, cycloalkyl and heterocycloalkyl is optionally substituted with one or more substituents, wherein each substituent is independently an halogen, or a (C1-C6) alkyl; or the side chain of a lysine, ornithine, diaminobutyric acid (Dab), diaminopropionic acid (Dap), citrulline, homolysine, histidine, norleucine, norvaline, glycine or glutamate; and $R_7$ is H or —$CH_3$; or $R_7$ is H, or a —$(CH_2)$p'—(C3-C8)alkyl, —$(CH_2)$p'—(C3-C8)heteroaryl, a —$(CH_2)$p'—(C3-C8)aryl, a —$(CH_2)$p'—(C3-C8)cycloalkyl, or a —$(CH_2)$p'—(C3-C8)heterocycloalkyl, wherein p' is 1 to 5, wherein the aryl or heteroaryl is optionally fused with one or two (C3-C8)aryl, and wherein the alkyl, heteroaryl, aryl, cycloalkyl and heterocycloalkyl is optionally substituted with one or more substituents, wherein each substituent is independently an halogen, or a (C1-C6)alkyl; or the side chain of a lysine, ornithine, diaminobutyric acid (Dab), diaminopropionic acid (Dap), citrulline, homolysine, histidine, norleucine, norvaline, glycine or glutamate; and $R_6$ is H or —$CH_3$;

(iv) (a) $R_{10}$ is H, or —$(CH_2)$q-(C3-C8)alkyl, —$(CH_2)$q-(C3-C8)heteroaryl, a —$(CH_2)$q-(C3-C8)aryl, a —$(CH_2)$q-(C3-C8)cycloalkyl, or a —$(CH_2)$q-(C3-C8) heterocycloalkyl, wherein q is 1 to 5, wherein the aryl or heteroaryl is optionally fused with one or two (C3-C8)aryl, and wherein the alkyl, heteroaryl, aryl, cycloalkyl and heterocycloalkyl is optionally substituted with one or more substituents, wherein each substituent is independently an halogen, or a (C1-C6) alkyl; or the side chain of an alanine (cyclopentyl), alanine (cyclohexyl), alanine (cyclobutyl), alanine (cyclopropyl), alanine (bromophenyl), alanine (thienyl), alanine (benzoylphenyl), alanine (styryl), alanine (styryl), alanine (pyridyl), alanine (benzothienyl), alanine(naphtyl), biphenylalanine, diphenylalanine, glycine (4-Hydroxyphenyl), alanine (homotyrosine), alanine (furyl), phenylalanine (4-amino), phenylalanine (4-nitro), phenylalanine (4-methyl), phenylalanine (2, 3, 4, 5, 6 pentafluoro), tyrosine, tyrosine (0-acetyl), tryptophan, lysine, m-tyrosine, tyrosine (O-methyl), phenylalanine, phenylalanine (4-fluoro), phenylalanine (4-tert-butyl), phenylalanine (4-iodo), phenylalanine (4-$CF_3$), phenylalanine (3-chloro), phenylalanine (4-chloro), phenylalanine (3-bromo), phenylalanine (4-bromo), phenylalanine (3-iodo) or phenylalanine (4-cyano); and $R_{11}$ is H or —$CH_3$; and $R_9$ is as defined in (vi); or (b) $R_{11}$ is H, —$(CH_2)$q-(C3-C8)alkyl, —$(CH_2)$q-(C3-C8)heteroaryl, a —$(CH_2)$q-(C3-C8)aryl, a —$(CH_2)$q-(C3-C8)cycloalkyl, or a —$(CH_2)$q-(C3-C8)heterocycloalkyl, wherein q is 1 to 5, wherein the aryl or heteroaryl is optionally fused with one or two (C3-C8)aryl, and wherein the alkyl, heteroaryl, aryl, cycloalkyl and heterocycloalkyl is optionally substituted with one or more substituents, wherein each substituent is independently an halogen, or a (C1-C6)alkyl; or the side chain of a alanine (cyclopentyl), alanine (cyclohexyl), alanine (cyclobutyl), alanine (cyclopropyl), alanine (bromophenyl), alanine (thienyl), alanine (benzoylphenyl), alanine (styryl), alanine (styryl), alanine (pyridyl), alanine (benzothienyl), alanine(naphtyl), biphenylalanine, diphenylalanine, glycine (4-Hydroxyphenyl), alanine (homotyrosine), alanine (furyl), phenylalanine (4-amino), phenylalanine (4-nitro), phenylalanine (4-methyl), phenylalanine (2, 3, 4, 5, 6 pentafluoro), tyrosine, tyrosine (0-acetyl), tryptophan, lysine, m-tyrosine, tyrosine (O-methyl), phenylalanine, phenylalanine (4-fluoro), phenylalanine (4-iodo), phenylalanine (4-tert-butyl), phenylalanine (4-$CF_3$), alanine (naphtyl), phenylalanine (3-chloro), phenylalanine (4-chloro), phenylalanine (3-bromo), phenylalanine (4-bromo), phenylalanine (3-iodo) or phenylalanine (4-cyano); and $R_{10}$ is H or —$CH_3$; and R9 is as defined in (vi); or (c) $R_9$ forms a ring or a ring system with $R_{10}$ or $R_{11}$, wherein the ring or ring system is a (C3-C8)cycloalkyl, a (C3-C8)heterocycloalkyl or an (C3-C8)heteroaryl, optionally fused to an additional (C3-C8) cycloalkyl, a (C3-C8)heterocycloalkyl or an (C3-C8) heteroaryl, wherein when R9 forms the ring or ring system with $R_{10}$, $R_{11}$ is H; and when R9 forms the ring or ring system with $R_{11}$, $R_{10}$ is H; and wherein the definition of R9 in (vi) does not apply;

(v) $R_{13}$ is H or —$CH_3$; and $R_{14}$ is H, —$(CH_2)$q'—(C3-C8)alkyl, —$(CH_2)$q'—(C3-C8)heteroaryl, a —$(CH_2)$q'—(C3-C8)aryl, —$(CH_2)$q'—(C3-C8)cycloalkyl, or a-$(CH_2)$q'—(C3-C8)heterocycloalkyl, wherein q' is 1 to 5, wherein the aryl or heteroaryl is optionally fused with one or two (C3-C8)aryl, and wherein the alkyl, heteroaryl, aryl, cycloalkyl and heterocycloalkyl is optionally substituted with one or more substituents, wherein each substituent is independently an halogen, or a (C1-C6)alkyl; or the side chain of a leucine, tert-leucine, norleucine, norvaline, valine, neopentylglycine, cyclohexylglycine, cyclohexylalanine, phenylalanine, tyrosine (O-methyl), 2, 4, 5-trifluoro phenylalanine, homocyclohexylalanine, cyclopropylalanine, cyclobutylalanine, cyclopentylalanine, cycloheptylalanine or glycine; or $R_{14}$ is H or —$CH_3$; and $R_{13}$ is H, —$(CH_2)$q'—(C3-C8) alkyl, —$(CH_2)$q'—(C3-C8)heteroaryl or a —$(CH_2)$q'—(C3-C8)aryl, —$(CH_2)$q'—(C3-C8)cycloalkyl, or a —$(CH_2)$q'—(C3-C8)heterocycloalkyl, wherein q' is 1 to 5, wherein the aryl or heteroaryl is optionally fused with one or two (C3-C8)aryl, and wherein the alkyl, heteroaryl, aryl, cycloalkyl and heterocycloalkyl is optionally substituted with one or more substituents, wherein each substituent is independently an halogen, or a (C1-C6)alkyl; or the side chain of a leucine, tert-leucine, norleucine, norvaline, valine, neopentylglycine, cyclohexylglycine, cyclohexylalanine, phenylalanine, tyrosine (O-methyl), 2, 4, 5, -trifluoro phenylalanine, homocyclohexylalanine, cyclopropylalanine, cyclobutylalanine, cyclopentylalanine, cycloheptylalanine or glycine;

(vi) (A) $R_2$, $R_5$, $R_8$, $R_9$, and $R_{12}$ are each independently H, (C1-12)alkyl, or (C4-C14)aralkyl; or (B) at least one of $R_2$, $R_5$, $R_8$, $R_9$, and $R_{12}$ is as follows:
  a) $R_2$ is an —$(CH_2)$p-(C3-C8)heteroaryl or a —$(CH_2)$p-(C3-C8)aryl, wherein p is 1 to 5; or the side chain of a lysine, ornithine, diaminobutyric acid (Dab), diaminopropionic acid (Dap), histidine, norleucine, norvaline, glycine or glutamate, with the proviso that $R_3$ and $R_4$ are then H;
  b) $R_5$ is a —$(CH_2)$p'—(C3-C8)heteroaryl or a —$(CH_2)$p'—(C3-C8)aryl, wherein p' is 1 to 5; or the side chain of a lysine, ornithine, diaminobutyric acid (Dab), diaminopropionic acid (Dap), histidine, norleucine, norvaline, glycine or glutamate, with the proviso that $R_6$ and $R_7$ are then H;
  c) $R_9$ is —$(CH_2)$q-(C3-C8)heteroaryl or a —$(CH_2)$q-(C3-C8)aryl, wherein q is 1 to 5; or the side chain of an alanine (cyclopentyl), alanine (furyl), phenylalanine (4-amino), phenylalanine (4-nitro), phenylalanine (4-methyl), phenylalanine (2, 3, 4, 5, 6 pentafluoro), tyrosine, tyrosine (OAc), tryptophan, lysine, m-tyrosine, tyrosine (Ome), phenylalanine, phenylalanine (4-fluoro), phenylalanine (4-iodo), phenylalanine (4-tert-butyl), phenylalanine (4-$CF_3$), alanine (naphtyl), phenylalanine (3-chloro), phenylalanine (4-chloro), phenylalanine (3-bromo), phenylalanine (4-bromo), phenylalanine (3-iodo) or phenylalanine (4-cyano), with the proviso that $R_{10}$ and $R_{11}$ are then H;
  d) $R_{12}$ is —$(CH_2)$q'—(C3-C8)heteroaryl or a —$(CH_2)$q'—(C3-C8)aryl, wherein q' is 1 to 5; or the side chain of a leucine, tert-leucine, norleucine, norvaline, valine, neopentylglycine, cyclohexylglycine, cyclohexylalanine, phenylalanine, tyrosine (Ome), 2, 4, 5,-trifluoro phenylalanine, homo cyclohexyl alanine, cyclopropyl alanine cyclobutyl alanine, cyclopentyl alanine or cycloheptyl alanine, with the proviso that $R_{13}$ and $R_{14}$ are then H;
  and the other ones of $R_2$, $R_5$, $R_8$, $R_9$, and $R_{12}$ are each independently H, (C1-12)alkyl, or (C4-C14)aralkyl, with the proviso that when (iv)(c), the definition of $R_9$ herein does not apply;

(vii) $R_{15}$ is H, or —$OR_{18}$ wherein $R_{18}$ is H, benzyl, (C4-C14)aralkyl or (C1-12)allyl;

(viii) $R_{16}$ is H, or —$CH_3$; and (ix) (a) X is —$(CH_2)$n, wherein n is 0-4; and Y is —$(CH_2)$m-, —CH=CH$(CH_2)$m-, —$C(R_{22})(R_{23})$—S—S—$C(R_{24})(R_{25})$— wherein $R_{22}$, $R_{23}$, $R_{24}$, and $R_{25}$— are independently H or (C1-C4)alkyl, —$NR_{19}$C(=O)$(CH_2)$m- or —C(=O)$NR_{19}(CH_2)$m-, wherein m is 1-4, wherein $R_{19}$ is H or (C1-C5)alkyl; or (b) X and Y form together —$(CH_2)$n-aryl-$(CH_2)$m-, wherein n and m are as defined above, wherein aryl is ortho, meta, or para benzene, or biaryl, substituted or not in at least one of positions 2, 3, 4, 2', 3', or 4', or a stereoisomer or a mixture thereof, or a pharmaceutically acceptable salt, ester or solvate thereof.

2. The compound, stereoisomer, mixture, pharmaceutically acceptable salt, ester or solvate thereof of item' 1, wherein:
  (iv) $R_{10}$ is a leucine or substituted or unsubstituted —$(CH_2)$q-(C3-C8)aryl or —$(CH_2)$q-(C3-C8)heteroaryl, wherein the aryl or heteroaryl is optionally fused with one or two (C3-C8)aryl, and wherein the aryl or heteroaryl is optionally substituted with one or more substituents, wherein each substituent is independently an halogen, or a (C1-C6)alkyl; and $R_{11}$ is H or —$CH_3$ or $R_{10}$ or $R_{11}$ forms with $R_9$ a (C3-C8)cycloalkyl fused with another (C3-C8)cycloalkyl; and
  (v) $R_{13}$ is H or —$CH_3$; and $R_{14}$ is a substituted or unsubstituted —$(CH_2)$q'—(C3-C8)cycloalkyl, —$(CH_2)$q'—(C3-C8)alkyl-$(CH_2)$q'—(C3-C8)heterocycloalkyl, or —$(CH_2)$q'—(C3-C8)aryl.

3. The compound, stereoisomer, mixture, pharmaceutically acceptable salt, ester or solvate thereof of item' 1, wherein the compound is any one of the compounds of the present invention e.g., compounds 14-17, 21, 27-34, 38-49, 51-156, 159-170 as defined herein.

4. The compound, stereoisomer, mixture, pharmaceutically acceptable salt, ester or solvate thereof of any one of items' 1-3, wherein the compound has a selectivity for the NTS2 receptor higher than 100.

5. The compound, stereoisomer, mixture, pharmaceutically acceptable salt, ester or solvate thereof of any one of items' 1-4, wherein:
  (ii) $R_{10}$ or $R_{11}$ is the side chain of a phenylalanine, leucine, biphenylalanine, tryptophan, thienylalanine, homotyrosine, tyrosine, benzothienylalanine, furylalanine, styrylalanine, cyclopentylalanine, pyridylalanine, cyclobutylalanine, or diphenylalanine; a —$CH_2$-naphtyl; or a —$CH_2$-cycloalkyl, wherein the side chain, naphtyl and cycloalkyl is optionally substituted with one or more substituents, each substituent being independently an halogen, or a (C1-C5)alkyl; and the other one of $R_{10}$ or $R_{11}$ is H or $CH_3$; and/or
  (iii) $R_{13}$ or $R_{14}$ is a-$(CH_2)$s-(C3-C7)cycloalkyl or —$(CH_2)$s-(C4-C7)alkyl wherein s is 1-3; or the side chain of a leucine, tyrosine, phenylalanine, or norleucine, wherein the side chain is optionally substituted with one or more substituents, each substituent being independently as defined above; and $R_{14}$ is H or —$CH_3$.

6. The compound, stereoisomer, mixture, pharmaceutically acceptable salt, ester or solvate thereof of item 1, wherein the compound is any one of compounds 43, 30, 101, 108, 86, 58, 57, 146, 84, 140, 72, 82, 147, 138, 55, 87, 92, 32, 28, 63, 54, 155, 65, 143, 52, 169, 149, 142, 53, 150, 74, 81, 62, 80, 132, 73, 161, 41, 120, 151, 168, 109, 167, 77, 47, 159, 31, 75, 76, 112, 126, 123, 79, 90, 51, 34, 118, 119, 122, 16, 139, 113, 111, 60, 135, 49, 114, 110, 136, 153, 93, 166, 117, 115, 131, 66, 162, 134, 116, 78, 129, 89, 91, 130, 137, 128, 64, 68, 156, 67, 133 and 127 as defined in item' 3.

7. The compound, stereoisomer, mixture, pharmaceutically acceptable salt, ester or solvate thereof of any one of items 1-3, wherein the compound is any one of compounds 34, 67, 116, 127, 128 and 133 as defined in item 3.

8. A composition comprising (a) the compound, stereoisomer, mixture, pharmaceutically acceptable salt, ester or solvate thereof defined in any one of items' 1 to 7; and (b) (i) at least another compound, stereoisomer, mixture, pharmaceutically acceptable salt, ester or solvate thereof defined in any one of items' 1 to 7; (ii) another antalgic agent; (iii) an anxiolytic agent; (iv) an antidepressant agent; (v) a pharmaceutically acceptable carrier; or (vi) a combination of at least two of (i) to (v).

9. A kit for preventing or treating pain, comprising (a) the compound, stereoisomer, mixture, pharmaceutically acceptable salt, ester or solvate thereof defined in any one of items' 1 to 7; and (b) (i) at least another compound, stereoisomer, mixture, pharmaceutically acceptable salt, ester or solvate thereof defined in any one of items' 1 to 7; (ii) another antalgic agent; (iii) an anxiolytic agent; (iv) an antidepressant agent; (v) a pharmaceutically acceptable carrier; (vi) instructions to use the kit in the prevention or treatment of pain or of a symptom thereof; or (vii) a combination of at least two of (i) to (vi).

10. A method of preventing or treating pain in a subject in need thereof, comprising administering to the subject an effective amount of the compound, stereoisomer, mixture, pharmaceutically acceptable salt, ester or solvate thereof defined in any one of items' 1 to 7; or of the composition defined in item' 8.

Other objects, advantages and features of the present disclosure will become more apparent upon reading of the following non-restrictive description of specific embodiments thereof, given by way of example only with reference to the accompanying drawings.

BRIEF DESCRIPTION OF THE DRAWINGS

In the appended drawings:

FIG. 2A: Dose-response curve of compound 34 in the acute thermal tail-flick test. Tail-flick latencies were measured each 10 min for up to 60 min following i.t. injection of compound 34 at different doses as compared to saline-injected rats. Error bars represent mean±SEM. A two-way ANOVA followed by Sidak's correction was performed. ****$p<0.0001$. FIG. 2B: Percentage of Maximal Possible Effect (% MPE) of compound 34 on acute (Tail-flick) test was calculated at 10 min post-injection, when the antinociceptive response was maximal as compared to saline-injected rats. Error bars represent mean±SEM. A one-way ANOVA followed by Dunnett's correction was performed. *$p<0.05$; ****$p<0.0001$.

Nonlinear regression using four parameters was performed for $ED_{50}$ calculation of the compound obtained from the resulting dose-response curve.

Figure 4A:
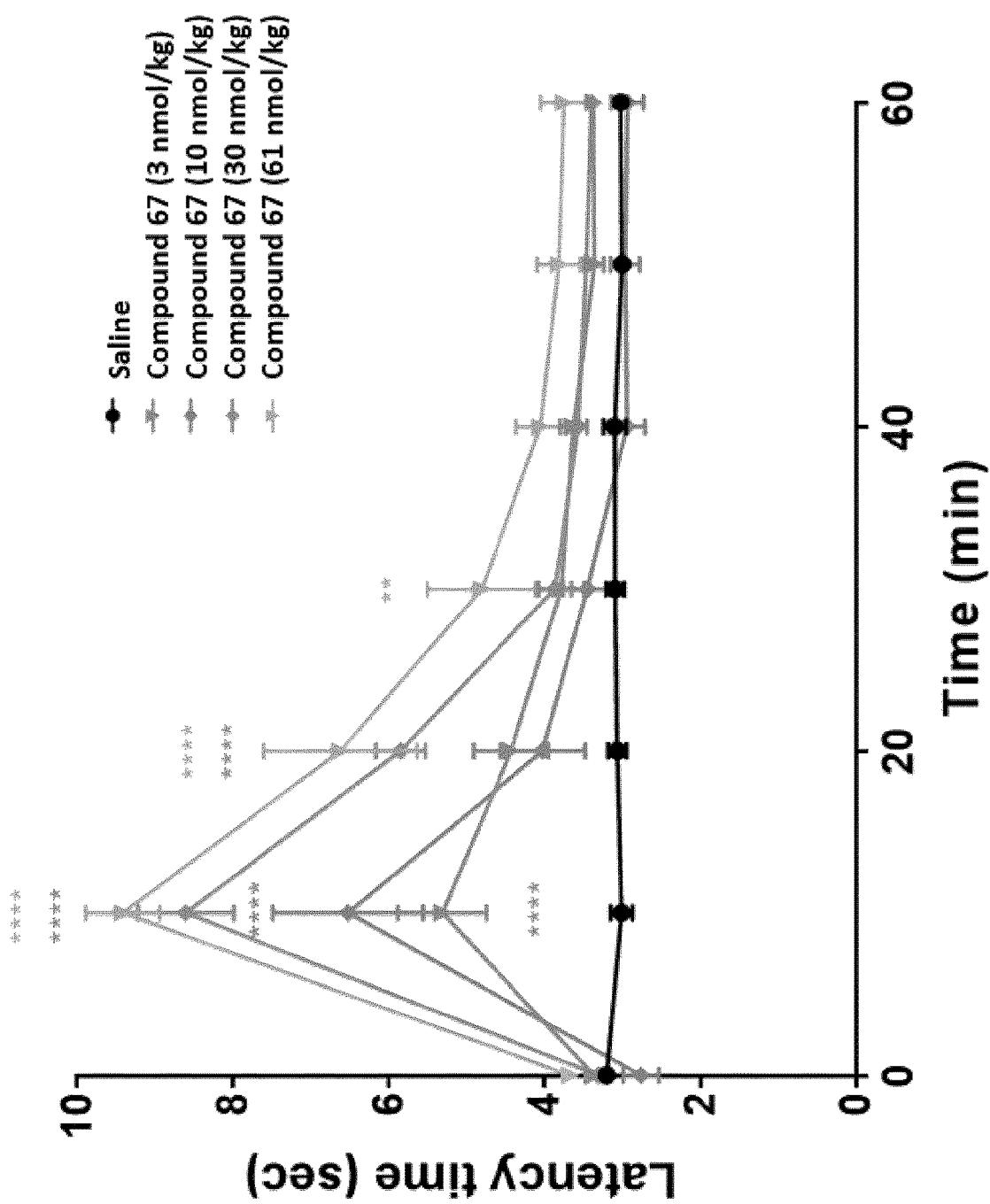
Figure 4B:
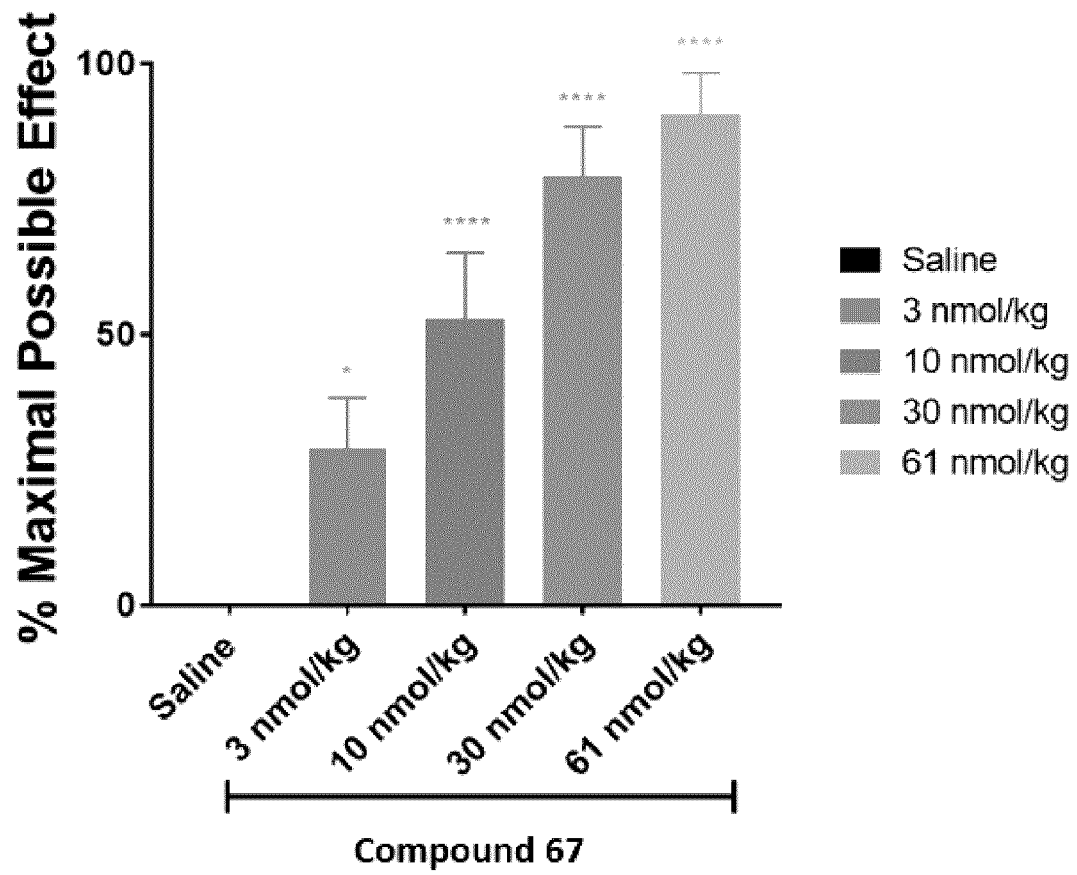

FIGS. 4A-B: FIG. 4A. Dose-response curve of compound 67 in the acute thermal tail-flick test. Tail-flick latencies were measured each 10 min for up to 60 min following i.t. injection of compound 67 at different doses as compared to saline-injected rats. Error bars represent mean±SEM, n=5-8 rats. A two-way ANOVA followed by Sidak's correction was performed. **$p<0.0001$. FIG. 4B: Percentage of Maximal Possible Effect (% MPE) of compound 67 on acute (Tail-flick) test was calculated at 10 min post-injection, when the antinociceptive response was maximal as compared to saline-injected rats. n=5-8 rats Error bars represent mean±SEM. **$p<0.0001$.

Figure 5:
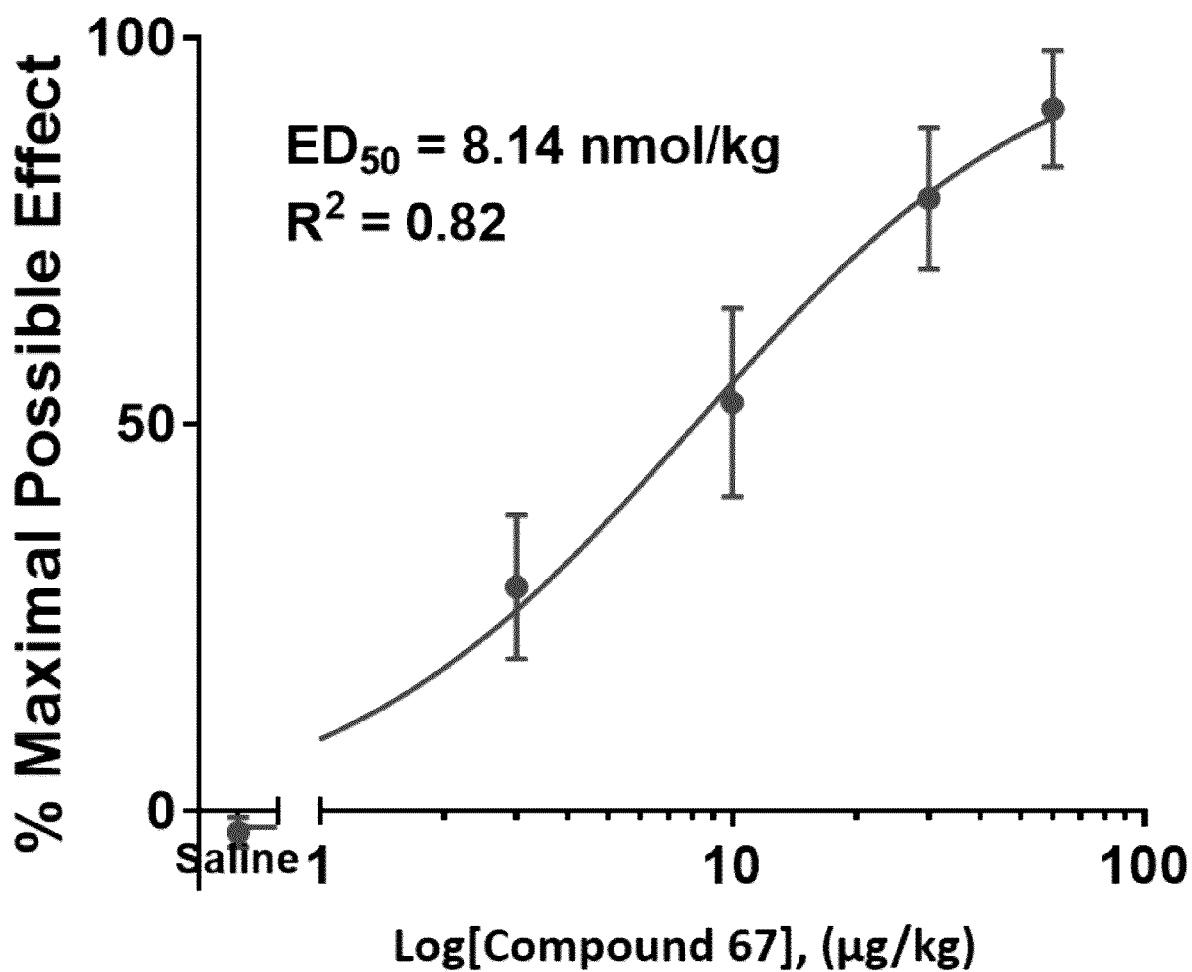
Figure 6A:
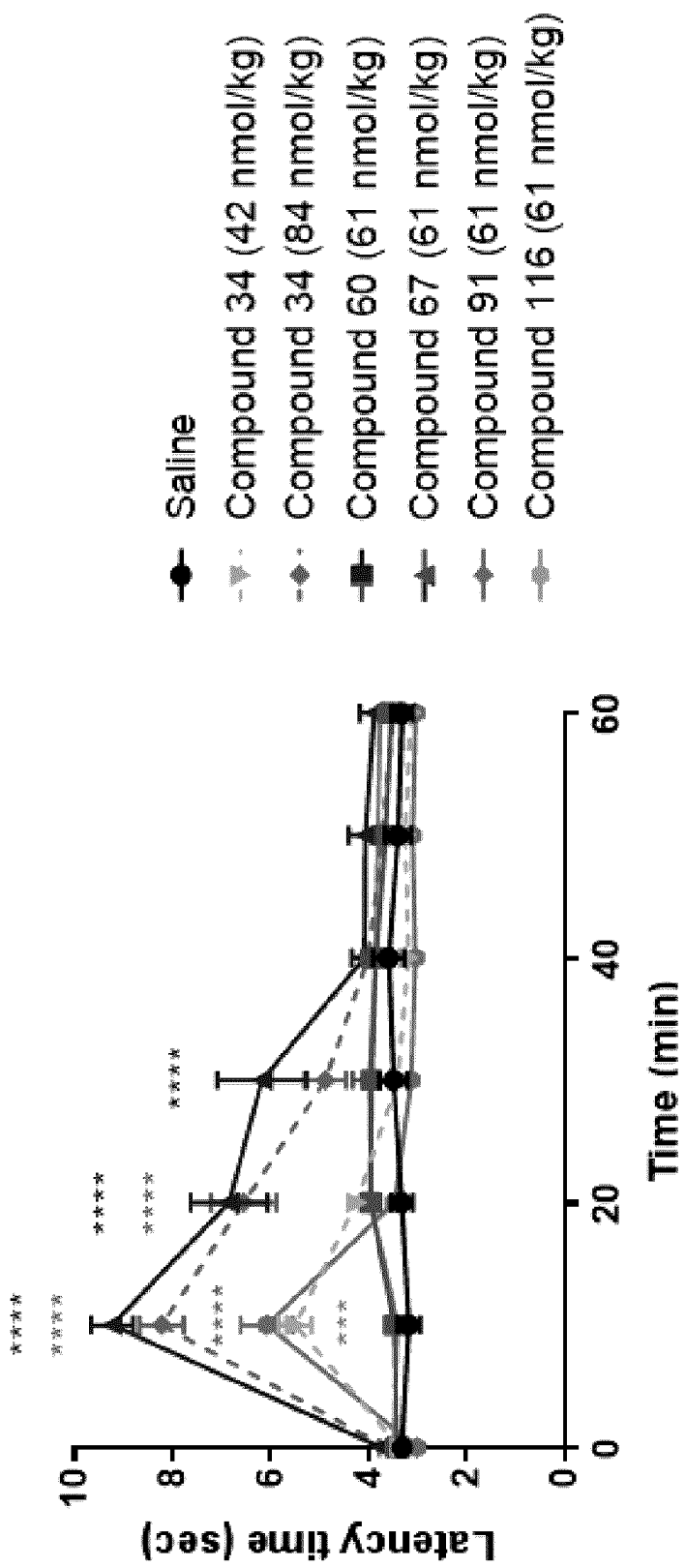
Figure 6B:
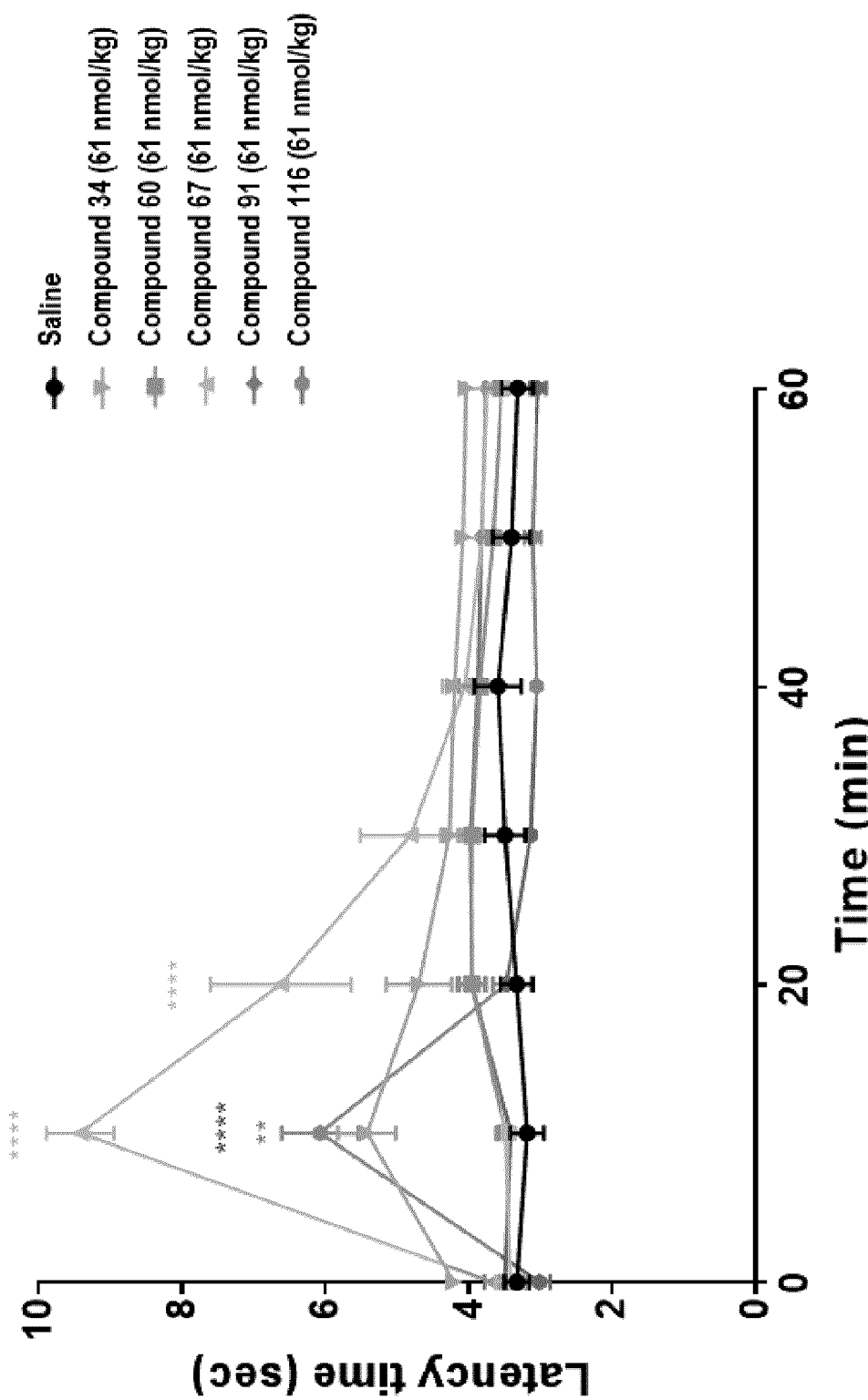
Figure 6C:
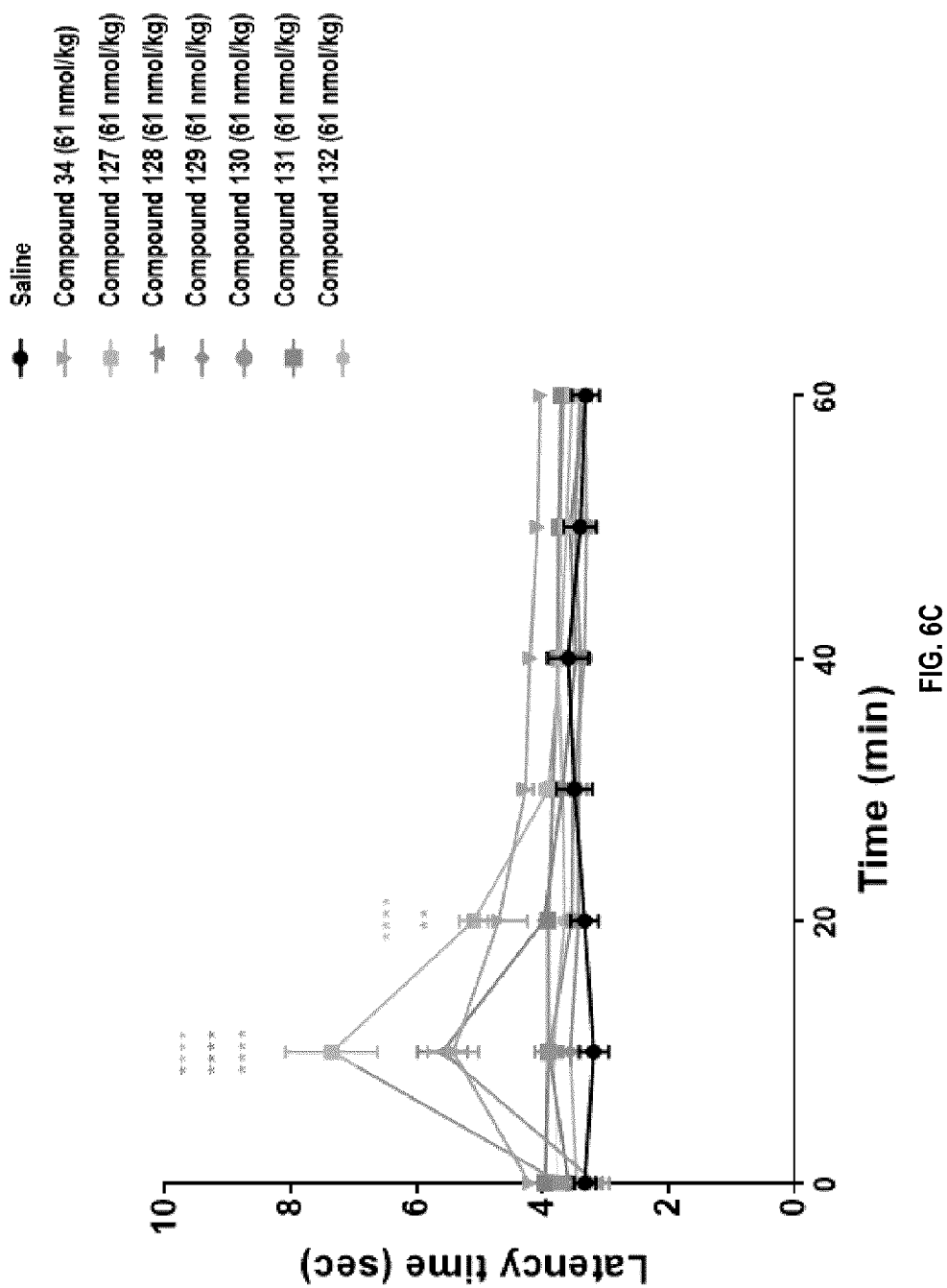
Figure 6D:
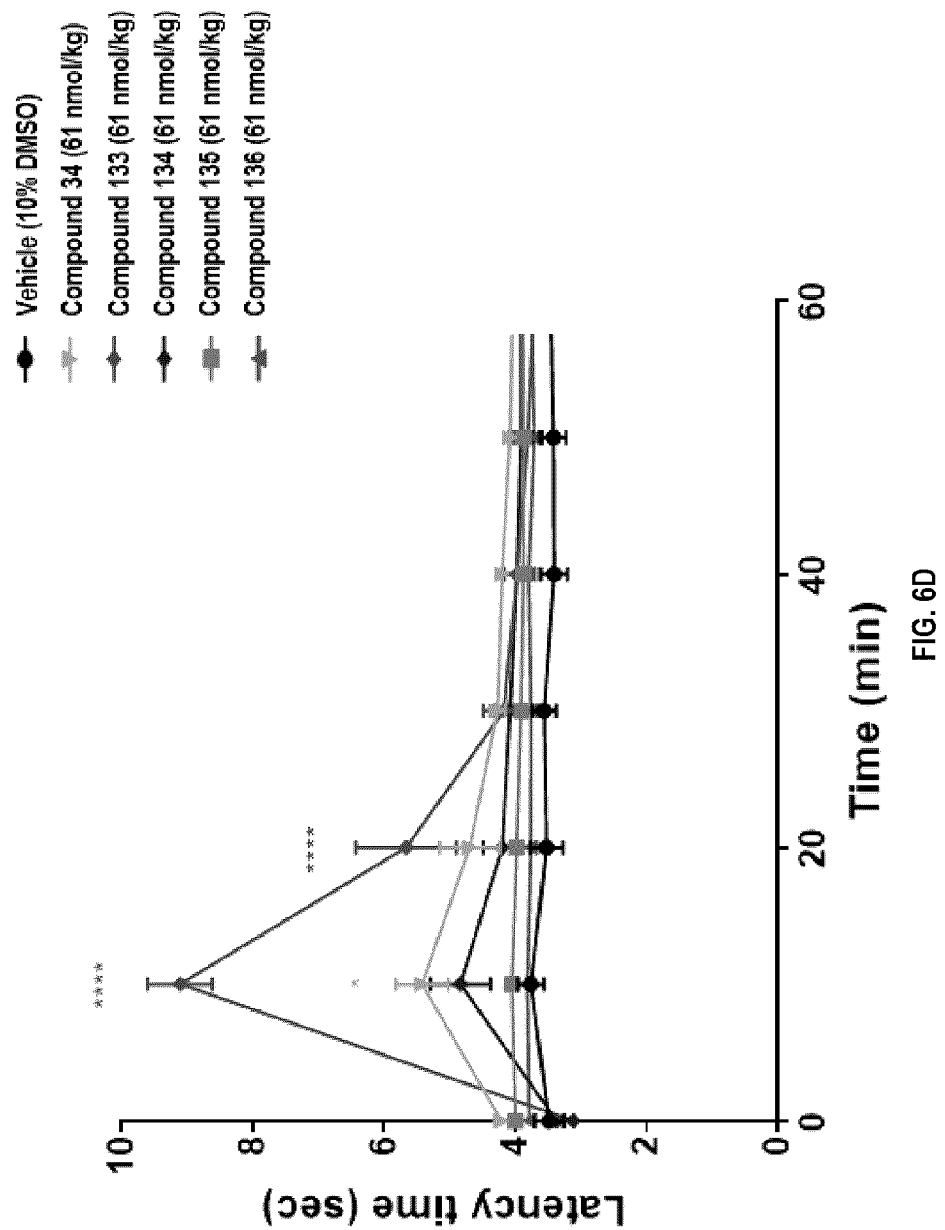
Figure 6E:
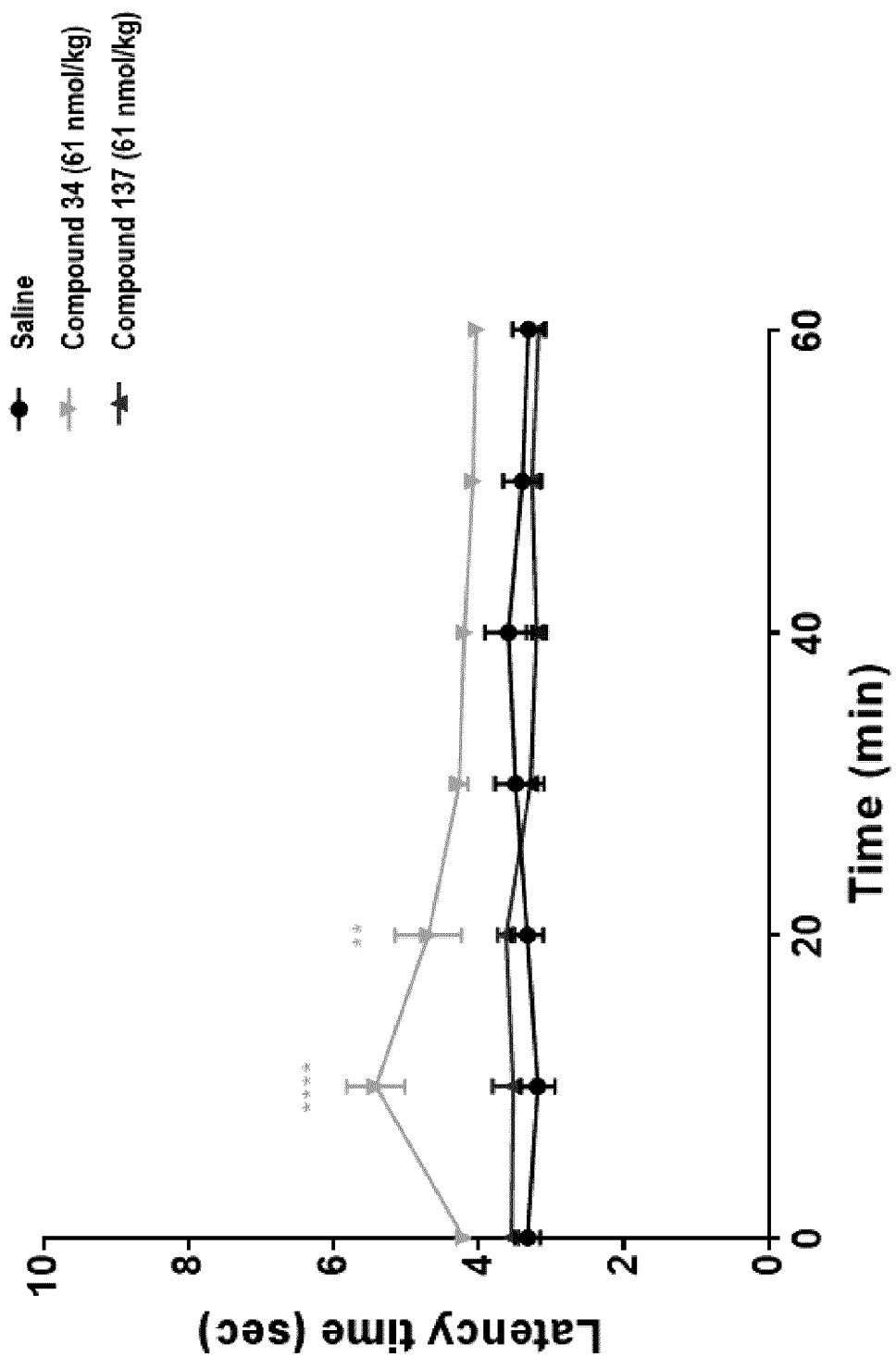

FIG. 5: Calculation of % MPE of compound 67 at 10 min post-injection allowed to determinate the half maximal effective dose ($ED_{50}$) of compound 67 to induce analgesia in acute pain. Error bars represent mean±SEM. Nonlinear regression using four parameters was performed for $ED_{50}$ calculation of the compound was obtained from the resulting dose-response curve n=5-8 rats.

FIGS. 6A-E: Analgesic efficacy of neurotensinergic agonists on acute pain. Tail-flick test on rats injected intrathecally at the $ED_{50}$ of compound 34 (48.52 μg/kg=61 nmol/kg), compounds 34 (42 nmol/kg, 84 nmol/kg and 61 nmol/kg), 60, 67, 91, and 116 (61 nmol/kg) (FIGS. 6A-B); compounds 34 and 127-132 (61 nmol/kg) (FIG. 6C); compounds 34 and 133-136 (61 nmol/kg) (FIG. 6D); or compounds 34 and 137 (61 nmol/kg) (FIG. 6E) as compared to saline-injected rats. Error bars represent mean±SEM. A two-way ANOVA followed by Sidak's correction was performed. *$p<0.05$; $p<0.01$; *$p<0.001$; ****$p<0.0001$.

Figure 7A:
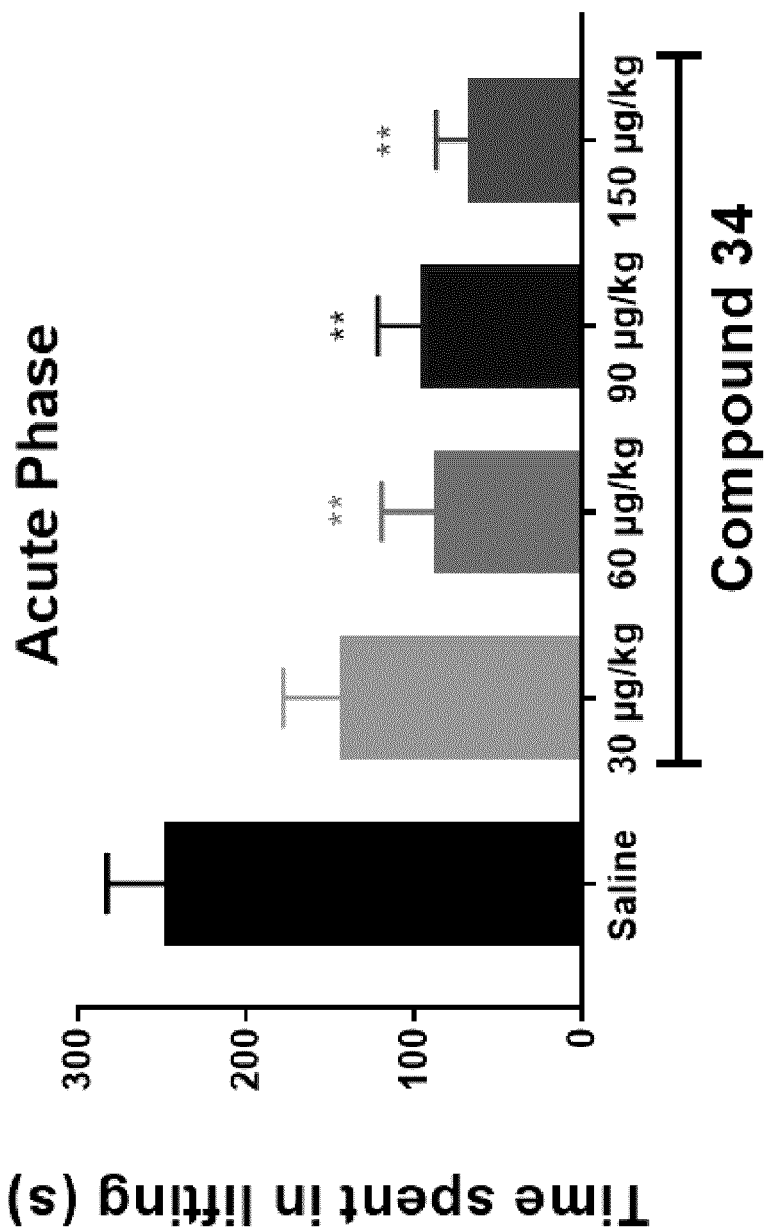
Figure 7B:
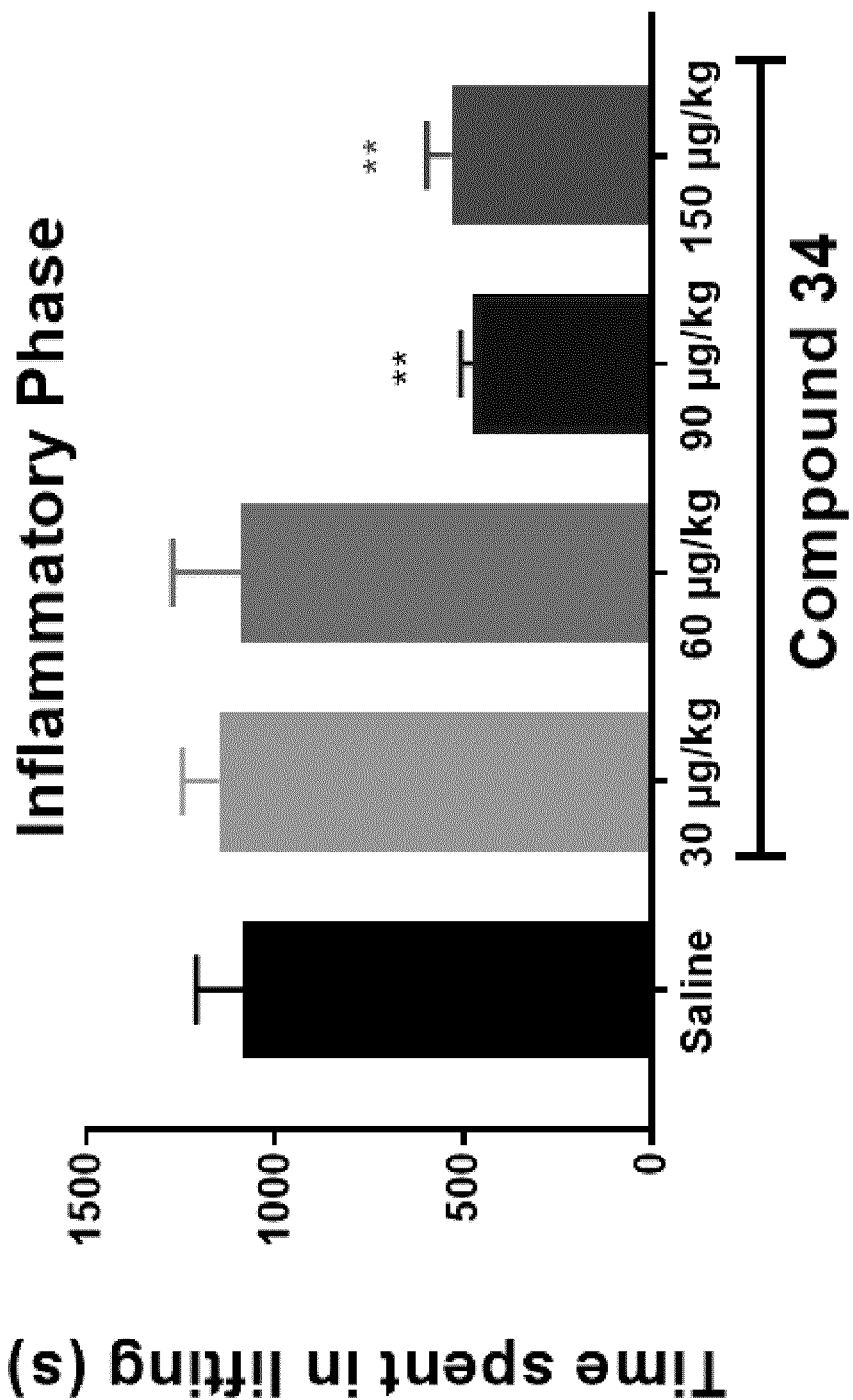

FIGS. 7A-B: Analgesic effect of acute intrathecal injection of 30 to 150 μg/kg of compound 34 on pain behaviors following intraplantar injection of formalin in rats. Areas Under the Curve (AUC) were calculated for category 2 of pain behaviors, for the acute phase (FIG. 7A) and the inflammatory phase (FIG. 78). Error bars represent mean±SEM (N=5-6/group). A one-way ANOVA followed by Dunnett's correction was performed. **$p<0.01$.

Figure 8A:
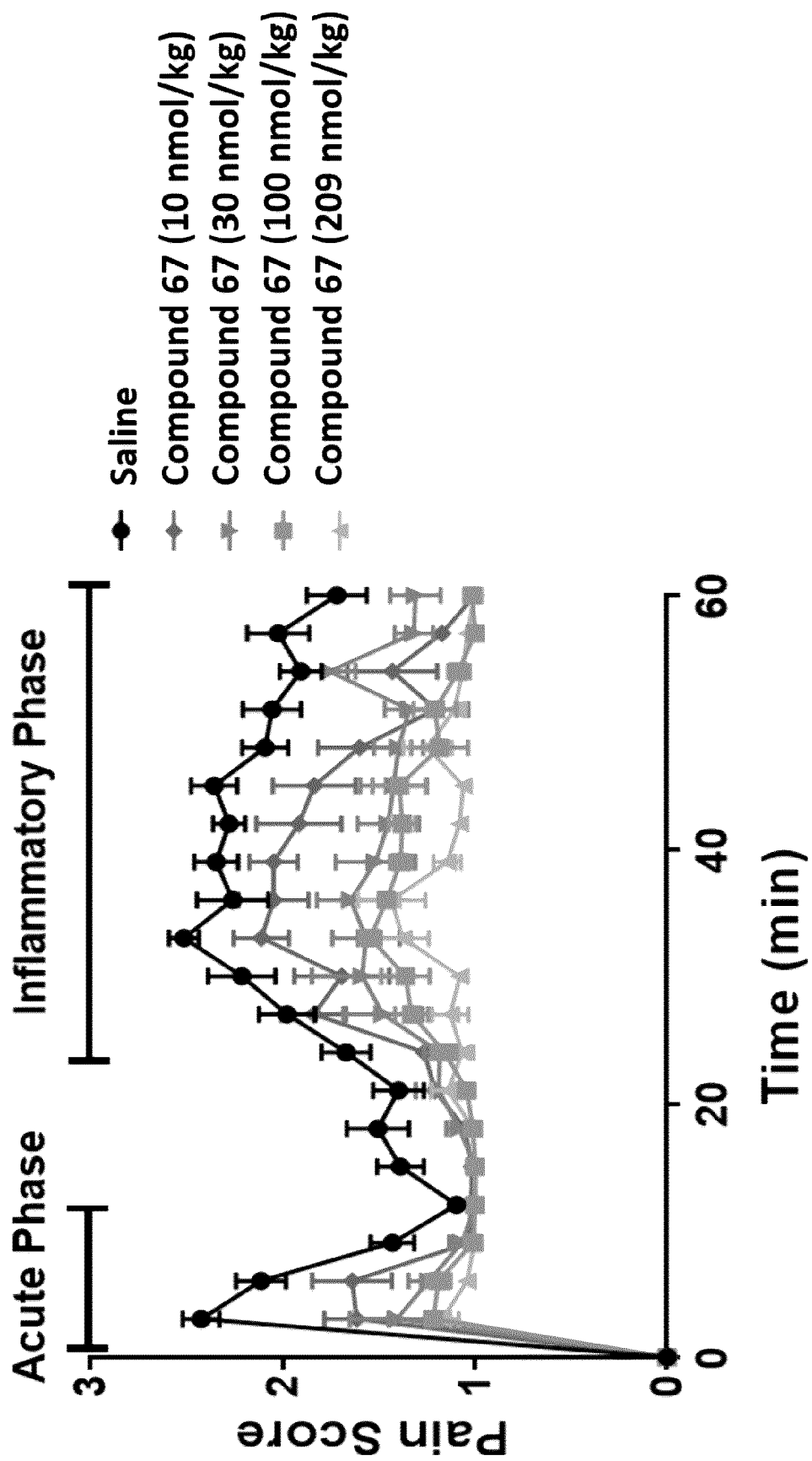
Figure 8C:
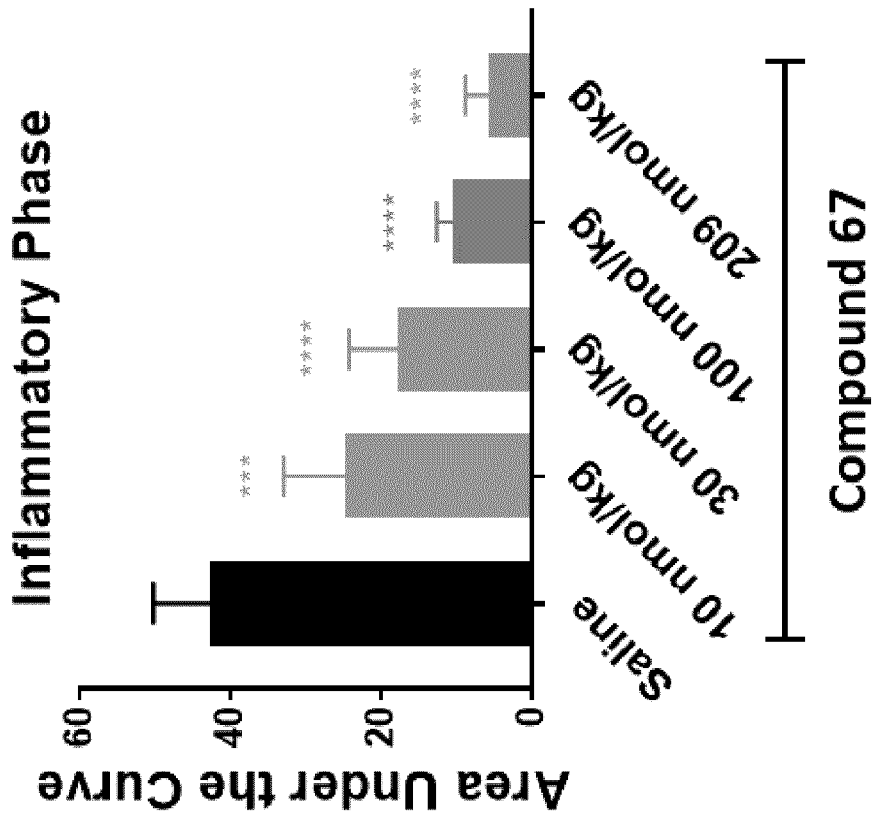
Figure 8B:
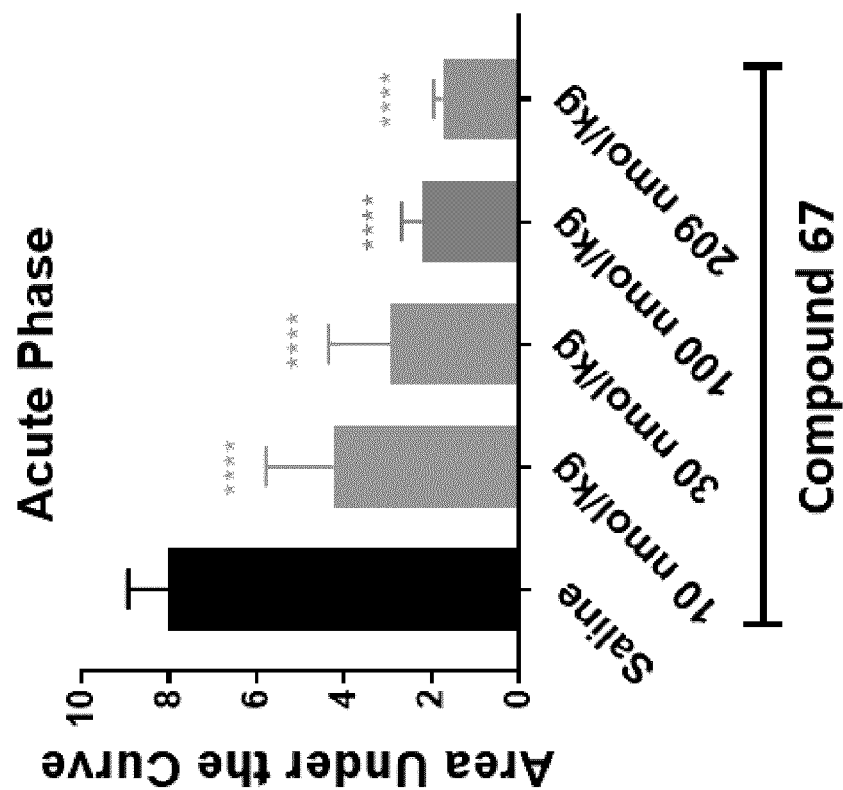
Figure 8D:
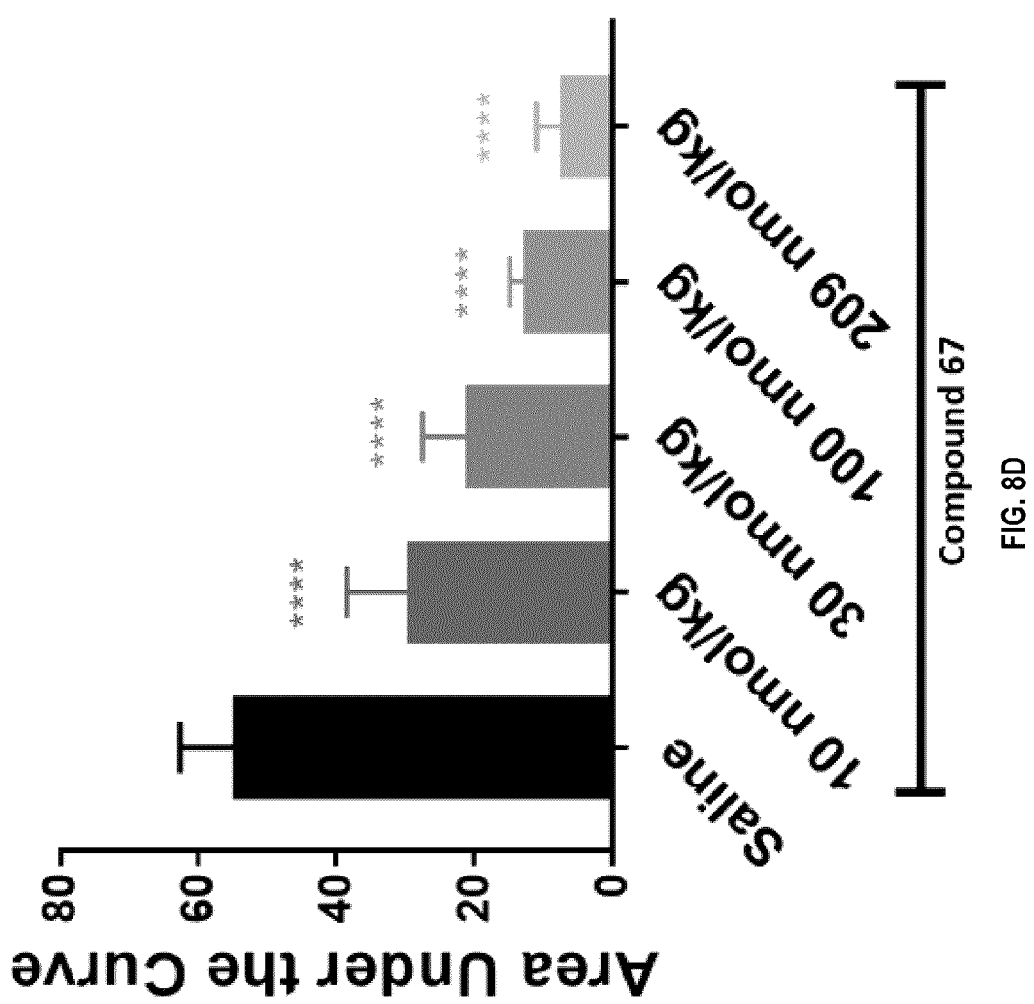
Figure 8E:
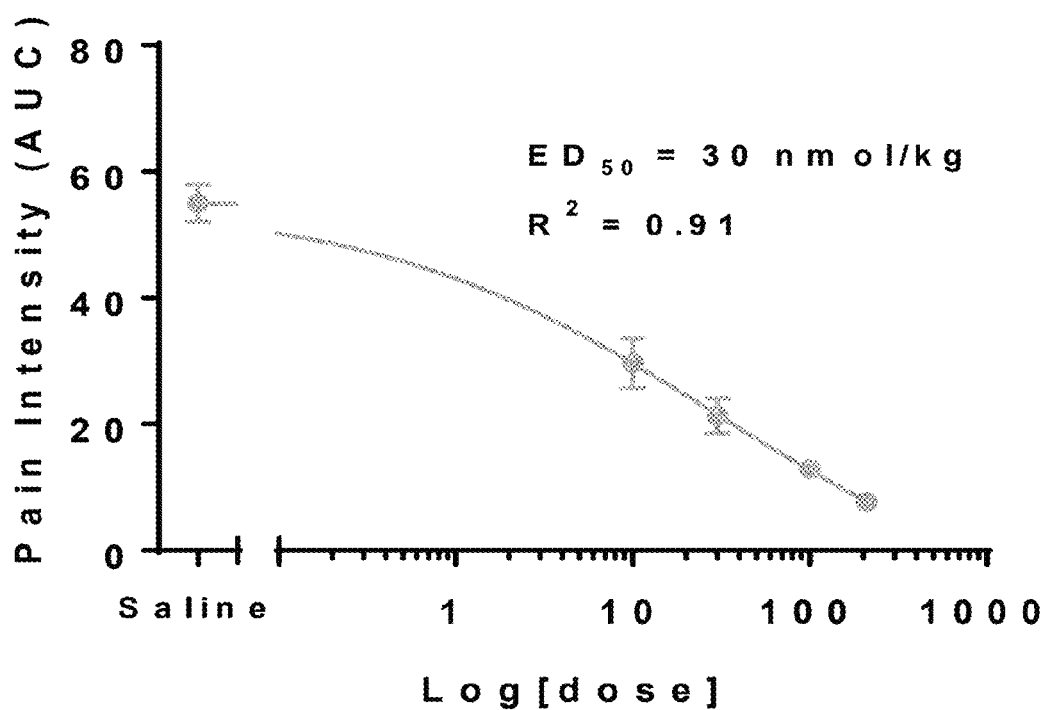

FIGS. 8A-E: Dose-response curve of compound 67 in the tonic pain model following intraplantar injection of formalin in the rat hind paw. FIG. 8A: The pain score was determined at each tested dose over 60 minutes and the corresponding Area Under the Curve (AUC) was calculated for all the duration of the test. FIGS. 8B-D: The AUC obtained with each dose in the acute phase, the inflammatory phase and combined was compared to that obtained with saline. FIG. 8E: Calculation of AUC (acute and inflammatory phases combined FIG. 8D) for each dose allowed to determinate the $ED_{50}$ of compound 67 as compared to saline-injected rats to induce analgesia in tonic pain. For FIGS. 8B-D, a one-way ANOVA followed by Dunnett's correction was performed. ****$p<0.0001$. For FIG. 8E, nonlinear regression using four parameters was performed for $ED_{50}$ calculation of the compound was obtained from the resulting dose-response curve. Error bars represent mean±SEM, n=5-6 rats.

Figure 9A:
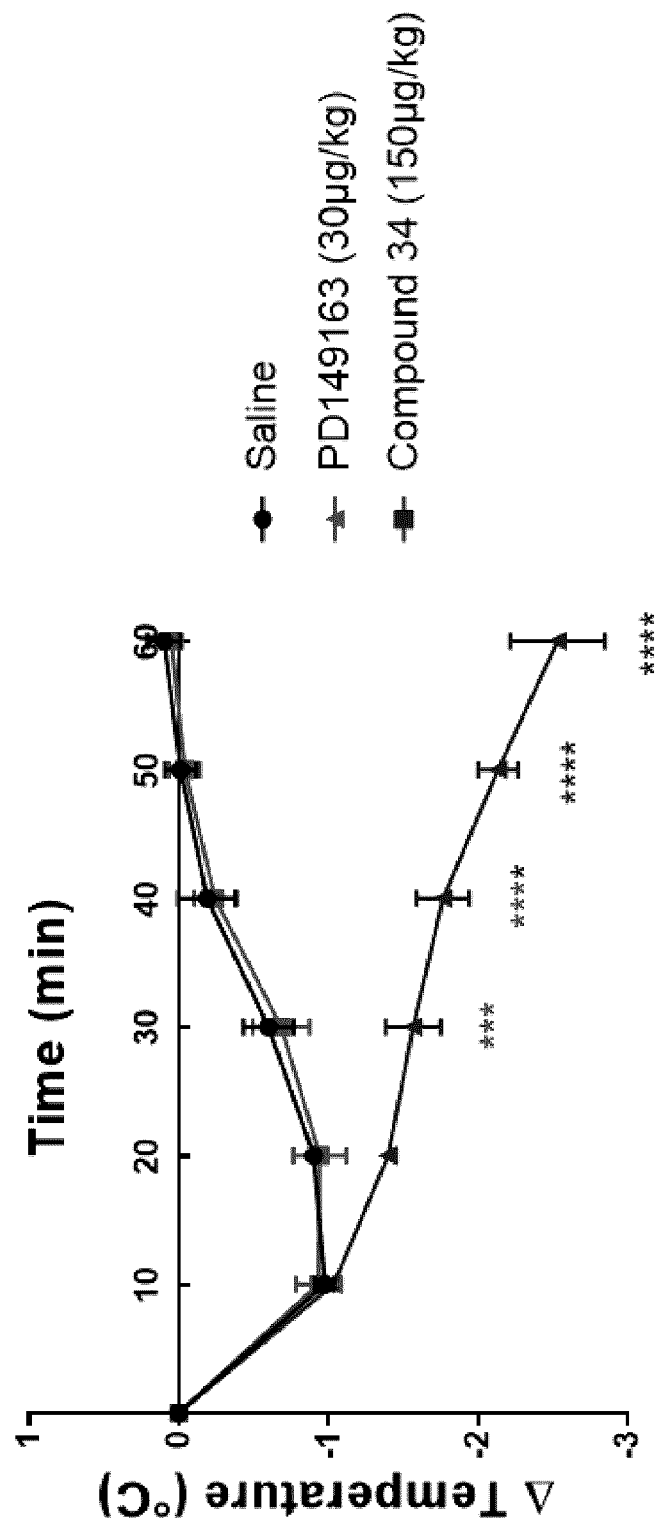
Figure 9B:
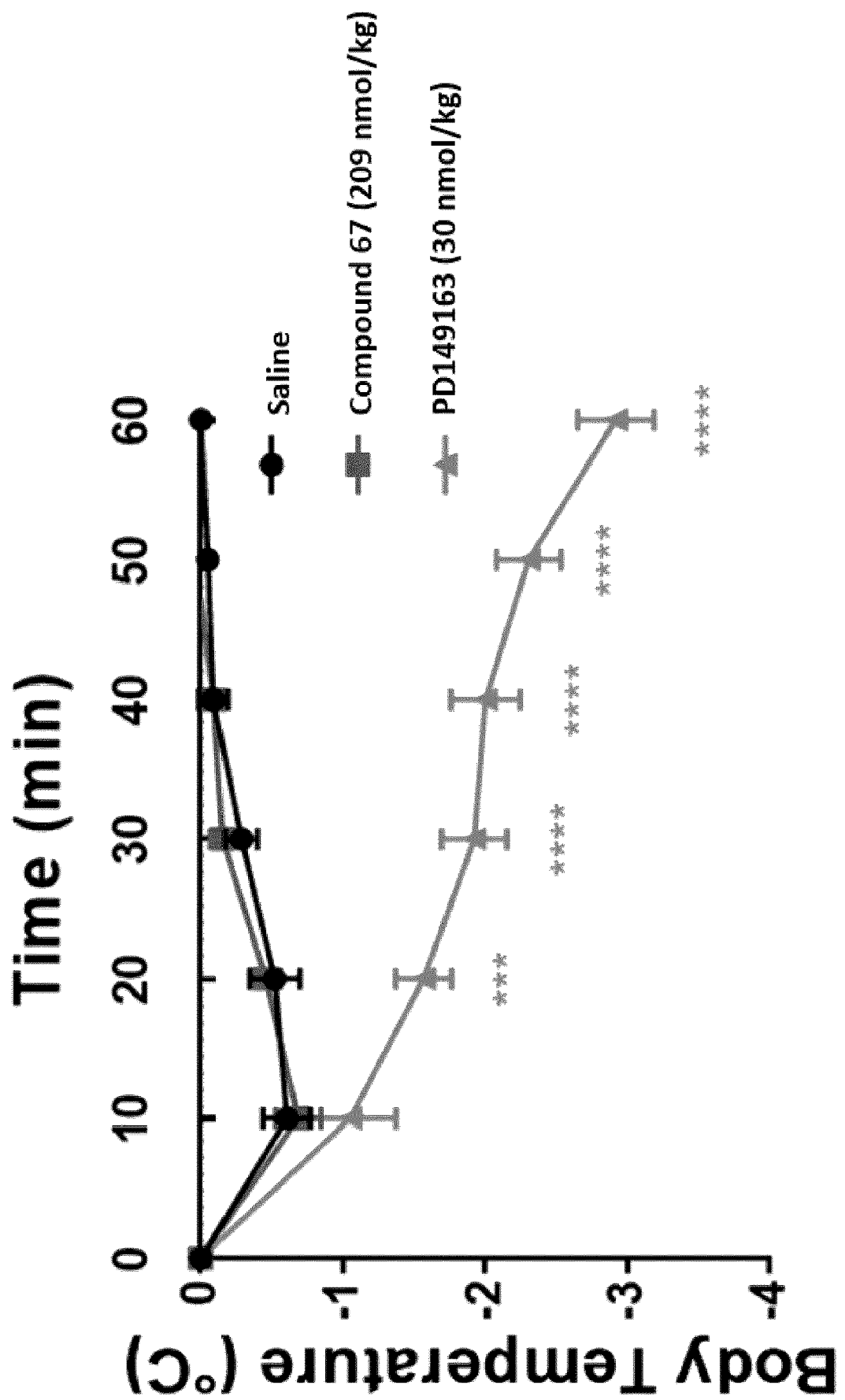

FIGS. 9A-B: Effect of compounds 34, 67 and PD149163 on body temperature. Change in body temperature (A Temperature or Body Temperature) was calculated every 10 min for up to 60 min following i.t. injection of compounds 34 (150 μg/kg), compound 67 (209 nmol/kg) and PD149163 (30 μg/kg) as compared to saline-injected rats. n=5-6 rats for each compound. Error bars represent mean±SEM, n=5-6 rats A two-way ANOVA followed by Tukey's correction was performed. *$p<0.001$; **$p<0.0001$.

Figure 10A:
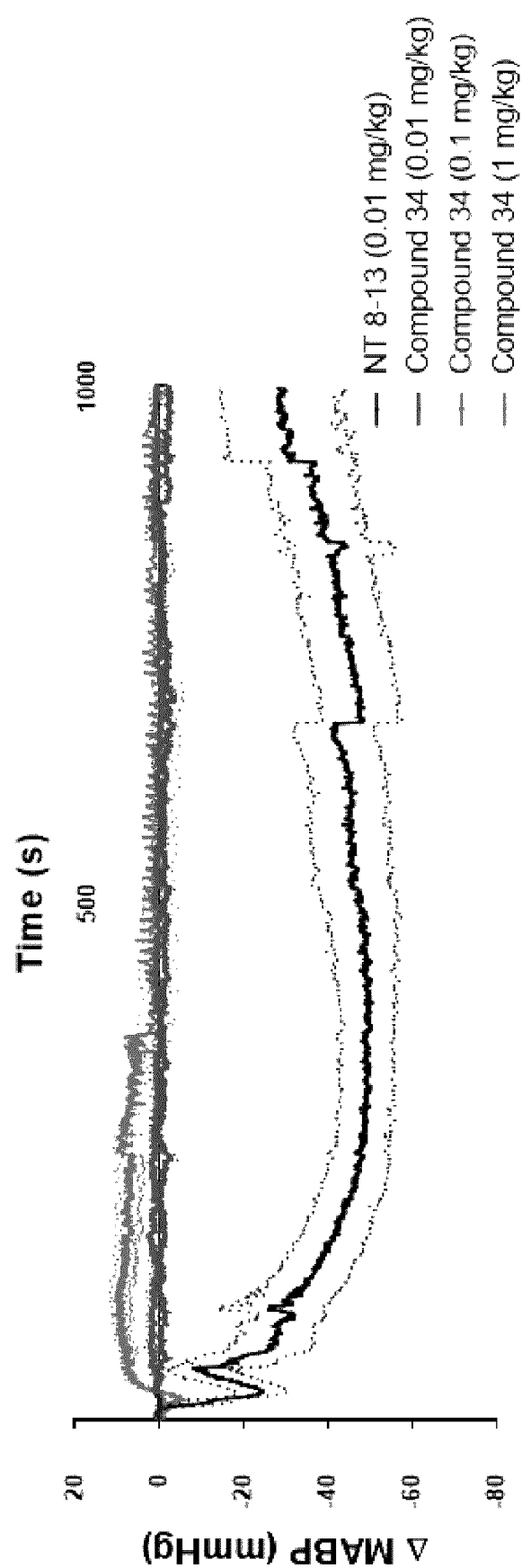
Figure 10B:
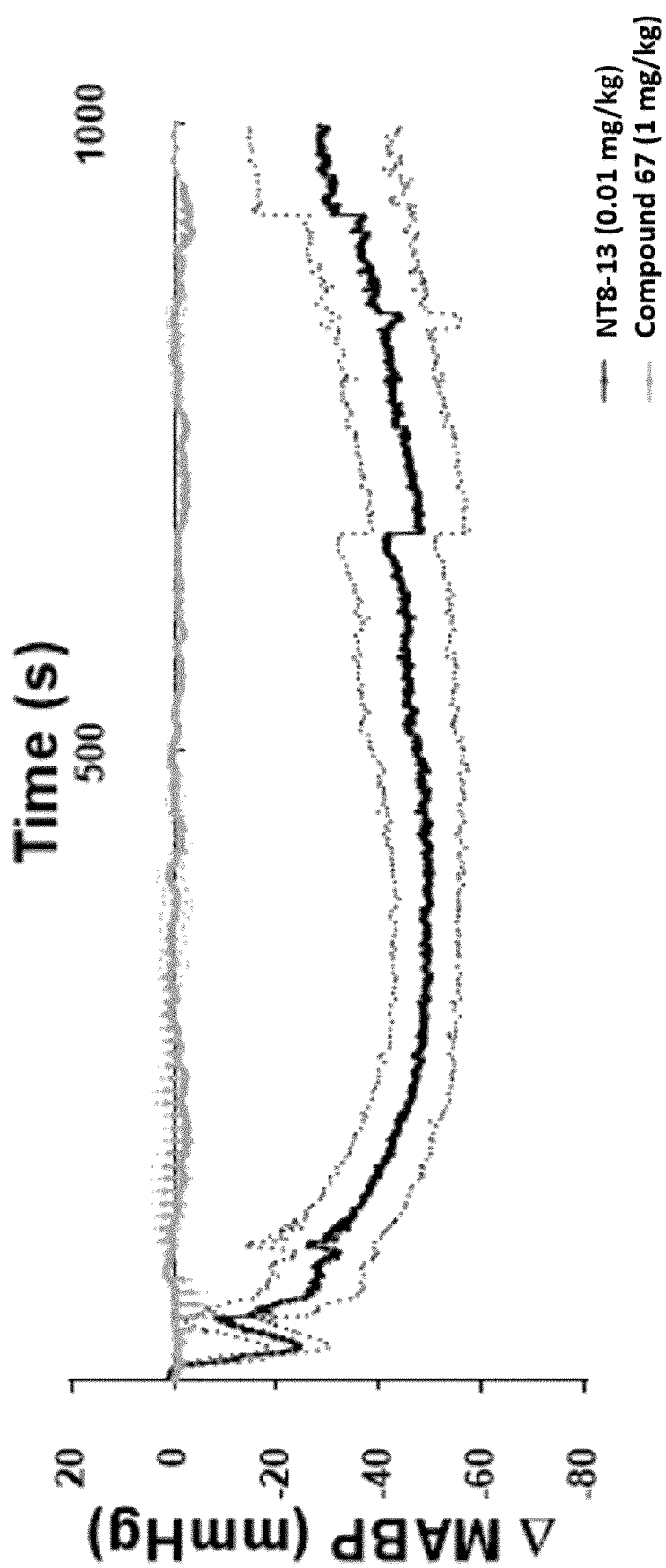

FIGS. 10A-B: Effect of compounds 34 and 67 and Neurotensin 8-13 on blood pressure. Change in mean arterial blood pressure (Δ MABP) was measured continuously every second up to 1000 s following i.v. injection of compounds 34 and 67 at different doses and Neurotensin 8-13 (0.01 mg/kg). n=5-6 rats for each compound. Error bars represent mean±SEM. Neurotensin $IC_{50}$ value was obtained from the resulting dose-response curve.

Figure 11:
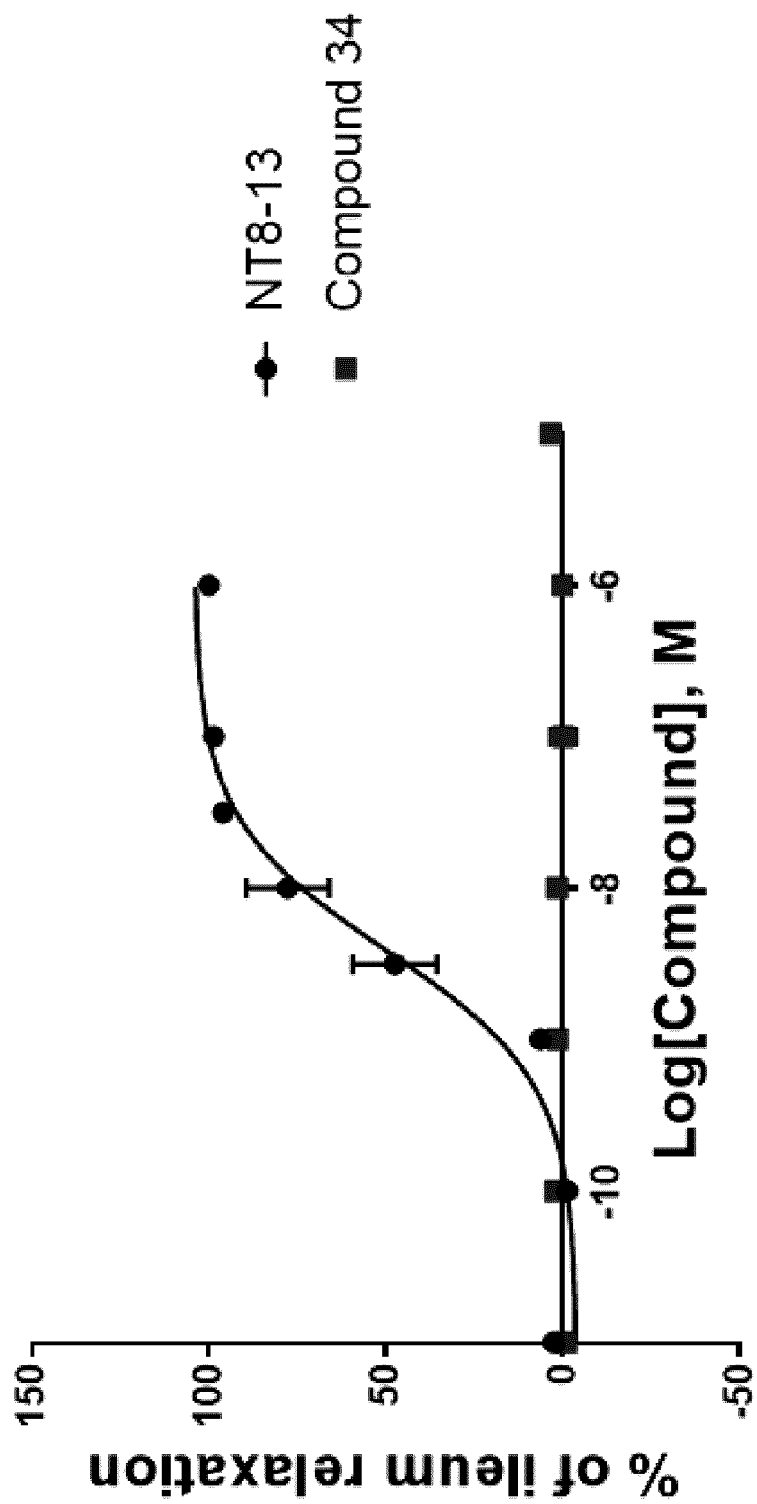

FIG. 11: Effect of compound 34 and Neurotensin 8-13 on ileum relaxation. % of ileum relaxation using Neurotensin 8-13 (NT8-13) at $10^{-11}$ to $10^{-6}$ M and compound 34 at $10^{-11}$ to $10^{-5}$ M. n=4-6 rats for each compound. Nonlinear regression using three parameters was performed for % of ileum relaxation. Neurotensin $IC_{50}$ value was obtained from the resulting dose-response curve. Error bars represent mean±SEM.

DESCRIPTION OF ILLUSTRATIVE EMBODIMENTS

The present disclosure relates to macrocyclic compounds that are specific agonists of the neurotensin 2 (NTS2) receptor. As such, they advantageously do not induce hypothermia, hypotension or ileum relaxation that may arise when NTS1 is activated. It also relates to method of using these compounds or compositions comprising these compounds to prevent or treat pain (e.g., acute or chronic pain).

Compounds of the Present Disclosure

In specific embodiments, macrocyclic compounds of the present disclosure are developed from the cyclization of a synthetic peptide (generally made from natural and/or non-natural amino acids) derived from the 7-13 fragment (RRPYIL) (SEQ ID NO: 1) of the neurotensin peptide (E-L-Y-E-N-K-P-R-R-P-Y-I-L) (SEQ ID NO: 2).

In specific embodiments, the cyclisation of the peptide is a side chain to side chain cyclisation. In specific embodiments, the cyclisation of the synthetic peptide is achieved through a reaction of ring-closing metathesis of alkene (or alkyne) groups at the end of each of the side chains of the N- and a central amino acid (or acid) moieties, the cyclisation resulting in a single carbon-carbon double bond (or single carbon-carbon triple bond if alkyne groups are used). The macrocycle may then further be modified to replace the double bond by a single bond through palladium-catalyzed hydrogenation. (see e.g., compound 47).

In other specific embodiments, the cyclisation of the peptide is achieved through a macrolactamisation reaction between an amine at the end of the side chain of one of the N-terminal amino acids and a carboxylic acid at the end of the side chain of the amino acid residue used to close the cycle (e.g., Xaa4) or the reverse.

In a specific embodiment, compounds of the present disclosure are of formula I, II or III, or are stereoisomers or a mixture thereof, or pharmaceutically acceptable salts, esters or solvates thereof. In case of discrepancies herein between the name and structure presented of compounds or parts thereof, the structure shall prevail when both structures and names are shown.

References herein to amino acids or acids that are part of molecules of the present disclosure should be understood to designate amino acid or acid residues. At least one of their ends is linked to another amino acid or acid to form e.g., a peptide bond thereby losing a hydroxy group and/or one hydrogen of an amine group. Hence, for example, an amino acid or acid listed in any one of the definitions of Xaa1, Xaa2, Xaa3, Xaa4, Xaa5 and Xaa6 should be understood to be the corresponding amino acid or acid residue.

In another specific embodiment, the macrocyclic compound has the following structure: c[Xaa1-Xaa2-Xaa3-Xaa4]-Xaa5-Xaa6 (SEQ ID NO: 3), wherein:

Xaa1 and Xaa4 close the ring and are identical or different and are aliphatic residues, alkenyl residues, acid residues or a natural or non-natural amino acid, a peptoid, or a derivative thereof, these moieties are optionally substituted. In specific embodiments, they are: [L-allylglycine-L-allylglycine], [L-allylglycine-D-allylglycine], [D-allylglycine-L-allylglycine], [D-allylglycine-D-allylglycine], [reduced allylglycine-allylglycine](allylglycines being reduced after the reaction) [L-alphamethyl (4-pentenyl)glycine-L-allylglycine], [D-alphamethyl (4-pentenyl)glycine-L-allylglycine], [L-allylglycine-L-alphamethyl (4-pentenyl)glycine], [L-allylglycine-D-alphamethyl (4-pentenyl)glycine], [L-alphamethyl (4-pentenyl)glycine-D-alphamethyl (4-pentenyl)glycine], [4-pentenoyl-L-allylglycine], [Dap-aspartate], [Dab-aspartate], [ornithine-aspartate], [lysine-aspartate], [Dap-glutamate], [Dab-glutamate], [ornithine-glutamate], [lysine-glutamate], [aspartate-Dap], [aspartate-Dab], [aspartate-ornithine], [aspartate-lysine], [glutamate-Dap], [glutamate-Dab], [glutamate-ornithine], [glutamate-lysine], [L-AllylGly-L-G(alpha-Me-(4-pentenyl))]; [L-Cys-L-Cys]; [L-Cys-L-penicillamine]; [L-Pentenoyl-L-AllylGly]; [L-Pentenoyl-L-AllylGly]; [L-Pentenoyl-L-G(alpha-Me-(4-pentenyl))]; [L-penicillamine-L-Cys]; and [L-penicillamine-L-penicillamine]. In specific embodiments, the pair Xaa1-Xaa2 can alternatively comprise one or two peptoids of any of the foregoing natural or non-natural amino acids, or derivative thereof. These natural or non-natural amino acids, peptoids or derivative thereof being optionally substituted. In all the foregoing combinations of two residues, they may be in the L, L; L-D; D, L; or D; D configurations. In specific embodiments, Xaa4 and Xaa1 are linked through their lateral chains. In specific embodiments, when Xaa1 is an amino acid, its N-terminal is linked to one or more additional amino acids that do not form part of the ring. Without being so limited, the macrocyclic compound has the following structure: (Xaa)r-c[Xaa1-Xaa2-Xaa3-Xaa4]-Xaa5-Xaa6, wherein r is 0, 1, 2 or 3.

Xaa2 is a natural or non-natural amino acid or a derivative thereof, these moieties are optionally substituted. In specific embodiments, it is a glycine(—(CH$_2$)p-(C3-C8)heteroaryl), glycine(—(CH$_2$)p-(C3-C8)aryl), glycine(—(CH$_2$)p-(C3-C8)heterocycloalkyl), glycine(—(CH$_2$)p-(C3-C8)cycloalkyl), glycine(-C1-C8 aminoalkyl), glycine(C1-C8 alkyl), or glycine(-C1-C8 alkyl-C(=O)OH), wherein p is 1 to 5. In other specific embodiments, it is a citrulline, arginine, histidine, lysine, ornithine, diaminobutyric acid (Dab), diaminopropionic acid (Dap), L-norleucine (Nle), norvaline (Nva), glycine, glutamate, homolysine, or a peptoid of any of the foregoing amino acids or a derivative thereof, this natural or non-natural amino acid, peptoid or derivative thereof being optionally substituted; and is more specifically alysine, ornithine, diaminobutyric acid (Dab), diaminopropionic acid (Dap), L-lysine, histidine, norleucine (Nle), norvaline (Nva), glycine, glutamate, or a derivative thereof, this natural or non-natural amino acid or derivative thereof being optionally substituted;

Xaa3 is a natural or non-natural amino acid or a derivative thereof, these moieties are optionally substituted. In specific embodiments, it is a glycine(—(CH$_2$)p'—(C3-C8)heteroaryl), glycine(—(CH$_2$)p'—(C3-C8)aryl), glycine(—(CH$_2$)p'—(C3-C8)heterocycloalkyl), glycine(—(CH$_2$)p'—(C3-C8)cycloalkyl), glycine(-C1-C8 aminoalkyl), glycine (C1-C8 alkyl), or glycine(-C1-C8 alkyl-C(=O)OH), wherein p' is 1 to 5. In specific embodiments, it is a citrulline, arginine, ornithine, diaminobutyric acid (Dab), diaminopropionic acid (Dap), lysine, histidine, norleucine, norvaline, glycine, glutamate, homolysine, or a peptoid of any of the foregoing amino acids, or a derivative thereof, this natural or non-natural amino acid, peptoid or derivative thereof being optionally substituted. In specific embodiments it is a lysine, ornithine, diaminobutyric acid (Dab), diaminopropionic acid (Dap), D-lysine, histidine, norleucine, norvaline, glycine, glutamate, or a derivative thereof, this natural or non-natural amino acid or derivative thereof being optionally substituted;

Xaa5 is a natural or non-natural amino acid or a derivative thereof, these moieties are optionally substituted. In specific embodiments, it is a glycine(—(CH$_2$)q-(C3-C8)heteroaryl), glycine(—(CH$_2$)q-(C3-C8)aryl), glycine(—(CH$_2$)q-(C3-C8)heterocycloalkyl), glycine(—(CH$_2$)q-(C3-C8)cycloalkyl), glycine(-C1-C8 aminoalkyl), glycine(C1-C8 alkyl), or glycine(-C1-C8 alkyl-C(=O)OH), wherein q is 1 to 5. In more specific embodiments, it is a glycine(thienyl), alanine (thienyl), glycine(thiazole), alanine(thiazole), glycine(pyridin), alanine(pyridin), glycine(quinoline), alanine(quinoline), serine (O-benzyl), Tyr(0-acetyl), tryptophan, lysine, D-tyrosine, m-tyrosine, D-tryptophan, alanine (furyl), phenylalanine (4-amino), phenylalanine (4-nitro), phenylalanine (2,3,4,5,6-trifluoro), phenylalanine (4-methyl), D-lysine, tyrosine-methyl, phenylalanine, phenylalanine (4-fluoro), phenylalanine (4-iodo), phenylalanine (4-Tbu), phenylalanine (4-CF3), naphthyl alanine, phenylalanine (3-chloro), phenylalanine (4-chloro), phenylalanine (3-bromo), phenylalanine (4-bromo), phenylalanine (3-iodo), phenylalanine (4-cyano), or a peptoid of any of the foregoing amino acids, or a derivative thereof, this natural or non-natural amino acid, peptoid or derivative thereof being optionally substituted. It is more preferably a tyrosine, Tyr(0-acetyl), tryptophan, lysine, D-tyrosine, m-tyrosine, D-tryptophan, D-lysine, tyrosine-O-methyl, phenylalanine, phenylalanine (4-fluoro), phenylalanine (4-iodo), phenylalanine (4-Tbu), phenylalanine (4-CF3), naphthyl alanine, phenylalanine (3-chloro), phenylalanine (4-chloro), phenylalanine (3-bromo), phenylalanine (4-bromo), phenylalanine (3-iodo), phenylalanine (4-cyano), or a derivative thereof, this natural or non-natural amino acid or derivative thereof being optionally substituted; More preferably is an aromatic amino acid exemplified by a tyrosine, Tyr(0-acetyl), tryptophan, lysine, D-tyrosine, m-tyrosine, D-tryptophan, tyrosine-methyl, phenylalanine, phenylalanine (4-fluoro), phenylalanine (4-iodo), phenylalanine (4-Tbu), phenylalanine (4-CF3), naphthylalanine, phenylalanine (3-chloro), phenylalanine (4-chloro), phenylalanine (3-bromo) phenylalanine, (4-bromo), phenylalanine (3-iodo), phenylalanine (4-cyano), 4-bromophenylalanine; homotyrosine; 4-hydroxyphenylglycine; alanine; anthracenealanine; benzocyclopentyl; biphenylalanine; cyclobutyl alanine; cyclopentyl alanine; cyclopropyl alanine; dihydroindolyl glycine; diphenylalanine; indolyl alanine; 2-thienylalanine; octahydroindol glycine; styrylalanine; benzoylphenylalanine; pyridyl alanine; Tic glycine, or a derivative thereof, this natural or non-natural amino acid or derivative thereof being optionally substituted;

Xaa6 is a natural or non-natural amino acid or a derivative thereof, these moieties are optionally substituted. It can also represent more than 1 amino acids (e.g., 2, 3 or 4 amino acids). In specific embodiments, it is a glycine(—(CH$_2$)q'—(C3-C8)heteroaryl), glycine(—(CH$_2$)q'—(C3-C8)aryl), glycine(—(CH$_2$)q'—(C3-C8)heterocycloalkyl), glycine(—(CH$_2$)q'—(C3-C8)cycloalkyl), glycine(-C1-C8 aminoalkyl), glycine(C1-C8 alkyl), or glycine(-C1-C8 alkyl-C(=O)OH), wherein q' is 1 to 5. In specific embodiments, it is a natural or non-natural amino acid, peptoid or derivative thereof having a single substituent attached to its beta carbon (see e.g., compounds 15-21, 28-29, 31-32, 34, 38-49, 51-70, 72-170). In a specific embodiment, it is a natural or non-natural amino acid, peptoid or derivative thereof that does not have 2 (or 3) substituents attached to its beta carbon. In other embodiments, it is a natural or non-natural amino acid, peptoid or derivative thereof having multiple substituents (at least 2) attached to its gamma carbon (see e.g., compounds 15-21, 28-29, 31-32, 34, 38-49, 51-70, 72-170). In more specific embodiments, it is an allo-isoleucine, a leucine, tert-leucine, norleucine, norvaline, valine, D-leucine, neopentylglycine, cyclohexylglycine, cyclohexylalanine, phenyl, tyrosine-O-methyl, phenylalanine (2,4,5-trifluoro), homo-cyclohexylalanine, cyclopropyl alanine, cyclobutyl alamine, cyclopentyl alanine, cycloheptyl alanine, or a peptoid of any of the foregoing amino acid or a derivative thereof, this natural or non-natural amino acid, peptoid or derivative thereof being optionally substituted or a derivative thereof, this natural or non-natural amino acid or derivative thereof being optionally substituted; and is more preferably a leucine, tert-leucine, norleucine, norvaline, valine, D-leucine, neopentylglycine, cyclohexylglycine, cyclohexylalanine, phenyl, tyrosine-O-methyl, 2,4,5-trifluoro-phenyl, homo-cyclohexylalanine, cyclopropyl alanine, cyclobutyl alamine, cyclopentyl alanine, cycloheptyl alanine, or a derivative thereof, this natural or non-natural amino acid or derivative thereof being optionally substituted; and In a specific embodiment, one of the end terminal non-natural amino acid residue used for closing the cycle (e.g., Xaa1—corresponding to position 7 in neurotensin) is, before ring-closure, an alkenyl-glycine (e.g., Xaa1 is a vinyl-glycine, Xaa1 is allyl-glycine (e.g., compounds 34, 40-42, 91 and 92); or alpha methyl (4-pentenyl)-glycine (e.g., compounds 89, 90 and 93)) and the other end (e.g., Xaa4) is, before ring-closure, an alkenyl residue (e.g., Xaa4 is a vinyl-glycine, allyl-glycine (e.g., compounds 34, 40-42, 89 and 90); or alpha methyl (4-pentenyl)-glycine (e.g., compounds 91-93), an acid residue or a non-natural amino acid residue, this alkenyl, acid or amino acid residue comprising an alkene moiety at its end (end of its lateral chain in the case of an amino acid residue). After closure, the double bonds (alkenes) of each moiety have merged into a single carbon-carbon double bond using, for example, a ring-closing metathesis reaction.

In other embodiments, one of the end terminal (natural or non-natural) amino acid residue used for closing the cycle (e.g., Xaa1 corresponding to position 7 in neurotensin or Xaa4 corresponding to position 10 in neurotensin) is, before ring-closure, an (natural or non-natural) amino acid having an amine on its lateral chain, and the other end terminal (e.g., Xaa4 corresponding to position 10 in neurotensin or Xaa1 corresponding to position 7 in neurotensin) is, before ring-closure, an (natural or non-natural) amino acid having a carboxylic acid on its lateral chain, so that the amine and the carboxylic acid react to form an amide through a macrolactamisation. More specifically, one of the end terminal (natural or non-natural) amino acid residue can be before ring-closure Dap (e.g., Xaa1 in compounds 94 and 98; and Xaa4 in compounds 102 and 103); Dab (e.g., Xaa1 in compounds 95 and 99; and Xaa4 in compounds 104 and 105); ornithine (e.g., Xaa1 in compounds 96 and 100; and Xaa4 in compounds 106 and 107); lysine (e.g., Xaa1 in compounds 97 and 101; and Xaa4 in compounds 108 and 109); and the other end terminal (natural or non-natural) amino acid residue can be before ring-closure aspartic acid (e.g., Xaa4 in compounds 94-97 and Xaa1 in compounds 103, 105, 107 and 109; or glutamic acid (e.g., Xaa4 in compounds 98-101 and Xaa1 in compounds 102, 104, 106 and 108. After closure, the lateral chain carboxylic acid, activated by a coupling agent, has reacted with the amino group of the lateral chain of the other residue to form a peptide bond using, for example, a macrolactamisation reaction.

In other embodiments, Xaa1 is, before ring-closure, an acid residue with an aliphatic tail of 4 to 11 carbon atoms comprising a terminal alkene (e.g., nonenoic acid residue) or an acid residue with an amino alkyl chain substituted with a terminal alkene (e.g., aminohex-6-enoic acid residue; a non-natural amino acid having an alkyl chain comprising a terminal alkene (e.g., an alpha-methyl-octenyl-alanine residue) or a non-natural amino acid having an amino alkyl chain comprising a terminal alkene (e.g., an N-allyl ornithine residue), an N-allyl Dab (diaminobutyric acid) residue, an N-butenyl Dab residue, an N-pentenyl Dap (diaminopropionic acid) residue, an N-allyl-lysine residue (N-allyl-L-lysine; or N-allyl-D-lysine), an N-butenyl-lysine residue or an N-pentenyl-lysine residue. Xaa1 may further be substituted e.g., on the endocyclic amine.

As used herein, the term "substituted" in reference to above listed natural or unnatural amino acid or acid residues in the c[Xaa1-Xaa2-Xaa3-Xaa4]-Xaa5-Xaa6 structure refers to a substitution by an halogen (e.g., Cl, F, Br, I), alkyl, aryl, arylalkyl, cycloalkyl, heteroaryl, heteroarylalkyl, heterocycloalkyl, aminoalkyl, aminoaryl, aminoarylalkyl, aminocycloalkyl, aminoheteroaryl, aminoheteroarylalkyl, or amino heterocycloalkyl.

In specific embodiments, the compounds of the present disclosure comprise the sequence of amino acid residues Xaa1-Xaa2-Xaa3-Xaa4-Xaa5-L (SEQ ID NO: 4), Xaa1-Xaa2-Xaa3-Xaa4-Y-Xaa6 (SEQ ID NO: 5), Xaa1-Xaa2-Xaa3-G-Xaa5-Xaa6 (SEQ ID NO: 6), Xaa1-Xaa2-K-Xaa4-Xaa5-Xaa6 (SEQ ID NO: 7), Xaa1-K-Xaa3-Xaa4-Xaa5-Xaa6 (SEQ ID NO: 8), or G-Xaa2-Xaa3-Xaa4-Xaa5-Xaa6 (SEQ ID NO: 9), wherein Xaa1, Xaa2, Xaa3, Xaa4, Xaa5 and Xaa6, are as defined above. In specific embodiments, the compounds of the present disclosure comprise the sequence of amino acid residues Xaa1-K-K-Xaa4-Y-L (SEQ ID NO: 10), Xaa1-Xaa2-K-Xaa4-Y-L (SEQ ID NO: 11), Xaa1-K-Xaa3-Xaa4-Y-L (SEQ ID NO: 12), Xaa1-K-K-Xaa4-Xaa5-L (SEQ ID NO: 13), Xaa1-K-K-Xaa4-Y-Xaa6 (SEQ ID NO: 14), wherein Xaa1, Xaa2, Xaa3, Xaa4, Xaa5 and Xaa6, are as defined above. In specific embodiments Xaa1 and Xaa4 comprise alkenes on their lateral chains. In other embodiments, Xaa1 and Xaa4 comprise respectively carboxylic acid or an amine on their lateral chains or vice versa. In other specific embodiments, the compounds of the present disclosure comprise the sequence of amino acid residues G-K-K-G-Y-L (SEQ ID NO: 15), Xaa1-K-K-G-Y-L (SEQ ID NO: 16), G-Xaa2-K-G-Y-L (SEQ ID NO: 17), G-K-Xaa3-G-Y-L (SEQ ID NO: 18), G-K-K-Xaa4-Y-L (SEQ ID NO: 19), G-K-K-G-Xaa5-L (SEQ ID NO: 20), G-K-K-G-Y-Xaa6 (SEQ ID NO: 21), wherein Xaa1, Xaa2, Xaa3, Xaa4, Xaa5 and Xaa6, are as defined above. In other specific embodiments, the compounds of the present disclosure comprise the sequence of amino acid residues G(Alkene)-K-K-G(Alkene)-Y-L (SEQ ID NO: 22), Xaa1-K-K-G(Alkene)-Y-L (SEQ ID NO: 23), G(Alkene)-Xaa2-K-G(alkene)-Y-L (SEQ ID NO: 24), G(Alkene)-K-Xaa3-G(Alkene)-Y-L (SEQ ID NO: 25), G(Alkene)-K-K-Xaa4-Y-L (SEQ ID NO: 26), -G(Alkene)-K-K-G(Alkene)-Xaa5-L (SEQ ID NO: 27), G(Alkene)-K-K-G(Alkene)-Y-Xaa6 (SEQ ID NO: 28), wherein Xaa1, Xaa2, Xaa3, Xaa4, Xaa5 and Xaa6, are as defined above. In other specific embodiments, the compounds of the present disclosure comprise any of the structures of Table I or a derivative of any of the foregoing comprising one or more substituents (e.g., on amino acid residues). In these certain compounds, the alkenes on the lateral chains of Xaa1 and Xaa4 share their double bond. In other compounds, the carboxylic acid (e.g., glutamate or aspartate) on the lateral chain of Xaa1 or Xaa4 form a peptide bond with the amine on the lateral chain of on the other one of Xaa1 and Xaa4 (e.g., lysine, ornithine, Dab or Dap).

In specific embodiments, the size of the macrocycle can be of 14 to 18-ring atoms, preferably 13-20-ring atoms. In specific embodiments, the size of the macrocycle can be of 14- to 18-ring atoms. In specific embodiments, the macrocycle size is of 13 ring atoms, 14 ring atoms (e.g., compounds 13-17, 21, 27-34, 38-49, 51-55, 57-88, 84, 103), 15 ring atoms (e.g., compounds 95, 98, 102, 105), 16 ring atoms (e.g., compound 89-92, 96, 99, 104, 107), 17 ring atoms (e.g., compounds 97, 100, 106, 109), 18 ring atoms (e.g., compounds 93, 101, 108), 19 ring atoms or 20 ring atoms.

In all the foregoing compounds, the residues (e.g., Xaa1 to Xaa6) may be in L or D configurations.

Compounds of the present invention are preferably selective NTS2 ligand As used herein the term "selective NTS2 ligand" or "selective for NTS2" is meant to convey that the ratio of the IC50 for NTS1: IC50 for NTS2 required to inhibit the NTS2 is more than 1; or 2 or more; 3 or more; 4 or more; 5 or more; 6 or more; 7 or more; 8 or more; 9 or more; 10 or more; 11 or more; 12 or more; 13 or more; 14 or more; 15 or more; 20 or more; 25 or more; 30 or more; 35 or more; 40 or more; 45 or more; 50 or more; 55 or more; 60 or more; 65 or more; 70 or more; 75 or more; 80 or more; 85 or more; 90 or more; 55 or more; and preferably 100 or more; 110 or more; 120 or more; 130 or more; 140 or more; 150 or more; 160 or more; 170 or more; 180 or more; 190 or more; 200 or more; 220 or more; 230 or more; 240 or more; 250 or more; 260 or more; 270 or more; 280 or more; 290 or more; more preferably 300 or more; 350 or more; 400 or more; 450 or more; 500 or more; 550 or more; 600 or more; 650 or more; 700 or more; 750 or more; 800 or more; 850 or more; 900 or more; even more preferably 1000 or more; 1500 or more; 2000 or more; 2500 or more; 3000 or more; 3500 or more; 4000 or more; 4500 or more; 5000 or more; 5500 or more; 6000 or more; 6500 or more; 7000 or more; 7500 or more; 8000 or more; 8500 or more; 9000 or more; 9500 or more; even more preferably 10000 or more; 20000 or more; or 30000 or more. Without being so limited, the selectivity of compounds in accordance with the present invention is provided in Table III.

Chemical Groups

As used herein, the term "alkyl" refers to a monovalent straight or branched chain, saturated or unsaturated aliphatic hydrocarbon radical having a number of carbon atoms in the specified range. Thus, for example, "(C1-12)alkyl" (or "C1-12 alkyl") refers to any alkyl of up to 12 carbon atom, including of the hexyl alkyl and pentyl alkyl isomers as well as n-, iso-, sec- and t-butyl, n- and iso-propyl, ethyl, and methyl. As another example, "(C1-4)alkyl" refers to n-, iso-, sec- and t-butyl, n- and isopropyl, ethyl, and methyl. As another example, "C1-3 alkyl" refers to n-propyl, isopropyl, ethyl, and methyl. Alkyl include unsaturated aliphatic hydrocarbon including alkyne (R—C≡C—R); and/or alkene (R—C=C—R).

The term "halogen" (or "halo") refers to fluorine, chlorine, bromine and iodine (alternatively referred to as fluoro, chloro, bromo, and iodo). The term "haloalkyl" refers to an alkyl group as defined above in which one or more of the hydrogen atoms have been replaced with a halogen (i.e., F, Cl, Br and/or I). Thus, for example, "C1-10 haloalkyl" (or "C1-C6 haloalkyl") refers to a C1 to C10 linear or branched alkyl group as defined above with one or more halogen substituents.

The term "fluoroalkyl" has an analogous meaning except that the halogen substituents are restricted to fluoro. Suitable fluoroalkyls include the series $(CH_2)_0 4CF_3$ (i.e., trifluoromethyl, 2,2,2-trifluoroethyl, 3,3,3-trifluoro-n-propyl, etc.).

The term "heteroalkyl" is given its ordinary meaning in the art and refers to alkyl groups as described herein in which one or more carbon atoms is replaced with a heteroatom (e.g., oxygen, nitrogen, sulfur, or derivatives thereof, and the like). Examples of heteroalkyl groups include, but are not limited to, alkoxy, alkyl-substituted amino, thiol such as methionine side group. Up to two heteroatoms may be consecutive. When a prefix such as $C_{2-6}$ is used to refer to a heteroalkyl group, the number of carbons (2-6, in this example) is meant to include the heteroatoms as well.

The term "aminoalkyl" refers to an alkyl group as defined above in which one or more of the hydrogen or carbon atoms has been replaced with a nitrogen or an amino derivative such as but not limited to guanidine. Thus, for example, "$C_{1-6}$ aminoalkyl" (or "C1-$C_6$ aminoalkyl") refers to a $C_1$ to $C_6$ linear or branched alkyl group as defined above with one or more amino derivatives (e.g., NH, amide, diazirin, azide, etc.).

The term "thioalkyl" refers to an alkyl group as defined above in which one or more of the hydrogen or carbon atoms has been replaced with a sulfur atom or thiol derivative. Thus, for example, "$C_{1-6}$ thioalkyl" (or "$C_1$-$C_6$ thioalkyl") refers to a $C_1$ to $C_6$ linear or branched alkyl group as defined above with one or more sulfur atoms or thiol derivatives (e.g., S, SH, etc.).

Aminoalkyl and thioalkyls are specific embodiments of and encompassed by the term "heteroalkyl" or substituted alkyl depending on the heteroatom replaces a carbon atom or an hydrogen atom.

The term "cycloalkyl" refers to saturated alicyclic hydrocarbon consisting of saturated 3-8 membered rings optionally fused with additional (1-3) aliphatic (cycloalkyl) or aromatic ring systems, each additional ring consisting of a 3-8 membered ring. It includes without being so limited cyclopropyl (e.g., compounds 65 and 144), cyclobutyl (e.g., compounds 66 and 143), cyclopentyl (e.g., compounds 67, 127-129, 133-135, 137, 142), cyclohexyl (e.g., compounds 30-31, 64) and cycloheptane (e.g., compound 68).

The term "heterocyclyl" refers to (i) a 4- to 7-membered saturated heterocyclic ring containing from 1 to 3 heteroatoms independently selected from N, O and S, or (ii) is a heterobicyclic ring (e.g., benzocyclopentyl, octahydroindol (e.g., compound 166)). Examples of 4- to 7-membered, saturated heterocyclic rings within the scope of this disclosure include, for example, azetidinyl, piperidinyl, morpholinyl, thiomorpholinyl, thiazolidinyl, isothiazolidinyl, oxazolidinyl, isoxazolidinyl, pyrrolidinyl, pyridine, imidazolidinyl, piperazinyl, tetrahydrofuranyl, tetrahydrothienyl, pyrazolidinyl, hexahydropyrimidinyl, thiazinanyl, thiazepanyl, azepanyl, diazepanyl, tetrahydropyranyl, tetrahydrothiopyranyl, and dioxanyl. Examples of 4- to 7-membered, unsaturated heterocyclic rings within the scope of this disclosure include mono-unsaturated heterocyclic rings corresponding to the saturated heterocyclic rings listed in the preceding sentence in which a single bond is replaced with a double bond (e.g., a carbon-carbon single bond is replaced with a carbon-carbon double bond).

The term "C(O)" refers to carbonyl. The terms "$S(O)_2$" and "$SO_2$" each refer to sulfonyl. The term "S(O)" refers to sulfinyl.

The term "aryl" refers to aromatic (unsaturated) compounds consisting of 3-8 membered rings, optionally fused with additional (1-3) aliphatic (cycloalkyl) or aromatic ring systems, each additional ring consisting of 3-8 membered ring (such as anthracene (e.g., compound 162), indane (e.g., compound 164), Tic (e.g., compound 163, 167), 3-benzothienylalanine (e.g., compound 168), dihydroindol (e.g., compound 170)). In a specific embodiment, it refers to phenyl (e.g., compounds 32, 62, 63, 34, 15, 21, 39, 75-78, 110-111, 113-118, 121-137, 139-141, 145-155, 157-158, 160-161), benzocyclopentyl, or naphthyl (e.g., compound 112). The term "heteroaryl" refers to (i) a 3-, 4-, 5-, 6-, 7- or 8-membered heteroaromatic ring (more specifically 3-7 or 3-6 membered ring) containing from 1 to 4 heteroatoms independently selected from N, O and S, such as thiophenyl (e.g., compound 159), thienyl (e.g., compound 168) pyridine (e.g., compounds 165, 169), or (ii) is a heterobicyclic ring selected from indolyl (e.g., compounds 43, 166, 168, 170), quinolinyl, isoquinolinyl, Tic (e.g., compounds 163, 167), dihydroindolylglycine (e.g., compound 170) and quinoxalinyl. Suitable 3-, 4-, 5- and 6-membered heteroaromatic rings include, for example, diazirin, pyridyl (also referred to as pyridinyl), pyrrolyl, diazine (e.g., pyrazinyl, pyrimidinyl, pyridazinyl), triazinyl, thienyl, furanyl, imidazolyl (e.g., compounds 55, 83-84), pyrazolyl, triazolyl (e.g., 1, 2, 3 triazolyl), tetrazolyl (e.g., 1, 2, 3, 4 tetrazolyl), oxazolyl, iso-oxazolyl, oxadiazolyl, oxatriazolyl, thiazolyl, isothiazolyl, and thiadiazolyl. Heteroaryls of particular interest are pyrrolyl, imidazolyl, pyridyl, pyrazinyl, quinolinyl (or quinolyl), isoquinolinyl (or isoquinolyl), and quinoxalinyl. Suitable heterobicyclic rings include indolyl.

The term "aralkyl" and more specifically "(C4-C14)aralkyl" or "C4-14 aralkyl" refers herein to compounds comprising a 3-7 ring-member aryl substituted by a 1 to 7 alkyl. In specific embodiments, it refers to a benzyl or a phenetyl.

As used herein, and unless otherwise specified, the terms "alkyl", "haloalkyl", "aminoalkyl", "cycloalkyl", "heterocyclyl", "aryl", "heteroalkyl" and "heteroaryl" and the terms designating their specific embodiments (e.g., butyl, fluoropropyl, aminobutyl, cyclopropane, morpholine, phenyl, pyrazole, etc.) encompass the substituted (i.e. in the case of haloalkyl and aminoalkyl, in addition to their halogen and nitrogen substituents, respectively) and unsubstituted embodiments of these groups. Hence for example, the term "phenyl" encompasses unsubstituted phenyl as well as fluorophenyl, hydroxyphenyl, methylsulfonyl phenyl (or biphenyl), diphenyl, trifluoromethyl-diazirin-phenyl, isopropylphenyl, trifluorohydroxy-phenyl. Similarly, the term pyrazole, encompass unsubstituted pyrazole as well as methylpyrazole. The one or more substituents may be an amine, halogen, hydroxyl, C1-6 aminoalkyl, C1-6 heteroalkyl, C1-6 alkyl, C3-8 cycloalkyl, C1-6 haloalkyl, aryl, heteroaryl and heterocyclyl groups (etc.).

It is understood that the specific rings listed above are not a limitation on the rings which can be used in the present disclosure. These rings are merely representative.

Unless expressly stated to the contrary in a particular context, any of the various cyclic rings and ring systems described herein may be attached to the rest of the compound at any ring atom (i.e., any carbon atom or any heteroatom) provided that a stable compound results therefrom.

Isomers, tautomers and polymorphs

As used herein, the term "isomers" refers to stereoisomers including optical isomers (enantiomers), diastereoisomers as well as the other known types of isomers.

The compounds of the disclosure have at least 5 asymmetric carbon atoms and can therefore exist in the form of optically pure enantiomers (optical isomers), and as mixtures thereof (racemates). The compounds have at least five asymmetric carbon atoms and can therefore exist in the form of pure diastereoisomers and as mixtures thereof. It is to be understood, that, unless otherwise specified, the present disclosure embraces the racemates, the enantiomers and/or the diastereoisomers of the compounds of the disclosure as well as mixtures thereof. For example, the compounds 40, 41 and 42 of the present disclosure are diastereoisomers; the compounds 89 and 90 of the present disclosure are diastereoisomers; the compounds 91 and 92 of the present disclosure are diastereoisomers; compounds 34 and 38, compounds 16 and 43, compounds 17 and 48, compounds 34 and 21, compounds 83 and 84, etc.

For further clarity, (S)—H or (S)—CH$_3$ indicates that the stereogenic center bearing the H or CH$_3$ substituent is of (S) stereochemistry.

In addition, the present disclosure embraces all geometric isomers. For example, when a compound of the disclosure incorporates a double bond or a fused ring, both the cis- and trans-forms, as well as mixtures, are embraced within the scope of the disclosure.

Within the present disclosure, it is to be understood that a compound of the disclosure may exhibit the phenomenon of tautomerism and that the formula drawings within this specification can represent only one of the possible tautomeric forms. It is to be understood that the disclosure encompasses any tautomeric form and is not to be limited merely to any one tautomeric form utilized within the formula drawings.

It is also to be understood that certain compounds of the disclosure may exhibit polymorphism, and that the present disclosure encompasses all such forms.

Salts

The present disclosure relates to the compounds of the disclosure as hereinbefore defined as well as to salts thereof. The term "salt(s)", as employed herein, denotes basic salts formed with inorganic and/or organic bases. Salts for use in pharmaceutical compositions will be pharmaceutically acceptable salts, but other salts may be useful in the production of the compounds of the disclosure. The term "pharmaceutically acceptable salts" refers to salts of compounds of the present disclosure that are pharmacologically acceptable and substantially non-toxic to the subject to which they are administered. More specifically, these salts retain the biological effectiveness and properties of the anti-atherosclerosis compounds of the disclosure and are formed from suitable non-toxic organic or inorganic acids or bases.

For example, where the compounds of the disclosure are sufficiently acidic, the salts of the disclosure include base salts formed with an inorganic or organic base. Such salts include alkali metal salts such as sodium, lithium, and potassium salts; alkaline earth metal salts such as calcium and magnesium salts; metal salts such as aluminum salts, iron salts, zinc salts, copper salts, nickel salts and a cobalt salts; inorganic amine salts such as ammonium or substituted ammonium salts, such as e.g., trimethylammonium salts; and salts with organic bases (for example, organic amines) such as chloroprocaine salts, dibenzylamine salts, dicyclohexylamine salts, dicyclohexylamines, diethanolamine salts, ethylamine salts (including diethylamine salts and triethylamine salts), ethylenediamine salts, glucosamine salts, guanidine salts, methylamine salts (including dimethylamine salts and trimethylamine salts), morpholine salts, morpholine salts, N,N'-dibenzylethylenediamine salts, N-benzyl-phenethylamine salts, N-methylglucamine salts, phenylglycine alkyl ester salts, piperazine salts, piperidine salts, procaine salts, t-butyl amines salts, tetramethylammonium salts, t-octylamine salts, tris-(2-hydroxyethyl) amine salts, and tris(hydroxymethyl)aminomethane salts. Preferred salts include those formed with sodium, lithium, potassium, calcium and magnesium.

Such salts can be formed routinely by those skilled in the art using standard techniques. Indeed, the chemical modification of a pharmaceutical compound (i.e. drug) into a salt is a technique well known to pharmaceutical chemists, (See, e.g., H. Ansel et. al., Pharmaceutical Dosage Forms and Drug Delivery Systems (6th Ed. 1995) at pp. 196 and 1456-1457, incorporated herein by reference). Salts of the compounds of the disclosure may be formed, for example, by reacting a compound of the disclosure with an amount of acid or base, such as an equivalent amount, in a medium such as one in which the salt precipitates or in an aqueous medium followed by lyophilization.

Esters

The present disclosure relates to the compounds of the disclosure as hereinbefore defined as well as to the esters thereof. The term "ester(s)", as employed herein, refers to compounds of the disclosure or salts thereof in which a carboxylic acid has been hydroxy groups have been converted to the corresponding esters using an alcohol and a coupling reagent. Esters for use in pharmaceutical compositions will be pharmaceutically acceptable esters, but other esters may be useful in the production of the compounds of the disclosure.

The term "pharmaceutically acceptable esters" refers to esters of the compounds of the present disclosure that are pharmacologically acceptable and substantially non-toxic to the subject to which they are administered. More specifically, these esters retain the biological effectiveness and properties of the anti-atherosclerosis compounds of the disclosure and act as prodrugs which, when absorbed into the bloodstream of a warm-blooded animal, cleave in such a manner as to produce the parent alcohol compounds.

Esters of the compounds of the present disclosure include among others the following groups (1) carboxylic acid esters obtained by esterification, in which the non-carbonyl moiety of the carboxylic acid portion of the ester grouping is selected from straight or branched chain alkyl (for example, ethyl, n-propyl, t-butyl, n-butyl, methyl, propyl, isopropyl, butyl, isobutyl, or pentyl), n-hexyl, alkoxyalkyl (for example, methoxymethyl, acetoxymethyl, and 2,2-dimethylpropionyloxymethyl), aralkyl (for example, benzyl), aryloxyalkyl (for example, phenoxymethyl), aryl (for example, phenyl optionally substituted with, for example, halogen, C1-4 alkyl, or C1-4 alkoxy, or amino).

Further information concerning examples of and the use of esters for the delivery of pharmaceutical compounds is available in Design of Prodrugs. Bundgaard H ed. (Elsevier, 1985) incorporated herein by reference. See also, H. Ansel et. al., 1995 at pp. 108-109; Krogsgaard-Larsen, 1996 at pp. 152-191; Jarkko Rautio, 2008; and Pen-Wei Hsieh, 2009, all incorporated herein by reference.

The compounds of this disclosure may be esterified by a variety of conventional procedures including the esters are formed from the acid of the molecule by reacting with a coupling agent such as DIC (diisopropyl carbodiimide) and a base, such as NN-dimethylaminopyridine (DMAP), and an alcohol, such as methanol (methyl ester), ethanol, longer chain alcohols or benzyl alcohol (benzyl ester). One skilled in the art would readily know how to successfully carry out these as well as other known methods of esterification of acid.

Esters of the compounds of the disclosure may form salts. Where this is the case, this is achieved by conventional techniques as described above.

Solvates

The compounds of the disclosure may exist in unsolvated as well as solvated forms with solvents such as water, ethanol, and the like, and it is intended that the disclosure embrace both solvated and unsolvated forms.

"Solvate" means a physical association of a compounds of this disclosure with one or more solvent molecules. This physical association involves varying degrees of ionic and covalent bonding, including hydrogen bonding. In certain instances, the solvate will be capable of isolation, for example when one or more solvent molecules are incorporated in the crystal lattice of the crystalline solid. "Solvate" encompasses both solution-phase and isolatable solvates. Solvates for use in pharmaceutical compositions will be pharmaceutically acceptable solvates, but other solvates may be useful in the production of the compounds of the disclosure.

As used herein, the term "pharmaceutically acceptable solvates" means solvates of compounds of the present disclosure that are pharmacologically acceptable and substantially non-toxic to the subject to which they are administered. More specifically, these solvates retain the biological effectiveness and properties of the anti-atherosclerosis compounds of the disclosure and are formed from suitable non-toxic solvents.

Non-limiting examples of suitable solvates include ethanolates, methanolates, and the like, as well as hydrates, which are solvates wherein the solvent molecules are $H_2O$.

Preparation of solvates is generally known. Thus, for example, Caira, 2004, incorporated herein by reference, describe the preparation of the solvates of the antifungal fluconazole in ethyl acetate as well as from water. Similar preparations of solvates, hemisolvate, hydrates and the like are described by van Tonder, 2004; Bingham, 2001, both incorporated herein by reference.

A typical, non-limiting, process for preparing a solvate involves dissolving the inventive compound in desired amounts of the desired solvent (organic or water or mixtures thereof) at a higher than ambient temperature, and cooling the solution at a rate sufficient to form crystals which are then isolated by standard methods. Analytical techniques such as, for example IR spectroscopy, can be used to show the presence of the solvent (or water) in the crystals as a solvate (or hydrate).

Compositions, Combination and Kits
Compositions

The present disclosure also relates to pharmaceutical compositions comprising the above-mentioned compounds of the disclosure or their pharmaceutically acceptable salts, esters and solvates thereof and optionally a pharmaceutically acceptable carrier.

As used herein, the terms "pharmaceutically acceptable" refer to molecular entities and compositions that are physiologically tolerable and do not typically produce an allergic or similar untoward reaction, such as gastric upset, dizziness and the like, when administered to subjects (e.g., humans). Preferably, as used herein, the term "pharmaceutically acceptable" means approved by regulatory agency of the federal or state government or listed in the U.S. Pharmacopeia or other generally recognized pharmacopeia for use in animals, and more particularly in humans.

The term "carrier" refers to a diluent, adjuvant, excipient, or vehicle with which the compounds of the present disclosure may be administered. Sterile water or aqueous saline solutions and aqueous dextrose and glycerol solutions may be employed as carriers, particularly for injectable solutions. Suitable pharmaceutical carriers are described in "Remington's Pharmaceutical Sciences" by E. W. Martin. The pharmaceutical compositions of the present disclosure may also contain excipients/carriers such as preserving agents, solubilizing agents, stabilizing agents, wetting agents, emulsifiers, sweeteners, colorants, odorants, salts for the variation of osmotic pressure, buffers, coating agents or antioxidants.

Any appropriate route of administration may be employed, include parenteral (by injection) and enteral (gastrointestinal route). More specifically, parenteral routes include for example, intravenous, intrathecal, intracerebroventricular, intradermal, transdermal (topical), subcutaneous, intramuscular, intramammary, intracranial, intraorbital, ophthalmic, intraventricular, intracapsular, intraarticular, intraspinal, intracisternal, and intraperitoneal; Enteral include oral, intranasal, sublingual, transmucosal or rectal administration.

Without being so limited, when the compound/pharmaceutical compositions of the disclosure is administered orally, it may take the form of tablets, coated tablets, dragees, hard or soft gelatin capsules, solutions, emulsions or suspensions for example; rectally using for example of suppositories; locally, topically, or percutaneously, for example using ointments, creams, gels or solutions; or parenterally, e.g., intravenously, intramuscularly, subcutaneously, intrathecally or transdermally, using for example injectable solutions. Furthermore, administration can be carried out sublingually, nasally, or as ophthalmological preparations or an aerosol, for example in the form of a spray, such as a nasal spray.

The compounds of the disclosure may be incorporated into dosage forms in conjunction with any of the vehicles which are commonly employed in pharmaceutical preparations. Methods for preparing appropriate formulations are well known in the art (see e.g., Remington's Pharmaceutical Sciences, 16th Ed., 1980, A. Oslo Ed., Easton, Pa. incorporated herein by reference). Common pharmaceutically acceptable carriers include, without limitation, sterile aqueous or non-aqueous solutions, suspensions, and emulsions. Examples of non-aqueous solvents include, without limitation, propylene glycol, polyethylene glycol, vegetable oils, and injectable organic esters. Aqueous carriers include, without limitation, water, alcohol, saline, and buffered solutions. Pharmaceutically acceptable carriers also can include physiologically acceptable aqueous vehicles (e.g., physiological saline) or other known carriers appropriate to specific routes of administration.

For the preparation of tablets, coated tablets, dragees or hard gelatin capsules, the compounds of the present disclosure may be admixed with any known pharmaceutically inert, inorganic or organic excipient and/or carrier. Examples of suitable excipients/carriers include lactose, maize starch or derivatives thereof, talc or stearic acid or salts thereof. Suitable excipients for use with soft gelatin capsules include for example vegetable oils, waxes, fats, semi-solid or liquid polyols etc. According to the nature of the active ingredients it may however be the case that no excipient is needed at all for soft gelatin capsules. For the preparation of solutions and syrups, excipients which may be used include for example water, polyols, saccharose, invert sugar and glucose.

For suppositories, and local or percutaneous application, excipients which may be used include for example natural or hardened oils, waxes, fats and semi-solid or liquid polyols.

In cases where parenteral administration is elected as the route of administration, preparations containing the compounds of the disclosure may be provided to patients in combination with pharmaceutically acceptable sterile aqueous or non-aqueous solvents, suspensions or emulsions. Examples of non-aqueous solvents are propylene glycol, polyethylene glycol, vegetable oil, fish oil, and injectable organic esters. Aqueous carriers include water, water-alcohol solutions, emulsions or suspensions, including saline and buffered medical parenteral vehicles including sodium chloride solution, Ringer's dextrose solution, dextrose plus sodium chloride solution, Ringer's solution containing lactose, or fixed oils. Intravenous vehicles may include fluid and nutrient replenishers, electrolyte replenishers, such as those based upon Ringer's dextrose, and the like.

The medicaments/pharmaceutical compositions may also contain preserving agents, solubilizing agents, stabilizing agents, wetting agents, emulsifiers, sweeteners, colorants, odorants, salts for the variation of osmotic pressure, buffers, coating agents or antioxidants. They may also contain other therapeutically active agents.

Any amount of a pharmaceutical composition can be administered to a subject. The dosages will depend on many factors including the age and the requirements of the patient and the mode of application. Typically, the amount of the compound of the disclosure contained within a single dose will be an amount that effectively prevent, delay or treat the disease or condition to be treated, delayed or prevented without inducing significant toxicity. Hence a "therapeutically effective amount" or "effective amount" or "therapeutically effective dosage" of a specific compound of the disclosure or composition thereof can result in a reduction of pain and/or body temperature in a subject. Intravenous, or oral administrations are preferred forms of use.

The effective amount of the compounds of the disclosure may also be measured directly. The effective amount may be given daily or weekly or fractions thereof. Typically, a pharmaceutical composition of the disclosure can be administered in an amount from about 0.001 mg up to about 500 mg per kg of body weight per day (e.g., 10 mg, 50 mg, 100 mg, or 250 mg). Dosages may be provided in either a single or multiple dosage regimen. For example, in some embodiments the effective amount may range from about 1 mg to about 25 grams of the composition per day, about 50 mg to about 10 grams of the composition per day, from about 100 mg to about 5 grams of the composition per day, about 1 gram of the composition per day, about 1 mg to about 25 grams of the composition per week, about 50 mg to about 10 grams of the composition per week, about 100 mg to about 5 grams of the composition every other day, and about 1 gram of the composition once a week.

These are simply guidelines since the actual dose must be carefully selected and titrated by the attending physician based upon clinical factors unique to each patient. The optimal daily dose will be determined by methods known in the art and will be influenced by factors such as the age of the patient and other clinically relevant factors. In addition, patients may be taking medications for other diseases or conditions. The other medications may be continued during the time that the pharmaceutical composition of the disclosure is given to the patient, but it is particularly advisable in such cases to begin with low doses to determine if adverse side effects are experienced.

Combinations

In accordance with another aspect, there is provided a combination of at least one of the compounds described herein with another of the compounds described herein and/or with another antalgic agent (e.g., analgesic) and/or with an agent that prevents or treats pain comorbidities such as anxiety (anxiolytic) and/or depression (antidepressant).

Without being so limited, other antalgic (e.g., analgesic) agents include acetylsalicylic acid, nonsteroidal anti-inflammatory drugs (NSAIDs) (e.g., ibuprofen, ketoprofen), acetaminophen, etc. Without being so limited, weak opioids such as codeine, dihydrocodeine, tramadol, and strong opioids such as morphine, buprenorphine, and fentanyl.

Without being so limited anxiolytic agents include benzodiazepine tetrazepam. Without being so limited antidepressant agents include anafranil, clomipramine, etc. In a specific embodiment, the combination of the compounds of the present disclosure with another active ingredient (e.g., an opioid), advantageously enables reducing the dose that would be required if each compound was used alone, thereby reducing the deleterious side effects of each. See for instance Eiselt et al., 2019.

In accordance with an aspect, there is provided a composition comprising at least one of the compounds as described herein, and (i) another of the compounds described herein; (ii) another analgesic and/or antalgic agent; (iii) a pharmaceutically acceptable carrier; or (iv) a combination of at least two of (i) to (iii).

In a specific embodiment, said composition is a pharmaceutical composition. In another specific embodiment, the composition comprises (i) a compound as described herein; and (ii) another analgesic and/or antalgic agent.

Kits

In accordance with another aspect of the present disclosure, there is provided a kit comprising the compound defined herein or the above-mentioned composition, and instructions to use same in the prevention or treatment of pain or of a symptom thereof.

In a specific embodiment of the kit, the kit comprises: (i) at least one of the compounds described herein; (ii) another antalgic agent (e.g., analgesic); (iii) instructions to use same in the prevention or treatment of pain or of a symptom thereof; or (iv) a combination of at least two of (i) to (iii).

Methods

The present disclosure also relates to a method of preventing or treating pain comprising administering to a subject in need thereof an effective amount of a compound described herein, or a composition described herein. In a specific embodiment, the method avoids or limits the risk for side effects such as hypothermia, hypotension and/or ileum relaxation.

As used herein the terms "subject" refers to an animal such as, but not limited to a human or a pet or other animal (e.g., pets such as cats, dogs, horses, etc.; and cattle, fishes, swine, poultry, etc.).

As used herein the terms "subject in need thereof" refer to a subject who would benefit from receiving an effective amount of the compound or composition of the present disclosure. In the context of the method of preventing or treating pain, it refers to a subject experiencing or at risk to experience pain (e.g., chronic or acute). In another specific embodiment, the subject at risk to experience pain, is, without being so limited, a subject immediately prior to surgery.

The use of the terms "a" and "an" and "the" and similar referents in the context of describing the disclosure (especially in the context of the following claims) are to be construed to cover both the singular and the plural, unless otherwise indicated herein or clearly contradicted by context.

The terms "comprising", "having", "including", and "containing" are to be construed as open-ended terms (i.e., meaning "including, but not limited to") unless otherwise noted.

Recitation of ranges of values herein are merely intended to serve as a shorthand method of referring individually to each separate value falling within the range, unless otherwise indicated herein, and each separate value is incorporated into the specification as if it were individually recited herein. All subsets of values within the ranges are also incorporated into the specification as if they were individually recited herein.

All methods described herein can be performed in any suitable order unless otherwise indicated herein or otherwise clearly contradicted by context.

The use of any and all examples, or exemplary language (e.g., "such as") provided herein, is intended merely to better illuminate the disclosure and does not pose a limitation on the scope of the disclosure unless otherwise claimed.

No language in the specification should be construed as indicating any non-claimed element as essential to the practice of the disclosure.

Herein, the term "about" has its ordinary meaning. In embodiments, it may mean plus or minus 10% of the numerical value qualified.

Unless otherwise defined, all technical and scientific terms used herein have the same meaning as commonly understood by one of ordinary skill in the art to which this disclosure belongs.

Other objects, advantages and features of the present disclosure will become more apparent upon reading of the following non-restrictive description of specific embodiments thereof, given by way of example only with reference to the accompanying drawings.

The present disclosure is illustrated in further details by the following non-limiting examples.

Example 1: Material and Method

Peptide Synthesis

All of the peptides were synthesized using standard procedures for solid phase synthesis on 200 mg of 2-chlorotrityl chloride resin (loaded at 0.25 mmol/g) obtained from Matrix Innovation. All commercially available Fmoc-protected amino acid were purchased from Chem-Impex and Matrix Innovation at the highest purity available. Peptide synthesis was performed on an orbital shaker at 150 RPM. 12 mL reactors with 20 um frit were purchased from Applied Separations and were used as vessels for the synthesis.

Standard Resin Wash Procedures

The resin was washed following this sequence, with 5 mL volumes: DMF x2, DCM x2, iPrOH x1, DCM x2, DMF x2. When a dried resin is needed, 2 additional washes with DCM or Et2O were performed, followed by at least 5 minutes of drying on vacuum.

Figure 1A:
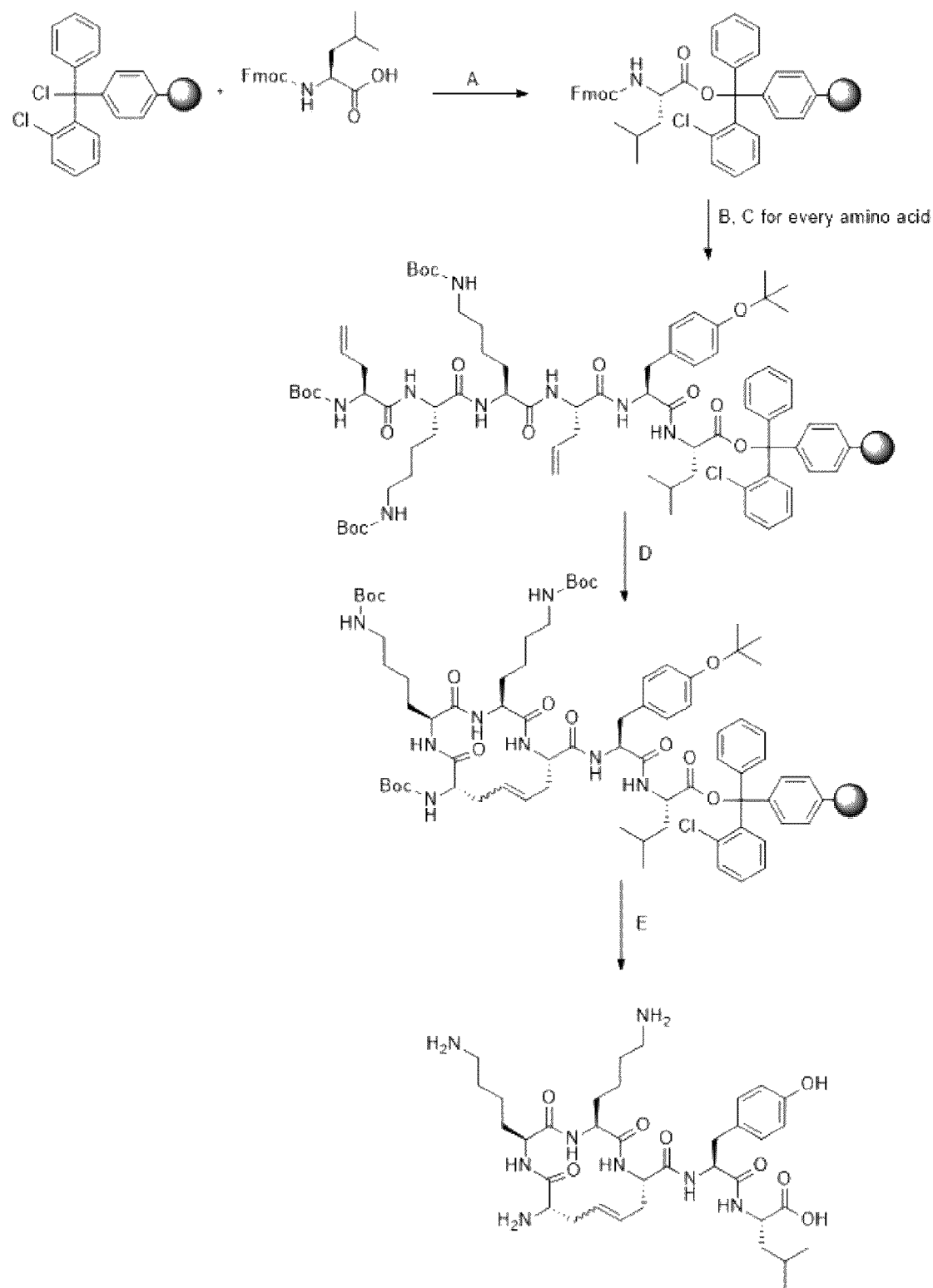
FIGS. 1A-B: Macrocyclization of (FIG. 1A) compound 34 by metathesis of olefins and of (FIG. 1B) compound 94 by macrolactamisation.
Figure 1B:
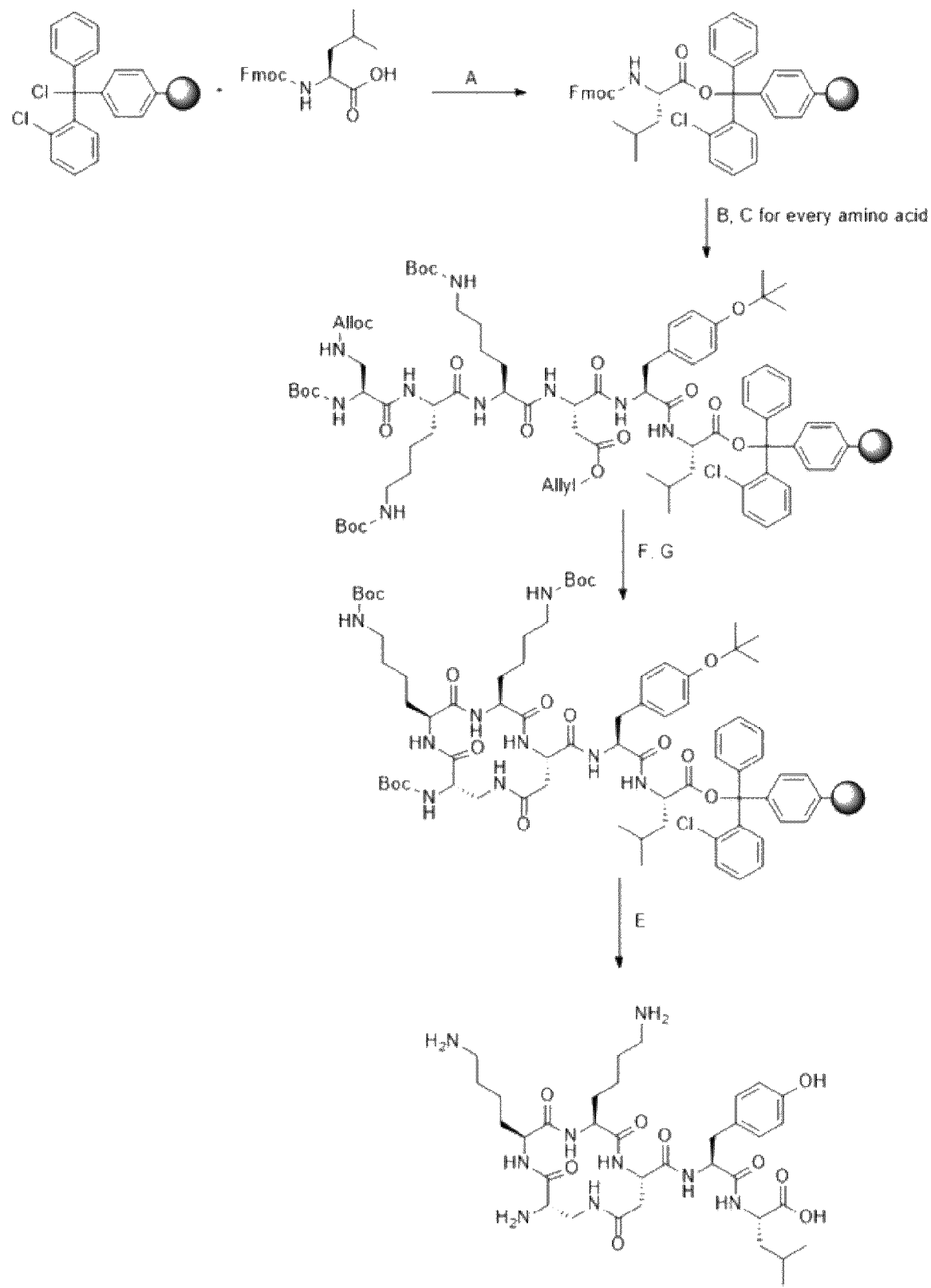

Coupling of the First Amino Acid (A, FIGS. 1A-B)

The resin and the first amino acid (1 eq. according to the loading, usually 0.25 mmol/g) were added together to a 12 mL reactor. 5 mL of dichloromethane was then added over and let to stir for 5 minutes or until the amino acid is completely dissolved. 2 eq. of diisopropylethylamine (DIPEA) was added to the mix which was then put on the orbital shaker to react for 2 hours or overnight. Unreacted sites on the resin were then capped with 5 mL of a mix 7/2/1 of DCM/MeOH/DIPEA for 45 minutes. Standard wash procedures were applied.

Fmoc Deprotection (B, FIGS. 1A-B)

Fmoc deprotection was made by adding 5 mL of a 20% solution of piperidine in DMF for 5 minutes, repeated once. Standard wash procedures were applied.

Fmoc-Deprotection of N-Methylated Amino Acids on the 2nd Position

Fmoc-deprotection of the 2nd coupled N-methylated amino acid was made by adding 5 mL of 50% piperidine in DMF and shaking vigorously for 30 seconds, repeated once. The resin was then washed rapidly 3 times with DCM and the next amino acid and HATU solution was immediately added to the resin, followed by DIPEA. This procedure diverges from the standard procedure because N-methylated amino acids on the 2nd position tend to make diketopiperazine, which cleaves the peptide from the resin.

Coupling of Non-Expensive Amino Acids (C, FIGS. 1A-B)

5 eq. of the Fmoc-protected amino acid and 5 eq. of hexafluorophosphate azabenzotriazole tetramethyl uronium (HATU) were added to ~8 mL of DMF and allowed to solubilise, sometimes needing a sonic bath. The mixture was then added to the washed resin and 6 eq. of DIPEA was added. The reactor was then sealed, the internal pressure was released after gentle hand shaking once or twice, then put on the orbital shaker for 30 minutes to an hour.

Coupling of Expensive Amino Acids (C, FIGS. 1A-B)

2 eq. of the Fmoc-protected amino acid and 2 eq. of HATU were added to ~8 mL of DMF and allowed to solubilise sometimes with a sonic bath. The mixture was then added to the washed resin and 3 eq. of DIPEA was added. The reactor was then sealed, the internal pressure was released after gentle hand shaking once or twice, then put on the orbital shaker for at least 2 hours, sometimes overnight.

Ring-Closing Metathesis (D, FIG. 1A)

To a flame dried microwave vial with a stir bar was added, 0.2 eq. of Grubbs-Hoveyda 2nd generation, 1 eq. of p-benzoquinone and the resin, which was previously dried with Et20. The solid mixture was then degassed with argon for 10 minutes, before adding 3 mL of DCE. The mixture was then subjected to microwave irradiation for 1 hour at 50° C. on a CEM Discover microwave.

Alloc/Allyl Deprotection (F, FIG. 1B)

To the pre-dried resin was added ~8 mL of DCM. 0.25 eq. of Pd(PPh3)4 were added to the mixture and 30 eq. of phenyl silane were added. The mixture was hand shaken and internal pressure was released several times before putting on the orbital shaker for 30 minutes.

Macrolactamisation (G, FIG. 1B)

Macrolactamisation was carried on using 5 eq. of HATU and 6 eq. of DIPEA in ~8 mL of DMF. The reaction was then put on the orbital shaker for at least 20 minutes, or until completion.

Cleavage from the Resin and Side-Chain Deprotection (E, FIGS. 1A-B)

The resin was transferred to a 8 mL glass vial and stirred for 2 h with ~2 mL of a TFA/H2O/TIPS (95:2,5:2,5) solution. The peptide was then precipitated in 20 mL of cold diethyl ether, centrifugated (3000 rpm, 10 min, 4° C.) and dried in vacuo.

Peptide Purification

The crude product was resuspended in water/acetonitrile (1:1) and purified on a preparative HPLC-MS system from Waters (column XSELECT™ CSH™ Prep C18 (19×100 mm) packed with 5 µm particles, UV detector 2998, MS SQ Detector 2, Sample manager 2767 and a binary gradient module) using acetonitrile and water+0.03% NH4OH, pH 10 as eluents. Purified fractions were then lyophilized and the purity of obtained compounds was assessed on an UPLC-MS system (column Acquity UPLC® CSH™ C18 (2.1×50 mm) packed with 1.7 µm particles) with the following gradient: acetonitrile and water with 0.1% TFA (0->0.2 min: 5% acetonitrile; 0.2->1.5 min: 5%->95%; 1.5->1.8 min: 95%; 1.8->2.0 min: 95%->5%; 2.0->2.5 min: 5%). High resolution mass spectra of all analogues were obtained using electrospray infusion ESI-Q-Tof™ from maXis.

Binding Assays

Cell Culture

CHO-K1 (Chinese Hamster Ovary) cells stably expressing hNTS1 and 1321N1 cells stably expressing hNTS2 (ES-690-C and ES-691-C from PerkinElmer, Montréal, Canada) were cultured respectively in Ham's F12 and in DMEM culture media. Culture media were supplemented with 10% FBS, 100 U/mL penicillin, 100 µg/mL streptomycin, 20 mM HEPES, and 0.4 mg/mL G418 at 37° C. in a humidified chamber at 5% $CO_2$.

Competitive Radioligand Binding Assay on the hNTS1 and hNTS2 Receptor

The cells expressing hNTS1 were frozen when they reached 80% confluency. They were scrapped off the dish with 10 mM Tris buffer, 1 mM EDTA, pH 7.5 and centrifuged at 15,000 g for 5 min at 4° C. The pellet was then re-suspended in 1 mL binding buffer. The cells expressing hNTS2 were also frozen when they reached 80% confluency. They were scraped off the dish with PBS, 0.5 mM EDTA, pH 7.5 and sonicated for 5 minutes (pulse 30 s/5 s off, amplitude 40%). They were ultracentrifuged at 100 000 g for 60 minutes at 4° C. The pellet was re-suspended in 1 mL freezing buffer (PBS, glycerol, 0.5 mM EDTA), sonicated for 1 minute (pulse 30 s/5 s off, amplitude 50%) and further diluted in binding buffer. Competitive radioligand binding experiments were performed by incubating 15 µg of cell membranes expressing the hNTS1 receptor with 45 µM of $^{125}I$-[$Tyr^3$]-NT (2200 Ci/mmol) or 50 µg of cell membranes expressing the hNTS2 receptor with 300 µM of $^{125}I$-[$Tyr^3$]-NT in binding buffer (50 mM Tris-HCl, pH 7.5, 0.2% BSA) in the presence of increasing concentrations of analogues ranging from $10^{-11}$ to $10^{-4}$ M for 60 min at 25° C. After incubation, the binding reaction mixture was transferred in PEI-coated 96-well filter plates (glass fiber filters GF/B, Millipore, Billerica, MA). Reaction was terminated by filtration, and plates were washed three times with 200 µL ice-cold binding buffer. Glass filters were then counted using a γ-counter (2470 Wizard2, PerkinElmer, Mississauga, Ontario, Canada). Non-specific binding was measured in the presence of $10^{-5}$ M unlabeled NT (8-13) and represented less than 5% of total binding. $IC_{50}$ values were determined from competition curves as the unlabeled ligand concentration inhibiting 50% of $^{125}I$-[$Tyr^3$]-NT-specific binding.

Competitive radioligand binding data were plotted using the nonlinear regression One-site-Fit Log($IC_{50}$) and represented the mean±SEM of at least three independent experiments in triplicates.

Plasma Stability Assay

Rat plasma is obtained by centrifugation of rat blood (13000 rpm, 5 min, 4° C.). 6 µL of a 1 mM aqueous solution (10% DMSO (Dimethylsulfoxide)) of peptide is incubated with 27 µL of rat plasma at 37° C. for 5, 10, 30 and 60 min (1, 3 and 5 min for NT (neurotensin) (8-13)). Proteolytic degradation is quenched by adding 70 µL of acetonitrile/ethanol (1:1), 0.5% nicotinamide solution and vortexing. Samples are centrifuged (13000 rpm, 5 min, 4° C.) and the supernatant is filtered on a 4-mm nylon 0.2 µm syringe filter and analyzed by UPLC-MS (Waters 2695 with ACE C18 column 2.0×100 mm, 2.7 µm spherical particle size and Electrospray micromass ZQ-2000™ from Waters). Data are analyzed using GraphPad Prism™ 7's one phase decay equation.

In Vivo Analgesic Assay

Animals, Housing, and Habituation

Experiments were performed with adults male Sprague-Dawley rats, weighing 225-300 g (Charles River laboratories, St Constant, Canada). Rats were housed two per cage on Aspen shavings in a quiet room and kept on a 12 h light/dark cycle and allowed ad libitum access to food and water. The experimental procedures in this study were approved by the Animal Care Committee of Université de Sherbrooke and were in accordance with policies and directives of the Canadian Council on Animal Care.

Intrathecal Administration

Rats were lightly anesthetized with isoflurane/oxygen (Baxter corporation, Mississauga, ON, Canada; 2 L/min) flow and injected intrathecally at the L5-L6 intervertebral space with concentrations ranging from 10 to 150 µg/kg of compound 34, 30 µg/kg of PD149163 or 61 nmol/kg of compounds 60, 67, 91 and 116 diluted in 0.9% saline or 0.9% saline alone.

Acute and Tonic Antinociceptive Effects

Tail-flick test: The tail flick test was used as outcome measures heat-induced pain in animals and as indicators of a compound's analgesic efficacy.

Acute pain was assessed using the Tail flick test (Tail Flick Analgesia meterV2.00, Colombus Instruments, Columbus, Ohio, USA). Tail flick test measures sensitivity to a high-intensity light beam focused on the rat tail. The tail flick apparatus was set at a light intensity of 6 and a cutoff of 10 seconds. The latency to flick the tail out of the path of the light beam corresponds to the measure of pain sensitivity or analgesia.

Before testing, animals were individually acclimatized to manipulations and behavioral apparatus 5 min/day for three consecutive days. On the test day, latencies baseline measures were taken before drug injection to provide a mean baseline. The compounds were diluted in 0.9% saline at the desired dose. The effects of the compound or saline on thermal nociception were assessed every 10 min for up to 60 min following i.t. administration.

For the MS03-174, Areas Under the Curve (AUC) were calculated during all the duration of the test (0-60 min). Moreover, tail flick latencies were converted into the percent maximal possible effect (% MPE) at the time of maximal peak of analgesia. % MPE were calculated according to the following formula: % MPE=[(Test latency)−(Saline latency)]/[(Cutoff)−(Saline latency)]×100. Data are expressed as mean±SEM of 5-8 animals for each dose.

The half maximal effective dose ($ED_{50}$) of the compound was determined on the AUC and the % MPE at 10 min, calculated for each dose in tail-flick test. Then, $ED_{50}$ values were determined using the dose-response stimulation log (agonist) vs response (four parameters).

Formalin test: The analgesic effect of compound 34 was assessed using the formalin test as a model of persistent pain. Before testing, animals were acclimatized to manipulations and to plexiglass chambers 30 min/day for three consecutive days. On test day, 5 minutes after intrathecal injection of compounds at increasing doses ranging from 30 to 150 µg/kg (FIGS. 7A-B) or 3 to 60 µg/kg (FIGS. 8A-D), the rats received a 50 µl of diluted 1.85% formaldehyde (i.e. 5% formalin; Bioshop, Burlington, Ontario) into the plantar surface of the right hind paw. Rats were then placed in clear plastic chambers (30×30×30 cm) positioned over a mirror angled at 45° in order to allow an unobstructed view of the paws and their behaviors were observed for the next 60 min. The intraplantar injection of formalin produced the biphasic nociceptive response typical of this tonic pain model (Tjolsen et al., 1992). The two distinct phases of spontaneous pain behaviors that occur in rodents are proposed to reflect first the direct effect of formalin on sensory receptors (acute phase, 0-9 min) and a longer lasting pain due to inflammation and central sensitization (inflammatory phase, 21-60 min). Nociceptive behavior was assessed using a weighted score as described previously (Dubuisson and Dennis 1977; Codere, 1993). Following injection of formalin into the hind paw, nociceptive mean score (pain score) was determined for each 3-min block during 60 min by measuring the amount of time spent in each of four behavioral categories: 0, the injected paw is comparable to the contralateral paw; 1, the injected paw has little or no weight placed on it; 2, the injected paw is elevated and is not in contact with any surface (lifting); 3, the injected paw is licked, bitten, or shaken. The behaviors believed to represent higher levels of pain intensity was given higher weighted scores. The weighted average pain intensity score ranging from 0 to 3 was then calculated by multiplying the time spent in each category by the category weight, summing these products, and dividing by the total time in a given time interval. The pain score was thus calculated from the following formula (1T1+2T2+3T3)/180 where T1, T2, and T3 are the durations (in seconds) spent in behavioral categories 1, 2, or 3, respectively, during each 180 second block. The Area Under the Curve (AUC) was calculated during all the duration of the test (0-60 min). Reduction in time spent in lifting (category 2 of nociceptive behaviors) was chosen to demonstrate the analgesic efficiency of the compound as previously described with NTS2-selective compounds (Roussy, G., Dansereau, M-A., Baudisson, S., Ezzoubaa, F., Belleville, K., Beaudet, N., Martinez, J., Richelson, E., Sarret, P. Evidence for a role of NTS2 receptors in the modulation of tonic pain sensitivity. Mol. Pain 2009, 5:38). Data represents the mean±SEM of 5-6 rats for each dose.

Body Temperature

Body temperature was measured using a thermistor probe inserted into the rectum of the rats. Animals were individually acclimatized to manipulations and thermistor probe 5 min/day for three consecutive days. On the test day, temperatures were measured before (baseline) and each 10 min for up to 60 min following intrathecal drug administration of compound 34. The compound was dissolved in 0.9% of saline and injected at the highest dose of 150 µg/kg. Changes in body temperature ($\Delta$ body temperature) were determined from baseline for each time and each animal. Data represents the mean±SEM of 5-6 rats for each condition.

Blood Pressure Measurements

Rats were anesthetized with ketamine/xylaxine (87 mg/kg: 13 mg/kg, i.m) and placed in supine position on a heating pad. Mean, systolic and diastolic arterial blood pressure and a heart rate were measured through a catheter (PE 50 filled with heparinized saline) inserted in the right carotid artery and connected to a Micro-Med transducer (model TDX-300, USA) linked to a blood pressure Micro-Med analyzer (model BPA-100c). Another catheter (PE 10 filled with heparinized saline) was inserted in the left jugular vein for injections of the compound 34 at 0.01, 0.1 and 1 mg/kg (volume 1 mL/kg, 5-10 s) or 0.9% saline. Blood pressure was recorded each second for up to 1000 seconds following intravenous injection. Changes in mean arterial blood pressure ($\Delta$ MABP) were determined from the basal pressure of rat. Data represents the mean±SEM of 4-5 rats for each condition.

Ileum Relaxation Assay

The functional ileum bioassay was carried out as described in detail elsewhere. (Van der Poorten, O., Van Den Hauwe, R., Eiselt, E., Betti, C., Guillemyn, K., Chung, N. N., Hall, F., Bihel, F., Schiller, P. W., Tourwé, D., Sarret, P., Gendron, L, . . . Ballet, S. (2017). X-Space Screening of Dermorphin-Based Tetrapeptides through Use of Constrained Arylazepinone and Quinolinone Scaffolds. ACS medicinal chemistry letters, 8(11), 1177-1182) Briefly, rats were euthanized, and 2 cm ileum segments were dissected out before removal of extraneous fat and connective tissue.

The ileum was then mounted under 0.5-g tension in a 10 mL organ bath containing warmed (37° C.) and oxygenated (95% $O_2$, 5% $CO_2$) Krebs solution (6.9 g/L NaCl, 0.145 g/L $MgSO_4$, 2.1 g/L $NaHCO_3$, 0.35 g/L KCl, 0.165 g/L $KH_2PO_4$, 1.98 g/L dextrose and 0.28 g/L $CaCl_2$)). One end of each ileum segment was suspended to a transducer and the other end was attached on an anodal electrode placed at the bottom of the bath. A stimulator (Power Lab 8/30, AD Instruments, Fairfax Alexandria, VA, USA) delivered repetitive field stimulation through platinum wire ring electrodes at the top and bottom of the bath (20 V, 10 ms delay, 1 ms duration). Contractions of the muscle were recorded via an isometric force transducer (159901A, Radnoti, Monrovia, CA, USA). The ileum was allowed to equilibrate for 30 minutes before viability was assessed with 50 µM carbachol in order to confirm that isolation and mounting of the ileum did not damage the tissue. The ability of relaxant agents tested was investigated after ileum contraction with carbachol.

Each concentration of the compounds tested were followed by 2×15-min washout periods in Krebs solution to allow full relaxation. Dose-response curves were obtained with NT (8-13) ($10^{-11}$ to $10^{-6}$) as standard for each ileum and for compound 34($10^{-11}$ to $10^{-5}$) and $IC_{50}$ values were determined. Data represented the mean±SEM of at least three individual experiments.

Statistical Analysis

Figure 2A:
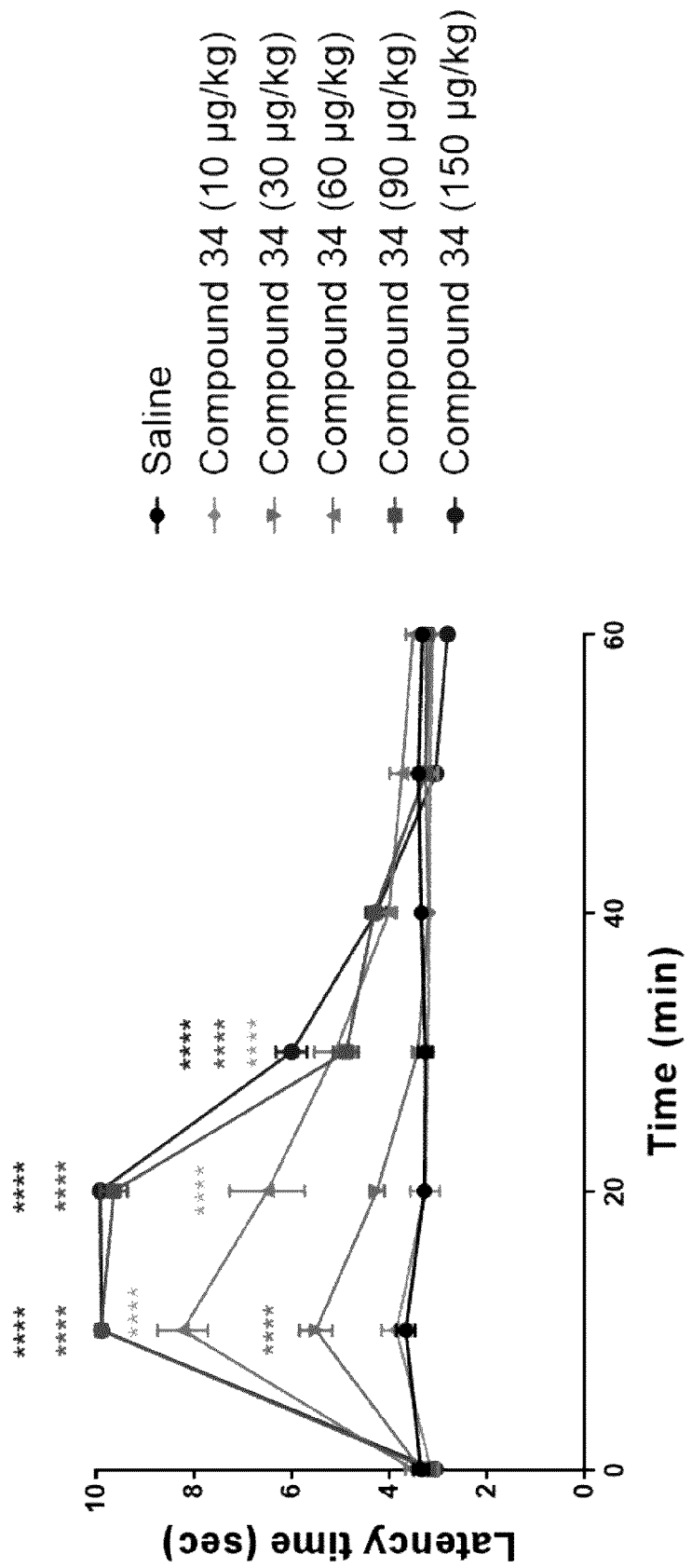
FIGS. 2A-B.

Data are expressed as mean±standard errors of the mean (SEM). All graphs and statistical analysis were performed using GraphPad Prism™ 7 (GraphPad software, La Jolla, CA, USA). A two-way ANOVA followed by Sidak's multiple comparisons test was used to determine the significant differences in tail-flick latencies between different concentrations of compounds 34, 60, 67, 91,116 and 127-137 and saline or vehicle (e.g., DMSO) (FIGS. 6A-E) or between different concentrations of compound 34 or 67 and saline (FIGS. 2A and 4A). A two-way ANOVA followed by Tukey's multiple comparisons test was used to determine the significant differences in changes in body temperature between different concentrations of compounds and saline (FIG. 9). The % MPE for the tail-flick test and the areas under the curve for the formalin test were analyzed using a one-way ANOVA followed by a Dunnett's multiple comparisons test to compare different concentrations of compounds and saline treatment (FIGS. 2B, 4B, 7A-B and 8B-D). Nonlinear regression using four parameters was performed for $ED_{50}$ calculation of the compound was obtained from the resulting dose-response curve for % MPE (FIGS. 3, 5 and 8E). Nonlinear regression using three parameters was performed for % of ileum relaxation and $IC_{50}$ value was obtained from the resulting dose-response curve (FIG. 11). A difference in response was considered significant with p-values *p<0.05, p<0.01, *p<0.001 and **p<0.0001.

Example 2: Peptide Synthesis

Compounds were synthesized as described in Example 1.
Compounds are presented in Table I below.

TABLE I structures of compounds

| Code | Structure |
|---|---|
| 13. c[G(All)KKG(All)]YLI (SEQ ID NO: 29) | 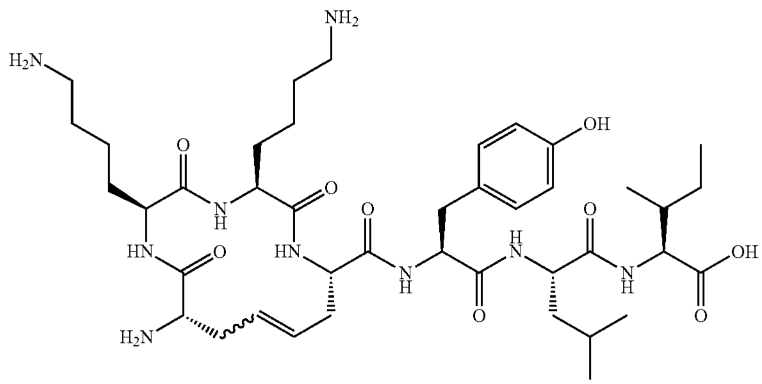 [SMILES: CCC(C)[C@H](NC(=O)[C@H](CC(C)C)NC(=O)[C@H](Cc1ccc(O)cc1)NC(=O)[C@@H]1CC=CC[C@H](N)C(=O)N[C@@H](CCCCN)C(=O)N[C@@H](CCCCN)C(=O)N1)C(=O)O] |
| 14. c[G(All)KKG(All)]YI (SEQ ID NO: 30) | 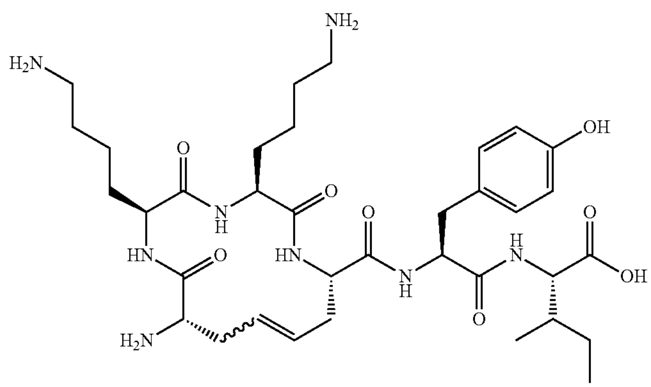 [SMILES: CCC(C)[C@H](NC(=O)[C@H](Cc1ccc(O)cc1)NC(=O)[C@@H]1CC=CC[C@H](N)C(=O)N[C@@H](CCCCN)C(=O)N[C@@H](CCCCN)C(=O)N1)C(=O)O] |
| 15. c[G(All)KKG(All)]Y(OAc)L (SEQ ID NO: 31) | 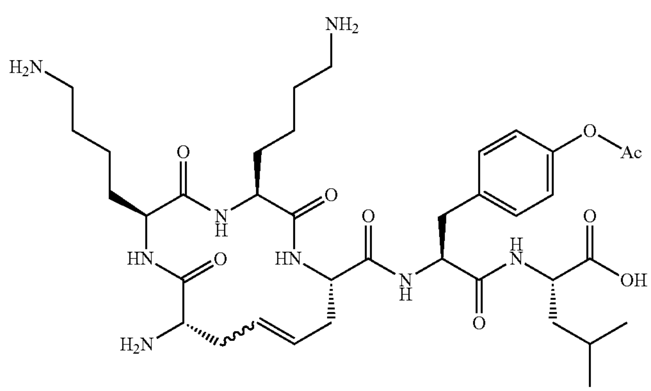 [SMILES: CC(=O)Oc1ccc(C[C@H](NC(=O)[C@@H]2CC=CC[C@H](N)C(=O)N[C@@H](CCCCN)C(=O)N[C@@H](CCCCN)C(=O)N2)C(=O)N[C@@H](CC(C)C)C(=O)O)cc1] |

Chemical Formula $C_{37}H_{55}N_8O_9$
Molecular Weight 758.92

TABLE I-continued
structures of compounds
| Code | Structure |
|---|---|
| 16. c[G(All)KKG(All)]WL (SEQ ID NO: 32) | 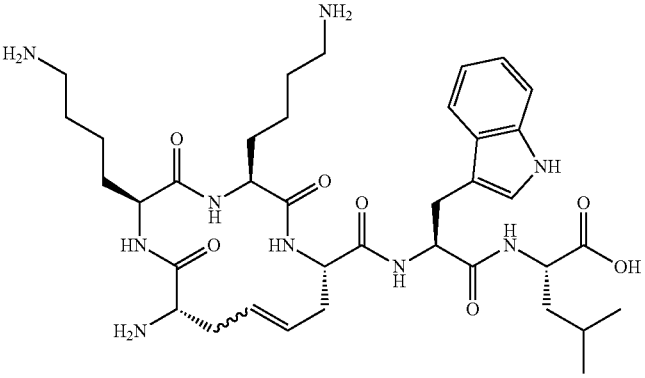 [SMILES: CC(C)C[C@H](NC(=O)[C@H](Cc1c[nH]c2ccccc12)NC(=O)[C@@H]1CC=CC[C@H](N)C(=O)N[C@@H](CCCCN)C(=O)N[C@@H](CCCCN)C(=O)N1)C(=O)O] Chemical Formula $C_{37}H_{57}N_9O_7$<br>Molecular Weight 739.92 |
| 17. c[G(All)KKG(All)]KL (SEQ ID NO: 33) (diastereoisomer of compound 48) | 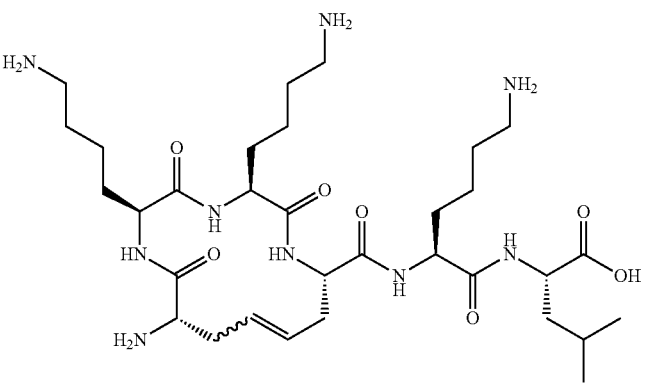 [SMILES: CC(C)C[C@H](NC(=O)[C@H](CCCCN)NC(=O)[C@@H]1CC=CC[C@H](N)C(=O)N[C@@H](CCCCN)C(=O)N[C@@H](CCCCN)C(=O)N1)C(=O)O] Chemical Formula $C_{32}H_{59}N_9O_7$<br>Molecular Weight 681.88 |
| 21. c[G(All)KKG(All)]Y*L (SEQ ID NO: 34) (diastereoisomer of compounds 34, 38, 40, 41, 42, 54, 141 and 145) | 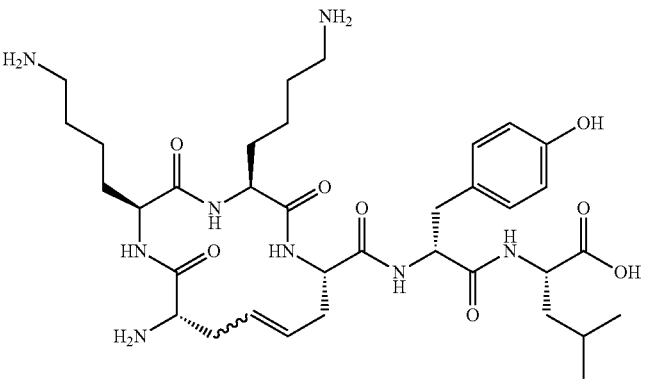 [SMILES: CC(C)C[C@H](NC(=O)[C@@H](Cc1ccc(O)cc1)NC(=O)[C@@H]1CC=CC[C@H](N)C(=O)N[C@@H](CCCCN)C(=O)N[C@@H](CCCCN)C(=O)N1)C(=O)O] Chemical Formula $C_{35}H_{56}N_5O_5$<br>Molecular Weight 716.88 |

TABLE I-continued
structures of compounds
| Code | Structure |
|---|---|
| 27. c[G(All)KKG(All)]YTle (SEQ ID NO: 35) | 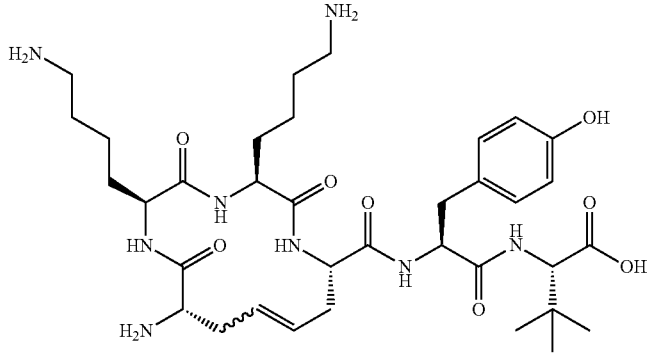 [SMILES: CC(C)(C)[C@H](NC(=O)[C@H](Cc1ccc(O)cc1)NC(=O)[C@@H]1CC=CC[C@H](N)C(=O)N[C@@H](CCCCN)C(=O)N[C@@H](CCCCN)C(=O)N1)C(=O)O]<br>Chemical Formula $C_{35}H_{56}N_8O_9$<br>Molecular Weight 716.88 |
| 28. c[G(All)KKG(All)]YNle (SEQ ID NO: 36) | 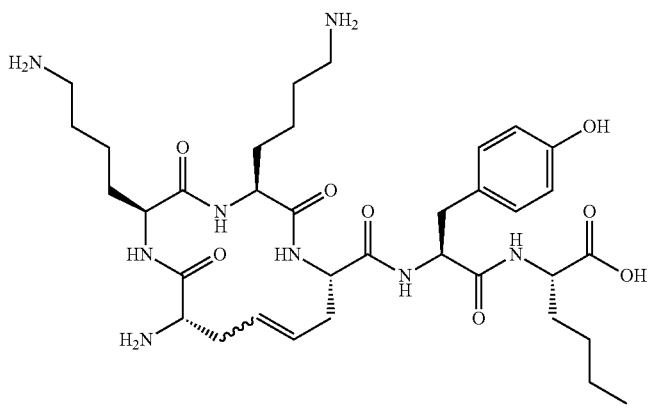 [SMILES: CCCC[C@H](NC(=O)[C@H](Cc1ccc(O)cc1)NC(=O)[C@@H]1CC=CC[C@H](N)C(=O)N[C@@H](CCCCN)C(=O)N[C@@H](CCCCN)C(=O)N1)C(=O)O]<br>Chemical Formula $C_{35}H_{56}N_8O_8$<br>Molecular Weight 716.88 |
| 29. c[G(All)KKG(All)]YNva (SEQ ID NO: 37) | 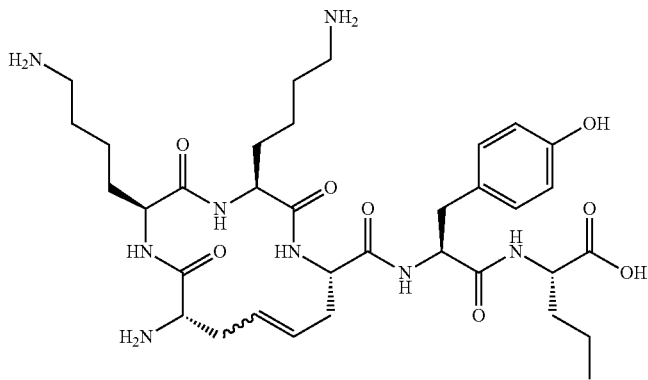<br>Chemical Formula $C_{34}H_{54}N_8O_8$<br>Molecular Weight 702.85 |

TABLE I-continued
structures of compounds
| Code | Structure |
|---|---|
| 30. c[G(All)KKG(All)]YChG (SEQ ID NO: 38) | 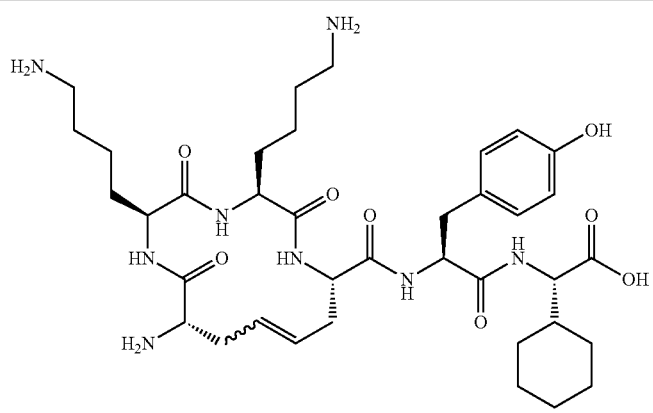Chemical Formula $C_{37}H_{58}N_8O_8$<br>Molecular Weight 742.92 |
| 31. c[G(All)KKG(All)]YA(Ch) (SEQ ID NO: 39) | 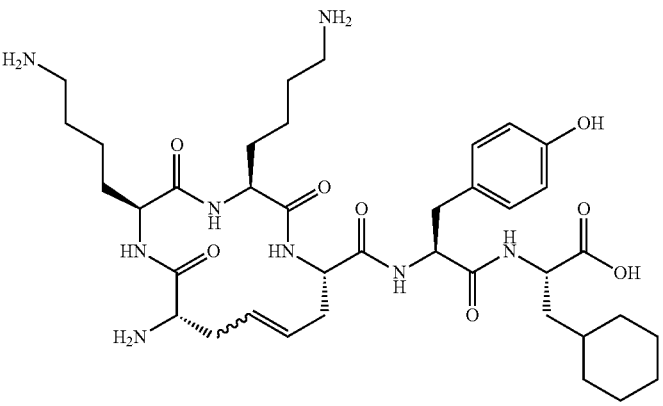Chemical Formula $C_{38}H_{60}N_8O_8$<br>Molecular Weight 756.895 |
| 32. c[G(All)KKG(All)]YF (SEQ ID NO: 40) | 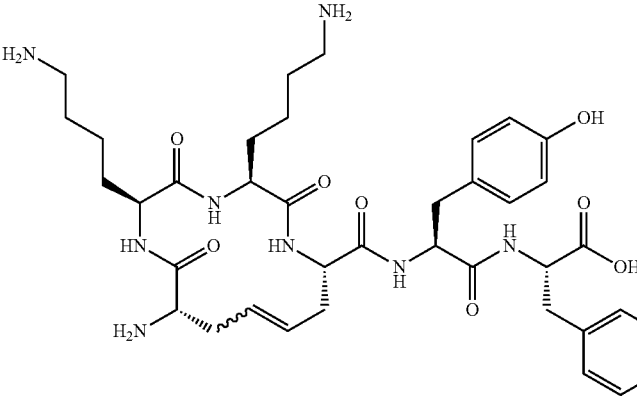Chemical Formula $C_{35}H_{54}N_8O_8$<br>Molecular Weight 750.90 |

TABLE I-continued
structures of compounds
| Code | Structure |
|---|---|
| 33. c[G(All)KKG(All)]YV (SEQ ID NO: 41) | 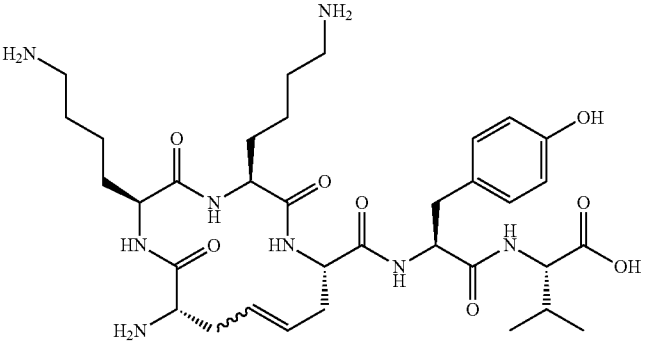<br>Chemical Formula $C_{34}H_{54}N_8O_8$<br>Molecular Weight 702.85 |
| 34. c[G(All)KKG(All)]YL (SEQ ID NO: 22) (diastereoisomer of compounds 21, 38, 40, 41, 42, 54, 141 and 145) | 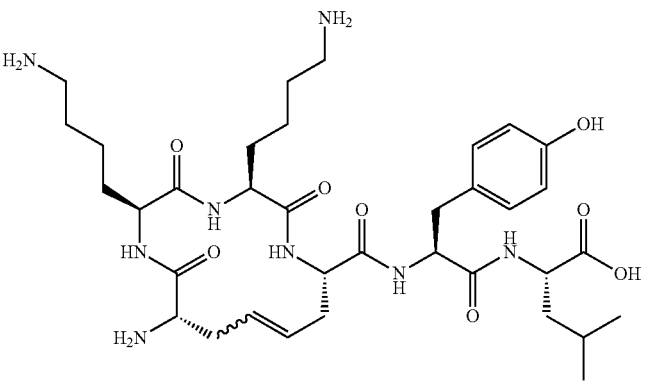<br>Chemical Formula $C_{35}H_{56}N_8O_8$<br>Molecular Weight 716.88 |
| 38. c[G(All)KKG(All)]YL* (SEQ ID NO: 42) (diastereoisomer of compounds 21, 34, 40, 41, 42, 54, 141 and 145) | 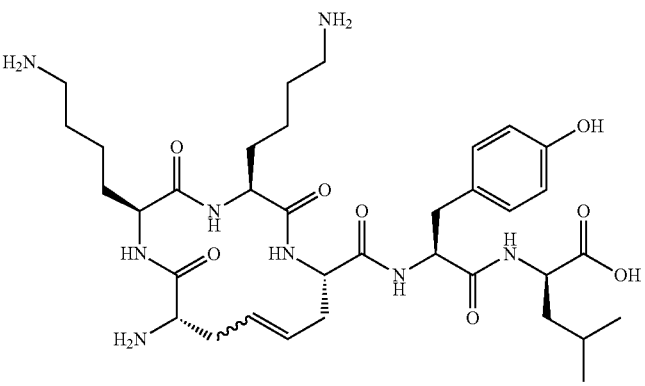<br>Chemical Formula $C_{35}H_{56}N_8O_8$<br>Molecular Weight 716.88 |

TABLE I-continued structures of compounds

| Code | Structure |
|---|---|
| 39.<br>c[G(All)KKG(All)]mYL<br>(SEQ ID NO: 43) | 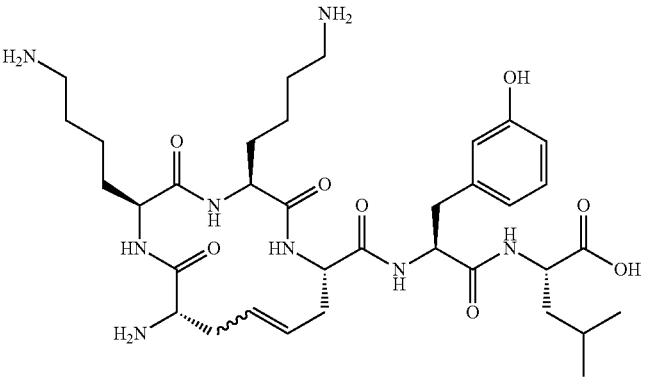<br>Chemical Formula C$_{35}$H$_{56}$N$_8$O$_8$<br>Molecular Weight 716.88 |
| 40.<br>c[G(All)KKG*(All)]YL<br>(SEQ ID NO: 44)<br>(diastereoisomer of compounds 21, 34, 38, 41, 42, 54, 141 and 145) | 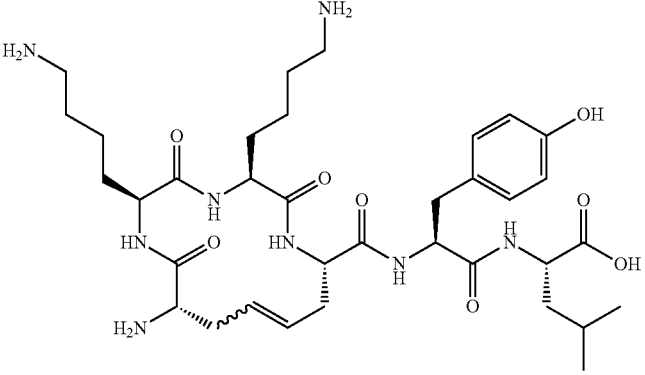<br>Chemical Formula C$_{35}$H$_{56}$N$_8$O$_8$<br>Molecular Weight 716.88 |
| 41.<br>c[G*(All)KKG(All)]YL<br>(SEQ ID NO: 45)<br>(diastereoisomer of compounds 21, 34, 38, 40, 42, 54, 141 and 145) | 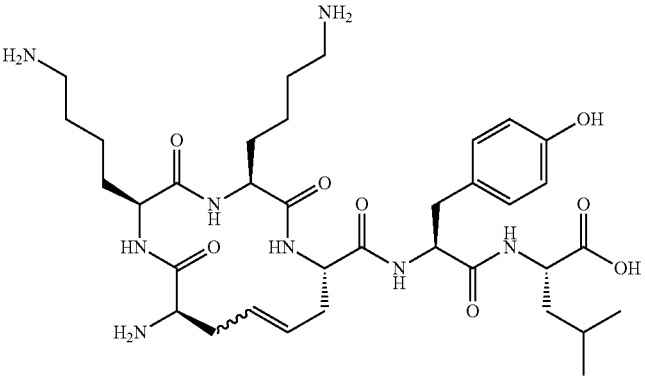<br>Chemical Formula C$_{35}$H$_{56}$N$_8$O$_8$<br>Molecular Weight 716.88 |

TABLE I-continued
structures of compounds
| Code | Structure |
|---|---|
| 42.<br>c[G*(All)KKG*(All)]YL<br>(SEQ ID NO: 46)<br>(diastereoisomer of compounds 21, 34, 38, 40, 41, 54, 141 and 145) | 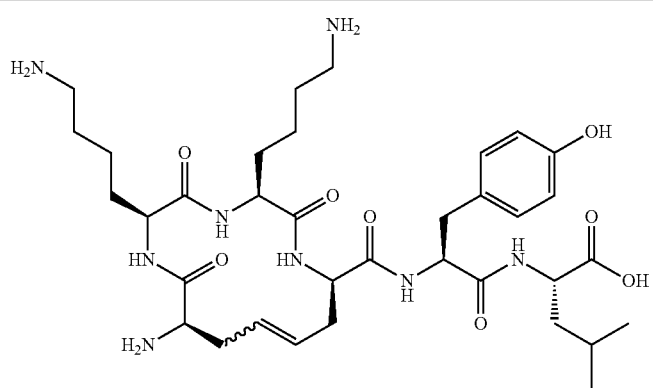<br>Chemical Formula $C_{35}H_{56}N_8O_8$<br>Molecular Weight 716.88 |
| 43.<br>c[G(All)KKG(All)]W*L<br>(SEQ ID NO: 47) | 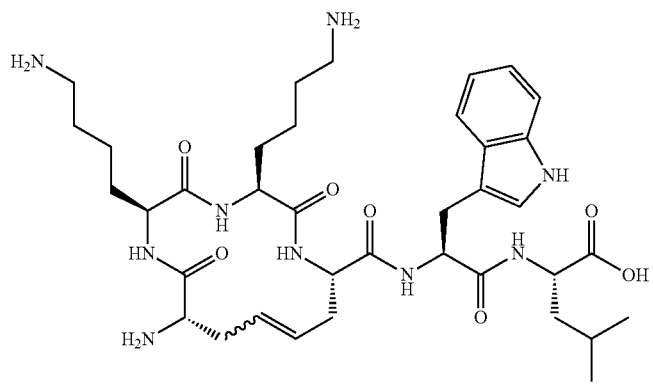<br>Chemical Formula $C_{37}H_{57}N_9O_7$<br>Molecular Weight 739.92 |
| 44.<br>c[G(All)KKG(All)]YL(NMe)<br>(SEQ ID NO: 48) | 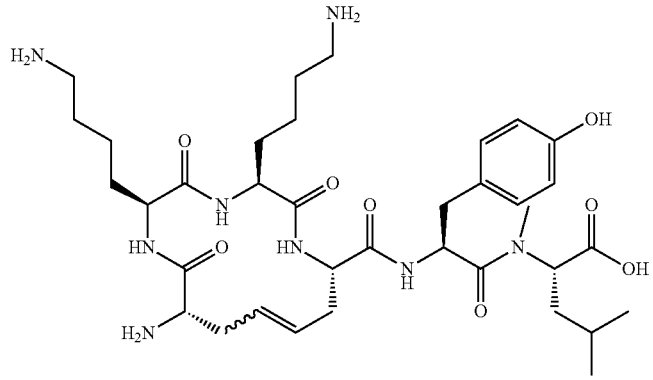<br>Chemical Formula $C_{36}H_{58}N_8O_8$<br>Molecular Weight 730.91 |

TABLE I-continued
structures of compounds
| Code | Structure |
|---|---|
| 45.<br>c[G(All)KKG(All)]Y(NMe)L<br>(SEQ ID NO: 49) | 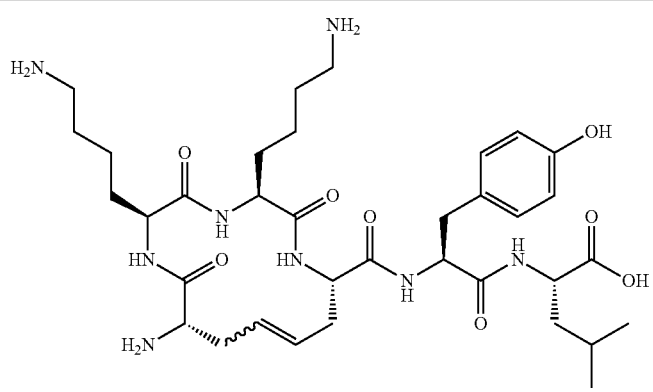<br>Chemical Formula $C_{36}H_{58}N_8O_8$<br>Molecular Weight 730.91 |
| 46.<br>c[G(All)KKG(All)]Y(NMe)L(NMe)<br>(SEQ ID NO: 50) | 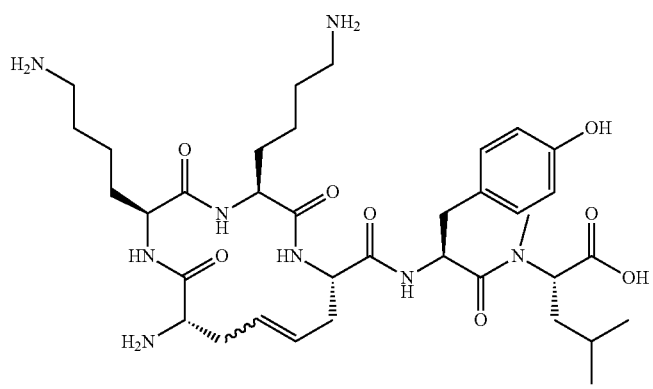<br>Chemical Formula $C_{37}H_{60}N_8O_8$<br>Molecular Weight 744.93 |
| 47.<br>Dihydro-c[G(All)KKG(All)]YL<br>(SEQ ID NO: 51) | 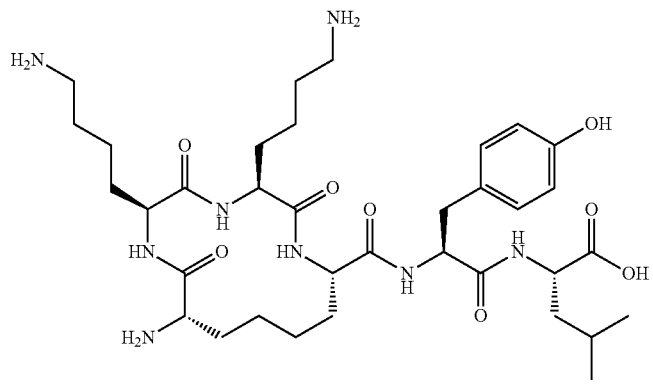<br>Chemical Formula $C_{35}H_{58}N_8O_8$<br>Molecular Weight 718.90 |

TABLE I-continued
structures of compounds
| Code | Structure |
|---|---|
| 48. c[G(All)KKG(All)]K*L (SEQ ID NO: 52) | 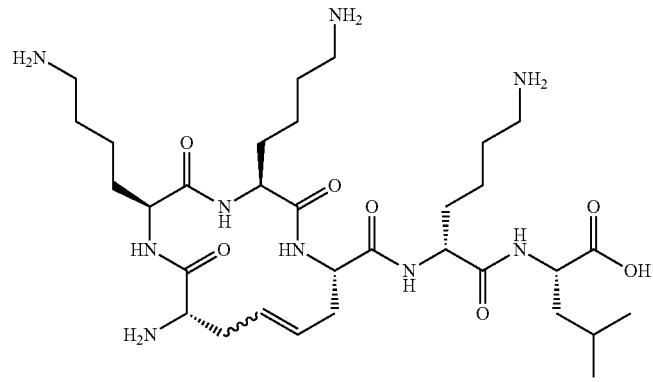 Chemical Formula $C_{32}H_{59}N_9O_7$<br>Molecular Weight 681.88 |
| 49. c[G(All)KKG(All)]YNpg (SEQ ID NO: 53) | 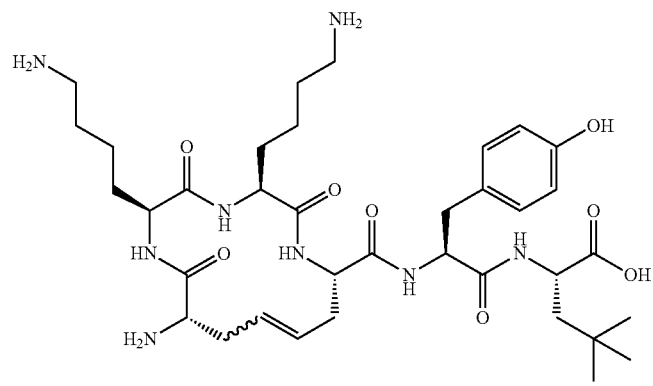 Chemical Formula $C_{36}H_{58}N_8O_8$<br>Molecular Weight 730.91 |
| 51. c[G(All)KOrnG(All)]YL (SEQ ID NO: 54) | 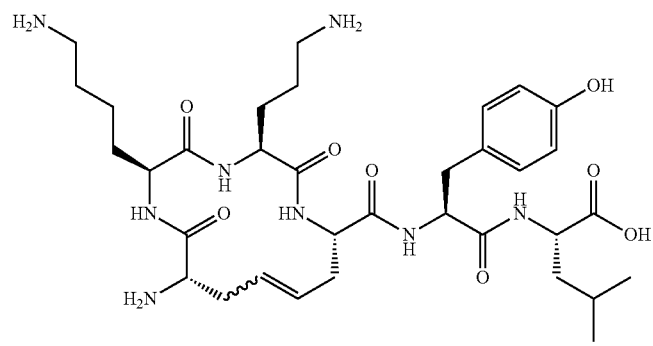 Chemical Formula $C_{34}H_{54}N_8O_8$<br>Molecular Weight 702.85 |

TABLE I-continued
structures of compounds
| Code | Structure |
|---|---|
| 52. c[G(All)KDabG(All)]YL (SEQ ID NO: 55) | 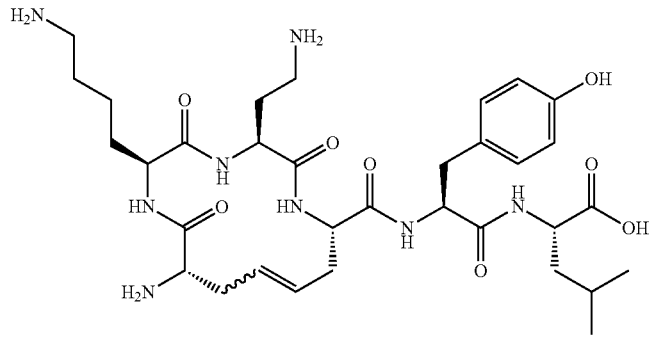<br>Chemical Formula $C_{33}H_{52}N_8O_8$<br>Molecular Weight 688.83 |
| 53. c[G(All)KDapG(All)]YL (SEQ ID NO: 56) | 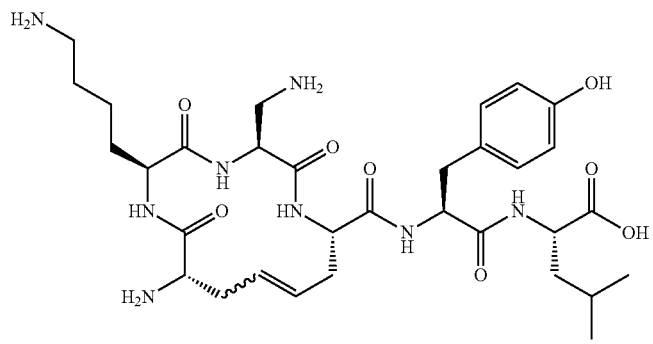<br>Chemical Formula $C_{32}H_{50}N_8O_8$<br>Molecular Weight 674.80 |
| 54. c[G(All)KK*G(All)]YL (SEQ ID NO: 57) (diastereoisomer of compounds 21, 34, 38, 40, 41, 42, 141 and 145) | 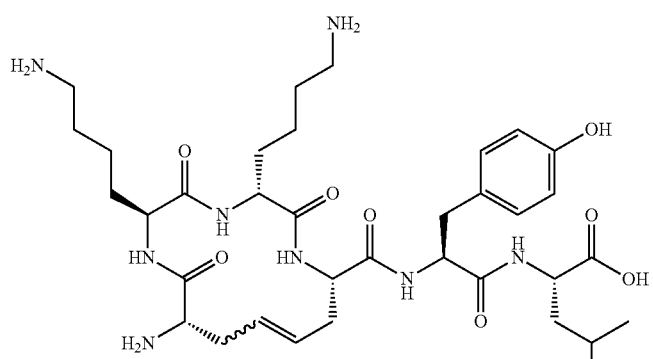<br>Chemical Formula $C_{35}H_{56}N_8O_8$<br>Molecular Weight 716.88 |

TABLE I-continued structures of compounds

| Code | Structure |
|---|---|
| 55. c[G(All)KHG(All)]YL (SEQ ID NO: 58) | Chemical Formula $C_{35}H_{51}N_9O_8$<br>Molecular Weight 725.85 |
| 57. c[G(All)KNleG(All)]YL (SEQ ID NO: 59) | Chemical Formula $C_{35}H_{55}N_7O_8$<br>Molecular Weight 701.87 |
| 58. c[G(All)KNvaG(All)]YL (SEQ ID NO: 60) | Chemical Formula $C_{34}H_{53}N_7O_8$<br>Molecular Weight 687.84 |

TABLE I-continued
structures of compounds
| Code | Structure |
|---|---|
| 59. c[G(All)KGG(All)]YL (SEQ ID NO: 61) | 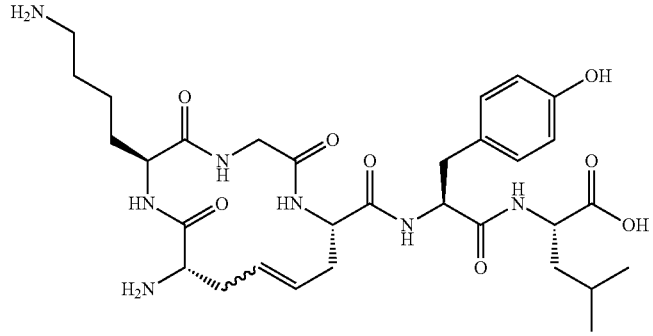<br>Chemical Formula $C_{31}H_{47}N_7O_8$<br>Molecular Weight 645.76 |
| 60. c[K(Pentenoyl)KG(All)]YL (SEQ ID NO: 62) | 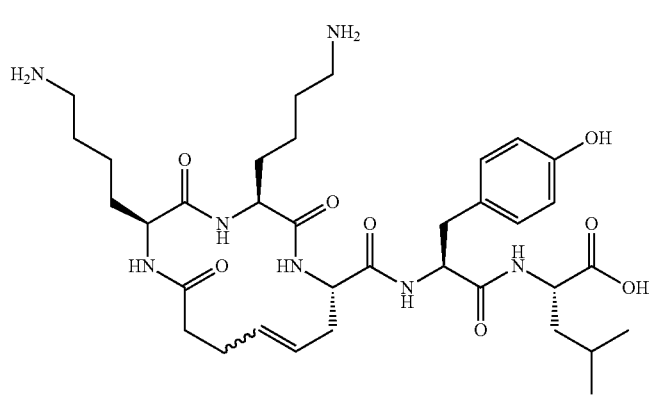<br>Chemical Formula $C_{35}H_{55}N_7O_8$<br>Molecular Weight 701.87 |
| 61. c[G(All)KEG(All)]YL (SEQ ID NO: 63) | 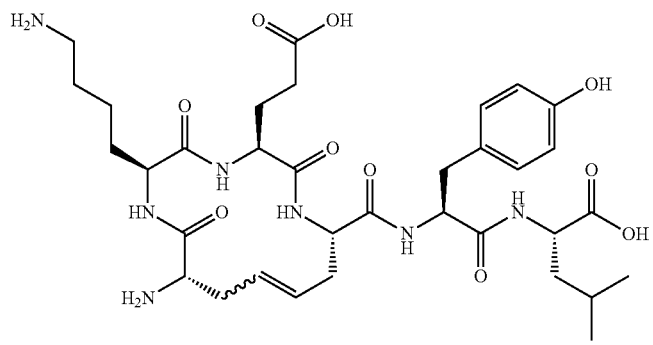<br>Chemical Formula $C_{34}H_{51}N_7O_{10}$<br>Molecular Weight 717.82 |

TABLE I-continued
structures of compounds
| Code | Structure |
|---|---|
| 62. c[G(All)KKG(All)]YY(OMe) (SEQ ID NO: 64) | 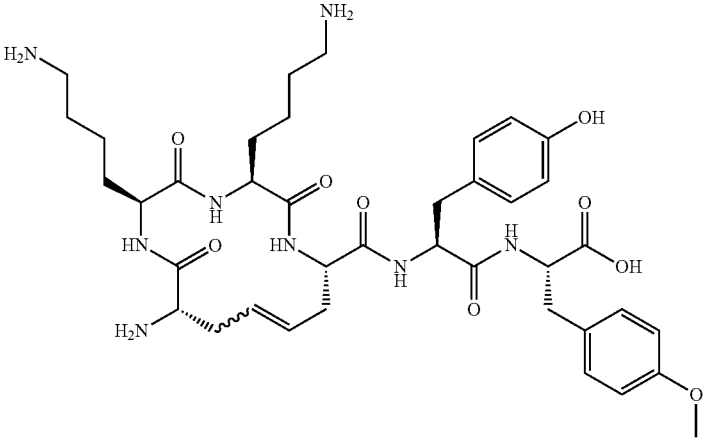 Chemical Formula $C_{39}H_{56}N_8O_9$<br>Molecular Weight 780.92 |
| 63. c[G(All)KKG(All)]YF(2,4,5-trifluoro) (SEQ ID NO: 65) | 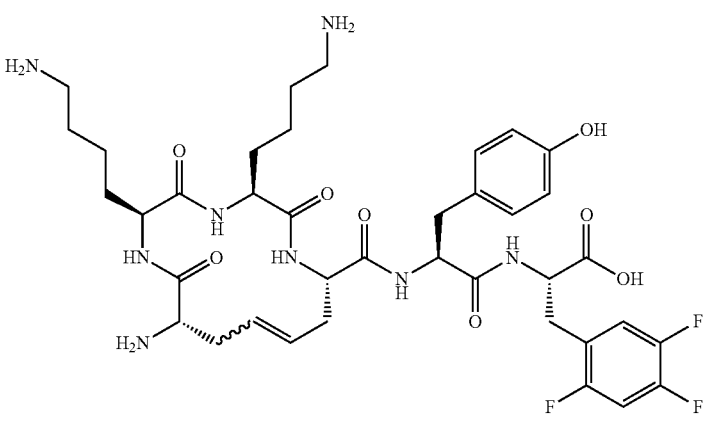 Chemical Formula $C_{38}H_{51}F_3N_8O_8$<br>Molecular Weight 804.87 |
| 64. c[G(All)KKG(All)]YA(homoChA) (SEQ ID NO: 66) | 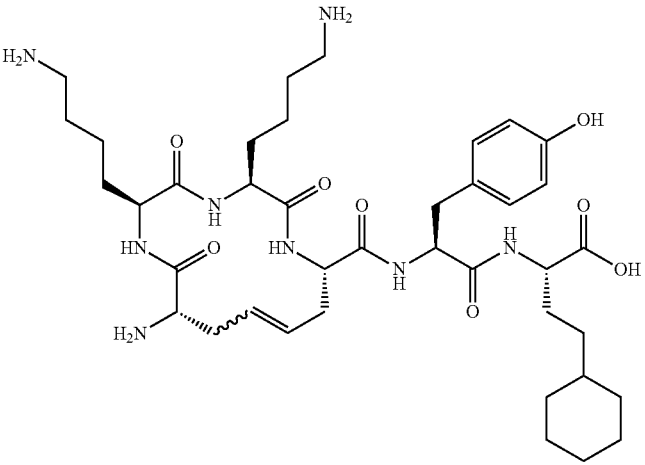 [SMILES: NCCCC[C@@H]1NC(=O)[C@H](CCCCN)NC(=O)[C@@H](N)CC=CC[C@@H](C(=O)N[C@@H](Cc2ccc(O)cc2)C(=O)N[C@@H](CCC2CCCCC2)C(=O)O)NC1=O] Chemical Formula $C_{39}H_{62}N_8O_8$<br>Molecular Weight 770.97 |

TABLE I-continued
structures of compounds
| Code | Structure |
|---|---|
| 65. c[G(All)KKG(All)]YA(cyclopropyl) (SEQ ID NO: 67) | 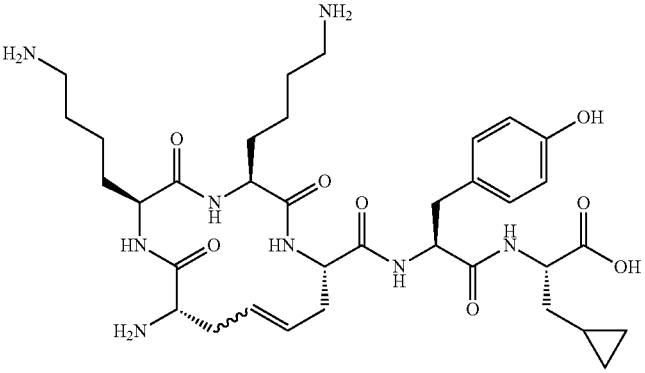 [SMILES: NCCCC[C@@H]1NC(=O)[C@H](CCCCN)NC(=O)[C@@H](N)CC=CC[C@@H](C(=O)N[C@@H](Cc2ccc(O)cc2)C(=O)N[C@@H](CC2CC2)C(=O)O)NC1=O] Chemical Formula $C_{35}H_{54}N_8O_8$<br>Molecular Weight 714.87 |
| 66. c[G(All)KKG(All)]YA(cyclobutyl) (SEQ ID NO: 68) | 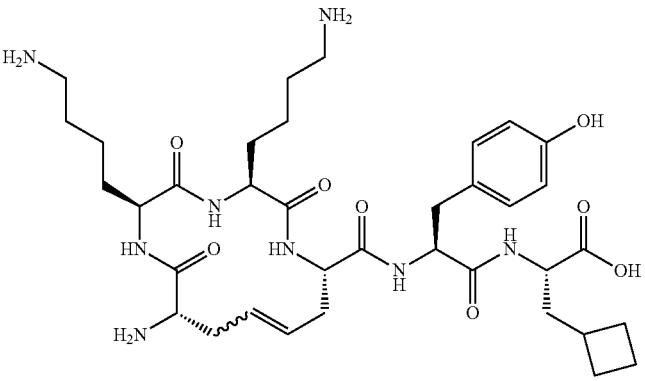 [SMILES: NCCCC[C@@H]1NC(=O)[C@H](CCCCN)NC(=O)[C@@H](N)CC=CC[C@@H](C(=O)N[C@@H](Cc2ccc(O)cc2)C(=O)N[C@@H](CC2CCC2)C(=O)O)NC1=O] Chemical Formula $C_{36}H_{56}N_8O_8$<br>Molecular Weight 728.89 |
| 67. c[G(All)KKG(All)]YA(cyclopentyl) (SEQ ID NO: 69) | 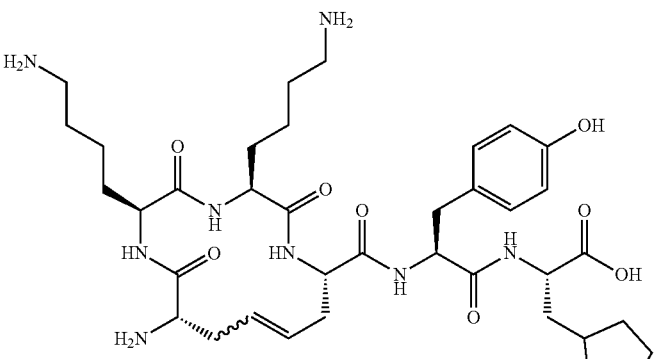 Chemical Formula $C_{37}H_{58}N_8O_8$<br>Molecular Weight 742.92 |

TABLE I-continued
structures of compounds
| Code | Structure |
|---|---|
| 68. c[G(All)KKG(All)]YA(cycloheptyl) (SEQ ID NO: 70) | 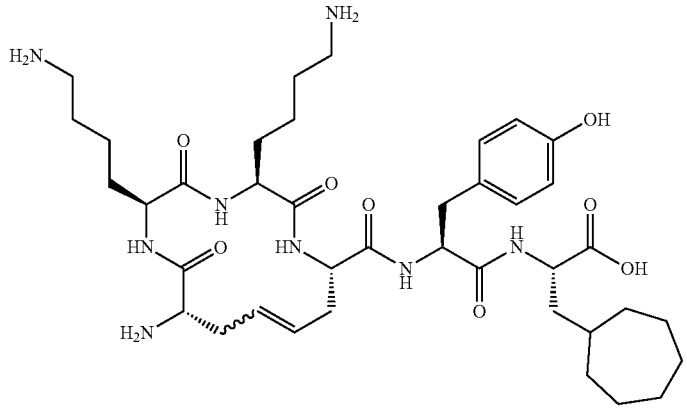 [SMILES: NCCCC[C@@H]1NC(=O)[C@H](CCCCN)NC(=O)[C@@H](N)CC=CC[C@@H](C(=O)N[C@@H](Cc2ccc(O)cc2)C(=O)N[C@@H](CC2CCCCCC2)C(=O)O)NC1=O]<br>Chemical Formula $C_{39}H_{62}N_8O_8$<br>Molecular Weight 770.97 |
| 69. c[G(All)KKG(All)]YG(N-isobutyl) (SEQ ID NO: 71) | 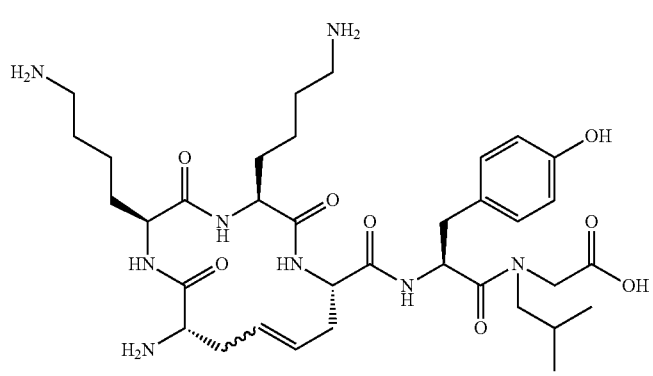 [SMILES: CC(C)CN(CC(=O)O)C(=O)[C@H](Cc1ccc(O)cc1)NC(=O)[C@@H]1CC=CC[C@H](N)C(=O)N[C@@H](CCCCN)C(=O)N[C@@H](CCCCN)C(=O)N1]<br>Chemical Formula $C_{35}H_{56}N_8O_8$<br>Molecular Weight 716.88 |
| 70. c[G(All)KKG(All)]G(N-(4-hydroxy)benzyl)L (SEQ ID NO: 72) | 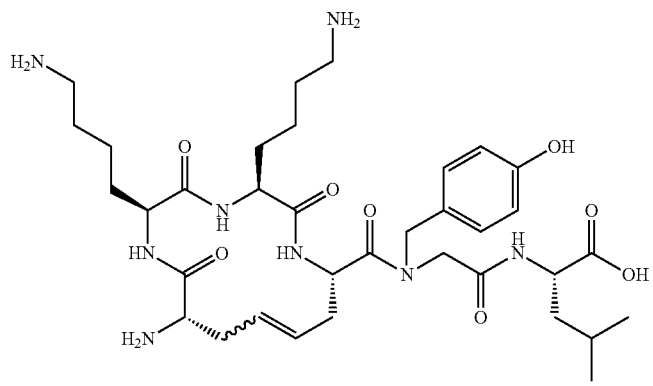 [SMILES: CC(C)C[C@H](NC(=O)CN(Cc1ccc(O)cc1)C(=O)[C@@H]1CC=CC[C@H](N)C(=O)N[C@@H](CCCCN)C(=O)N[C@@H](CCCCN)C(=O)N1)C(=O)O]<br>Chemical Formula $C_{35}H_{56}N_8O_8$<br>Molecular Weight 716.88 |

TABLE I-continued
structures of compounds
| Code | Structure |
|---|---|
| 71. c[G(All)KKG(All)]G(N-(4-hydroxybenzyl))G(N-isobutyl) (SEQ ID NO: 73) | 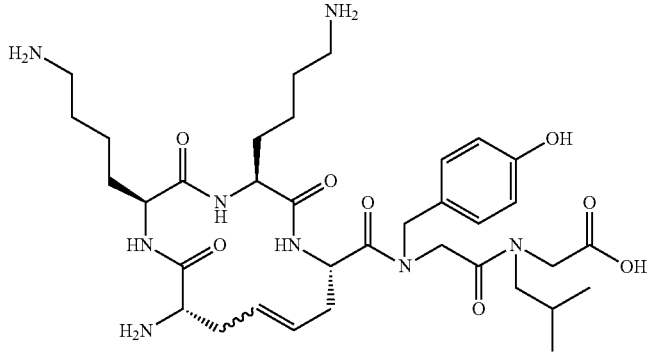 [SMILES: CC(C)CN(CC(=O)O)C(=O)CN(Cc1ccc(O)cc1)C(=O)[C@@H]1CC=CC[C@H](N)C(=O)N[C@@H](CCCCN)C(=O)N[C@@H](CCCCN)C(=O)N1]<br>Chemical Formula $C_{35}H_{56}N_8O_8$<br>Molecular Weight 716.88 |
| 72. c[G(All)KK(NMe)G(All)]YL (SEQ ID NO: 74) | 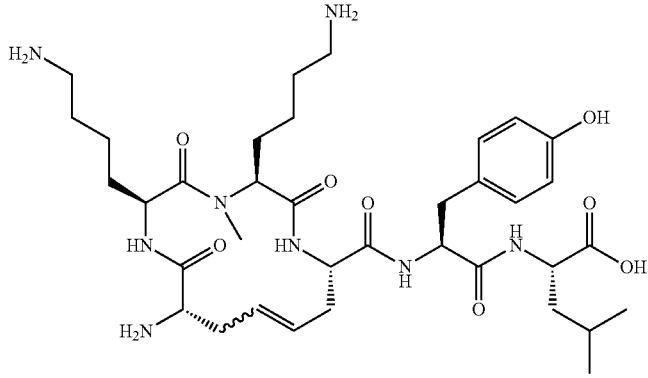 [SMILES: CC(C)C[C@H](NC(=O)[C@H](Cc1ccc(O)cc1)NC(=O)[C@@H]1CC=CC[C@H](N)C(=O)N[C@@H](CCCCN)C(=O)N(C)[C@@H](CCCCN)C(=O)N1)C(=O)O]<br>Chemical Formula $C_{36}H_{58}N_8O_8$<br>Molecular Weight 730.91 |
| 73. c[G(All)K(NMe)KG(All)]YL (SEQ ID NO: 75) | 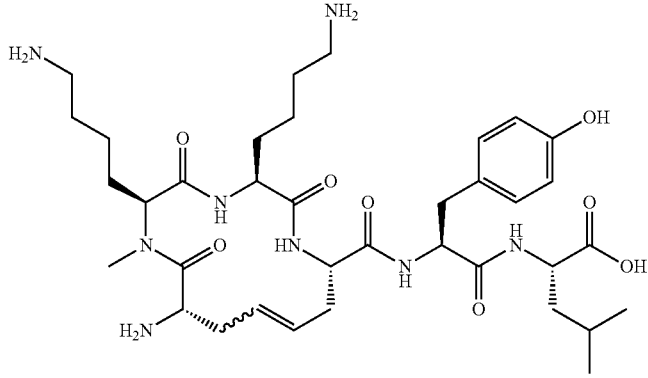 [SMILES: CC(C)C[C@H](NC(=O)[C@H](Cc1ccc(O)cc1)NC(=O)[C@@H]1CC=CC[C@H](N)C(=O)N(C)[C@@H](CCCCN)C(=O)N[C@@H](CCCCN)C(=O)N1)C(=O)O]<br>Chemical Formula $C_{36}H_{58}N_8O_8$<br>Molecular Weight 730.91 |

TABLE I-continued
structures of compounds
| Code | Structure |
|---|---|
| 74. c[G(All)K(NMe)K(NMe)G(All)]YL (SEQ ID NO: 76) | 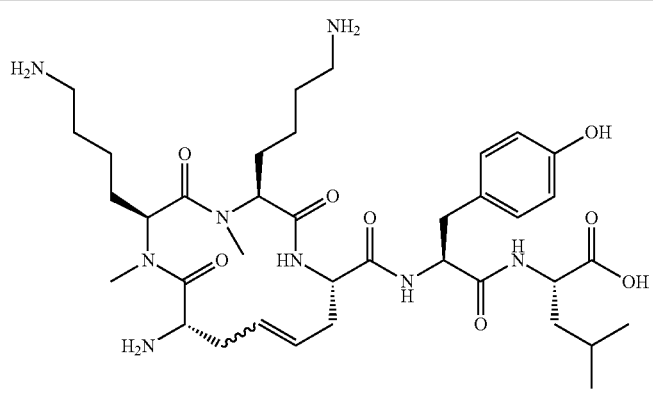<br>Chemical Formula $C_{37}H_{60}N_8O_8$<br>Molecular Weight 744.93 |
| 75. c[G(All)KKG(All)]Y(OMe)L (SEQ ID NO: 77) | 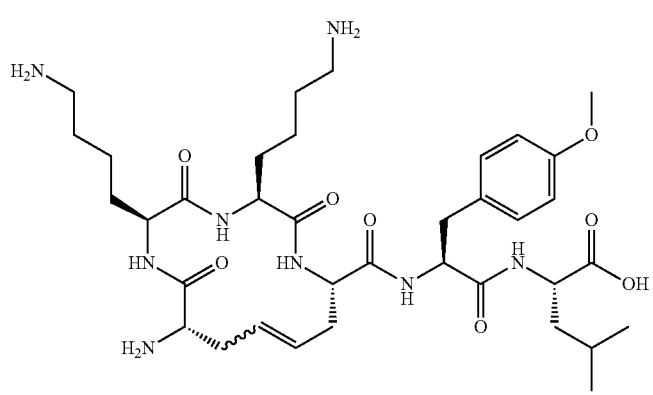 [SMILES: COc1ccc(C[C@H](NC(=O)[C@@H]2CC=CC[C@H](N)C(=O)N[C@@H](CCCCN)C(=O)N[C@@H](CCCCN)C(=O)N2)C(=O)N[C@@H](CC(C)C)C(=O)O)cc1]<br>Chemical Formula $C_{36}H_{58}N_8O_8$<br>Molecular Weight 730.91 |
| 76. c[G(All)KKG(All)FL (SEQ ID NO: 78) | 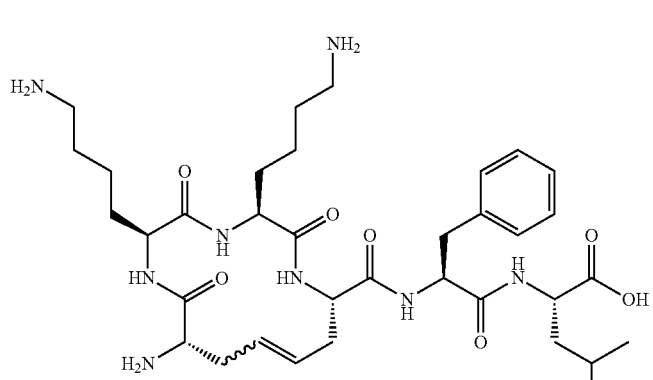<br>Chemical Formula $C_{35}H_{56}N_8O_7$<br>Molecular Weight 700.88 |

TABLE I-continued
structures of compounds
| Code | Structure |
|---|---|
| 77. c[G(All)KKG(All)]F(4-fluoro)L (SEQ ID NO: 79) | 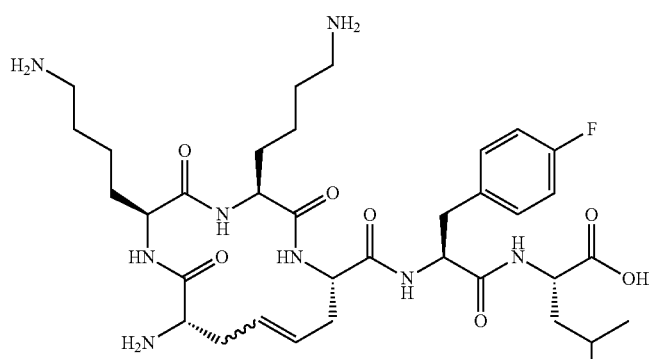<br>Chemical Formula $C_{35}H_{55}FN_8O_7$<br>Molecular Weight 718.87 |
| 78. c[G(All)KKG(All)]F(4-iodo)L (SEQ ID NO: 80) | 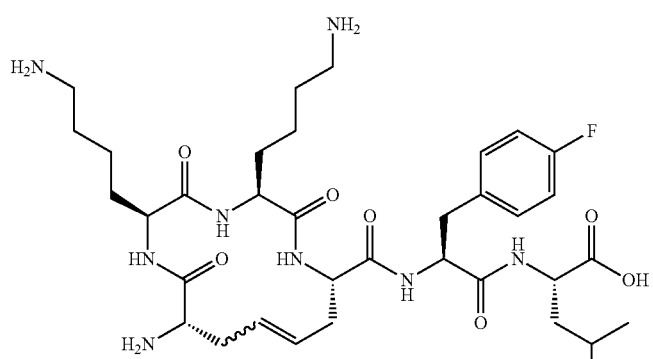<br>Chemical Formula $C_{35}H_{55}IN_8O_7$<br>Molecular Weight 826.78 |
| 79. c[G(All)OrnKG(All)]YL (SEQ ID NO: 81) | 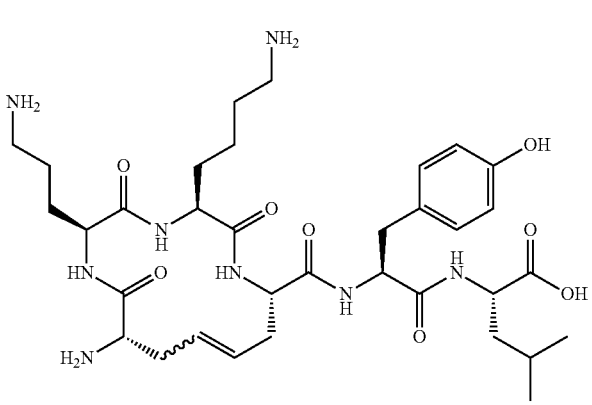<br>Chemical Formula $C_{34}H_{54}N_8O_8$<br>Molecular Weight 702.85 |

TABLE I-continued
structures of compounds
| Code | Structure |
|---|---|
| 80. c[G(All)DabKG(All)]YL (SEQ ID NO: 82) | 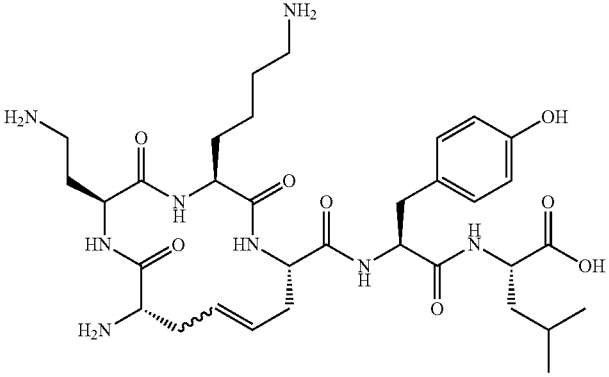 Chemical Formula $C_{33}H_{52}N_8O_8$<br>Molecular Weight 688.83 |
| 81. c[G(All)DapKG(All)]YL (SEQ ID NO: 83) | 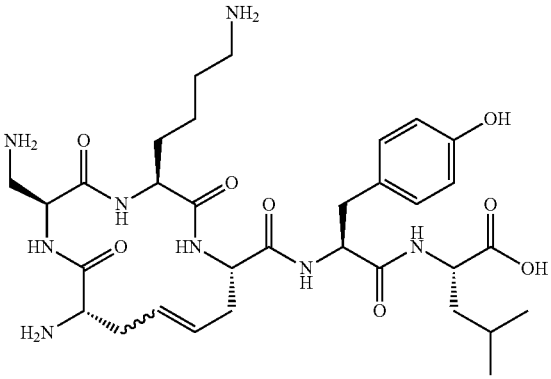 Chemical Formula $C_{32}H_{50}N_8O_8$<br>Molecular Weight 674.80 |
| 82. c[G(All)K*KG(All)]YL (SEQ ID NO: 84) | 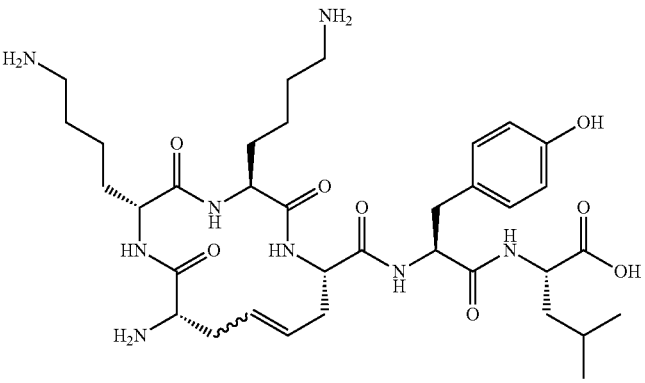 Chemical Formula $C_{35}H_{56}N_8O_8$<br>Molecular Weight 716.88 |

TABLE I-continued
structures of compounds
| Code | Structure |
|---|---|
| 83. c[G(All)HKG(All)]YL (SEQ ID NO: 85) (stereoisomer of compound 84) | 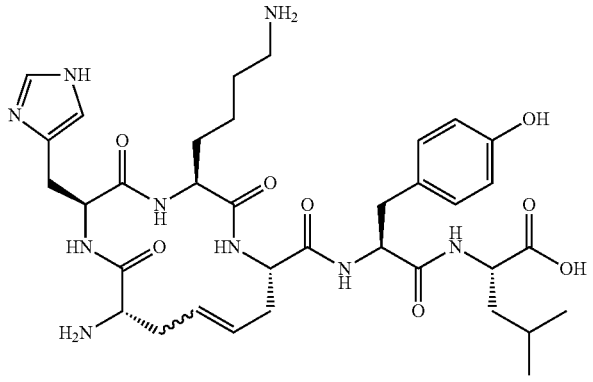 Chemical Formula $C_{35}H_{51}N_9O_8$ Molecular Weight 725.85 |
| 84. c[G(All)H*KG(All)]YL (SEQ ID NO: 86) (stereoisomer of compound 83) | 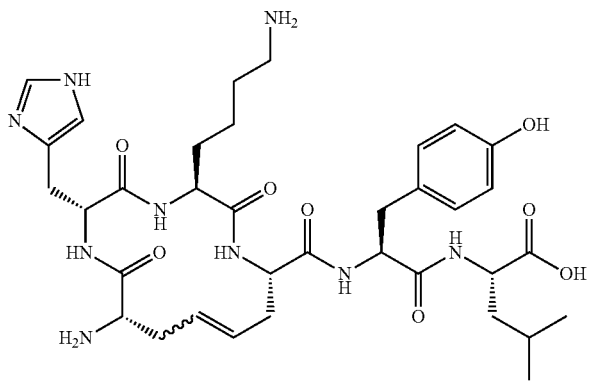 Chemical Formula $C_{35}H_{51}N_9O_8$ Molecular Weight 725.85 |
| 85. c[G(All)NleKG(All)]YL (SEQ ID NO: 87) | 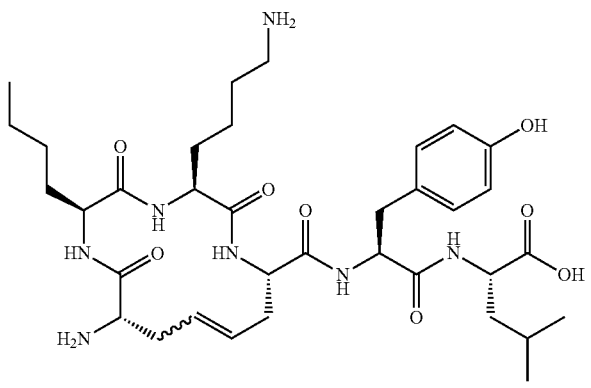 Chemical Formula $C_{35}H_{55}N_7O_8$ Molecular Weight 701.87 |

TABLE I-continued
structures of compounds
| Code | Structure |
|---|---|
| 86. c[G(All)NvaKG(All)]YL (SEQ ID NO: 88) | 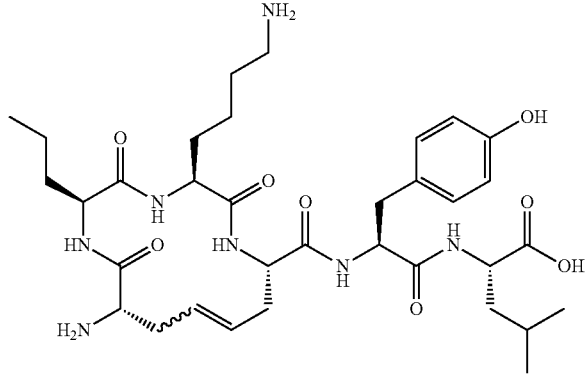<br>Chemical Formula $C_{34}H_{53}N_7O_8$<br>Molecular Weight 687.84 |
| 87. c[G(All)GKG(All)]YL (SEQ ID NO: 89) | 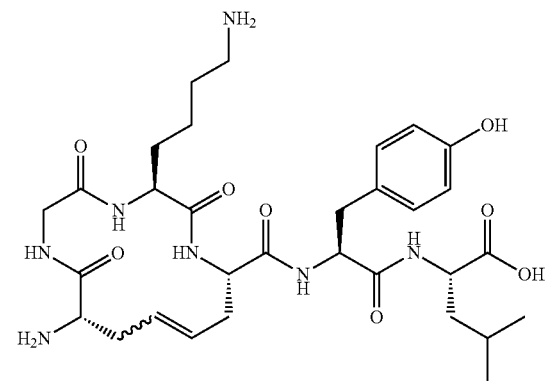<br>Chemical Formula $C_{31}H_{47}N_7O_8$<br>Molecular Weight 645.76 |
| 88. c[G(All)EKG(All)]YL (SEQ ID NO: 90) | 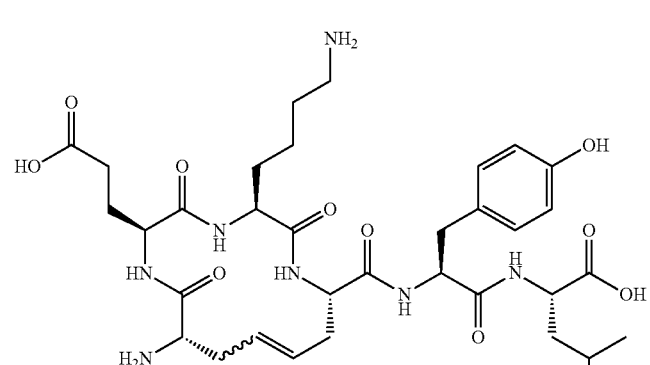<br>Chemical Formula $C_{34}H_{51}N_7O_{10}$<br>Molecular Weight 717.82 |

TABLE I-continued structures of compounds

| Code | Structure |
|---|---|
| 89. c[G(alpha-Me-(4-Pentenyl))KKG(All)]YL (SEQ ID NO: 91) (diastereoisomer of compound 90) | 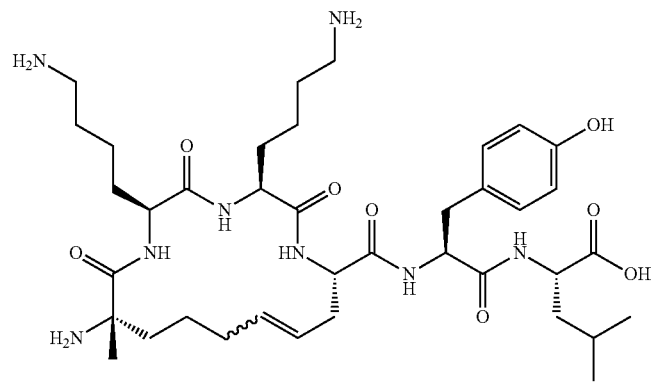<br>Chemical Formula $C_{38}H_{62}N_8O_8$<br>Molecular Weight 758.96 |
| 90. c[G*(alpha-Me-(4-Pentenyl))KKG(All)]YL (SEQ ID NO: 92) (diastereoisomer of compound 89) | 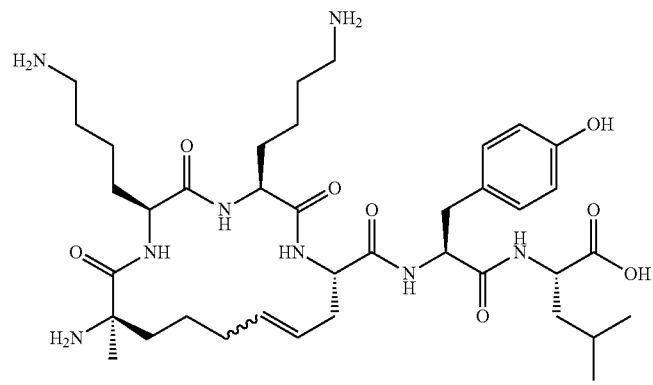<br>Chemical Formula $C_{38}H_{62}N_8O_8$<br>Molecular Weight 758.96 |
| 91. c[G(All)KKG(alpha-Me-(4-Pentenyl))]YL (SEQ ID NO: 93) | 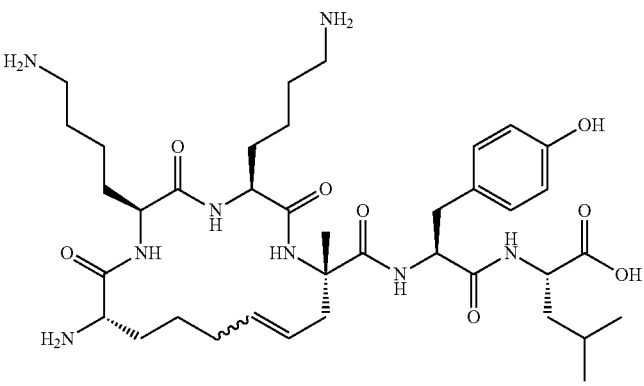<br>Chemical Formula $C_{38}H_{62}N_8O_8$<br>Molecular Weight 758.96 |

TABLE I-continued
structures of compounds
| Code | Structure |
|---|---|
| 92. c[G(All)KKG*(alpha-Me-(4-Pentenyl))]YL (SEQ ID NO: 94) | 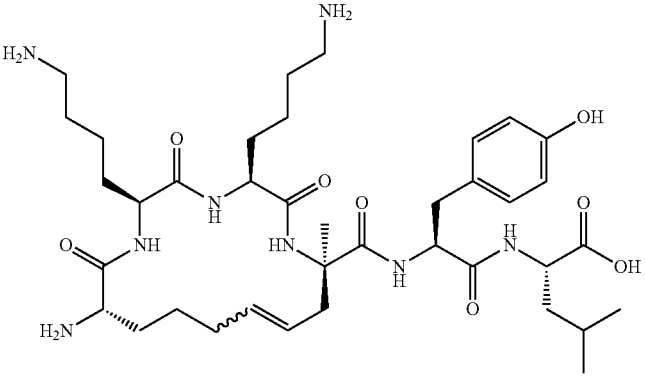<br>Chemical Formula C$_{38}$H$_{62}$N$_8$O$_8$<br>Molecular Weight 758.96 |
| 93. c[G(alpha-Me-(4-Pentenyl))KKG*(alpha-Me(4-Pentenyl))]YL (SEQ ID NO: 95) | 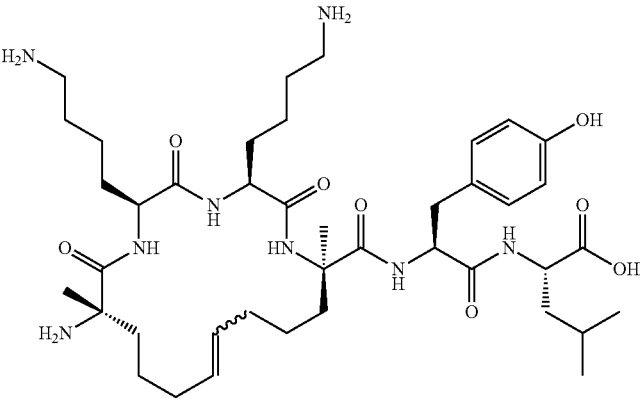<br>Chemical Formula C$_{41}$H$_{68}$N$_8$O$_8$<br>Molecular Weight 801.04 |
| 94. c[DapKKD]YL (SEQ ID NO: 96) | 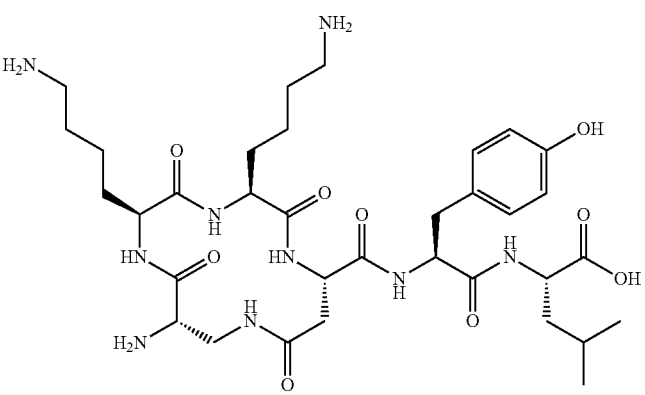<br>Chemical Formula: C$_{34}$H$_{55}$N$_9$O$_9$<br>Molecular Weight: 733.87 |

TABLE I-continued structures of compounds

| Code | Structure |
|---|---|
| 95. c[DabKKD]YL (SEQ ID NO: 97) | Chemical Formula: $C_{35}H_{57}N_9O_9$<br>Molecular Weight: 747.89 |
| 96. c[OrnKKD]YL (SEQ ID NO: 98) | Chemical Formula: $C_{36}H_{59}N_9O_9$<br>Molecular Weight: 761.92 |
| 97. c[KKKD]YL (SEQ ID NO: 99) | Chemical Formula: $C_{37}H_{61}N_9O_9$<br>Molecular Weight: 775.95 |

TABLE I-continued
structures of compounds
| Code | Structure |
|---|---|
| 98. c[DapKKE]YL (SEQ ID NO: 100) | 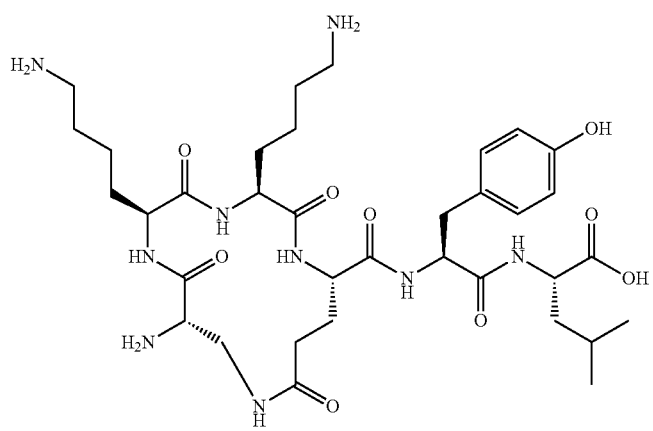 Chemical Formula: $C_{35}H_{57}N_9O_9$<br>Molecular Weight: 747.89 |
| 99. c[DabKKE]YL (SEQ ID NO: 101) | 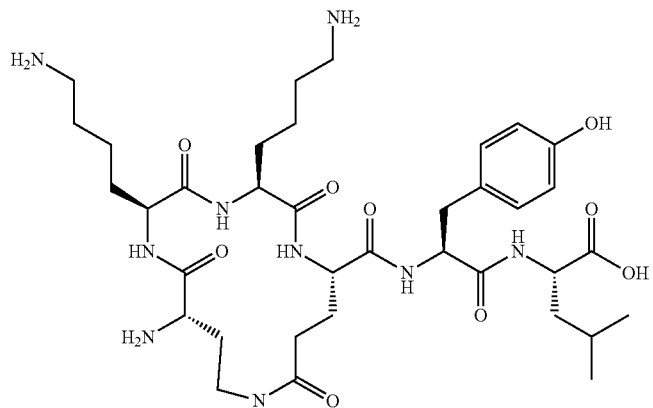 Chemical Formula: $C_{36}H_{59}N_9O_9$<br>Molecular Weight: 761.92 |
| 100. c[OrnKKE]YL (SEQ ID NO: 102) | 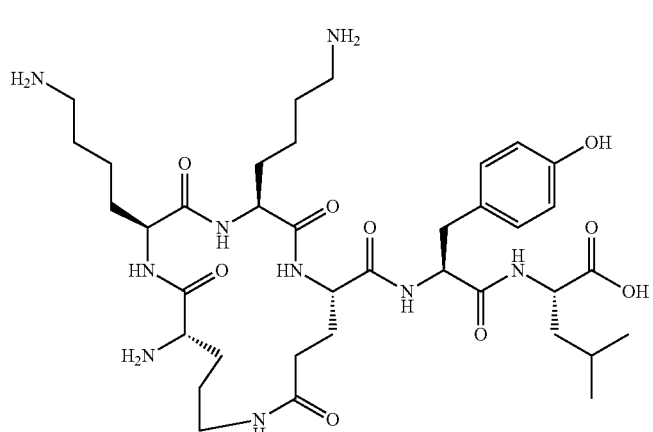 Chemical Formula: $C_{37}H_{61}N_9O_9$<br>Molecular Weight: 775.95 |

TABLE I-continued
structures of compounds
| Code | Structure |
|---|---|
| 101. c[KKKE]YL (SEQ ID NO: 103) | 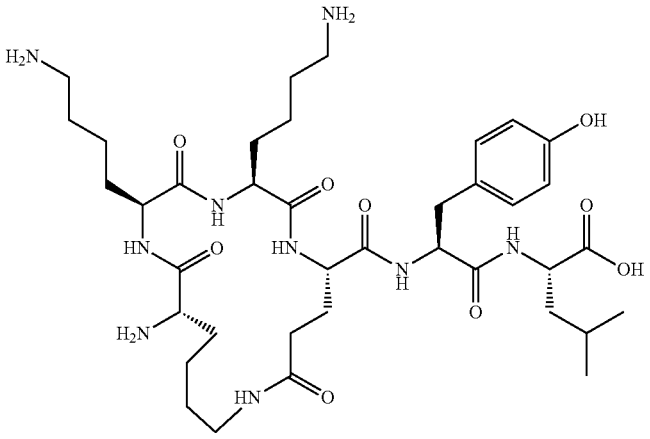<br>Chemical Formula: $C_{38}H_{63}N_9O_9$<br>Molecular Weight: 789.98 |
| 102. c[EKKDap]YL (SEQ ID NO: 104) | 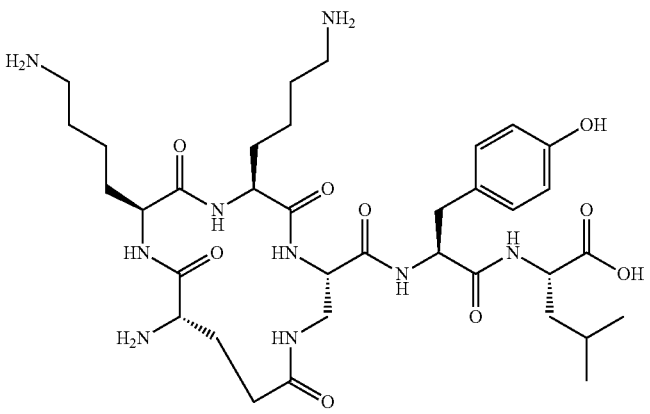<br>Chemical Formula: $C_{35}H_{57}N_9O_9$<br>Molecular Weight: 747.89 |
| 103. c[DKKDap]YL (SEQ ID NO: 105) | 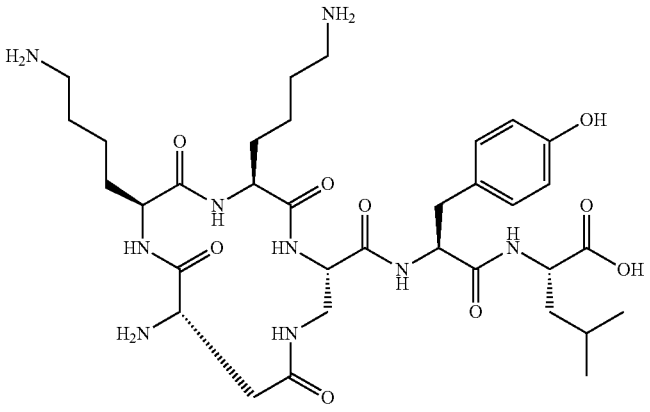<br>Chemical Formula: $C_{34}H_{55}N_9O_9$<br>Molecular Weight: 733.87 |

TABLE I-continued
structures of compounds
| Code | Structure |
|---|---|
| 104. c[EKKDab]YL (SEQ ID NO: 106) | 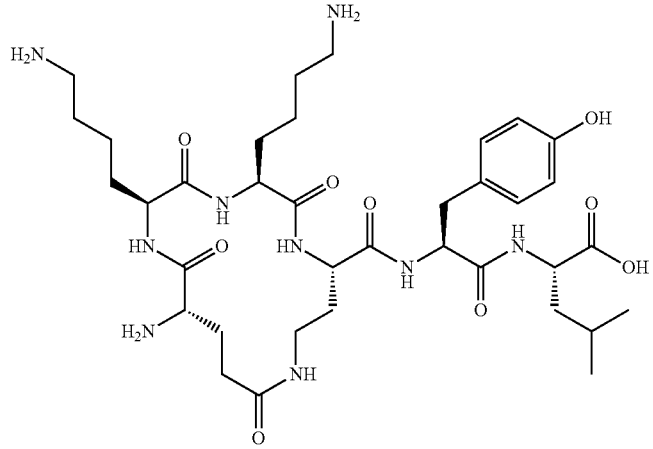<br>Chemical Formula: $C_{36}H_{59}N_9O_9$<br>Molecular Weight: 761.92 |
| 105. c[DKKDab]YL (SEQ ID NO: 107) | 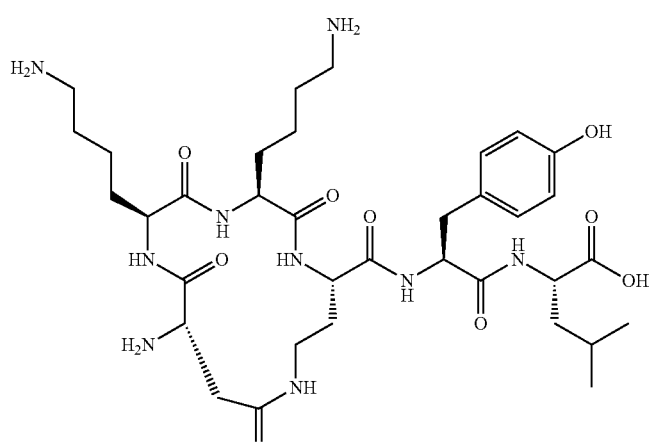<br>Chemical Formula: $C_{35}H_{57}N_9O_9$<br>Molecular Weight: 747.89 |
| 106. c[EKKOrn]YL (SEQ ID NO: 108) | 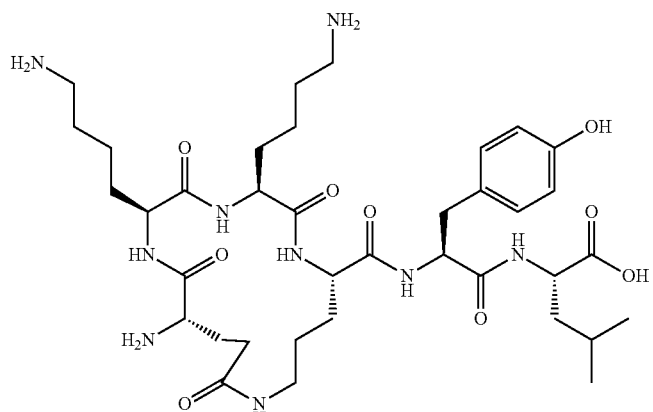<br>Chemical Formula: $C_{37}H_{61}N_9O_9$<br>Molecular Weight: 775.95 |

TABLE I-continued
structures of compounds
| Code | Structure |
|---|---|
| 107. c[DKKOrn]YL (SEQ ID NO: 109) | 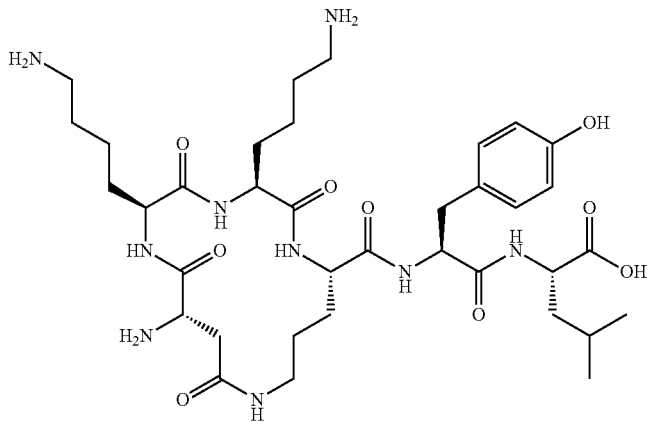  Chemical Formula: $C_{36}H_{59}N_9O_9$<br>Molecular Weight: 761.92 |
| 108. c[EKKK]YL (SEQ ID NO: 110) | 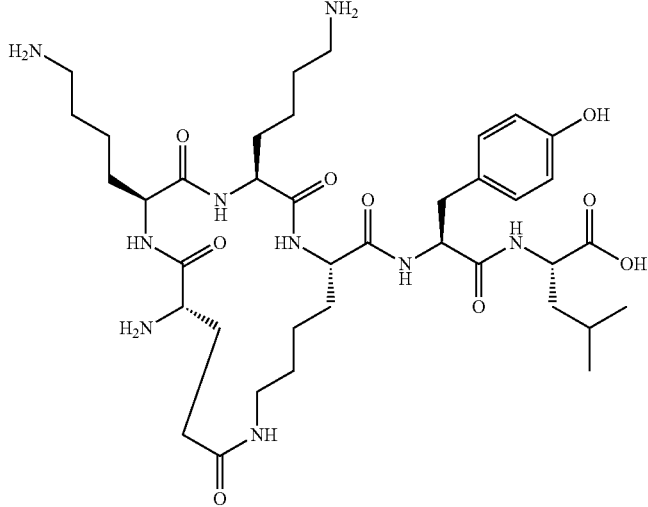  Chemical Formula: $C_{38}H_{63}N_9O_9$<br>Molecular Weight: 789.98 |

TABLE I-continued
structures of compounds
| Code | Structure |
|---|---|
| 109.<br>c[DKKK]YL<br>(SEQ ID NO: 111) | 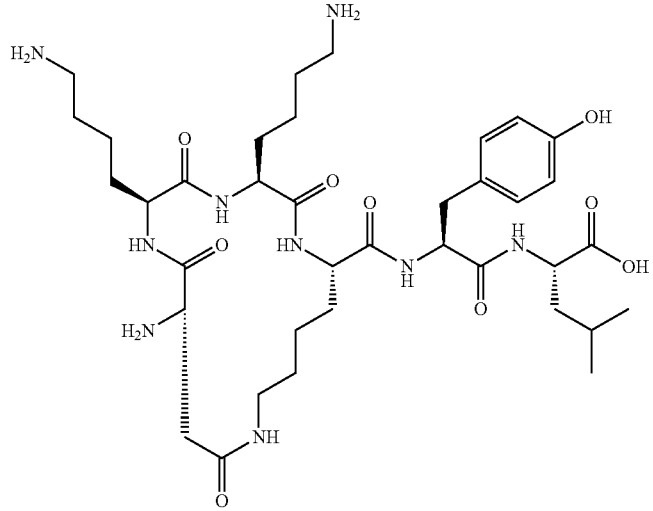<br>Chemical Formula: $C_{37}H_{61}N_9O_9$<br>Molecular Weight: 775.95 |
| 110.<br>c[G(All)KKG(All)]F(4-tbu)L<br>(SEQ ID NO: 112) | 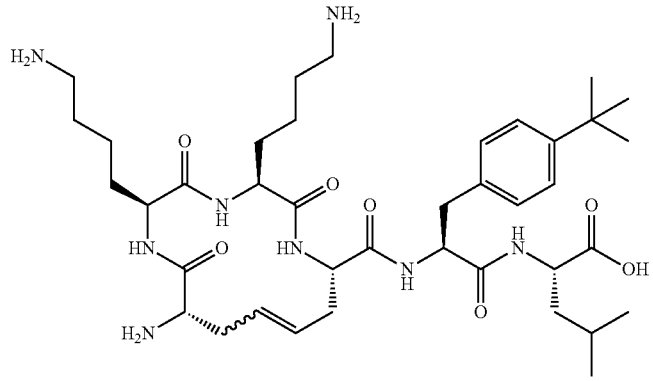<br>Chemical Formula: $C_{39}H_{64}N_8O_7$<br>Molecular Weight: 756.99 |
| 111.<br>c[G(All)KKG(All)]F(4-CF$_3$)L<br>(SEQ ID NO: 113) | 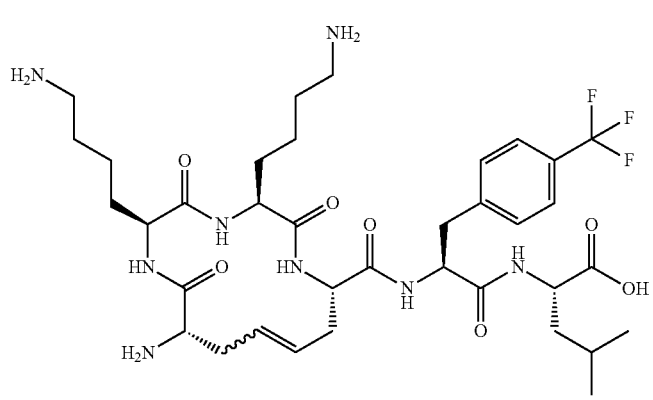<br>Chemical Formula: $C_{36}H_{55}F_3N_8O_7$<br>Molecular Weight: 768.88 |

TABLE I-continued
structures of compounds
| Code | Structure |
|------|-----------|
| 112. c[G(All)KKG(All)]A(naphtyl)L (SEQ ID NO: 114) | 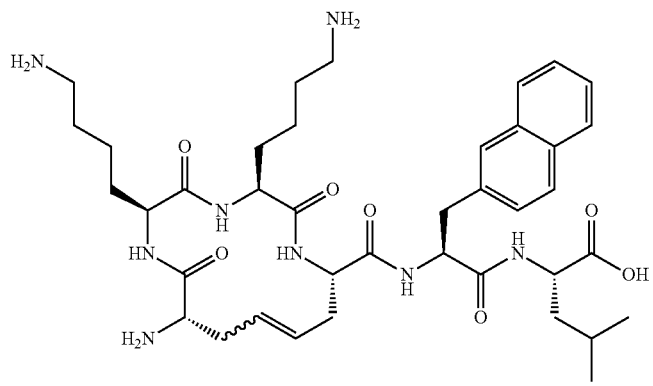<br>Chemical Formula: $C_{39}H_{58}N_8O_7$<br>Molecular Weight: 750.94 |
| 113. c[G(All)KKG(All)]F(3-chloro)L (SEQ ID NO: 115) | 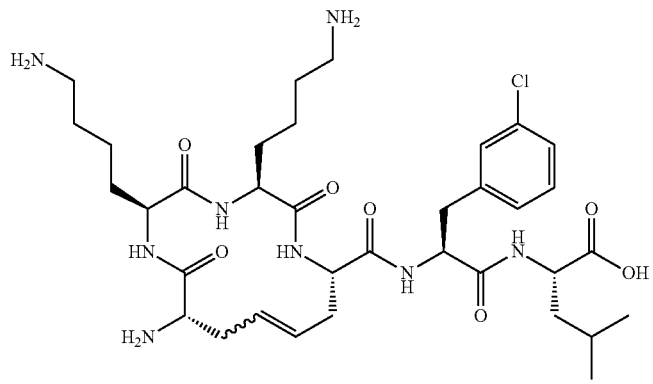<br>Chemical Formula: $C_{35}H_{55}ClN_8O_7$<br>Molecular Weight: 735.32 |
| 114. c[G(All)KKG(All)]F(4-chloro)L (SEQ ID NO: 116) | 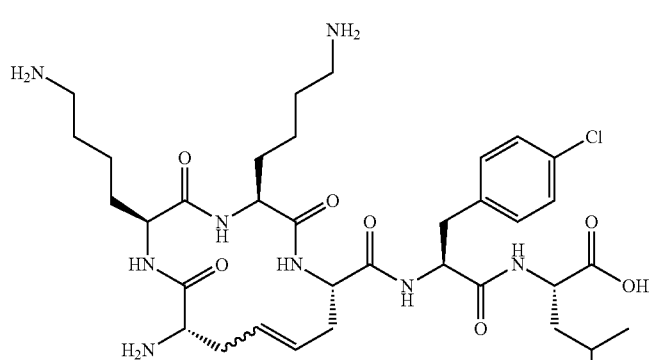<br>Chemical Formula: $C_{35}H_{55}ClN_8O_7$<br>Molecular Weight: 735.32 |

TABLE I-continued
structures of compounds
| Code | Structure |
|---|---|
| 115. c[G(All)KKG(All)]F(3-bromo)L (SEQ ID NO: 117) | 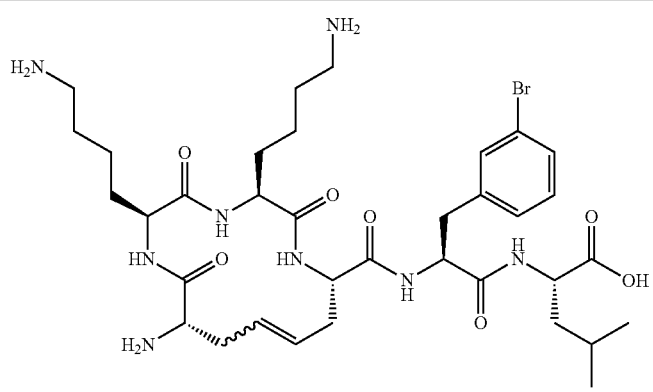<br>Chemical Formula: $C_{35}H_{55}BrN_8O_7$<br>Molecular Weight: 779.78 |
| 116. c[G(All)KKG(All)]F(4-bromo)L (SEQ ID NO: 118) | 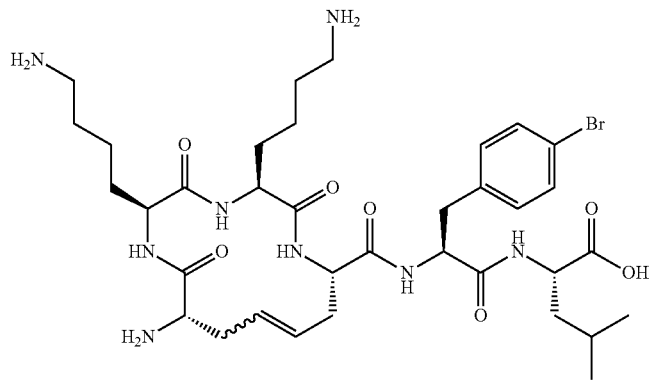<br>Chemical Formula: $C_{35}H_{55}BrN_8O_7$<br>Molecular Weight: 779.78 |
| 117. c[G(All)KKG(All)]F(3-iodo)L (SEQ ID NO: 119) | 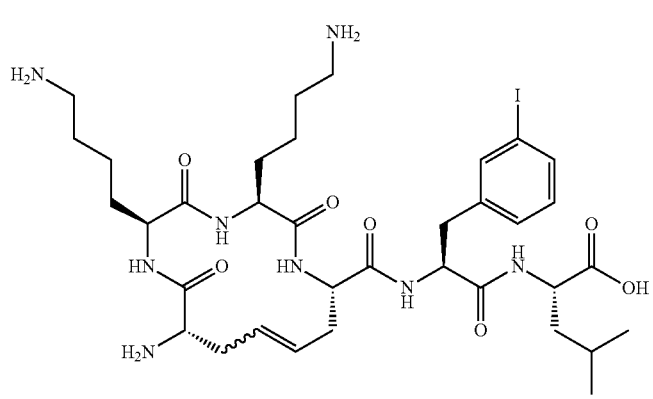<br>Chemical Formula: $C_{35}H_{55}IN_8O_7$<br>Molecular Weight: 826.78 |

TABLE I-continued
structures of compounds
| Code | Structure |
|---|---|
| 118. c[G(All)KKG(All)]F(4-cyano)L (SEQ ID NO: 120) | 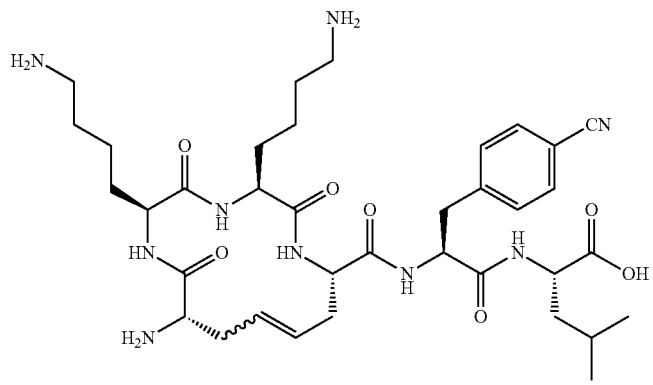<br>Chemical Formula: $C_{36}H_{55}N_9O_7$<br>Molecular Weight: 725.89 |
| 119. c[G(All)KKG(All)](Ch)L (SEQ ID NO: 121) | 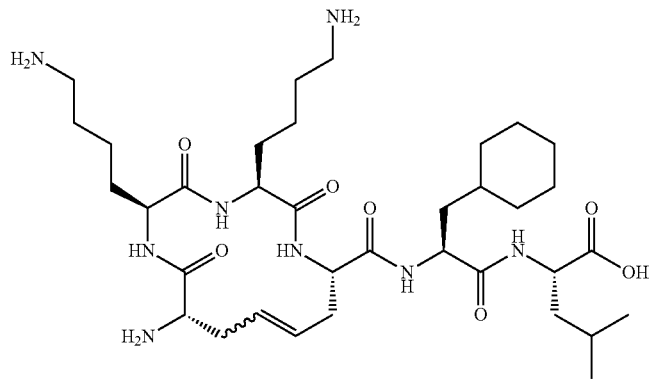<br>Chemical Formula: $C_{35}H_{62}N_8O_7$<br>Molecular Weight: 706.93 |
| 120. c[G(All)KKG(All)]A(2-furyl)L (SEQ ID NO: 122) | 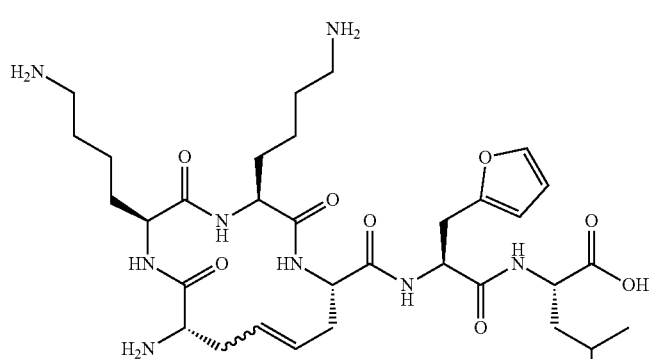<br>Chemical Formula: $C_{33}H_{54}N_8O_8$<br>Molecular Weight: 690.84 |

TABLE I-continued structures of compounds

| Code | Structure |
|---|---|
| 121. c[G(All)KKG(All)]F(4-amino)L (SEQ ID NO: 123) | Chemical Formula: $C_{35}H_{57}N_9O_7$<br>Molecular Weight: 715.90 |
| 122. c[G(All)KKG(All)]F(4-nitro)L (SEQ ID NO: 124) | Chemical Formula: $C_{35}H_{55}N_9O_9$<br>Molecular Weight: 745.88 |
| 123. c[G(All)KKG(All)]F(4-Me)L (SEQ ID NO: 125) | Chemical Formula: $C_{36}H_{58}N_8O_7$<br>Molecular Weight: 714.91 |

TABLE I-continued
structures of compounds
| Code | Structure |
|---|---|
| 124. c[G(All)KKG(All)]F(2,3,4,5,6-pentafluoro)L (SEQ ID NO: 126) | 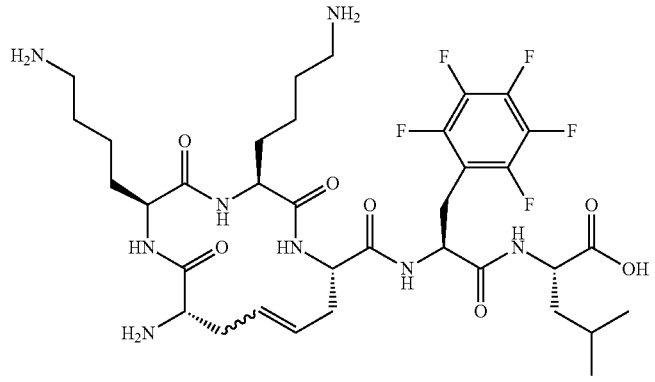 Chemical Formula C$_{35}$H$_{51}$F$_5$N$_8$O$_7$ Molecular Weight 790.83 |
| 125. c[G(All)KKG(All)] hydroxyphenyl)L (SEQ ID NO: 127) | 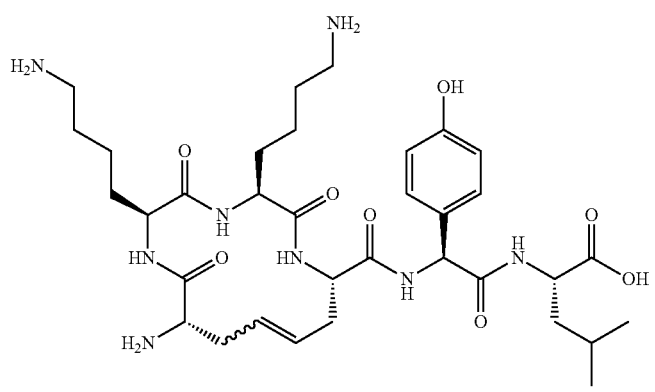 Chemical Formula C$_{34}$H$_{54}$N$_8$O$_8$ Molecular Weight 702.85 |
| 126. c[G(All)KKG(All)]homoYL (SEQ ID NO: 128) | 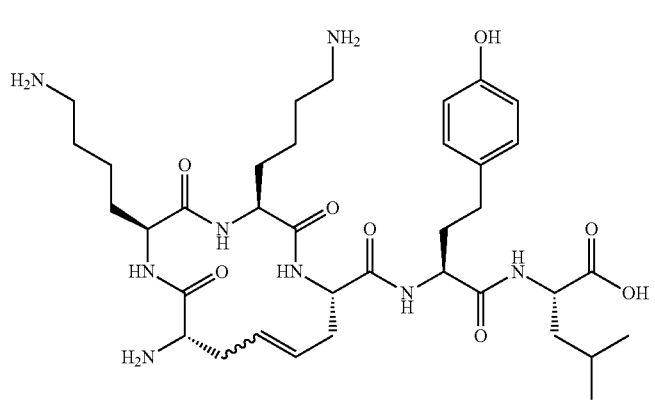 Chemical Formula C$_{36}$H$_{58}$N$_8$O$_8$ Molecular Weight 730.91 |

TABLE I-continued
structures of compounds
| Code | Structure |
|---|---|
| 127. c[G(All)KKG(All)]F(4-bromo)A(cyclopentyl) (SEQ ID NO: 129) | 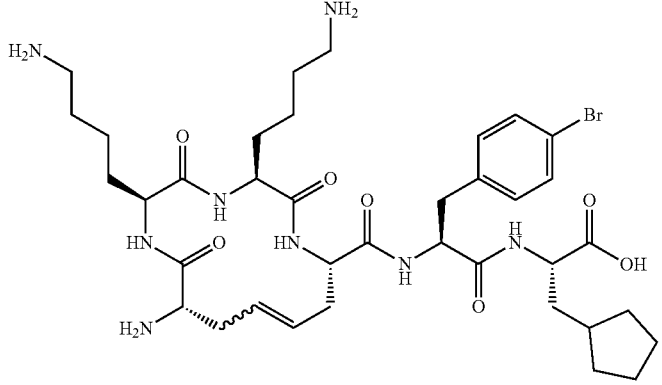<br>Chemical Formula $C_{37}H_{57}BrN_8O_7$<br>Molecular Weight 805.82 |
| 128. c[G(All)KKG((S)-alpha-Me-(4-pentenyl))]YA(cyclopentyl) (SEQ ID NO: 130) | 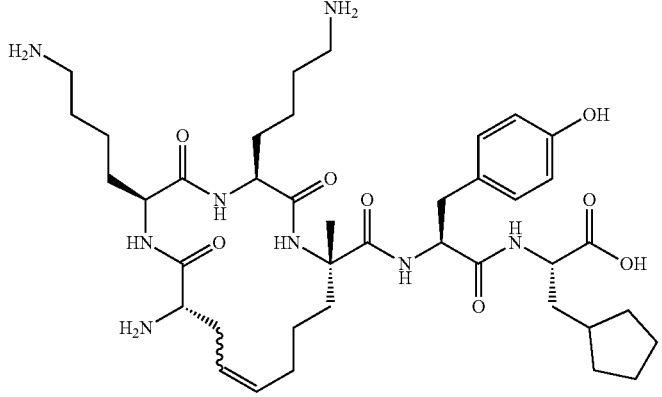<br>Chemical Formula $C_{40}H_{64}BrN_8O_8$<br>Molecular WeighT 785.00 |
| 129. c[pK(pentenoyl)KG(All)]YA(cyclopentyl) (SEQ ID NO: 131) | 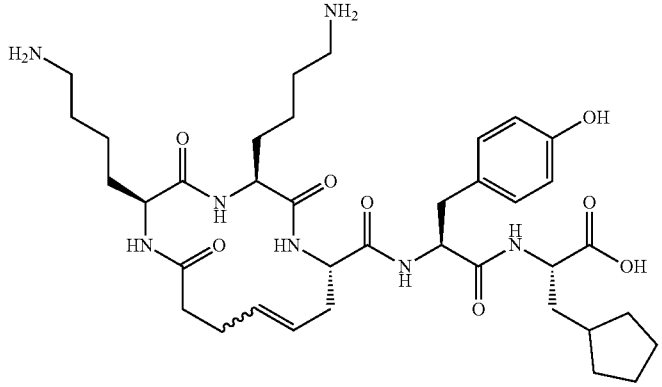<br>Chemical Formula $C_{37}H_{57}N_7O_8$<br>Molecular Weight 727.90 |

TABLE I-continued
structures of compounds
| Code | Structure |
|---|---|
| 130. c[G(All)KKG(alpha-Me-(4-pentenyl))]F(4-bromo)L (SEQ ID NO: 132) | 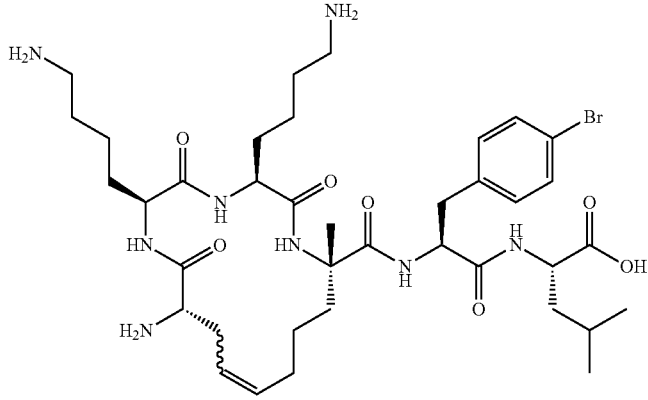<br>Chemical Formula $C_{38}H_{61}BrN_8O_7$<br>Molecular Weight 821.86 |
| 131. c[K(pentenoyl)KG(All)](4-bromo)L (SEQ ID NO: 133) | 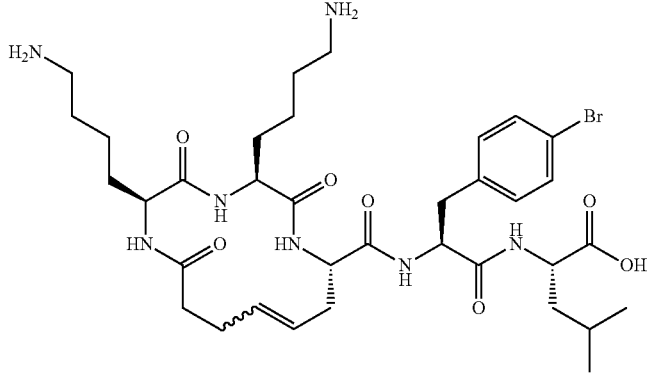<br>Chemical Formula $C_{35}H_{54}BrN_7O_7$<br>Molecular Weight 764.76 |
| 132. c[K(Pentenoyl)KG(alpha-Me-(4-pentenyl))]YL (SEQ ID NO: 134) | 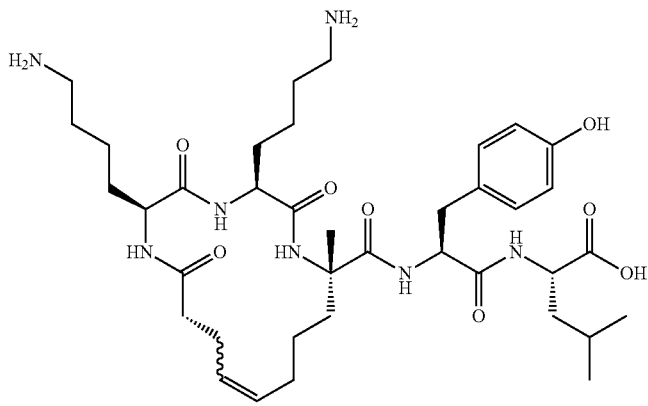<br>Chemical Formula $C_{38}H_{61}N_7O_8$<br>Molecular Weight 743.95 |

TABLE I-continued structures of compounds

| Code | Structure |
|---|---|
| 133. c[G(All)KKG(alpha-Me-(4-pentenyl))]F(4-bromo)A (cyclopentyl) (SEQ ID NO: 135) | 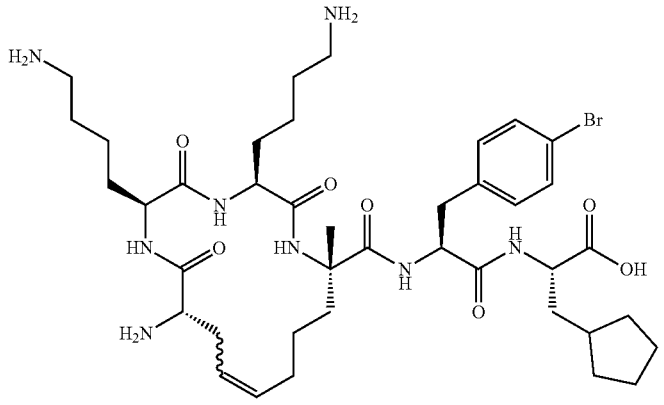<br>Chemical Formula $C_{40}H_{63}BrN_8O_7$<br>Molecular Weight 847.90 |
| 134. cK([Pentenoyl)KG(All)]F(4-bromo)A (cyclopentyl) (SEQ ID NO: 136) | 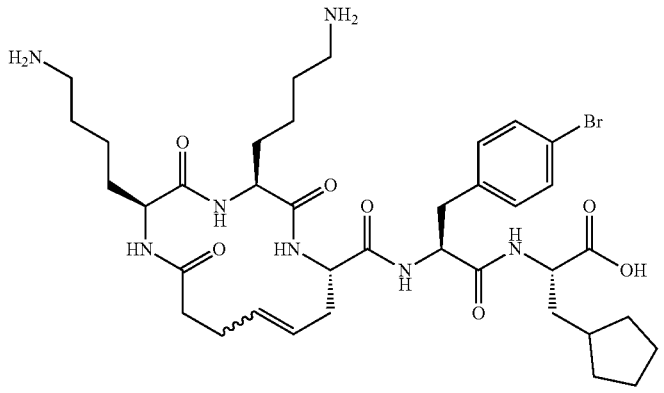<br>Chemical Formula $C_{37}H_{56}BrN_7O_7$<br>Molecular Weight: 790.80 |
| 135. c[K(Pentenoyl)KG(alpha-Me-(4-pentenyl))]YA(cyclopentyl) (SEQ ID NO: 137) | 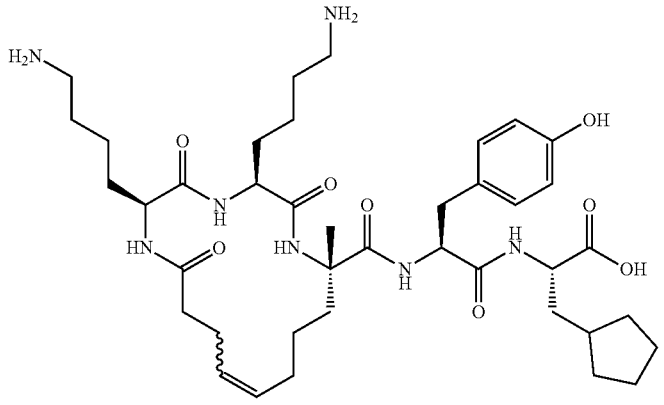<br>Chemical Formula $C_{40}H_{63}N_7O_8$<br>Molecular Weight 769.98 |

TABLE I-continued
structures of compounds
| Code | Structure |
|---|---|
| 136. c[PentenoylKKG(alpha-Me-(4-pentenyl))]F(4-bromo)L (SEQ ID NO: 138) | 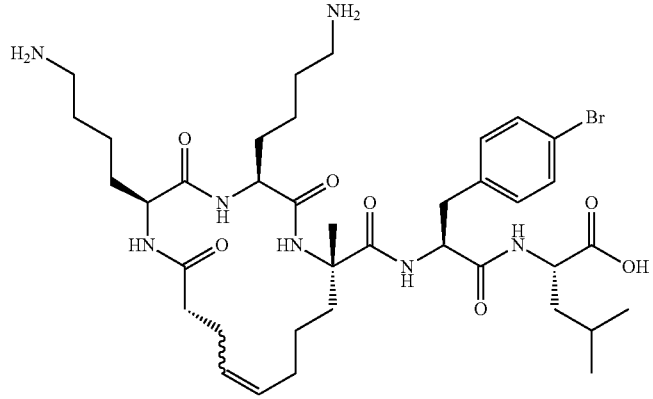<br>Chemical Formula $C_{38}H_{60}BrN_7O_7$<br>Molecular Weight 806.84 |
| 137. c[K(Pentenoyl)KG(alpha-Me-(4-pentenyl))]F(4-bromo)A (cyclopentyl) (SEQ ID NO: 139) | 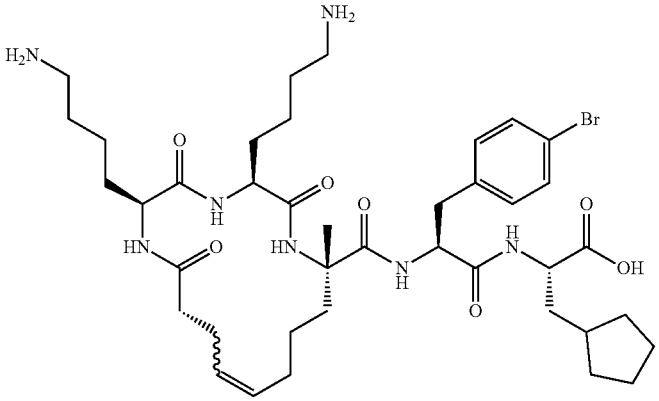<br>Chemical Formula $C_{40}H_{62}BrN_7O_7$<br>Molecular Weight 832.88 |
| 138. c[G(All)KKG(All)]AL (SEQ ID NO: 140) | 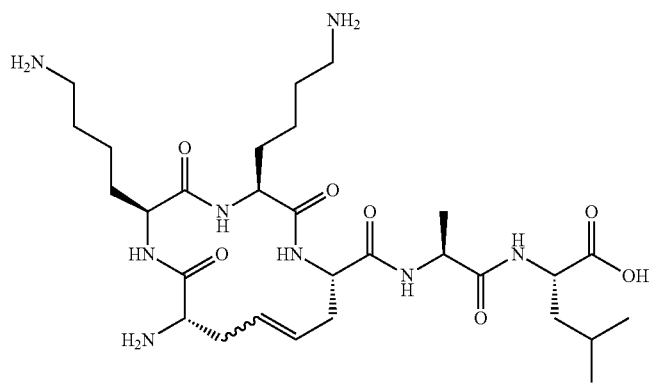<br>Chemical Formula $C_{29}H_{52}N_8O_7$<br>Molecular Weight 624.78 |

TABLE I-continued structures of compounds

| Code | Structure |
|------|-----------|
| 139. c[G(All)KKG(All)]A(biphenyl)L (SEQ ID NO: 141) | 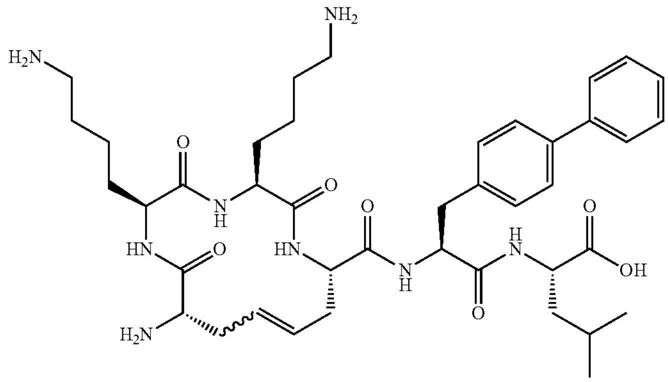 [SMILES: CC(C)C[C@H](NC(=O)[C@H](Cc1ccc(-c2ccccc2)cc1)NC(=O)[C@@H]1CC=CC[C@H](N)C(=O)N[C@@H](CCCCN)C(=O)N[C@@H](CCCCN)C(=O)N1)C(=O)O] |
| 140. c[G(All)KKG(All)]A(diphenyl)L (SEQ ID NO: 142) | 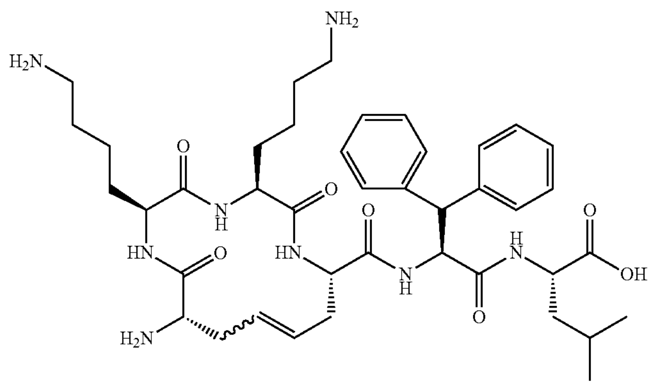 [SMILES: CC(C)C[C@H](NC(=O)[C@@H](NC(=O)[C@@H]1CC=CC[C@H](N)C(=O)N[C@@H](CCCCN)C(=O)N[C@@H](CCCCN)C(=O)N1)C(c1ccccc1)c1ccccc1)C(=O)O] |
| 141. c[G(All)KKG(All)]Y*L* (SEQ ID NO: 143) (diastereoisomer of compounds 21, 34, 38, 40, 41, 42, 54 and 145) | Chemical Formula $C_{35}H_{56}N_8O_8$ <br> Molecular Weight 716.88 |
| 142. c[G(All)KKG(All)]A(cyclopentyl)L (SEQ ID NO: 144) | 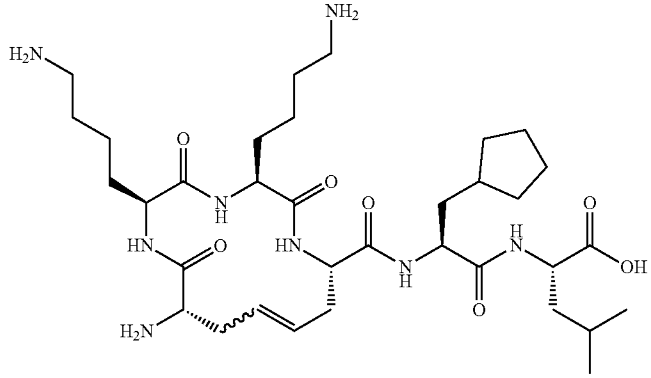 [SMILES: CC(C)C[C@H](NC(=O)[C@H](CC1CCCC1)NC(=O)[C@@H]1CC=CC[C@H](N)C(=O)N[C@@H](CCCCN)C(=O)N[C@@H](CCCCN)C(=O)N1)C(=O)O] |

TABLE I-continued structures of compounds

| Code | Structure |
|---|---|

143.
c[G(All)KKG(All)]A
(cyclobutyl)L
(SEQ ID NO: 145)

Chemical Formula $C_{34}H_{60}N_8O_7$
Molecular Weight 692.90

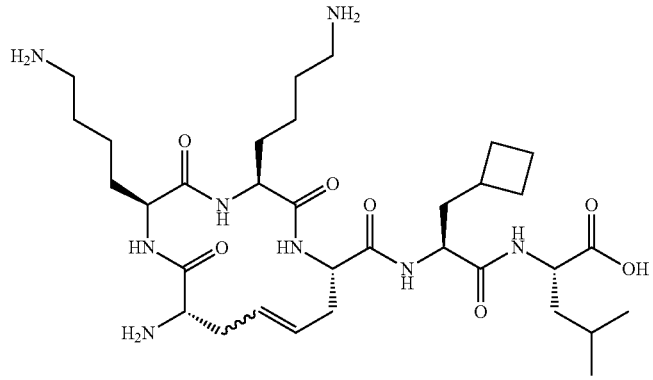 [SMILES: CC(C)C[C@H](NC(=O)[C@H](CC1CCC1)NC(=O)[C@@H]1CC=CC[C@H](N)C(=O)N[C@@H](CCCCN)C(=O)N[C@@H](CCCCN)C(=O)N1)C(=O)O]

144.
c[G(All)KKG(All)]A
(cyclopropyl)L
(SEQ ID NO: 146)

Chemical Formula $C_{33}H_{58}N_8O_7$
Molecular Weight 678.88

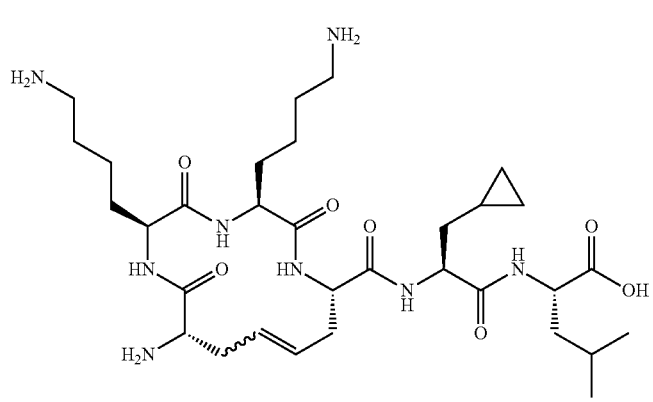 [SMILES: CC(C)C[C@H](NC(=O)[C@H](CC1CC1)NC(=O)[C@@H]1CC=CC[C@H](N)C(=O)N[C@@H](CCCCN)C(=O)N[C@@H](CCCCN)C(=O)N1)C(=O)O]

145.
c[G*(All)K*K*G*(All)]Y*L*
(SEQ ID NO: 147)
(diastereoisomer of compounds
21, 34, 38, 40, 41, 42 and 141)

Chemical Formula $C_{32}H_{56}N_8O_7$
Molecular Weight 664.85

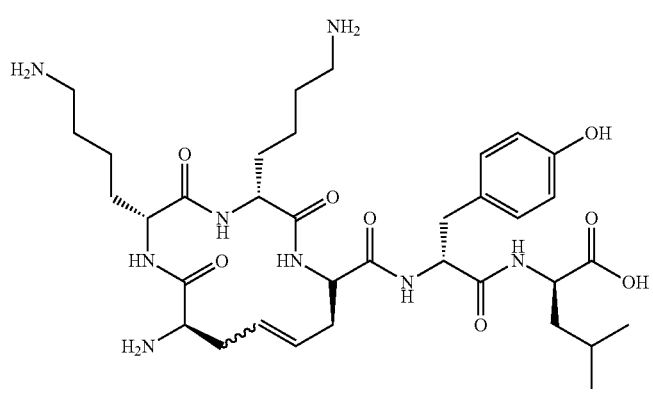

Chemical Formula $C_{35}H_{56}N_8O_8$
Molecular Weight 716.88

TABLE I-continued
structures of compounds
| Code | Structure |
|---|---|
| 146. c[G(All)KcitrullineG(All)]YL (SEQ ID NO: 148) | 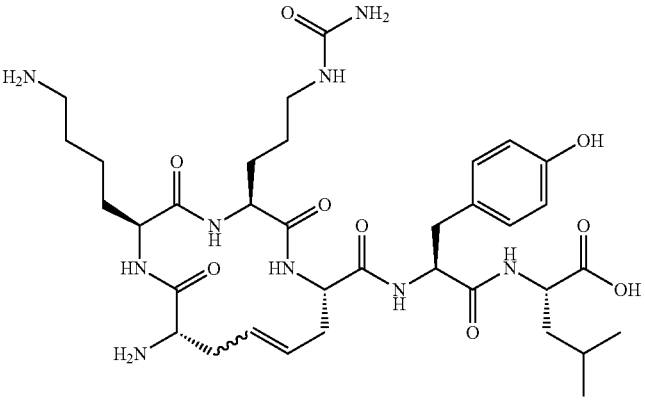 [SMILES: CC(C)C[C@H](NC(=O)[C@H](Cc1ccc(O)cc1)NC(=O)[C@@H]1CC=CC[C@H](N)C(=O)N[C@@H](CCCCN)C(=O)N[C@@H](CCCNC(N)=O)C(=O)N1)C(=O)O] Chemical Formula $C_{35}H_{55}N_9O_9$ <br> Molecular Weight 745.88 |
| 147. c[G(All)citrullineKG(All)]YL (SEQ ID NO: 149) | 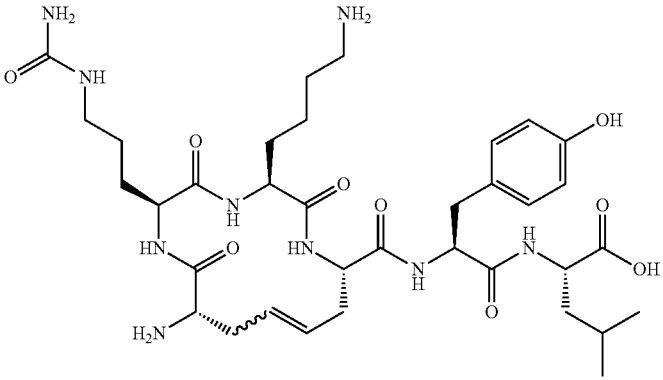 [SMILES: CC(C)C[C@H](NC(=O)[C@H](Cc1ccc(O)cc1)NC(=O)[C@@H]1CC=CC[C@H](N)C(=O)N[C@@H](CCCNC(N)=O)C(=O)N[C@@H](CCCCN)C(=O)N1)C(=O)O] Chemical Formula $C_{35}H_{55}N_9O_9$ <br> Molecular Weight 745.88 |
| 148. c[G(All)citrulline-citrullineG (All)]YL (SEQ ID NO: 150) | 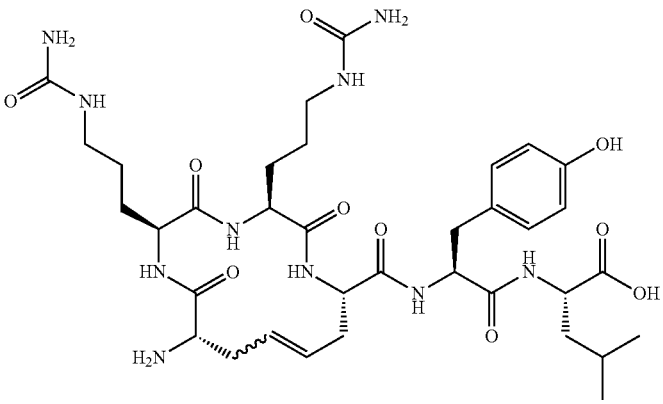 [SMILES: CC(C)C[C@H](NC(=O)[C@H](Cc1ccc(O)cc1)NC(=O)[C@@H]1CC=CC[C@H](N)C(=O)N[C@@H](CCCNC(N)=O)C(=O)N[C@@H](CCCNC(N)=O)C(=O)N1)C(=O)O] Chemical Formula $C_{35}H_{54}N_{10}O_{10}$ <br> Molecular Weight 774.88 |

TABLE I-continued
structures of compounds
| Code | Structure |
|---|---|
| 149. c[G(All)KhomolysineG(All)]YL (SEQ ID NO: 151) | 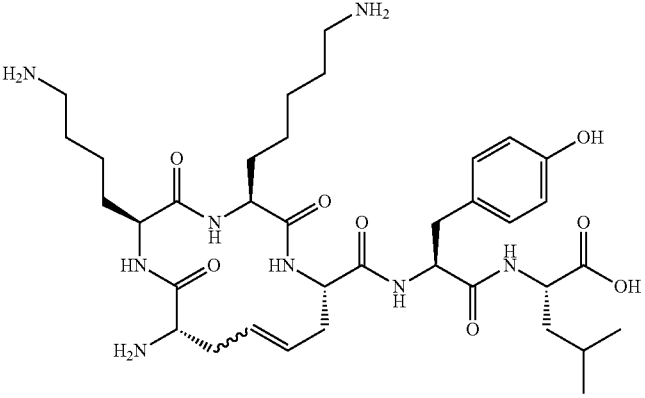 [SMILES: CC(C)C[C@H](NC(=O)[C@H](Cc1ccc(O)cc1)NC(=O)[C@@H]1CC=CC[C@H](N)C(=O)N[C@@H](CCCCN)C(=O)N[C@@H](CCCCCN)C(=O)N1)C(=O)O]<br>Chemical Formula $C_{36}H_{58}N_8O_8$<br>Molecular Weight 730.91 |
| 150. c[G(All)homolysineKG(All)]YL (SEQ ID NO: 152) | 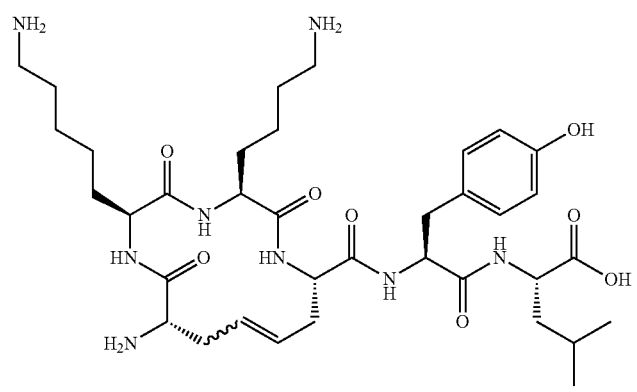 [SMILES: CC(C)C[C@H](NC(=O)[C@H](Cc1ccc(O)cc1)NC(=O)[C@@H]1CC=CC[C@H](N)C(=O)N[C@@H](CCCCCN)C(=O)N[C@@H](CCCCN)C(=O)N1)C(=O)O]<br>Chemical Formula $C_{36}H_{58}N_8O_8$<br>Molecular Weight 730.91 |
| 151. c[G(All)K(homo)K(homo)G(All)]YL (SEQ ID NO: 153) | 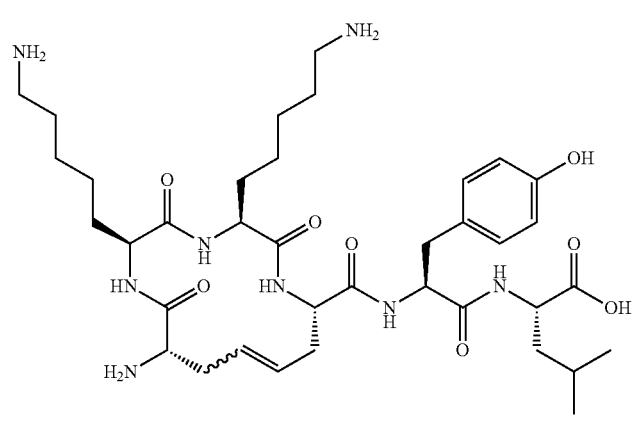 [SMILES: CC(C)C[C@H](NC(=O)[C@H](Cc1ccc(O)cc1)NC(=O)[C@@H]1CC=CC[C@H](N)C(=O)N[C@@H](CCCCCN)C(=O)N[C@@H](CCCCCN)C(=O)N1)C(=O)O]<br>Chemical Formula $C_{37}H_{60}N_8O_8$<br>Molecular Weight 744.93 |

TABLE I-continued
structures of compounds
| Code | Structure |
|---|---|
| 152. c[CKKC]YL (SEQ ID NO: 154) | 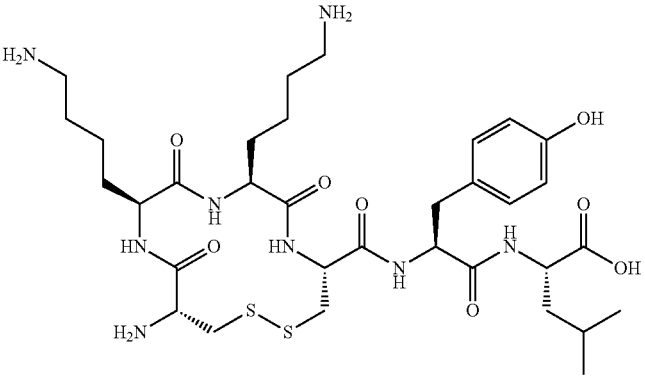 [SMILES: CC(C)C[C@H](NC(=O)[C@H](Cc1ccc(O)cc1)NC(=O)[C@@H]1CSSC[C@H](N)C(=O)N[C@@H](CCCCN)C(=O)N[C@@H](CCCCN)C(=O)N1)C(=O)O]<br>Chemical Formula $C_{33}H_{54}N_8O_8S_2$<br>Molecular Weight 754.96 |
| 153. c[CKKPen]YL (SEQ ID NO: 155) | 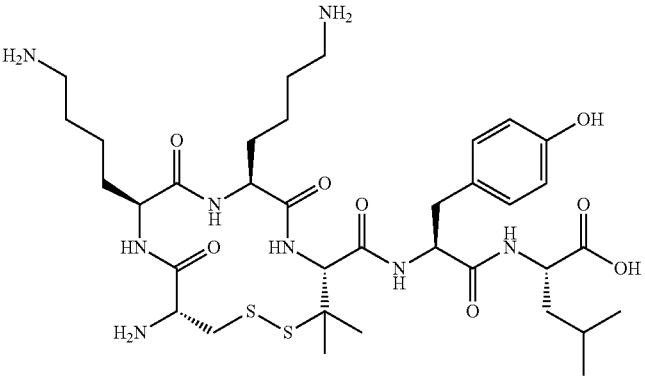 [SMILES: CC(C)C[C@H](NC(=O)[C@H](Cc1ccc(O)cc1)NC(=O)[C@H]1NC(=O)[C@H](CCCCN)NC(=O)[C@H](CCCCN)NC(=O)[C@@H](N)CSSC1(C)C)C(=O)O]<br>Chemical Formula $C_{35}H_{58}N_8O_8S_2$<br>Molecular Weight 783.02 |
| 154. c[PenKKC]YL (SEQ ID NO: 156) | 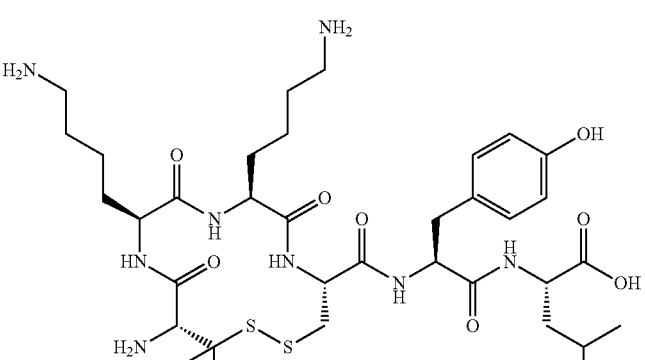<br>Chemical Formula $C_{35}H_{58}N_8O_8S_2$<br>Molecular Weight 783.02 |

TABLE I-continued
structures of compounds
| Code | Structure |
|---|---|
| 155. c[(Pen)KK(Pen)]YL (SEQ ID NO: 157) | 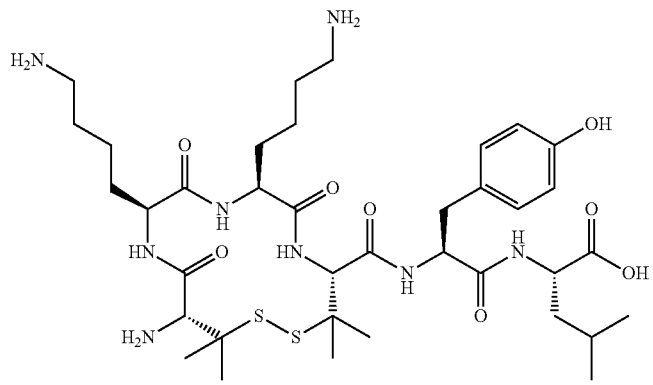<br>Chemical Formula $C_{37}H_{62}N_8O_8S_2$<br>Molecular Weight 811.07 |
| 156. Kc[G(All)KKG(All)]YL (SEQ ID NO: 158) | 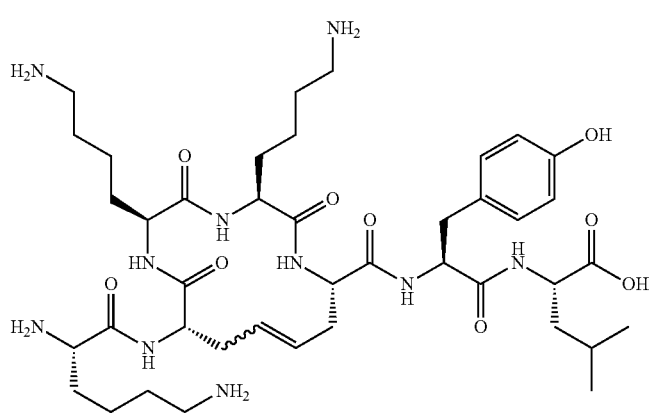<br>Chemical Formula $C_{41}H_{68}N_{10}O_9$<br>Molecular Weight 845.06 |
| 159. c[G(All)KKG(All)]A(2-thienyl)L (SEQ ID NO: 159) | 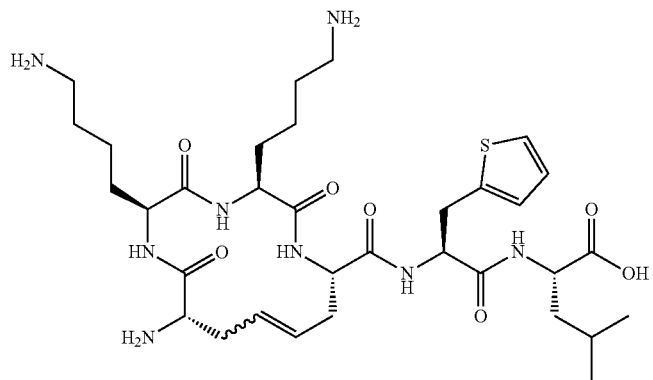<br>Chemical Formula $C_{33}H_{54}N_8O_7S$<br>Molecular Weight 706.90 |

TABLE I-continued
structures of compounds
| Code | Structure |
|---|---|
| 160. c[G(All)KKG(All)]F(benzoyl)L (SEQ ID NO: 160) | 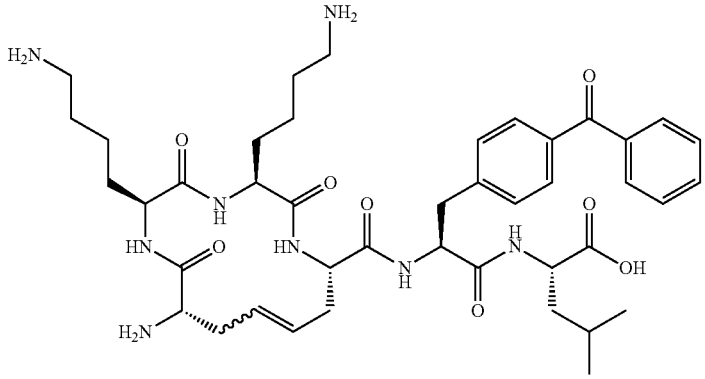<br>Chemical Formula $C_{42}H_{60}N_8O_8$<br>Molecular Weight 804.99 |
| 161. c[G(All)KKG(All)]A(styryl)L (SEQ ID NO: 161) | 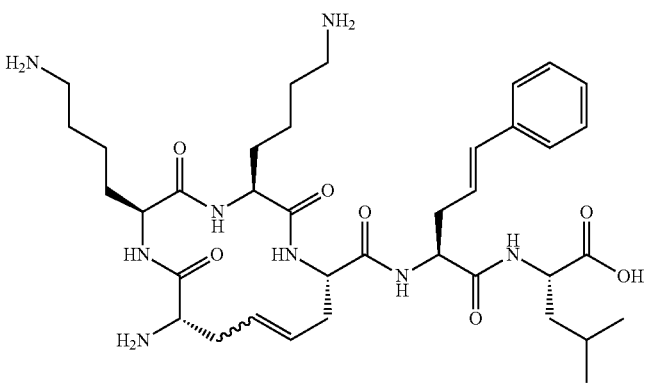<br>Chemical Formula $C_{37}H_{58}N_8O_7$<br>Molecular Weight 726.92 |
| 162. c[G(All)KKG(All)]A(anthryl-)L (SEQ ID NO: 162) | 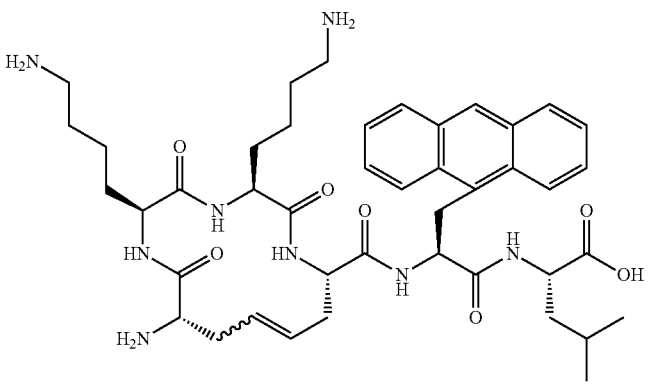<br>Chemical Formula $C_{43}H_{60}N_8O_7$<br>Molecular Weight 801.00 |

TABLE I-continued
structures of compounds
| Code | Structure |
|---|---|
163.
c[G(All)KKG(All)]G(Tic)L
(SEQ ID NO: 163)
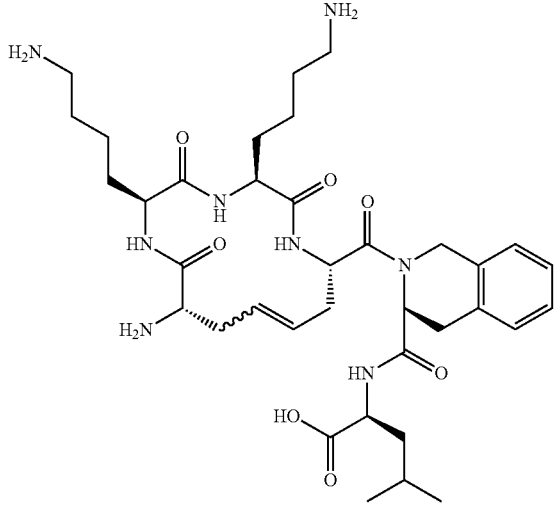
Chemical Formula $C_{36}H_{56}N_8O_7$
Molecular Weight 712.89
164.
c[G(All)KKG(All)]G(indanyl)L
(SEQ ID NO: 164)
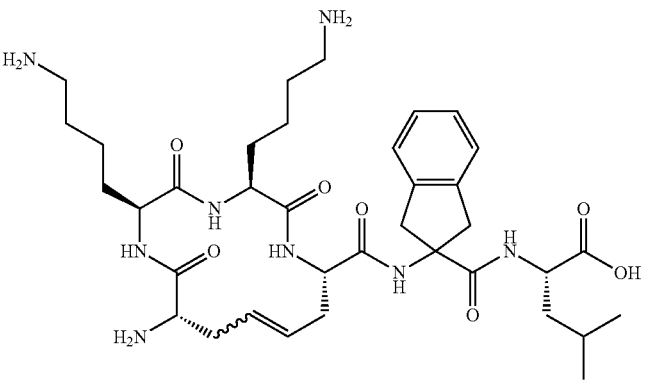
Chemical Formula $C_{36}H_{56}N_8O_7$
Molecular Weight 712.89
165.
c[G(All)KKG(All)]A(2-pyridyl)L
(SEQ ID NO: 165)
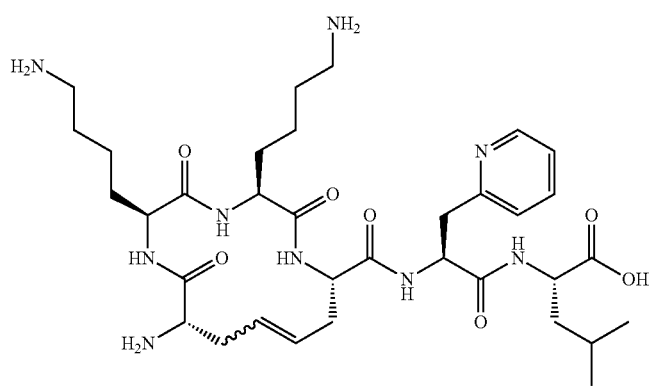
Chemical Formula $C_{34}H_{55}N_9O_7$
Molecular Weight 701.87

TABLE I-continued
structures of compounds
| Code | Structure |
|---|---|
| 166. c[G(All)KKG(All)p(octahydroindol)L (SEQ ID NO: 166) | 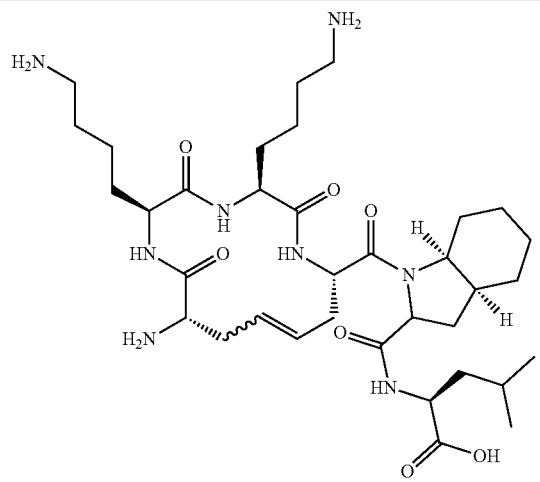<br>Chemical Formula C$_{35}$H$_{60}$N$_8$O$_7$<br>Molecular Weight 704.91 |
| 167. c[G(All)KKG(All)]G(Tic)*L* (SEQ ID NO: 167) | 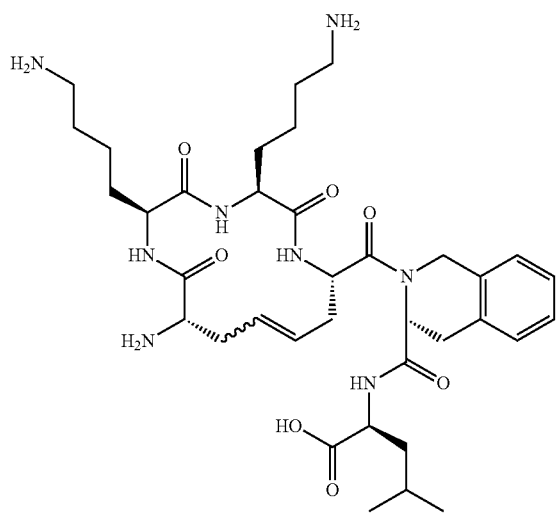<br>Chemical Formula C$_{36}$H$_{56}$N$_8$O$_7$<br>Molecular Weight 712.89 |
| 168. c[G(All)KKG(All)]A(3-benzothienyl)L (SEQ ID NO: 168) | 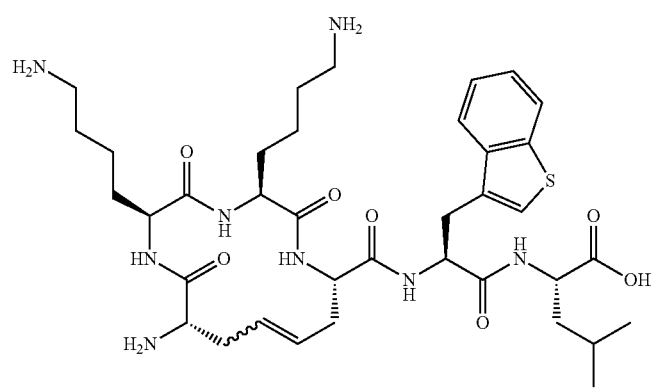<br>Chemical Formula C$_{37}$H$_{56}$N$_8$O$_7$<br>Molecular Weight 756.96 |

TABLE I-continued structures of compounds

| Code | Structure |
|---|---|
| 169. c[G(All)KKG(All)]A(3-pyridyl)L (SEQ ID NO: 169) | 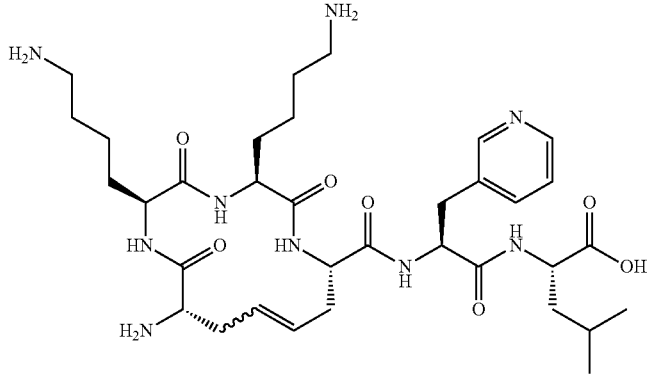<br>Chemical Formula $C_{34}H_{55}N_9O_7$<br>Molecular Weight 701.87 |
| 170. c[G(All)KKG(All)]G(dihydroindolyl)L (SEQ ID NO: 35) | 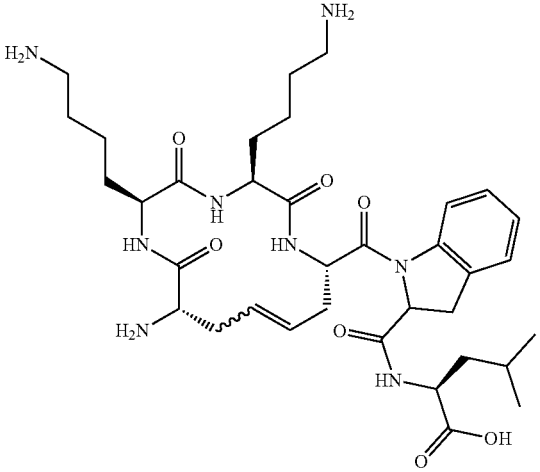<br>Chemical Formula $C_{35}H_{54}N_8O_7$<br>Molecular Weight 698.87 |

All: Allyl

Tle: Tert-Leucine

Tbu: Tert butyl

Tic: tetrahydroisoquinoline

Nle: Norleucine

Nva: NorValine

Npg: Neopentylglycine

Pen: penicillamine

ChG: CyclohexylGlycine

ChA: CyclohexylAlanine

Y(OMe): O-methyl tyrosine

Homo-ChA: homo-cyclohexylalanine

*following an amino acid residue means that residue in D/(R) configuration

Y(OAc): O-acetyl tyrosine mY: meta-tyrosine

Example 7: Chemical Characterization of Compounds

The purity, theoretical mass, ultra-performance liquid chromatography mass spectrometry (UPLC-MS) in terms of mass-to-charge ratio m/z, and ionization state were determined for the listed compounds and are presented in Table II below.

TABLE 2

Compounds biochemical characterization

| # compound | purity | Theoretical mass MW (g/mol) | m/z (UPLC-MS) | Ion |
|---|---|---|---|---|
| 14. | | | | |
| 15. | 91% | 758.92 | 380.4 | [M + 2]2+ |
| 16. | 91% | 758.92 | 380.4 | [M + 2]2+ |
| 17. | 95% (ELSD) | 681.88 | 342 | [M + 2]2+ |
| 21. | 95% | 716.88 | 359.7 | [M + 2]2+ |
| 27. | 99% | 716.88 | 359.7 | [M + 2]2+ |
| 28. | 99% | 716.88 | 359.7 | [M + 2]2+ |
| 29. | 99% | 702.85 | 352.7 | [M + 2]2+ |
| 30. | 99% | 742.92 | 372.4 | [M + 2]2+ |
| 31. | 99% | 756.95 | 379.4 | [M + 2]2+ |
| 32. | 99% | 750.9 | 376.3 | [M + 2]2+ |
| 33. | 99% | 702.85 | 352.3 | [M + 2]2+ |
| 34. | 99% | 716.88 | 359.3 | [M + 2]2+ |
| 38. | 99% | 716.88 | 359.3 | [M + 2]2+ |
| 39. | | | | |
| 40. | 99% | 716.88 | 359.3 | [M + 2]2+ |
| 41. | 99% | 716.88 | 359.3 | [M + 2]2+ |
| 42. | 99% | 716.88 | 359.3 | [M + 2]2+ |
| 43. | 99% | 739.92 | 371.1 | [M + 2]2+ |
| 44. | 95% | 730.91 | 366.5 | [M + 2]2+ |
| 45. | 97% | 730.91 | 366.5 | [M + 2]2+ |
| 46. | 99% | 744.93 | 373.4 | [M + 2]2+ |
| 47. | 98% | 718.9 | 360.4 | [M + 2]2+ |
| 48. | 95% (ELSD) | 681.88 | 341.9 | [M + 2]2+ |
| 49. | 99% | 730.91 | 366.6 | [M + 2]2+ |
| 51. | 98% | 702.85 | 352.4 | [M + 2]2+ |
| 52. | 99% | 689.3 | 689.3 | [M + 2]2+ |
| 53. | 99% | 674.8 | 675.3 | [M + 1] |
| 54. | 95% | 716.88 | 359.3 | [M + 2]2+ |
| 55. | 98% | 725.85 | 363.8 | [M + 2]2+ |
| 57. | 95% | 701.87 | 351.8 | [M + 2]2+ |
| 58. | 99% | 687.84 | 688.8 | [M + 1] |
| 59. | 97% | 645.76 | 646.8 | [M + 1] |
| 60. | 99% | 701.87 | 352 | [M + 2]2+ |
| 61. | 99% | 717.82 | 718.2 | [M + 1] |
| 62. | 99% | 780.92 | 781.3 | [M + 2]2+ |
| 63. | 95% | 804.87 | 403.3 | [M + 2]2+ |
| 64. | 99% | 770.97 | 771.4 | [M + 1] |
| 65. | 99% | 714.87 | 715.2 | [M + 1] |
| 66. | 99% | 728.89 | 365.3 | [M + 2]2+ |
| 67. | 99% | 742.92 | 372.3 | [M + 2]2+ |
| 68. | 99% | 770.97 | 386.4 | [M + 2]2+ |
| 69. | | 716.88 | | |
| 70. | | 716.88 | | |
| 71. | | 716.88 | | |
| 72. | 99% | 730.91 | 731.4 | [M + 1] |
| 73. | 99% | 730.91 | 366.1 | [M + 2]2+ |
| 74. | 99% | 744.93 | 373.2 | [M + 2]2+ |
| 75. | 99% | 730.91 | 731.4 | [M + 2]2+ |
| 76. | 99% | 700.88 | 701.4 | [M + 2]2+ |
| 77. | 95% | 718.87 | 719.4 | [M + 2]2+ |
| 78. | 99% | 826.78 | 827.1 | [M + 2]2+ |
| 79. | 99% | 702.85 | 703.3 | [M + 1] |
| 80. | 99% | 688.83 | 689.2 | [M + 1] |
| 81. | 99% | 674.8 | 675.2 | [M + 1] |
| 82. | 99% | 716.88 | 359 | [M + 2]2+ |
| 83. | 99% | 725.85 | 726.3 | [M + 2]2+ |
| 84. | 95% | 725.85 | 726.3 | [M + 2]2+ |
| 85. | 95% | 701.87 | 702.3 | [M + 2]2+ |
| 86. | 95% | 687.84 | 688.2 | [M + 2]2+ |
| 87. | 98% | 645.76 | 646.2 | [M + 1] |
| 88. | 98% | 717.82 | 718.3 | [M + 2]2+ |
| 89. | 92% | 758.96 | 380.1 | [M + 2]2+ |
| 90. | 99% | 758.96 | 380.1 | [M + 2]2+ |
| 91. | 99% | 758.96 | 380.1 | [M + 2]2+ |
| 92. | 99% | 758.96 | 380.2 | [M + 2]2+ |
| 93. | 95% | 801.04 | 401.4 | [M + 2]2+ |
| 94. | 99% | 733.87 | 367.8 | [M + 2]2+ |
| 95. | 95% | 747.89 | 374.8 | [M + 2]2+ |
| 96. | 95% | 761.92 | 381.8 | [M + 2]2+ |
| 97. | 99% | 775.95 | 388.8 | [M + 2]2+ |
| 98. | 95% | 747.89 | 374.8 | [M + 2]2+ |
| 99. | 95% | 761.92 | 381.9 | [M + 2]2+ |
| 100. | 98% | 775.95 | 388.8 | [M + 2]2+ |
| 101. | 90% | 789.98 | 395.8 | [M + 2]2+ |
| 102. | 90% | 747.89 | 374.7 | [M + 2]2+ |
| 103. | 90% | 733.87 | 367.8 | [M + 2]2+ |
| 104. | 95% | 761.92 | 381.8 | [M + 2]2+ |
| 105. | 90% | 747.89 | 374.8 | [M + 2]2+ |
| 106. | 99% | 775.95 | 388.8 | [M + 2]2+ |
| 107. | 97% | 761.92 | 381.8 | [M + 2]2+ |
| 108. | 99% | 789.98 | 395.8 | [M + 2]2+ |
| 109. | 99% | 775.95 | 388.8 | [M + 2]2+ |
| 110. | 99% | 756.99 | 379.3 | [M + 2]2+ |
| 111. | 99% | 768.88 | 385.3 | [M + 2]2+ |
| 112. | 99% | 750.94 | 376.2 | [M + 2]2+ |
| 113. | 99% | 735.32 | 368.6 | [M + 2]2+ |
| 114. | 99% | 735.32 | 386.6 | [M + 2]2+ |
| 115. | 99% | 779.78 | 390.7 | [M + 2]2+ |
| 116. | 99% | 779.78 | 390.8 | [M + 2]2+ |
| 117. | 99% | 826.78 | 414.2 | [M + 2]2+ |
| 118. | 99% | 725.89 | 363.8 | [M + 2]2+ |
| 119. | 99% | 706.93 | 354.3 | [M + 2]2+ |
| 120. | 99% | 690.84 | 346.3 | [M + 2]2+ |
| 121. | | 715.9 | 358.8 | [M + 2]2+ |
| 122. | 99% | 745.88 | 373.8 | [M + 2]2+ |
| 123. | 99% | 714.91 | 358.3 | [M + 2]2+ |
| 124. | 99% | 790.83 | 396.3 | [M + 2]2+ |
| 125 | 99% | 702.85 | 352.3 | [M + 2]2+ |
| 126 | 99% | 730.91 | 366.3 | [M + 2]2+ |
| 127 | 99% | 805.82 | 403.7 | [M + 2]2+ |
| 128 | 99% | 785 | 393.3 | [M + 2]2+ |
| 129 | 99% | 727.9 | 364.8 | [M + 2]2+ |
| 130 | 99% | 821.86 | 288.4 | [M + 2]2+ |
| 131 | 99% | 764.76 | 383.2 | [M + 2]2+ |
| 132 | 99% | 743.95 | 372.9 | [M + 2]2+ |
| 133 | 96% | 847.9 | 424.8 | [M + 2]2+ |
| 134 | 99% | 790.8 | 396.2 | [M + 2]2+ |
| 135 | 99% | 769.98 | 385.8 | [M + 2]2+ |
| 136 | 99% | 806.84 | 404.3 | [M + 2]2+ |
| 137 | 95% | 832.88 | 417.3 | [M + 2]2+ |
| 138 | 95% | 624.78 | 313.1 | |
| 139 | 95% | 776.98 | 389.2 | |
| 140 | 95% | 776.98 | 389.2 | |
| 141 | | 916.88 | | |
| 142 | 95% | 692.9 | 347.3 | |
| 143 | 95% | 678.88 | 340.3 | |
| 144 | | 664.85 | | |
| 145 | 95% | 716.88 | 359.1 | |
| 146 | 99% | 745.88 | 746.5 | |
| 147 | 99% | 745.88 | 373.8 | |
| 148 | | 774.88 | | |
| 149 | 99% | 730.91 | 366.3 | |
| 150 | 99% | 730.91 | 366.3 | |
| 151 | 95% | 744.93 | 373.4 | |
| 152 | 95% | 754.96 | 378.3 | |
| 153 | 99% | 783.02 | 392.4 | |
| 154 | 99% | 783.02 | 392.4 | |
| 155 | 99% | 811.07 | 406.5 | |
| 156 | | 845.06 | | |
| 159 | 90% | 706.9 | 354.2 | |
| 160 | 97% | 804.99 | 403.4 | |
| 161 | 99% | 726.92 | 364.3 | |
| 162 | 90% | 801 | 401.4 | |
| 163 | 99% | 712.89 | 357.3 | |
| 164 | | 712.89 | 357.2 | |
| 165 | | 701.87 | 351.7 | |

TABLE 2-continued

Compounds biochemical characterization

| # compound | purity | Theoretical mass MW (g/mol) | m/z (UPLC-MS) | Ion |
|---|---|---|---|---|
| 166 | 97% | 704.91 | 353.3 | |
| 167 | 99% | 712.89 | 713.4 | |
| 168 | 97% | 756.96 | 379.3 | |
| 169 | | 701.87 | 351.8 | |
| 170 | | 698.87 | | |

Example 8: Binding and Stability Assays

Compounds of Table I were cyclized between residues at positions Xaa1 and Xaa4. The affinity for the NTS1 and NTS2 receptors was evaluated (see Table III).

These experiments allowed to determine that this series of macrocycles was selective for NTS2 i.e. able to bind to the NTS2 to a much stronger extent than to the NTS1 receptor.

TABLE III

Variation of position Xaa6 (or 12 when using neurotensin numbering) vs. compound 34

| Macrocycle | Amino acid or derivative | Side chain | $IC_{50}$ NTS1 (µM) | $IC_{50}$ NTS2 (nM) | Selectivity |
|---|---|---|---|---|---|
| 34 | Leu | | 100 | 59.6 | 1685 |
| 14 | Ile | | 100 | 10200 | 10 |
| 27 | Tle | | >100 | 77800 | >1.3 |
| 28 | Nle | | >100 | 381 | >262 |
| 29 | Nva | | >100 | 3300 | >30.3 |
| 33 | Val | | >100 | 79800 | >1.25 |
| 38 | D-Leu | | >100 | 239 883 | >2.4 |

TABLE III-continued
| | | | | | |
|---|---|---|---|---|---|
| 49 | Neopentylglycine (Npg) | 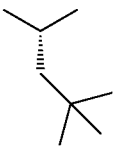 | >100 | 44.4 | >2252 |
| 30 | Cyclohexyl glycine (Chg) | 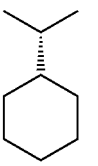 | >100 | 955 | >104 |
| 31 | Cyclohexyl alanine (Cha) | 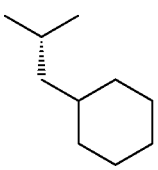 | >100 | 8.67 | >11534 |
| 32 | Phe | 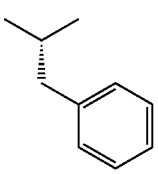 | >100 | 453 | >220 |
| 62 | Tyr(Ome) | 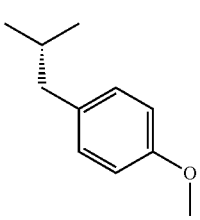 | >100 | 166 | >602 |
| 63 | 2.4.5-trifluoroPhe | 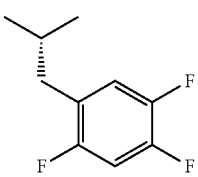 | >100 | 366 | >273 |
| 64 | Homo-Cha | 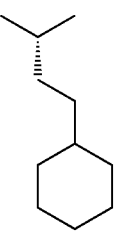 | >100 | 7.74 | >12 920 |
| 65 | Cyclopropyl Ala | 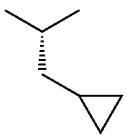 | >100 | 311.89 | >321 |
| 66 | Cyclobutyl Ala | 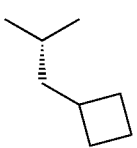 | >100 | 27.16 | >3682 |

TABLE III-continued
| | | | | | |
|---|---|---|---|---|---|
| 67 | Cyclopentyl Ala | 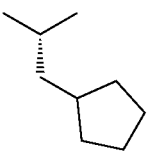 | >100 | 3.06 | >32 680 |
| 68 | Cycloheptyl Ala | 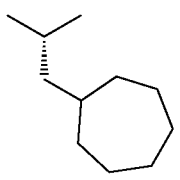 | >100 | 6.85 | >14 600 |
| 127 | Cyclopentyl Ala | 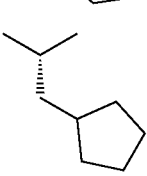 | >100 | 2.0 | 49505 |
| 128 | | | >100 | 7.8 | 12788 |
| 129 | | | >100 | 13.9 | 7194 |
| 133 | | | >100 | 3.0 | 33333 |
| 134 | | | >100 | 17.7 | 5650 |
| 135 | | | >100 | 45.9 | 2179 |
| 137 | | | >100 | 9.6 | 10428 |
Variation of position Xaa5 (or 11 when using neurotensin numbering) vs. compound 34
| | | | | | |
|---|---|---|---|---|---|
| 34 | Tyr | 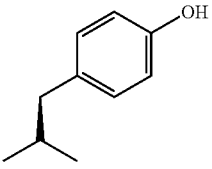 | 199 | 59.6 | 3339 |
| 15 | Tyr(OAc) | 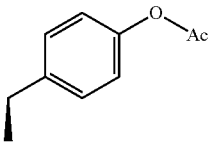 | >100 | | |
| 16 | Trp | 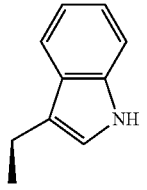 | >100 | 53.6 | 1865 |
| 17 | Lys | 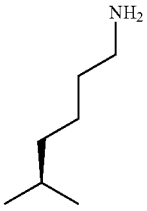 | >100 | 1100 | 90.9 |
| 21 | D-Tyr | 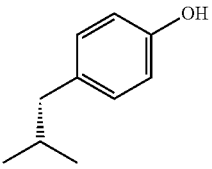 | >100 | 4700 | |

TABLE III-continued

| # | Name | Structure | | | |
|---|---|---|---|---|---|
| 39 | m-Tyr | 3-hydroxybenzyl with isobutyl | | | |
| 43 | D-Trp | indol-3-ylmethyl amide | >100 | 968 | >103.3 |
| 48 | D-Lys | 5-aminopentyl with isopropyl | >100 | 10 100 | >10 |
| 75 | Tyr(OMe) | 4-methoxybenzyl with isobutyl | >100 | 86.3 | >1159 |
| 76 | Phe | benzyl with isobutyl | >100 | 85.1 | >1175 |
| 77 | 4-F-Phe | 4-fluorobenzyl with isobutyl | >100 | 95.6 | >1046 |
| 78 | 4-I-Phe | 4-iodobenzyl with isobutyl | >100 | 15.5 | >6452 |
| 110 | 4-tBu-Phe | 4-tert-butylbenzyl with isobutyl | >100 | 40.2 | >2488 |

TABLE III-continued
| | | | | | |
|---|---|---|---|---|---|
| 111 | 4-CF$_3$-Phe | 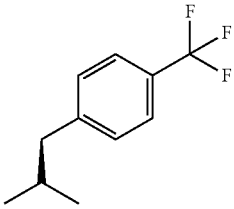 | >100 | 47.9 | >2087 |
| 112 | 2-NaI | 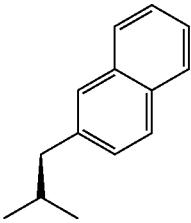 | >100 | 83.6 | >1196 |
| 113 | 3-Cl-Phe | 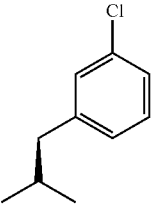 | >100 | 48 | >2084 |
| 114 | 4-Cl-Phe | 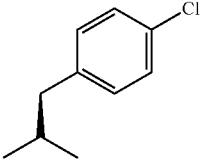 | >100 | 40.6 | >2466 |
| 115 | 3-Br-Phe | 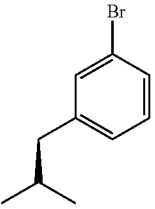 | >100 | 28.4 | >3523 |
| 116 | 4-Br-Phe | 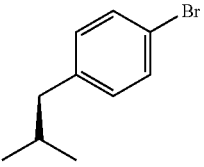 | >100 | 15.5 | >6443 |
| 117 | 3-I-Phe | 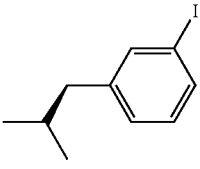 | >100 | 32.3 | >3097 |
| 118 | 4-CN-Phe | 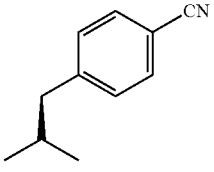 | >100 | 57.8 | >1729 |

TABLE III-continued
| | | | | | |
|---|---|---|---|---|---|
| 125 | 4-Hydroxyphenylglycine |  | >100 | 1800 | 56 |
| 126 | homotyrosine | 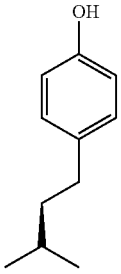 | >100 | 81.7 | 1224 |
| 127 | 4-bromophenylalanine | 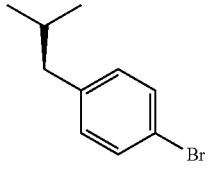 | >100 | 2 | 49505 |
| 130 | | | >100 | 10.2 | 9843 |
| 131 | | | >100 | 27.4 | 3650 |
| 133 | 4-bromophenylalanine | 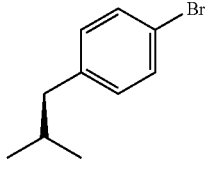 | >100 | 3 | 33333 |
| 134 | | | >100 | 17.7 | 5650 |
| 136 | | | >100 | 37.7 | 2653 |
| 137 | | | >100 | 9.6 | 10428 |
| 138 | Ala |  | >100 | 582.1 | 172 |
| 139 | biphenylalanine | 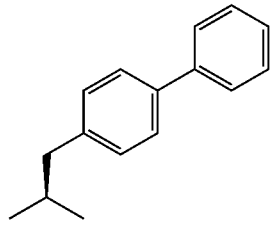 | >100 | 48.5 | 2061 |
| 140 | diphenylalanine | 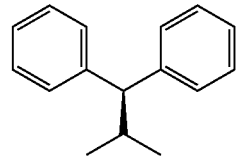 | >100 | 631.0 | 158 |
| 142 | Cyclopentyl Ala | 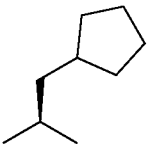 | >100 | 204.2 | 490 |

TABLE III-continued

| | | | | | |
|---|---|---|---|---|---|
| 143 | Cyclobutyl Ala | | >100 | 276.1 | 362 |
| 144 | Cyclopropyl Ala | | >100 | | |
| 159 | 2-thienylalanine | | >100 | 90.0 | 1112 |
| 160 | benzoylphenylalanine | | >100 | 115.1 | 2 |
| 161 | styrylalanine | | >100 | 130.6 | 766 |
| 162 | anthracenealanine | | >100 | 19.1 | 5249 |
| 163 | Tic glycine | | >100 | 10000 | 10 |
| 164 | benzocyclopentyl | | >100 | 10000 | 10 |
| 165 | pyridyl alanine | | >100 | 509.3 | 20 |

TABLE III-continued

| | | | | | |
|---|---|---|---|---|---|
| 166 | octahydroindol glycine | | >100 | 33.3 | 3006 |
| 167 | Tic glycine | | >100 | 96.2 | 1040 |
| 168 | Indolyl alanine | | >100 | 102.1 | 979 |
| 169 | Pyridyl alanine | | >100 | 234.4 | 427 |
| 170 | Dihydroindolyl glycine | | | | |

Variation of position Xaa3 (or 9 when using neurotensin numbering) vs. compound 34

| | | | | | |
|---|---|---|---|---|---|
| 34 | Lys | | 199 | 59.6 | 3339 |
| 51 | Orn | | >100 | 70.3 | >1422 |
| 52 | Dab | | >100 | 244.3 | >409.3 |
| 53 | Dap | | >100 | 203.7 | >490.9 |

TABLE III-continued
| | | | | | |
|---|---|---|---|---|---|
| 54 | D-Lys | 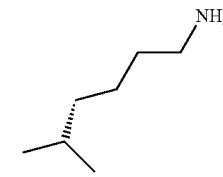 | >100 | 320.6 | >311.9 |
| 55 | His | 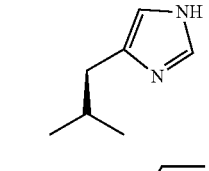 | >100 | 570.16 | >175 |
| 57 | Nle | 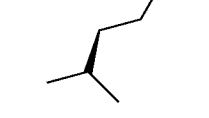 | >100 | 716.14 | >140 |
| 58 | Nva | 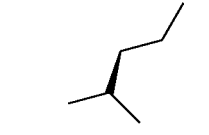 | >100 | 729.46 | >137 |
| 59 | Gly | | >100 | 2 128 | >47 |
| 61 | Glu | 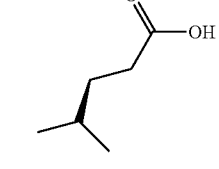 | >100 | 12417 | >8. |
| 146 | citrulline | 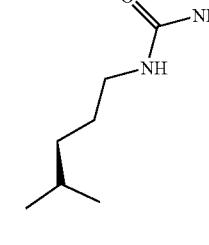 | >100 | 698.2 | 143 |
| 148 | | | >100 | 7900 | 13 |
| 149 | homolysine | 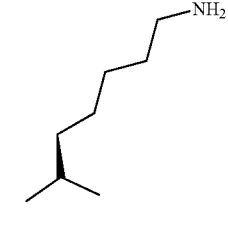 | >100 | 213.5 | 468 |
| 151 | | | >100 | 104.0 | 962 |
Variation of position Xaa2 (or 8 when using neurotensin numbering) vs. compound 34
| | | | | | |
|---|---|---|---|---|---|
| 34 | Lys | 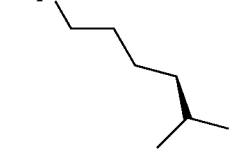 | 199 | 59.6 | 3339 |

TABLE III-continued

| | | | | | |
|---|---|---|---|---|---|
| 79 | Orn | H₂N-[CH₂CH₂CH(CH₃)-] | >100 | 77.5 | >1291 |
| 80 | Dab | H₂N-[CH₂CH(CH₃)-] | >100 | 137.1 | >729 |
| 81 | Dap | H₂N-[CH(CH₃)-] | >100 | 179.5 | >557.2 |
| 82 | D-Lys | H₂N-[CH₂CH₂CH₂CH(CH₃)-] | >100 | 621 | >161 |
| 83 | His | imidazole-CH₂CH(CH₃)- | >100 | 1324 | >76 |
| 84 | D-His | imidazole-CH₂CH(CH₃)- | >100 | 645.7 | >154.9 |
| 85 | Nle | CH₃CH₂CH₂CH₂CH(CH₃)- | >100 | 1072 | >93 |
| 86 | Nva | CH₃CH₂CH₂CH(CH₃)- | >100 | 743.0 | >135 |
| 87 | Gly | | >100 | 516.4 | >194 |
| 88 | Glu | HOOC-CH₂CH₂CH(CH₃)- | >100 | 10617 | >9.4 |

TABLE III-continued

| | | | IC$_{50}$ NTS1 (μM) | IC$_{50}$ NTS2 (nM) | Selectivity |
|---|---|---|---|---|---|
| 147 | citrulline | 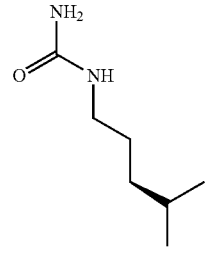 | >100 | 599.8 | 167 |
| 148 | | | >100 | 7900 | 13 |
| 150 | homolysine | 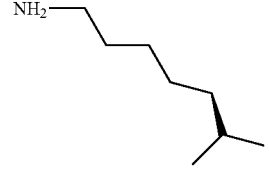 | >100 | 187.5 | 533 |
| 151 | | | >100 | 104.0 | 962 |

Variation of N-terminal of position Xaa1 (or 7 when using neurotensin numbering) vs. compound 34

| | | | | | |
|---|---|---|---|---|---|
| 34 | Amine | —NH$_2$ | 199 | 59.6 | 3339 |
| 60 | Des-amino | absent | >100 | 47.0 | >2127.7 |
| 129 | | | >100 | 13.9 | 7194 |
| 131 | | | >100 | 27.4 | 3650 |
| 132 | | | >100 | 136.5 | 733 |
| 134 | | | >100 | 17.7 | 5650 |
| 135 | | | >100 | 45.9 | 2179 |
| 136 | | | >100 | 37.7 | 2653 |
| 137 | | | >100 | 9.6 | 10428 |
| 156 | Des-amino | 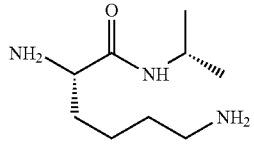 | >100 | 6.6 | 15244 |

Variation of linked positions Xaa1-Xaa4 (or linked 7-10 when using neurotensin numbering) vs. compound 34

| Macrocycle | Amino acid or derivative | Illustration of Xaa1-Xaa4 bond | IC$_{50}$ NTS1 (μM) | IC$_{50}$ NTS2 (nM) | Selectivity |
|---|---|---|---|---|---|
| 34 | [L-AllylGly-L-AllylGly] | | 199 | 59.6 | 3339 |
| 40 | [L-AllylGly-D-AllylGly] | | >100 | 1200 | >85 |
| 41 | [D-AllylGly-L-AllylGly] | | >100 | 112.5 | >889 |

TABLE III-continued

| | | | | | |
|---|---|---|---|---|---|
| 42 | [D-AllylGly-D-AllylGly] | | >100 | 2300 | >42 |
| 47 | Reduced link | | >100 | 94 | >1064 |
| 89 | [L-PentenylGly-L-AllylGly] | | >100 | 13.2 | >7553 |
| 90 | [D-PentenylGly-L-AllylGly] | | >100 | 76.9 | >1300 |
| 91 | [L-AllylGly-L-PentenylGly] | | >100 | 10.6 | >9399 |
| 92 | [L-AllylGly-D-PentenylGly] | | >100 | 510.6 | >196 |
| 93 | [L-PentenylGly-D-PentenylGly] | | >100 | 34.4 | >2907 |
| 129 | [L-Pentenoyl-L-AllylGly] | | >100 | 13.9 | 7194 |
| 131 | [L-Pentenoyl-L-AllylGly] | | >100 | 27.4 | 3650 |

TABLE III-continued

| | | | | | |
|---|---|---|---|---|---|
| 132 | [L-Pentenoyl-L-G(alpha-Me-(4-pentenyl))] | | >100 | 136.5 | 733 |
| 133 | [L-AllylGly-L-G(alpha-Me-(4-pentenyl))] | | >100 | 3.0 | 33333 |
| 134 | [L-Pentenoyl-L-AllylGly] | | >100 | 17.7 | 5650 |
| 135 | [L-Pentenoyl-L-G(alpha-Me-(4-pentenyl))] | | >100 | 45.9 | 2179 |
| 136 | [L-Pentenoyl-L-G(alpha-Me-(4-pentenyl))] | | >100 | 37.7 | 2653 |
| 137 | [L-Pentenoyl-L-G(alpha-Me-(4-pentenyl))] | | >100 | 9.6 | 10428 |
| 152 | [L-Cys-L-Cys] | | >1000 | 1400 | 7 |
| 153 | [L-Cys-L-Pen] | | >100 | 34.8E | 2871 |

TABLE III-continued

| | | | | | |
|---|---|---|---|---|---|
| 154 | [L-Pen-L-Cys] | | >100 | 1200 | 81 |
| 155 | [L-Pen-L-Pen] | | >100 | 317.7 | 315 |

Variation of linked positions Xaa1-Xaa4 (or linked 7-10 when using neurotensin numbering) vs. compound 34 using a macrolactamisation reaction. Resulting macrocycles 94-101 satisfy the formula II below

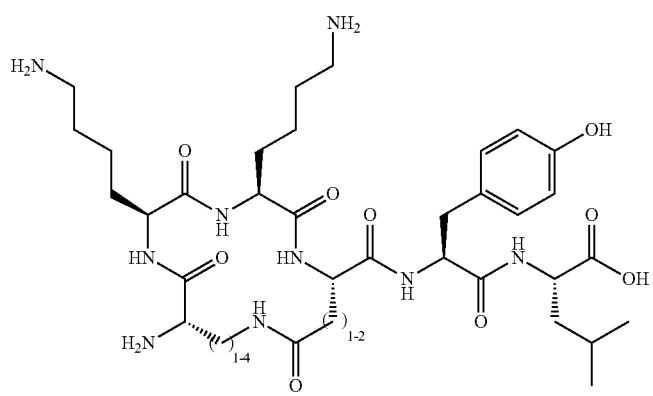

II

Resulting macrocycles 102-109 satisfy formula III below

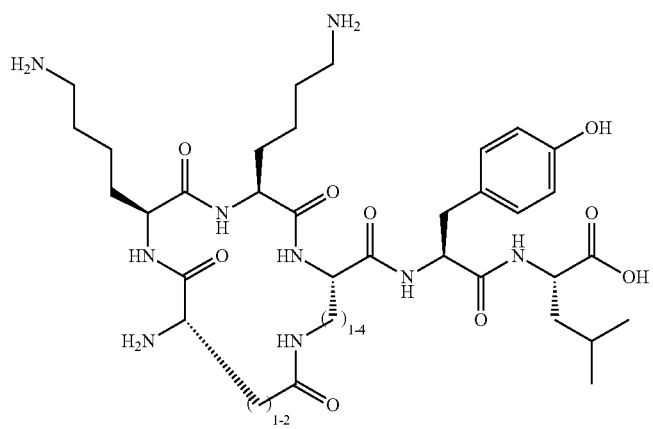

III

| | | | | | |
|---|---|---|---|---|---|
| 94 | Asp | Dap | >100 | 22750 | >4.4 |
| 95 | Asp | Dab | >100 | 8811 | >11.4 |
| 96 | Asp | Orn | >100 | 1930 | >51.8 |
| 97 | Asp | Lys | >100 | 1016 | >98.4 |
| 98 | Glu | Dap | >100 | 8185 | >12.2 |
| 99 | Glu | Dab | >100 | 11000 | >9 |
| 100 | Glu | Orn | >100 | 4500 | >22 |
| 101 | Glu | Lys | >100 | 889 | >111 |
| 102 | Dap | Asp | >100 | | |
| 103 | Dap | Glu | >100 | 9100 | >11.0 |
| 104 | Dab | Asp | >100 | 16480 | >6.1 |

TABLE III-continued

| 105 | Dab | Glu | >100 | 1450 | >67.0 |
| 106 | Orn | Asp | >100 | | |
| 107 | Orn | Glu | >100 | | |
| 108 | Lys | Asp | >100 | | |
| 109 | Lys | Glu | >100 | | |

*structures showing the side chains of compounds at positions Xaa5, Xaa3 and Xaa2 also show parts of the rest of the structure. For clarity, reference should be made to Table I above.
"PentenylGly" in the table above refers to alpha-methyl (4-pentenyl) glycine.

Example 9: Analgesic Profile In Vivo-Acute Pain Models

Compounds 34 and 67 were tested in an in vivo test of acute pain, the tail-flick test, measuring their ability to extend the response latency to thermal noxious stimuli in Sprague-Dawley rats. Following an intrathecal injection at 10 to 150 µg/kg (compound 34) or 3 nmol/kg to 61 nmol/kg (compound 67), the latency time observed was significantly increased compared to the saline injection, indicating the presence of an analgesic effect (FIGS. 2A and 4A, respectively). There was no apparent increase in latency with compound 34 for the lowest dose of 10 µg/kg (data not shown) and the analgesic effect reached a plateau around 90 µg/kg (FIG. 2A). Similarly, there was no apparent increase in latency with compound 67 for doses inferior to 3 nmol/kg (data not shown. Similar results were also evidenced by analyzing % Maximal Possible Effect (% MPE) of compounds 34 and 67 (FIGS. 3 and 5, respectively). Compound 34 exhibited a dose-dependent increase in % MPE, with ED50 of 43.8 µg/kg (FIG. 3).

Figure 2B:
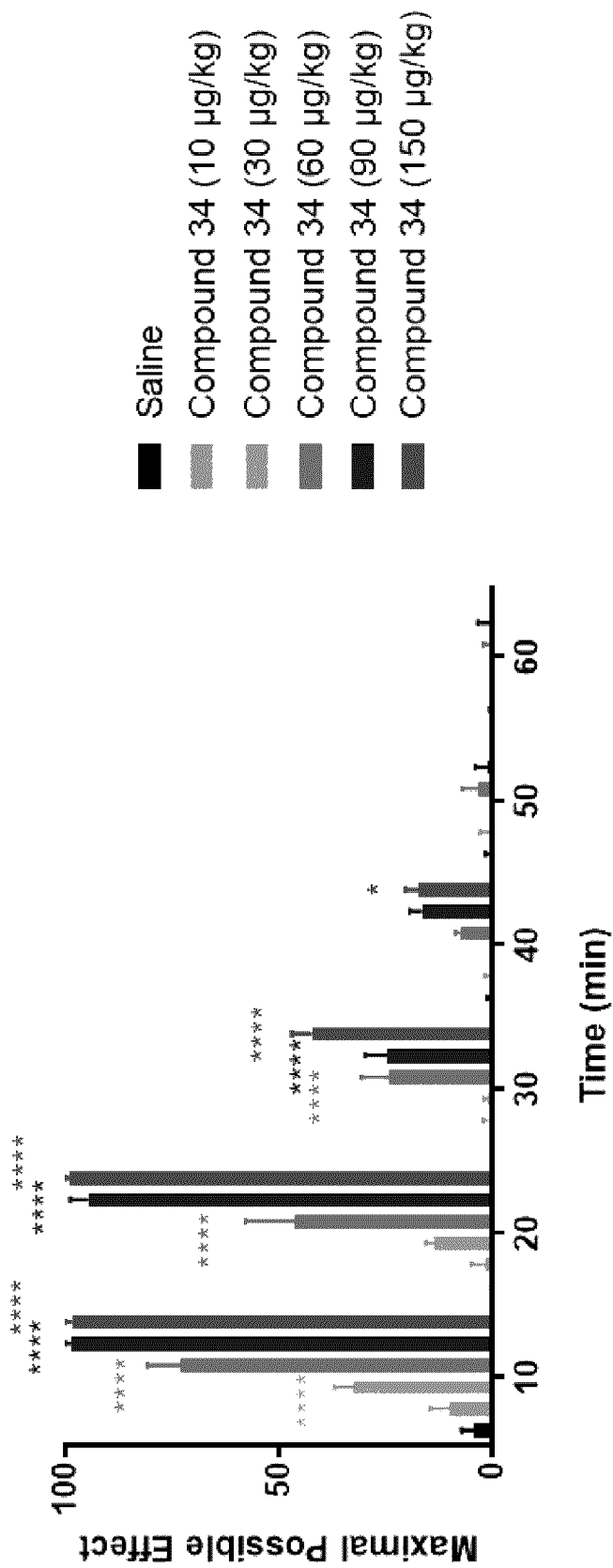
Figure 3:
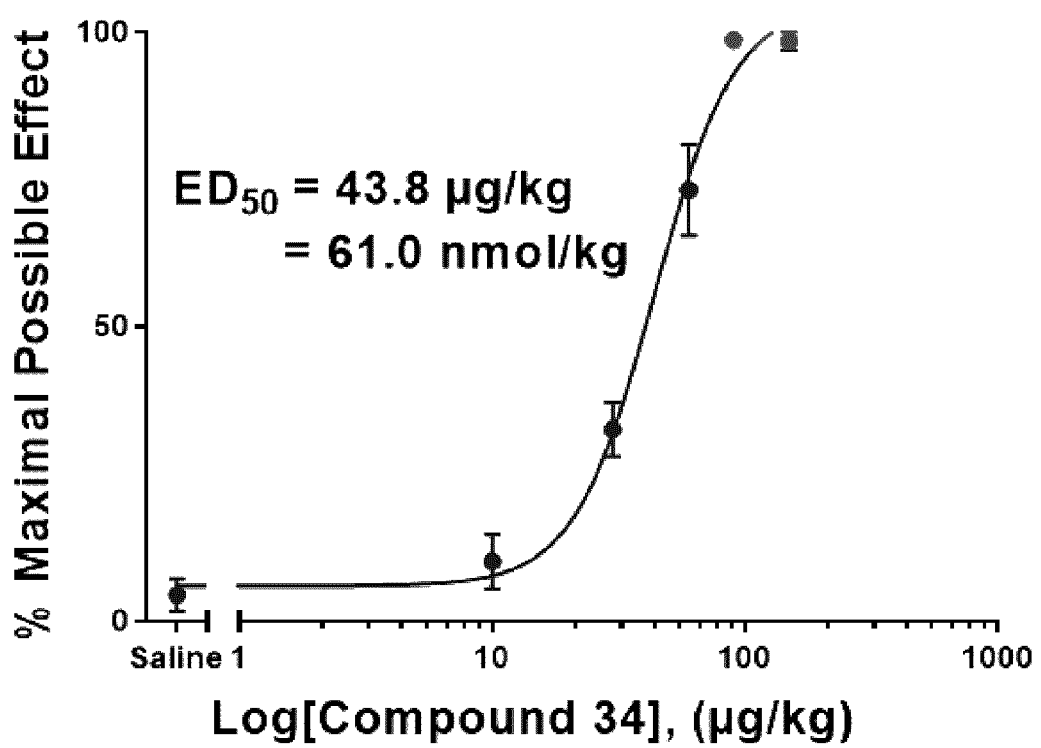
FIG. 3: Calculation of % MPE of compound 34 at 10 min post-injection allowed to determinate the half maximal effective$^{dose}$ ($ED_{50}$) of compound 34 to induce analgesia in acute pain. Error bars represent mean±SEM.

MPE reached a plateau around 90 µg/kg and raised at least 98% for the two higher doses (FIG. 2B). Compound 67 also exhibited a dose-dependent increase in % MPE, with ED50 of 8.14 nmol/kg (FIG. 5). MPE did not reach a plateau at the tested doses, and raised at least 91% for the highest dose (FIG. 4B). A comparison of the analgesic efficacy of compound 34 (at 42 nmol/kg and 84 nmol/kg or 61 nmol/kg), with compounds 60, 67, 91, 116, and 127-137, each at 61 nmol/kg (namely the $ED_{50}$ of compound 34) is shown in FIGS. 6A-E. Compounds 67, 116, 127, 128 and 133 sustainably increased latency of the tail-flick reflex compared to baseline after i.t. injection whereas the other shown compounds displayed no significant analgesic effects. At equimolar doses, compound 67 induced the highest antinociceptive effect of the tested compounds.

The antinociceptive effect of compounds 34 and 67 was also tested in the formalin tonic pain model (FIGS. 7A-B and 8A-D, respectively). Following intraplantar injection of formalin into the right hind paw of saline-pretreated rats, a biphasic nociceptive behavioral response is observed characterized by an acute phase (0-9 min) before a sustained inflammatory phase.

For the experiment conducted with compound 34, formalin-induced pain related behavior was quantified for the 2 phases by measuring the duration of episodes behavioral responses such as lifting. Compound 34 significantly decreased the time spent in lifting, from 60 µg/kg and from 90 µg/kg respectively for the acute and the inflammatory phases (FIGS. 7A-B).

For the experiment conducted with compound 67, formalin-induced pain related behavior was quantified for the 2 phases by measuring the pain score as described above. Compound 67 significantly decreased the pain score at all tested doses (i.e. from 10 nmol/kg) (FIGS. 8A-C). Compound 67 exhibited a dose-dependent decrease in pain intensity, with $ED_{50}$ of 30 nmol/kg (FIG. 8D).

Example 10: Hypothermia In Vivo

Following i.t. administration of compounds 34 and 67, no significant variation in body temperature at the higher doses injected (150 µg/kg and 209 nmol/kg, respectively) was observed as compared to saline treatment (FIGS. 9A-B, respectively and Table IV). Conversely, the NTS1 agonist PD149163 significantly decreased body temperature at a dose 5 times lower (30 µg/kg). These results confirm that hypothermia is not mediated by NTS2 receptor.

Example 11: Hypotension In Vivo

Monitoring arterial blood pressure after i.v. injection of compound 34 at 0.01 to 1 mg/kg and of compound 67 at 1 mg/kg showed no significant hypotension (FIGS. 10A-B and Table IV). However, NT(8-13) administered at 0.01 µg/kg i.v. produced a sharp blood pressure drop characterized by a triphasic response. The first phase is a short drop (about –25 mmHg) rapidly followed by a swift return to baseline level (second phase) before a sustained depression (third phase). These observations evidenced that hypotension is triggered by NTS1 activation.

Example 12: Ileum Relaxation Ex Vivo

Any change in ileum spontaneous contractile activity was noticed for compound 34 as compared to NT(8-13) which dose-dependently relaxed ileum with $IC_{50}$ of 3.9 nM, indicating that ileum relaxation is mediated via NTS1 receptor. Compound 34 doesn't impact gut motility (FIG. 11 and Table IV).

Results of examples 9-12 are summarized in Table IV below.

TABLE IV

In vivo effect of compounds of the disclosure on pain, hypothermia, hypotension and ileum relaxation.

| Compound | Acute pain (tail beam) (i.t.) | Tonic Pain (formalin test) (i.t.) | Hypothermia (i.t.) | Hypotension (i.v.) | Ileum relaxation |
|---|---|---|---|---|---|
| 34 | % MPE at 10, 20, 30, 40, 50 and 60 min<br>+++ 10, 30, 60, 90, 150 µg/kg<br>$ED_{50}$ = 48.52 µg/kg = 61 nmol/kg | +++ 60, 90, 150 µg/kg (acute phase)<br>+++ 90, 150 µg/kg (inflammatory phase) | No hypothermia (150 µg/kg) | No hypotension (0.01, 0.1, 1 mg/kg) | No ileum relaxation |

TABLE IV-continued

In vivo effect of compounds of the disclosure on pain, hypothermia, hypotension and ileum relaxation.

| Compound | Acute pain (tail beam) (i.t.) | Tonic Pain (formalin test) (i.t.) | Hypothermia (i.t.) | Hypotension (i.v.) | Ileum relaxation |
|---|---|---|---|---|---|
| 60 | No effect (61 nmol/kg) | | | | |
| 67 | % MPE at 3, 10, 30, 61 nmol/kg +++ 3, 10, 30, 61 nmol/kg $ED_{50}$ = 8.14 nmol/kg | +++ 10, 30, 100, 209 nmol/kg (acute phase) +++ 10, 30, 100, 209 nmol/kg (inflammatory phase) $ED_{50}$ = 30 nmol/kg | No hypothermia (209 nmol/kg) | No hypotension (1 mg/kg) | |
| 91 | No effect (61 nmol/kg) | | | | |
| 116 | +++ (61 nmol/kg) | | | | |

The scope of the claims should not be limited by the preferred embodiments set forth in the examples but should be given the broadest interpretation consistent with the description as a whole

The invention claimed is:
1. A compound of formula (I)

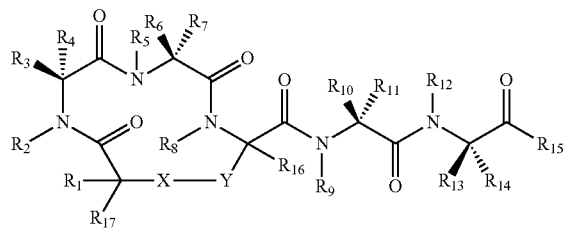

wherein:
(i) $R_1$ is H, —$CH_3$, —$NH_2$ or —NH—C(=O)—C($NH_2$)(aminoalkyl) and $R_{17}$ is H or $CH_3$; or $R_{17}$ is H, —$CH_3$, —$NH_2$ or —NH—C(=O)—C($NH_2$)(aminoalkyl); and $R_1$ is H or $CH_3$;
(ii) $R_3$ is a —(C1-C5)aminoalkyl, wherein the aminoalkyl is optionally substituted with one or more substituents, wherein each substituent is independently an halogen, amine, hydroxy, oxo, or a (C1-C5)alkyl; or the side chain of a histidine, norleucine, norvaline, glycine or glutamate; and $R_4$ is H or —$CH_3$; or
  $R_4$ is a —(C1-C5)aminoalkyl, wherein the aminoalkyl is optionally substituted with one or more substituents, wherein each substituent is independently an halogen, amine, hydroxy, oxo, or a (C1-C5)alkyl; or the side chain of a histidine, norleucine, norvaline, glycine or glutamate; and $R_3$ is H or —$CH_3$;
(iii) $R_6$ is a —(C1-C5)aminoalkyl, wherein the aminoalkyl is optionally substituted with one or more substituents, wherein each substituent is independently an halogen, amine, hydroxy, oxo, or a (C1-C5)alkyl; or the side chain of a histidine, norleucine, norvaline, glycine or glutamate; and $R_7$ is H or —$CH_3$; or
  $R_7$ is a —(C1-C5)aminoalkyl, wherein aminoalkyl is optionally substituted with one or more substituents, wherein each substituent is independently an halogen, amine, hydroxy, oxo, or a (C1-C5)alkyl; or the side chain of a histidine, norleucine, norvaline, glycine or glutamate; and $R_6$ is H or —$CH_3$;
(iv) (a) $R_{10}$ is H, or —(C1-C5)alkyl, —($CH_2$)q-(C3-C8)heteroaryl, a —($CH_2$)q-(C3-C8)aryl, a —($CH_2$)q-(C3-C8)cycloalkyl, or a —($CH_2$)q-(C3-C8)heterocycloalkyl, wherein q is 1 to 5, wherein the aryl or heteroaryl is optionally fused with one or two (C3-C8)aryl, and wherein the alkyl, heteroaryl, aryl, cycloalkyl and heterocycloalkyl is optionally substituted with one or more substituents, wherein each substituent is independently an halogen, hydroxy, amino, trifluoromethyl, cyano, nitro, or a (C1-C6)alkyl; or the side chain of an alanine (cyclopentyl), alanine (cyclohexyl), alanine (cyclobutyl), alanine (cyclopropyl), alanine (bromophenyl), alanine (thienyl), alanine (benzoylphenyl), alanine (anthryl), alanine (styryl), alanine, alanine (pyridyl), alanine (benzothienyl), alanine(naphtyl), biphenylalanine, diphenylalanine, glycine (4-Hydroxyphenyl), alanine (homotyrosine), alanine (furyl), phenylalanine (4-amino), phenylalanine (4-nitro), phenylalanine (4-methyl), phenylalanine (2, 3, 4, 5, 6 pentafluoro), tyrosine, tyrosine (O-acetyl), tryptophan, lysine, m-tyrosine, tyrosine (O-methyl), phenylalanine, phenylalanine (4-fluoro), phenylalanine (4-iodo), phenylalanine (4-tert-butyl), phenylalanine (4-$CF_3$), phenylalanine (3-chloro), phenylalanine (4-chloro), phenylalanine (3-bromo), phenylalanine (4-bromo), phenylalanine (3-iodo) or phenylalanine (4-cyano); and $R_{11}$ is H or —$CH_3$; and $R_9$ is as defined in (vi); or (b) $R_{11}$ is H, —(C1-C5)alkyl, —($CH_2$)$_q$—(C3-C8)heteroaryl, a —($CH_2$)$_q$—(C3-C8)aryl, a —($CH_2$)$_q$—(C3-C8)cycloalkyl, or a —($CH_2$)$_q$—(C3-C8)heterocycloalkyl, wherein q is 1 to 5, wherein the aryl or heteroaryl is optionally fused with one or two (C3-C8)aryl, and wherein the alkyl, heteroaryl, aryl, cycloalkyl and heterocycloalkyl is optionally substituted with one or more substituents, wherein each substituent is independently an halogen, hydroxy, amino, trifluoromethyl, cyano, nitro, or a (C1-C6)alkyl; or the side chain of a alanine (cyclopentyl), alanine (cyclohexyl), alanine (cyclobutyl), alanine (cyclopropyl), alanine (bromophenyl), alanine (thienyl), alanine (benzoylphenyl), alanine (anthryl), alanine (styryl), alanine, alanine (pyridyl), alanine (benzothienyl), alanine(naphtyl), biphenylalanine, diphenylalanine, glycine (4-Hydroxyphenyl), alanine (homotyrosine), alanine (furyl), phenylalanine (4-amino), phenylalanine (4-nitro), phenylalanine (4-methyl), phenylalanine (2, 3, 4, 5, 6 pentafluoro), tyrosine, tyrosine (O-acetyl), tryptophan, lysine, m-tyrosine, tyrosine (O-methyl), phenylalanine, phenylalanine (4-fluoro), phenylalanine (4-iodo), phenylalanine (4-tert-butyl), phenylalanine (4-$CF_3$), alanine (naphtyl), phenylalanine (3-chloro), phenylalanine (4-chloro), phenylalanine (3-bromo), phenylalanine (4-bromo), phenylalanine (3-iodo) or phenylalanine (4-cyano); and $R_{10}$ is H or —$CH_3$; and $R_9$ is as defined in (vi); or
  (c) $R_{10}$ or $R_{11}$ forms a ring with $R_9$, wherein the ring is a (C3-C8)heterocycloalkyl, optionally fused to a (C3-C8)cycloalkyl, a (C3-C8)heterocycloalkyl, a (C3-C8)aryl or a (C3-C8)heteroaryl, wherein when $R_9$ forms the ring with $R_{10}$, $R_{11}$ is H; and when $R_9$ forms the ring with $R_{11}$, $R_{10}$ is H; and wherein the definition of $R_9$ in (vi) does not apply;
(v) $R_{13}$ is H or —$CH_3$; and $R_{14}$ is H, —(C1-C5)alkyl, —($CH_2$)q'—(C3-C8)heteroaryl, a —($CH_2$)q'—(C3-C8)aryl, —($CH_2$)q'—(C3-C8)cycloalkyl, or a —($CH_2$)q'—(C3-C8)heterocycloalkyl, wherein q' is 1 to 5, wherein the aryl or heteroaryl is optionally fused with one or two (C3-C8)aryl, and wherein the alkyl, heteroaryl, aryl, cycloalkyl and heterocycloalkyl is optionally substituted with one or more substituents, wherein each substituent is independently an halogen, hydroxy, alkoxy, or a (C1-C6)alkyl; or the side chain of a leucine, tert-leucine, norleucine, norvaline, valine, neopentylglycine, cyclohexylglycine, cyclohexylalanine, phenylalanine, tyrosine (O-methyl), 2, 4, 5-trifluoro phenylalanine, homocyclohexylalanine, cyclopropylalanine, cyclobutylalanine, cyclopentylalanine, cycloheptylalanine or glycine; or $R_{14}$ is H or —$CH_3$; and $R_{13}$ is H, —(C1-C5)alkyl, —$(CH_2)q'$—(C3-C8)heteroaryl, a —$(CH_2)q'$—(C3-C8)aryl, —$(CH_2)q'$—(C3-C8)cycloalkyl, or a —$(CH_2)q'$—(C3-C8)heterocycloalkyl, wherein q' is 1 to 5, wherein the aryl or heteroaryl is optionally fused with one or two (C3-C8)aryl, and wherein the alkyl, heteroaryl, aryl, cycloalkyl and heterocycloalkyl is optionally substituted with one or more substituents, wherein each substituent is independently an halogen, hydroxy, alkoxy, or a (C1-C6)alkyl; or the side chain of a leucine, tert-leucine, norleucine, norvaline, valine, neopentylglycine, cyclohexylglycine, cyclohexylalanine, phenylalanine, tyrosine (O-methyl), 2, 4, 5, -trifluoro phenylalanine, homocyclohexylalanine, cyclopropylalanine, cyclobutylalanine, cyclopentylalanine, cycloheptylalanine or glycine;

(vi) $R_2$, $R_5$, $R_8$, $R_9$, and $R_{12}$ are each independently H, (C1-12)alkyl, or (C4-C14)aralkyl;

(vii) $R_{15}$ is H or —OH;

(viii) $R_{16}$ is H or —$CH_3$; and (ix) X is —$(CH_2)n$, wherein n is 0-4; and Y is —$(CH_2)m$-, —CH=CH$(CH_2)m$-, —$NR_{19}C(=O)(CH_2)m$- or —$C(=O)NR_{19}(CH_2)m$-, wherein m is 1-4, wherein Rig is H or (C1-C5)alkyl, or a stereoisomer or a mixture thereof, or a pharmaceutically acceptable salt, ester or solvate thereof.

2. The compound, stereoisomer, mixture, pharmaceutically acceptable salt, ester or solvate thereof of claim 1, wherein:

(iv) $R_{10}$ is a substituted or unsubstituted —$(CH_2)_q$—(C3-C8)aryl or —$(CH_2)_q$—(C3-C8)heteroaryl, wherein the aryl or heteroaryl is optionally fused with one or two (C3-C8)aryl, and wherein the aryl or heteroaryl is optionally substituted with one or more substituents, wherein each substituent is independently an halogen, hydroxy, amino, trifluoromethyl, cyano, nitro, or a (C1-C6)alkyl, and $R_{11}$ is H or —$CH_3$; or $R_{10}$ or $R_{11}$ forms a ring with $R_9$, wherein the ring is a (C3-C8) heterocycloalkyl fused with an (C3-C8)cycloalkyl or a (C3-C8)aryl, wherein when $R_{10}$ forms the ring with $R_9$, $R_{11}$ is H; and when $R_{11}$ forms the ring with $R_9$, $R_{10}$ is H; and (v) $R_{13}$ is H, or —(C1-C5)alkyl; and $R_{14}$ is H, a substituted or unsubstituted —$(CH_2)q'$—(C3-C8)cycloalkyl, —(C1-C5)alkyl, —$(CH_2)q'$—(C3-C8)heterocycloalkyl, or —$(CH_2)q'$—(C3-C8)aryl, wherein q' is 1 to 5, and wherein the aryl is optionally substituted with one or more substituents, wherein each substituent is independently an halogen, hydroxy, or alkoxy.

3. The compound, stereoisomer, mixture, pharmaceutically acceptable salt, ester or solvate thereof of claim 1, wherein the compound is:

| Code | Structure |
|---|---|
| 14. (SEQ ID NO: 30) | 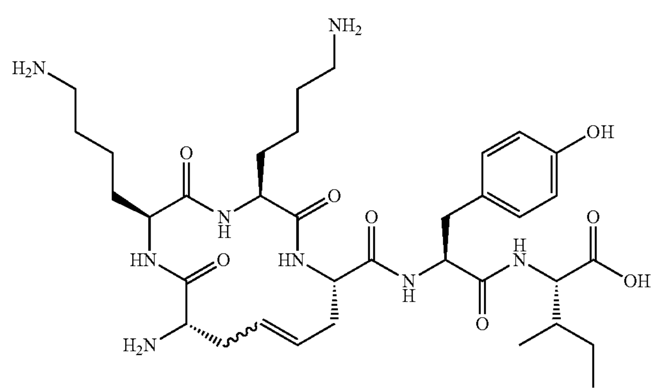 [SMILES: CCC(C)[C@H](NC(=O)[C@H](Cc1ccc(O)cc1)NC(=O)[C@@H]1CC=CC[C@H](N)C(=O)N[C@@H](CCCCN)C(=O)N[C@@H](CCCCN)C(=O)N1)C(=O)O] |
| 15. (SEQ ID NO: 31) | 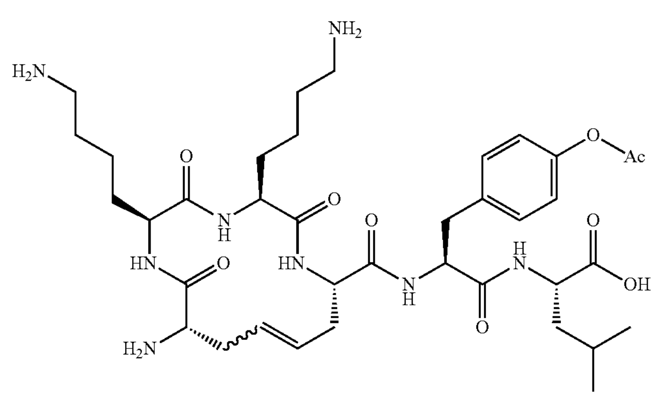 [SMILES: CC(=O)Oc1ccc(C[C@H](NC(=O)[C@@H]2CC=CC[C@H](N)C(=O)N[C@@H](CCCCN)C(=O)N[C@@H](CCCCN)C(=O)N2)C(=O)N[C@@H](CC(C)C)C(=O)O)cc1] |

| Code | Structure |
|---|---|
| 16. (SEQ ID NO: 32) | 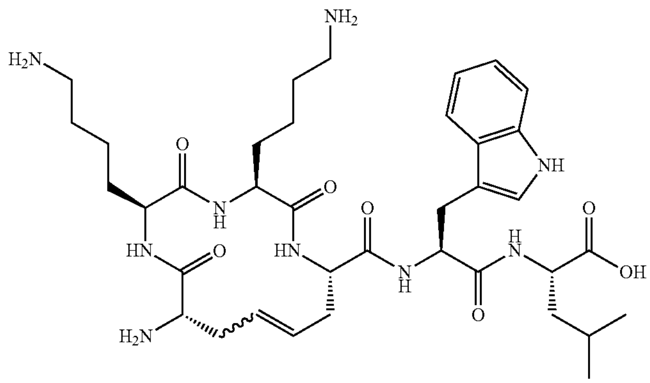 [SMILES: CC(C)C[C@H](NC(=O)[C@H](Cc1c[nH]c2ccccc12)NC(=O)[C@@H]1CC=CC[C@H](N)C(=O)N[C@@H](CCCCN)C(=O)N[C@@H](CCCCN)C(=O)N1)C(=O)O] |
| 17. (SEQ ID NO: 33) | 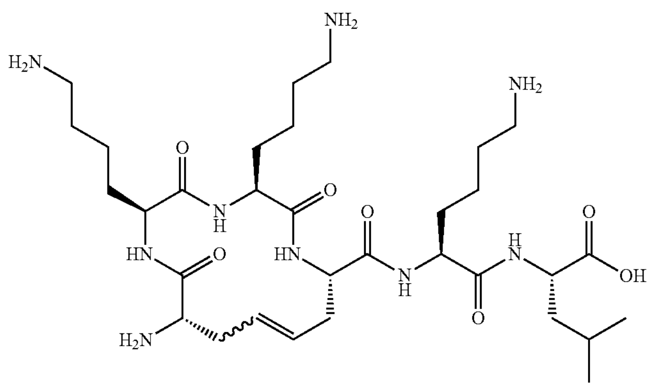 [SMILES: CC(C)C[C@H](NC(=O)[C@H](CCCCN)NC(=O)[C@@H]1CC=CC[C@H](N)C(=O)N[C@@H](CCCCN)C(=O)N[C@@H](CCCCN)C(=O)N1)C(=O)O] |
| 21. (SEQ ID NO: 34) | 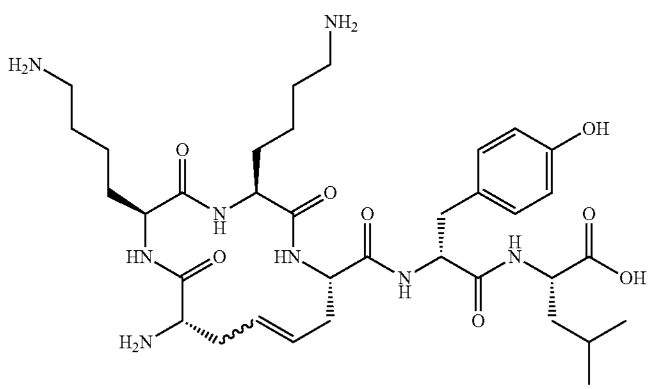 [SMILES: CC(C)C[C@H](NC(=O)[C@@H](Cc1ccc(O)cc1)NC(=O)[C@@H]1CC=CC[C@H](N)C(=O)N[C@@H](CCCCN)C(=O)N[C@@H](CCCCN)C(=O)N1)C(=O)O] |
| 27. (SEQ ID NO: 35) | 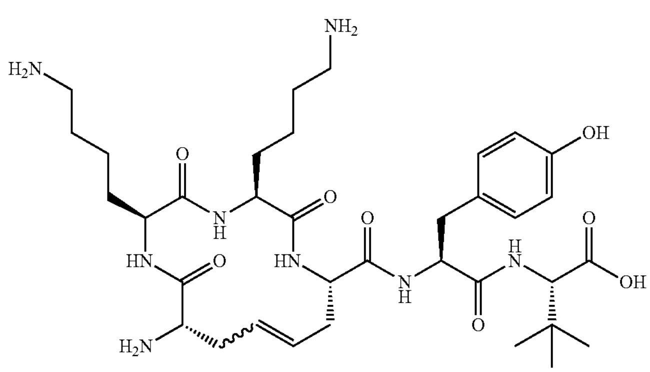 [SMILES: CC(C)(C)[C@H](NC(=O)[C@H](Cc1ccc(O)cc1)NC(=O)[C@@H]1CC=CC[C@H](N)C(=O)N[C@@H](CCCCN)C(=O)N[C@@H](CCCCN)C(=O)N1)C(=O)O] |

| Code | Structure |
|---|---|
| 28. (SEQ ID NO: 36) | 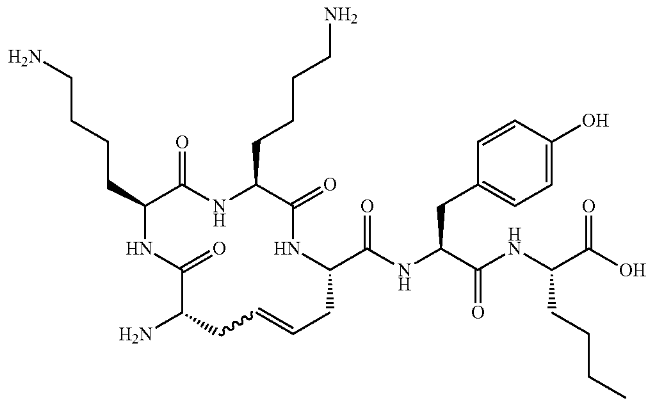 [SMILES: CCCC[C@H](NC(=O)[C@H](Cc1ccc(O)cc1)NC(=O)[C@@H]1CC=CC[C@H](N)C(=O)N[C@@H](CCCCN)C(=O)N[C@@H](CCCCN)C(=O)N1)C(=O)O] |
| 29. (SEQ ID NO: 37) | 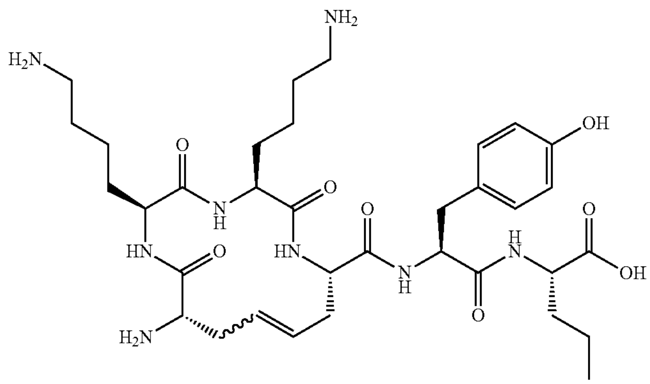 [SMILES: CCC[C@H](NC(=O)[C@H](Cc1ccc(O)cc1)NC(=O)[C@@H]1CC=CC[C@H](N)C(=O)N[C@@H](CCCCN)C(=O)N[C@@H](CCCCN)C(=O)N1)C(=O)O] |
| 30. (SEQ ID NO: 38) | 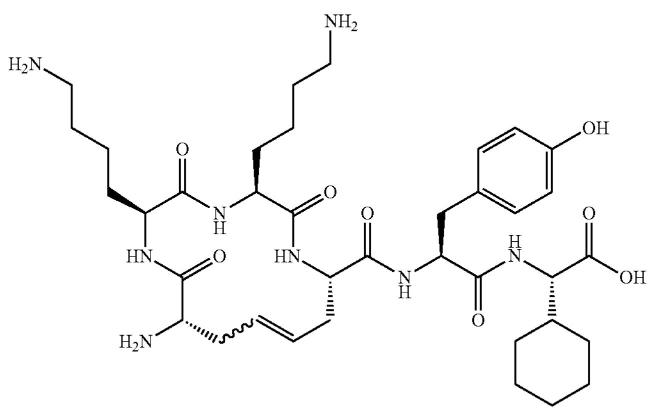 [SMILES: NCCCC[C@@H]1NC(=O)[C@H](CCCCN)NC(=O)[C@@H](N)CC=CC[C@@H](C(=O)N[C@@H](Cc2ccc(O)cc2)C(=O)N[C@H](C(=O)O)C2CCCCC2)NC1=O] |
| 31. (SEQ ID NO: 39) | 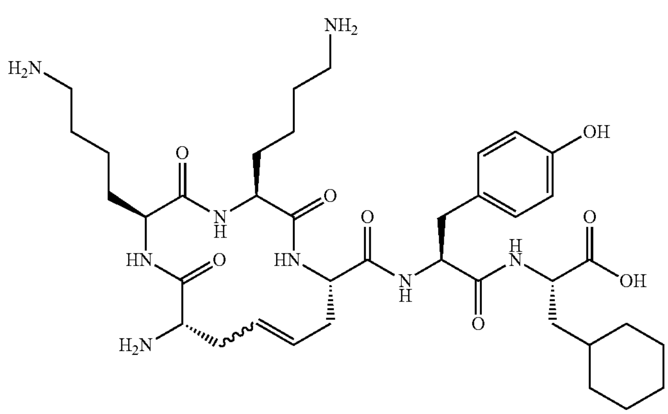 [SMILES: NCCCC[C@@H]1NC(=O)[C@H](CCCCN)NC(=O)[C@@H](N)CC=CC[C@@H](C(=O)N[C@@H](Cc2ccc(O)cc2)C(=O)N[C@@H](CC2CCCCC2)C(=O)O)NC1=O] |

-continued

| Code | Structure |
|---|---|
| 32. (SEQ ID NO: 40) | 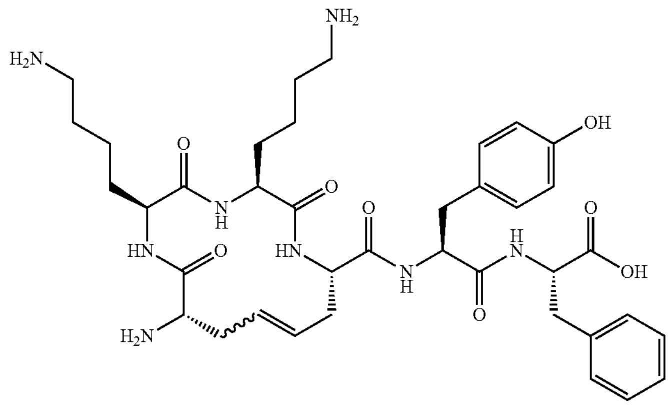 [SMILES: NCCCC[C@@H]1NC(=O)[C@H](CCCCN)NC(=O)[C@@H](N)CC=CC[C@@H](C(=O)N[C@@H](Cc2ccc(O)cc2)C(=O)N[C@@H](Cc2ccccc2)C(=O)O)NC1=O] |
| 33. (SEQ ID NO: 41) | 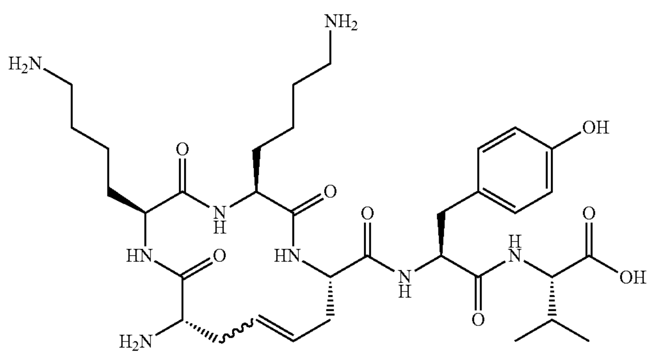 [SMILES: CC(C)[C@H](NC(=O)[C@H](Cc1ccc(O)cc1)NC(=O)[C@@H]1CC=CC[C@H](N)C(=O)N[C@@H](CCCCN)C(=O)N[C@@H](CCCCN)C(=O)N1)C(=O)O] |
| 34. (SEQ ID NO: 22) | 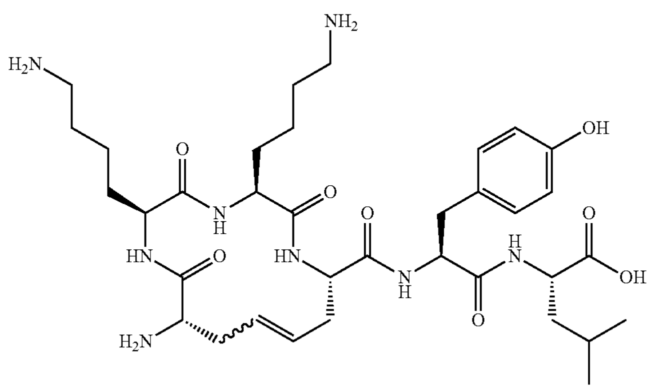 |
| 38. (SEQ ID NO: 42) | 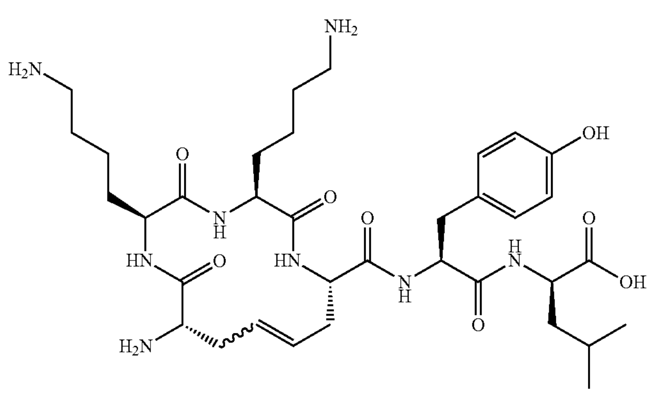 [SMILES: CC(C)C[C@@H](NC(=O)[C@H](Cc1ccc(O)cc1)NC(=O)[C@@H]1CC=CC[C@H](N)C(=O)N[C@@H](CCCCN)C(=O)N[C@@H](CCCCN)C(=O)N1)C(=O)O] |

-continued

| Code | Structure |
|---|---|
| 39. (SEQ ID NO: 43) | 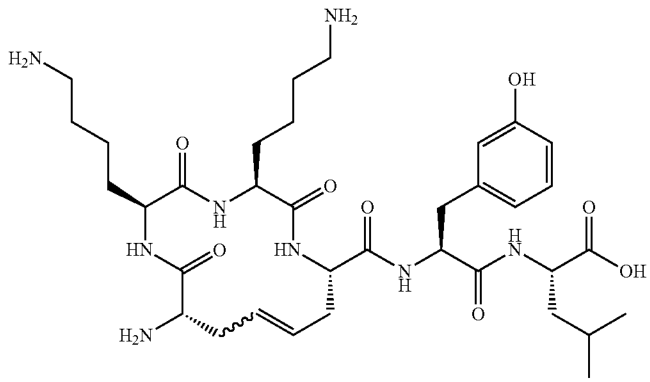 [SMILES: CC(C)C[C@H](NC(=O)[C@H](Cc1cccc(O)c1)NC(=O)[C@@H]1CC=CC[C@H](N)C(=O)N[C@@H](CCCCN)C(=O)N[C@@H](CCCCN)C(=O)N1)C(=O)O] |
| 40. (SEQ ID NO: 44) | 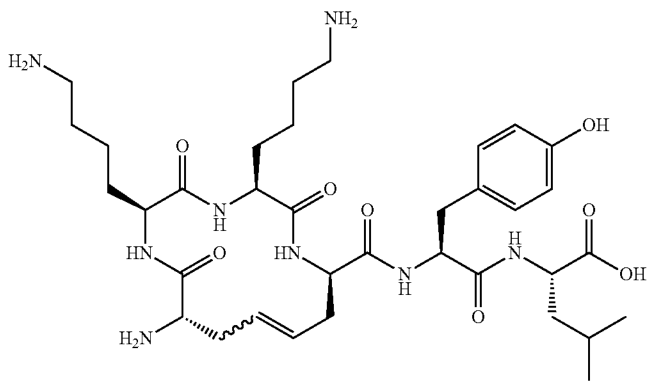 [SMILES: CC(C)C[C@H](NC(=O)[C@H](Cc1ccc(O)cc1)NC(=O)[C@H]1CC=CC[C@H](N)C(=O)N[C@@H](CCCCN)C(=O)N[C@@H](CCCCN)C(=O)N1)C(=O)O] |
| 41. (SEQ ID NO: 45) | 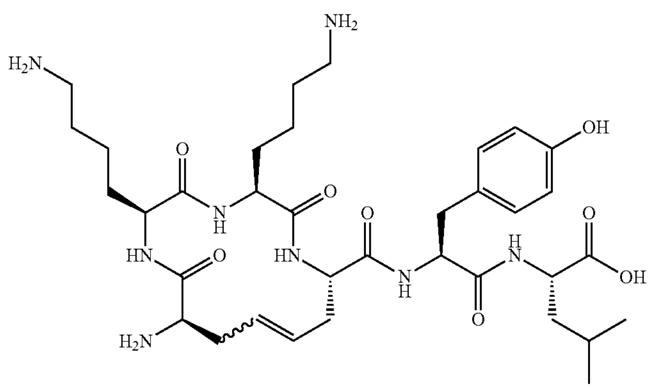 [SMILES: CC(C)C[C@H](NC(=O)[C@H](Cc1ccc(O)cc1)NC(=O)[C@@H]1CC=CC[C@@H](N)C(=O)N[C@@H](CCCCN)C(=O)N[C@@H](CCCCN)C(=O)N1)C(=O)O] |
| 42. (SEQ ID NO: 46) | 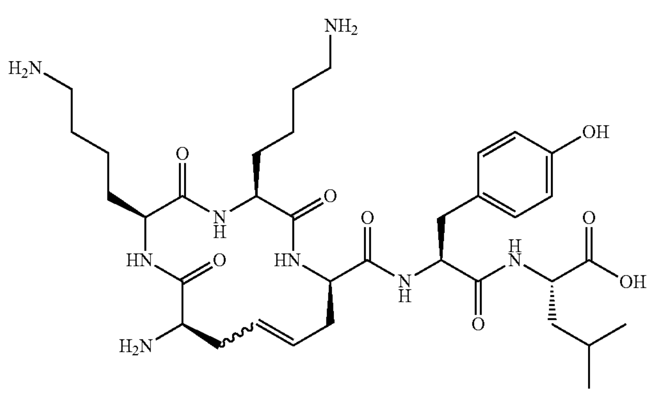 [SMILES: CC(C)C[C@H](NC(=O)[C@H](Cc1ccc(O)cc1)NC(=O)[C@H]1CC=CC[C@@H](N)C(=O)N[C@@H](CCCCN)C(=O)N[C@@H](CCCCN)C(=O)N1)C(=O)O] |

| Code | Structure |
|------|-----------|
| 43. (SEQ ID NO: 47) | 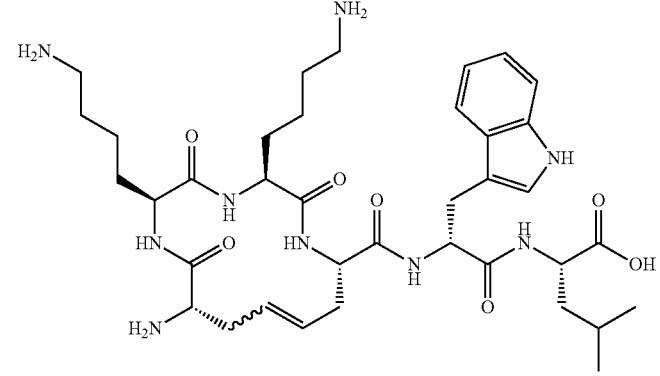 [SMILES: CC(C)C[C@H](NC(=O)[C@@H](Cc1c[nH]c2ccccc12)NC(=O)[C@@H]1CC=CC[C@H](N)C(=O)N[C@@H](CCCCN)C(=O)N[C@@H](CCCCN)C(=O)N1)C(=O)O] |
| 44. (SEQ ID NO: 48) | 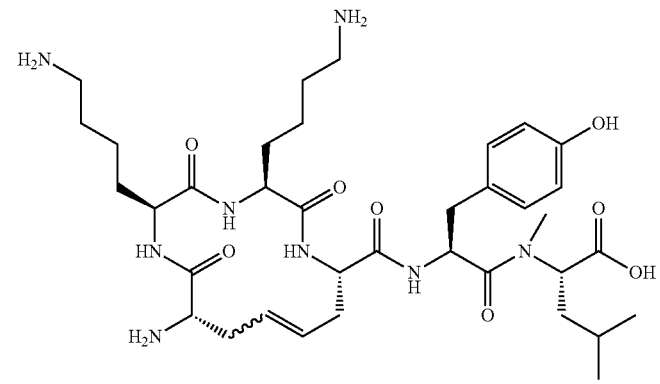 [SMILES: CC(C)C[C@@H](C(=O)O)N(C)C(=O)[C@H](Cc1ccc(O)cc1)NC(=O)[C@@H]1CC=CC[C@H](N)C(=O)N[C@@H](CCCCN)C(=O)N[C@@H](CCCCN)C(=O)N1] |
| 45. (SEQ ID NO: 49) | 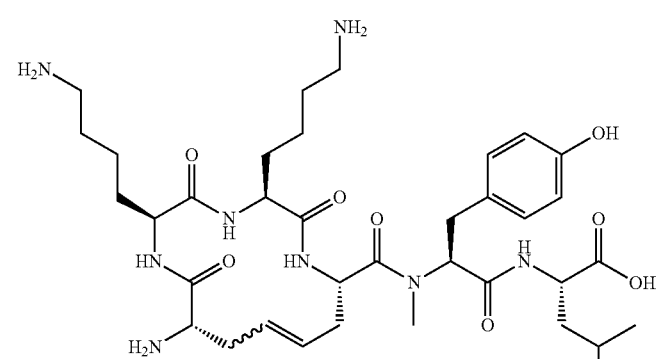 |
| 46. (SEQ ID NO: 50) | 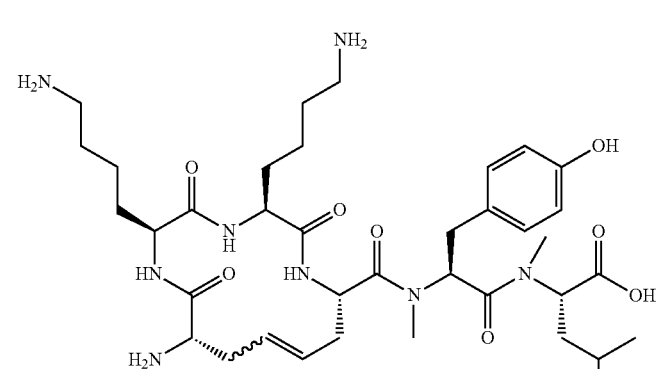 |

| Code | Structure |
|---|---|
| 47. (SEQ ID NO: 51) | 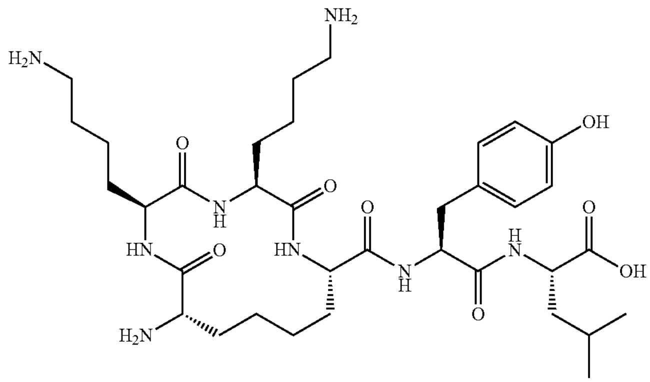 [SMILES: CC(C)C[C@H](NC(=O)[C@H](Cc1ccc(O)cc1)NC(=O)[C@@H]1CCCC[C@H](N)C(=O)N[C@@H](CCCCN)C(=O)N[C@@H](CCCCN)C(=O)N1)C(=O)O] |
| 48. (SEQ ID NO: 52) | 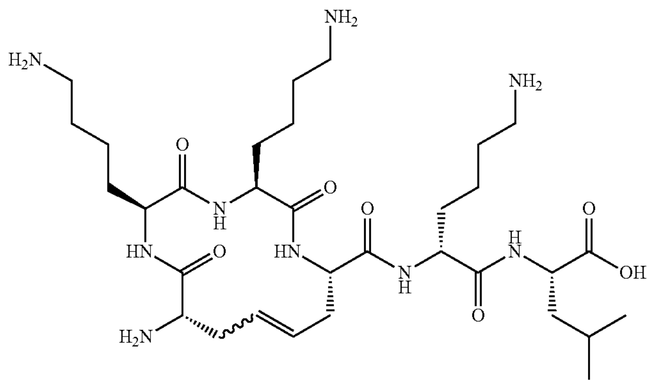 [SMILES: CC(C)C[C@H](NC(=O)[C@@H](CCCCN)NC(=O)[C@@H]1CC=CC[C@H](N)C(=O)N[C@@H](CCCCN)C(=O)N[C@@H](CCCCN)C(=O)N1)C(=O)O] |
| 49. (SEQ ID NO: 53) | 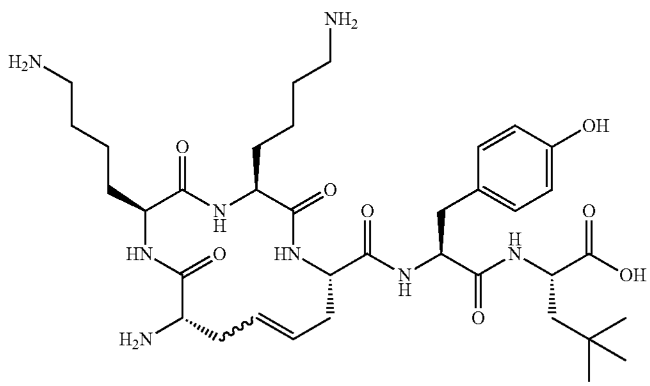 [SMILES: CC(C)(C)C[C@H](NC(=O)[C@H](Cc1ccc(O)cc1)NC(=O)[C@@H]1CC=CC[C@H](N)C(=O)N[C@@H](CCCCN)C(=O)N[C@@H](CCCCN)C(=O)N1)C(=O)O] |
| 51. (SEQ ID NO: 54) | 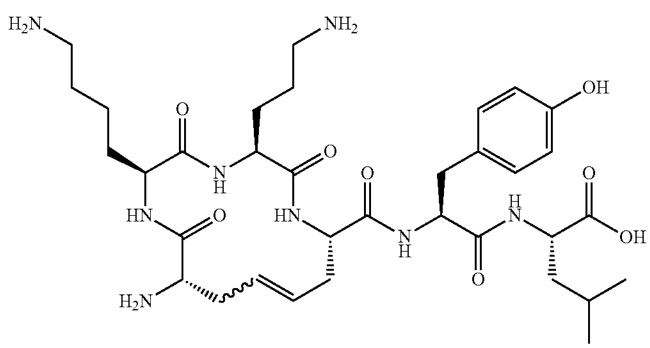 [SMILES: CC(C)C[C@H](NC(=O)[C@H](Cc1ccc(O)cc1)NC(=O)[C@@H]1CC=CC[C@H](N)C(=O)N[C@@H](CCCCN)C(=O)N[C@@H](CCCN)C(=O)N1)C(=O)O] |

| Code | Structure |
|---|---|
| 52. (SEQ ID NO: 55) | 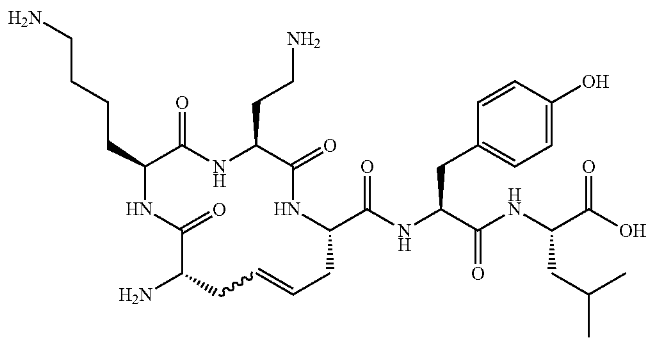 [SMILES: CC(C)C[C@H](NC(=O)[C@H](Cc1ccc(O)cc1)NC(=O)[C@@H]1CC=CC[C@H](N)C(=O)N[C@@H](CCCCN)C(=O)N[C@@H](CCN)C(=O)N1)C(=O)O] |
| 53. (SEQ ID NO: 56) | 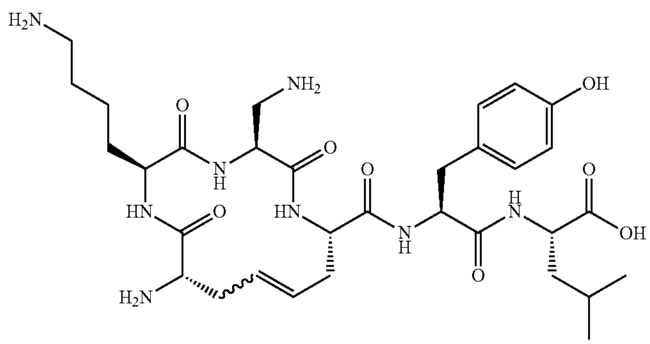 [SMILES: CC(C)C[C@H](NC(=O)[C@H](Cc1ccc(O)cc1)NC(=O)[C@@H]1CC=CC[C@H](N)C(=O)N[C@@H](CCCCN)C(=O)N[C@@H](CN)C(=O)N1)C(=O)O] |
| 54. (SEQ ID NO: 57) | 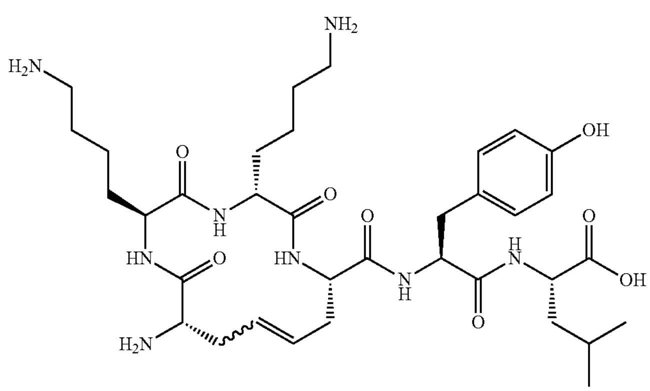 [SMILES: CC(C)C[C@H](NC(=O)[C@H](Cc1ccc(O)cc1)NC(=O)[C@@H]1CC=CC[C@H](N)C(=O)N[C@@H](CCCCN)C(=O)N[C@H](CCCCN)C(=O)N1)C(=O)O] |
| 55. (SEQ ID NO: 58) | 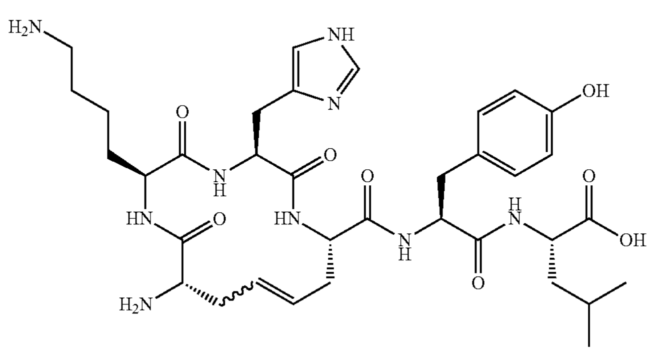 [SMILES: CC(C)C[C@H](NC(=O)[C@H](Cc1ccc(O)cc1)NC(=O)[C@@H]1CC=CC[C@H](N)C(=O)N[C@@H](CCCCN)C(=O)N[C@@H](Cc2c[nH]cn2)C(=O)N1)C(=O)O] |

| Code | Structure |
|---|---|
| 57. (SEQ ID NO: 59) | 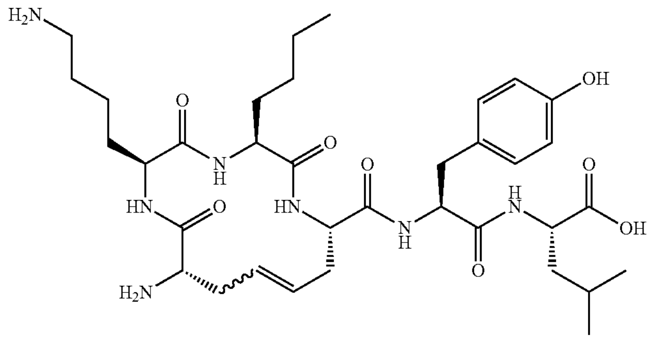 [SMILES: CCCC[C@@H]1NC(=O)[C@H](CCCCN)NC(=O)[C@@H](N)CC=CC[C@@H](C(=O)N[C@@H](Cc2ccc(O)cc2)C(=O)N[C@@H](CC(C)C)C(=O)O)NC1=O] |
| 58. (SEQ ID NO: 60) | 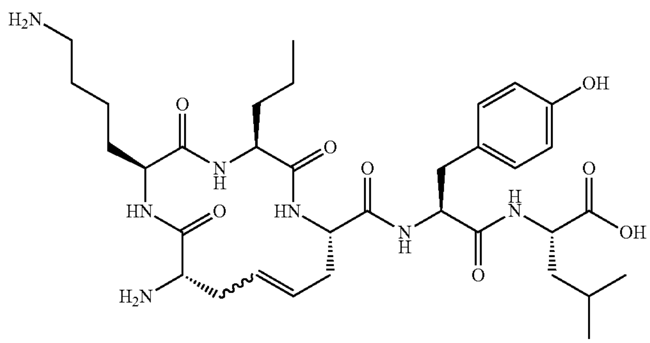 [SMILES: CCC[C@@H]1NC(=O)[C@H](CCCCN)NC(=O)[C@@H](N)CC=CC[C@@H](C(=O)N[C@@H](Cc2ccc(O)cc2)C(=O)N[C@@H](CC(C)C)C(=O)O)NC1=O] |
| 59. (SEQ ID NO: 61) | 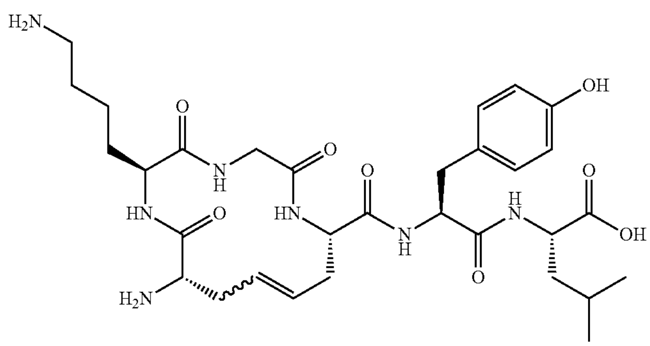 [SMILES: CC(C)C[C@H](NC(=O)[C@H](Cc1ccc(O)cc1)NC(=O)[C@@H]1CC=CC[C@H](N)C(=O)N[C@@H](CCCCN)C(=O)NCC(=O)N1)C(=O)O] |
| 60. (SEQ ID NO: 62) | 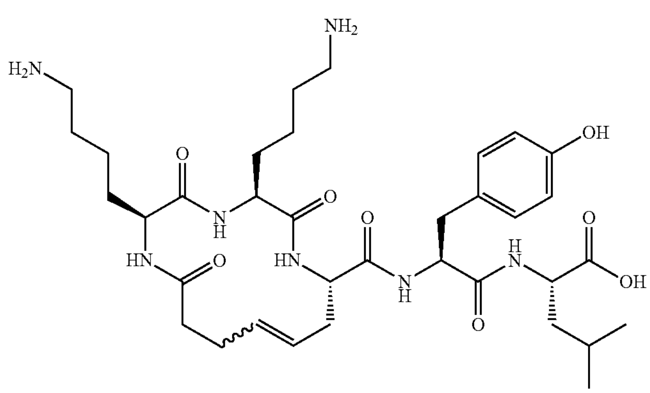 |

| Code | Structure |
|---|---|
| 61. (SEQ ID NO: 63) | 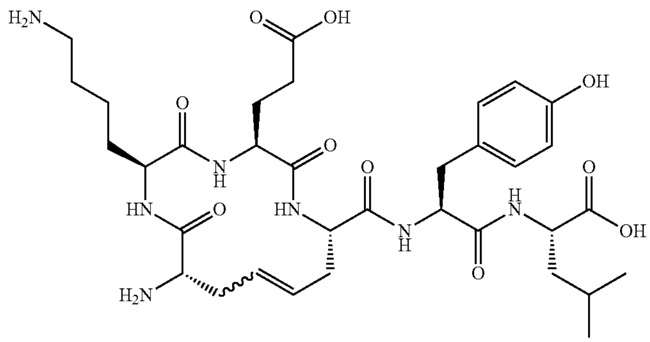 [SMILES: CC(C)C[C@H](NC(=O)[C@H](Cc1ccc(O)cc1)NC(=O)[C@@H]1CC=CC[C@H](N)C(=O)N[C@@H](CCCCN)C(=O)N[C@@H](CCC(=O)O)C(=O)N1)C(=O)O] |
| 62. (SEQ ID NO: 64) | 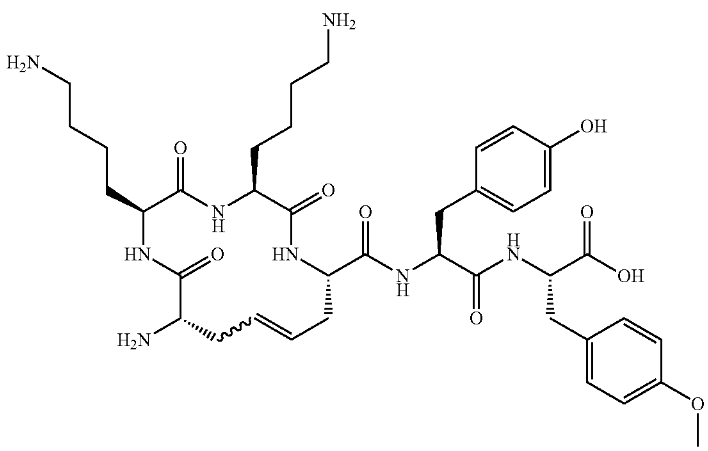 [SMILES: COc1ccc(C[C@H](NC(=O)[C@H](Cc2ccc(O)cc2)NC(=O)[C@@H]2CC=CC[C@H](N)C(=O)N[C@@H](CCCCN)C(=O)N[C@@H](CCCCN)C(=O)N2)C(=O)O)cc1] |
| 63. (SEQ ID NO: 65) | 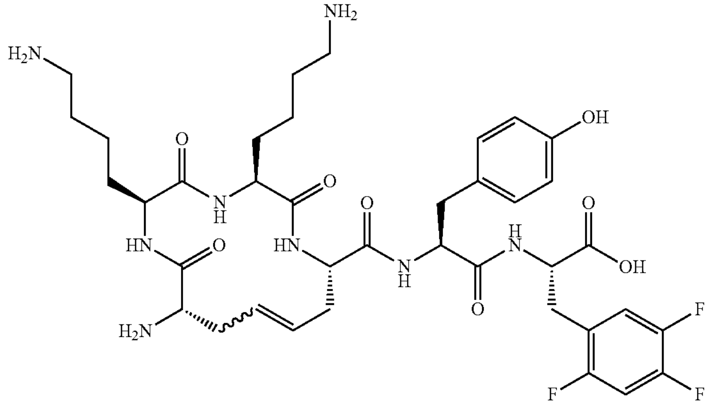 [SMILES: NCCCC[C@@H]1NC(=O)[C@H](CCCCN)NC(=O)[C@@H](N)CC=CC[C@@H](C(=O)N[C@@H](Cc2ccc(O)cc2)C(=O)N[C@@H](Cc2cc(F)c(F)cc2F)C(=O)O)NC1=O] |

-continued
| Code | Structure |
|---|---|
| 64. (SEQ ID NO: 66) | 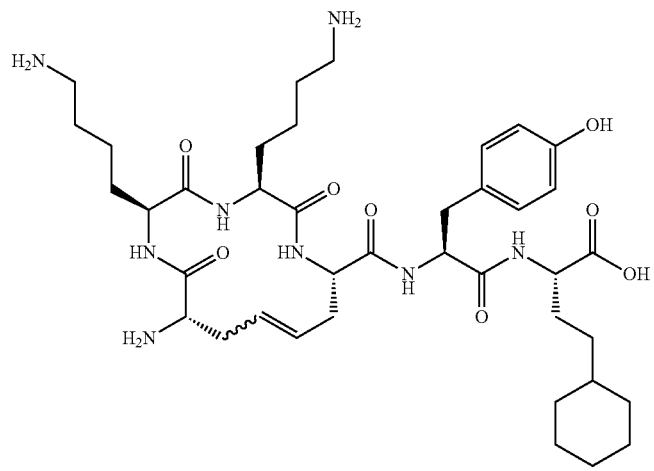 [SMILES: NCCCC[C@@H]1NC(=O)[C@H](CCCCN)NC(=O)[C@@H](N)CC=CC[C@@H](C(=O)N[C@@H](Cc2ccc(O)cc2)C(=O)N[C@@H](CCC2CCCCC2)C(=O)O)NC1=O] |
| 65. (SEQ ID NO: 67) | 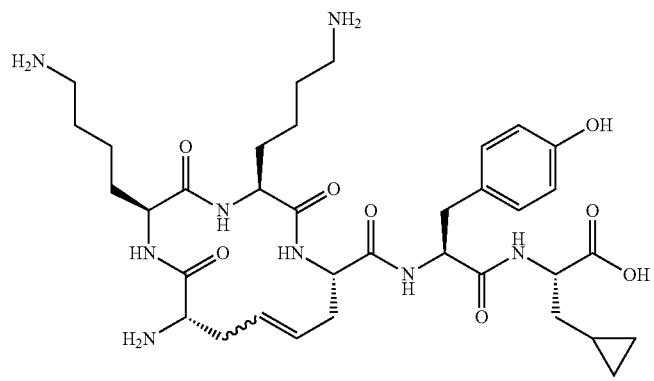 [SMILES: NCCCC[C@@H]1NC(=O)[C@H](CCCCN)NC(=O)[C@@H](N)CC=CC[C@@H](C(=O)N[C@@H](Cc2ccc(O)cc2)C(=O)N[C@@H](CC2CC2)C(=O)O)NC1=O] |
| 66. (SEQ ID NO: 68) | 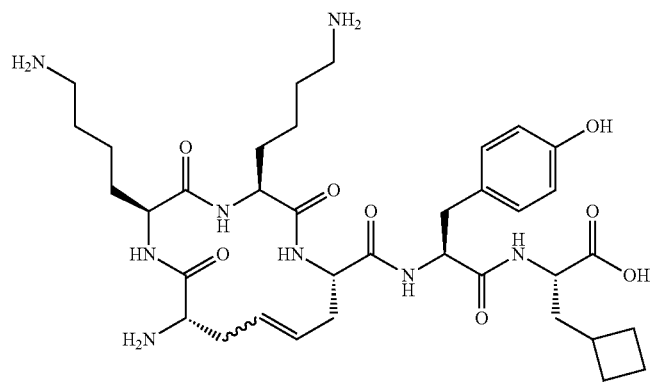 [SMILES: NCCCC[C@@H]1NC(=O)[C@H](CCCCN)NC(=O)[C@@H](N)CC=CC[C@@H](C(=O)N[C@@H](Cc2ccc(O)cc2)C(=O)N[C@@H](CC2CCC2)C(=O)O)NC1=O] |

| Code | Structure |
|---|---|
| 67. (SEQ ID NO: 69) | 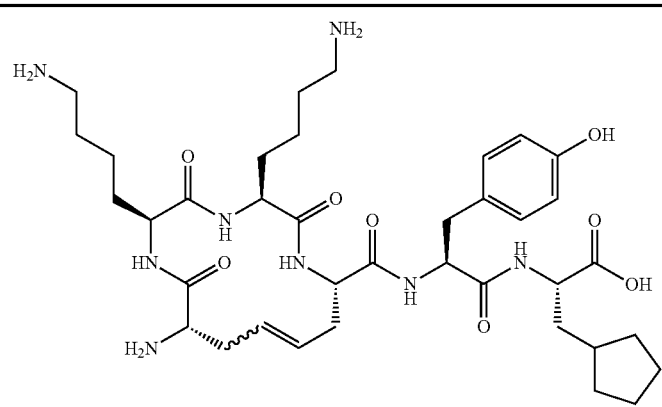 |
| 68. (SEQ ID NO: 70) | 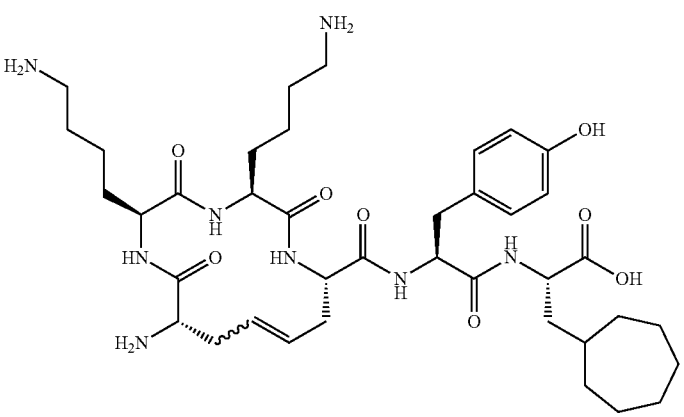 [SMILES: NCCCC[C@@H]1NC(=O)[C@H](CCCCN)NC(=O)[C@@H](N)CC=CC[C@@H](C(=O)N[C@@H](Cc2ccc(O)cc2)C(=O)N[C@@H](CC2CCCCCC2)C(=O)O)NC1=O] |
| 69. (SEQ ID NO: 71) | 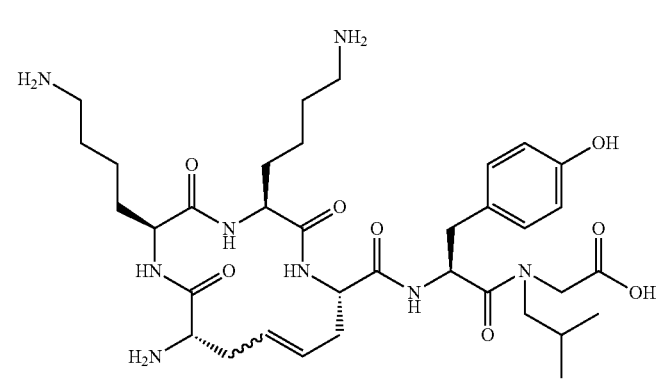 [SMILES: CC(C)CN(CC(=O)O)C(=O)[C@H](Cc1ccc(O)cc1)NC(=O)[C@@H]1CC=CC[C@H](N)C(=O)N[C@@H](CCCCN)C(=O)N[C@@H](CCCCN)C(=O)N1] |
| 70. (SEQ ID NO: 72) | 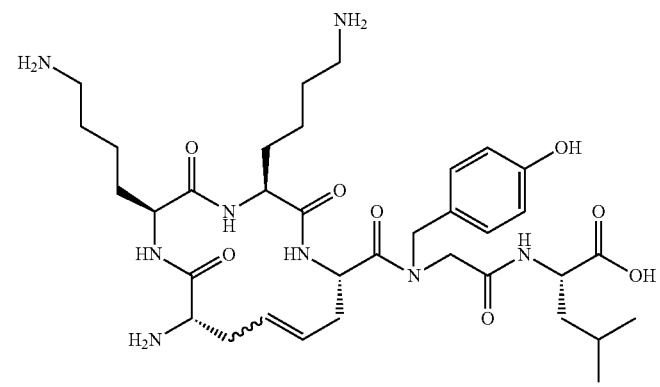 [SMILES: CC(C)C[C@H](NC(=O)CN(Cc1ccc(O)cc1)C(=O)[C@@H]1CC=CC[C@H](N)C(=O)N[C@@H](CCCCN)C(=O)N[C@@H](CCCCN)C(=O)N1)C(=O)O] |

| Code | Structure |
|---|---|
| 71. (SEQ ID NO: 73) | 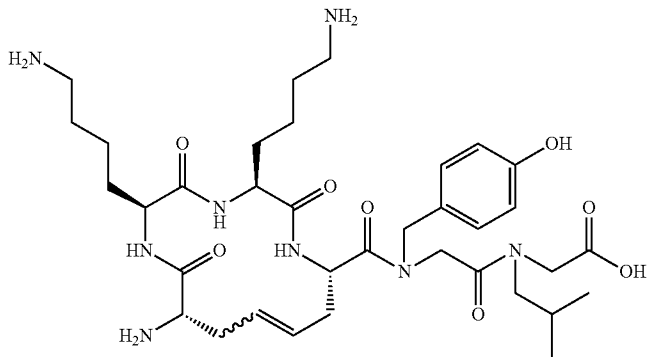 [SMILES: CC(C)CN(CC(=O)O)C(=O)CN(Cc1ccc(O)cc1)C(=O)[C@@H]1CC=CC[C@H](N)C(=O)N[C@@H](CCCCN)C(=O)N[C@@H](CCCCN)C(=O)N1] |
| 72. (SEQ ID NO: 74) | 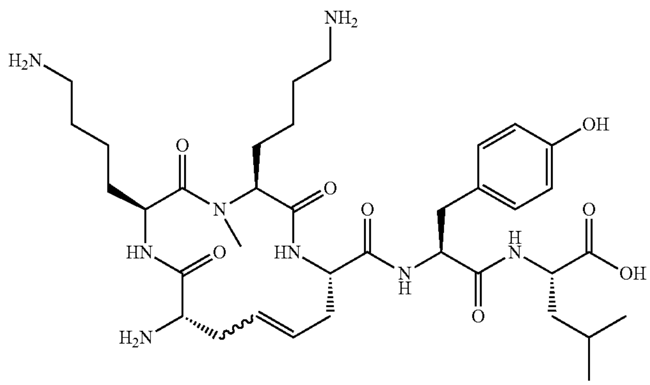 [SMILES: CC(C)C[C@H](NC(=O)[C@H](Cc1ccc(O)cc1)NC(=O)[C@@H]1CC=CC[C@H](N)C(=O)N[C@@H](CCCCN)C(=O)N(C)[C@@H](CCCCN)C(=O)N1)C(=O)O] |
| 73. (SEQ ID NO: 75) | 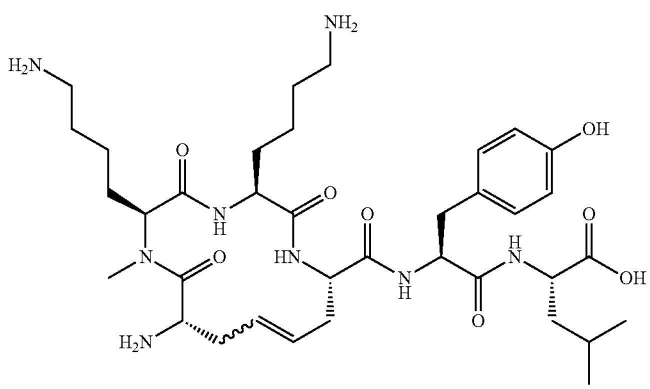 [SMILES: CC(C)C[C@H](NC(=O)[C@H](Cc1ccc(O)cc1)NC(=O)[C@@H]1CC=CC[C@H](N)C(=O)N(C)[C@@H](CCCCN)C(=O)N[C@@H](CCCCN)C(=O)N1)C(=O)O] |
| 74. (SEQ ID NO: 76) | 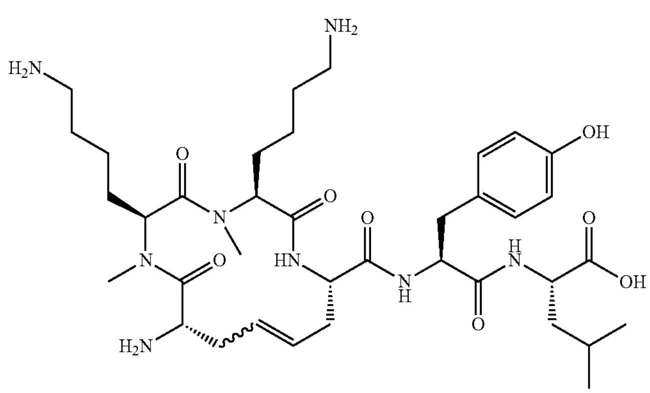 [SMILES: CC(C)C[C@H](NC(=O)[C@H](Cc1ccc(O)cc1)NC(=O)[C@@H]1CC=CC[C@H](N)C(=O)N(C)[C@@H](CCCCN)C(=O)N(C)[C@@H](CCCCN)C(=O)N1)C(=O)O] |

-continued
| Code | Structure |
|---|---|
| 75. (SEQ ID NO: 77) | 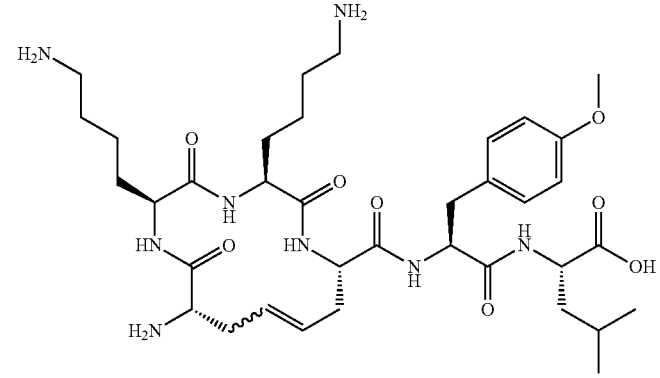 [SMILES: COc1ccc(C[C@H](NC(=O)[C@@H]2CC=CC[C@H](N)C(=O)N[C@@H](CCCCN)C(=O)N[C@@H](CCCCN)C(=O)N2)C(=O)N[C@@H](CC(C)C)C(=O)O)cc1] |
| 76. (SEQ ID NO: 78) | 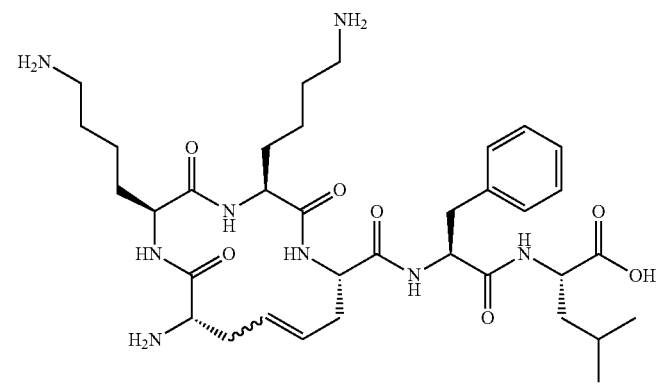 |
| 77. (SEQ ID NO: 79) | 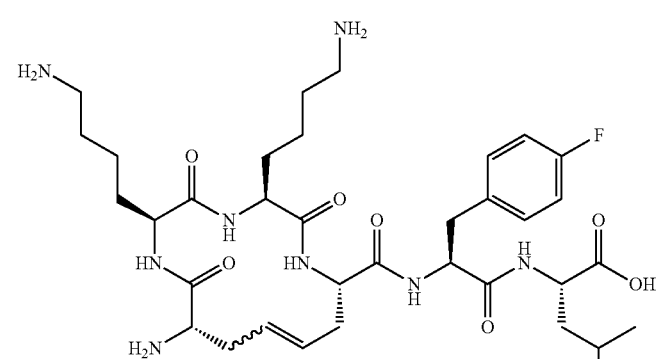 |
| 78. (SEQ ID NO: 80) | 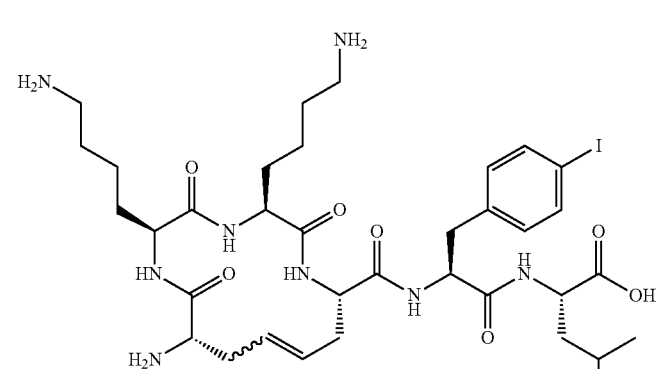 |

| Code | Structure |
|---|---|
| 79. (SEQ ID NO: 81) | 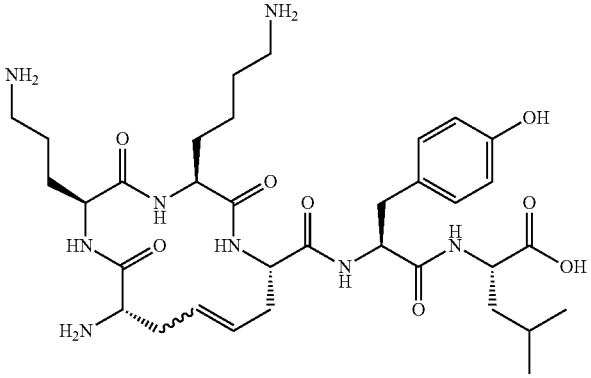 [SMILES: CC(C)C[C@H](NC(=O)[C@H](Cc1ccc(O)cc1)NC(=O)[C@@H]1CC=CC[C@H](N)C(=O)N[C@@H](CCCN)C(=O)N[C@@H](CCCCN)C(=O)N1)C(=O)O] |
| 80. (SEQ ID NO: 82) | 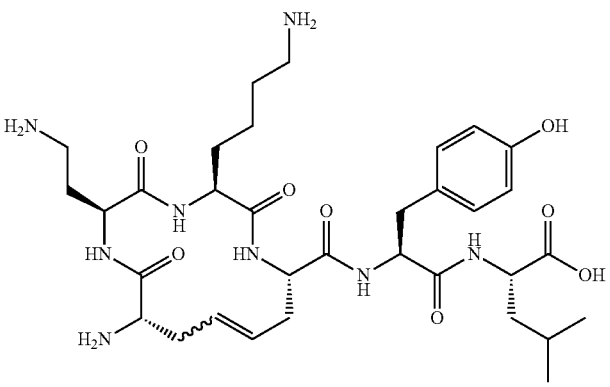 [SMILES: CC(C)C[C@H](NC(=O)[C@H](Cc1ccc(O)cc1)NC(=O)[C@@H]1CC=CC[C@H](N)C(=O)N[C@@H](CCN)C(=O)N[C@@H](CCCCN)C(=O)N1)C(=O)O] |
| 81. (SEQ ID NO: 83) | 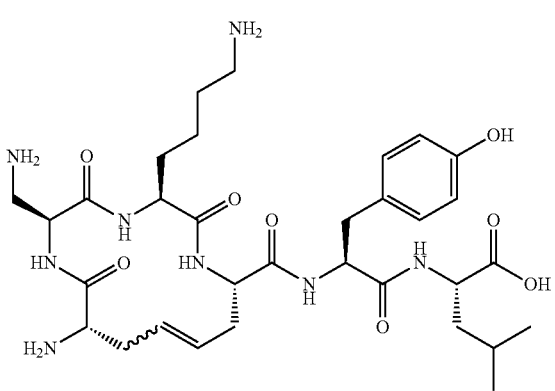 [SMILES: CC(C)C[C@H](NC(=O)[C@H](Cc1ccc(O)cc1)NC(=O)[C@@H]1CC=CC[C@H](N)C(=O)N[C@@H](CN)C(=O)N[C@@H](CCCCN)C(=O)N1)C(=O)O] |
| 82. (SEQ ID NO: 84) | 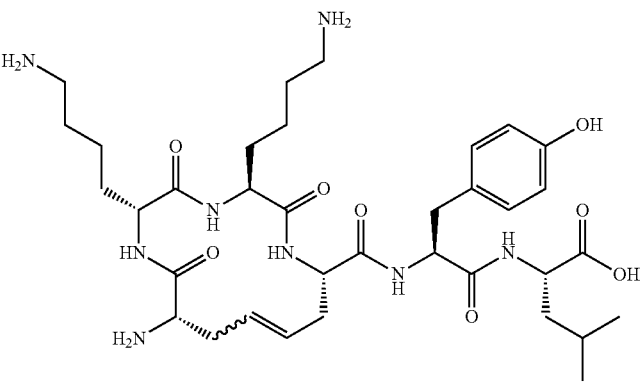 [SMILES: CC(C)C[C@H](NC(=O)[C@H](Cc1ccc(O)cc1)NC(=O)[C@@H]1CC=CC[C@H](N)C(=O)N[C@H](CCCCN)C(=O)N[C@@H](CCCCN)C(=O)N1)C(=O)O] |

| Code | Structure |
|---|---|
| 83. (SEQ ID NO: 85) | 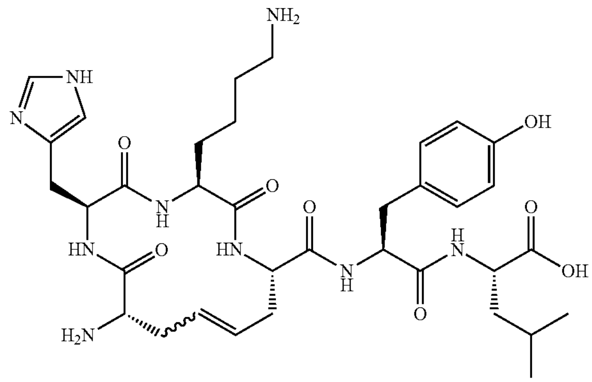 [SMILES: CC(C)C[C@H](NC(=O)[C@H](Cc1ccc(O)cc1)NC(=O)[C@@H]1CC=CC[C@H](N)C(=O)N[C@@H](Cc2c[nH]cn2)C(=O)N[C@@H](CCCCN)C(=O)N1)C(=O)O] |
| 84. (SEQ ID NO: 86) | 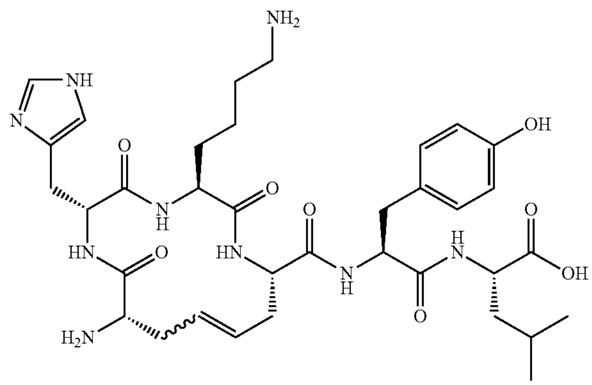 [SMILES: CC(C)C[C@H](NC(=O)[C@H](Cc1ccc(O)cc1)NC(=O)[C@@H]1CC=CC[C@H](N)C(=O)N[C@H](Cc2c[nH]cn2)C(=O)N[C@@H](CCCCN)C(=O)N1)C(=O)O] |
| 85. (SEQ ID NO: 87) | 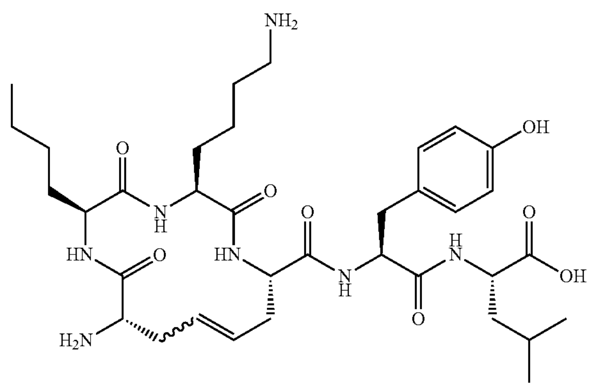 [SMILES: CCCC[C@@H]1NC(=O)[C@@H](N)CC=CC[C@@H](C(=O)N[C@@H](Cc2ccc(O)cc2)C(=O)N[C@@H](CC(C)C)C(=O)O)NC(=O)[C@H](CCCCN)NC1=O] |
| 86. (SEQ ID NO: 88) | 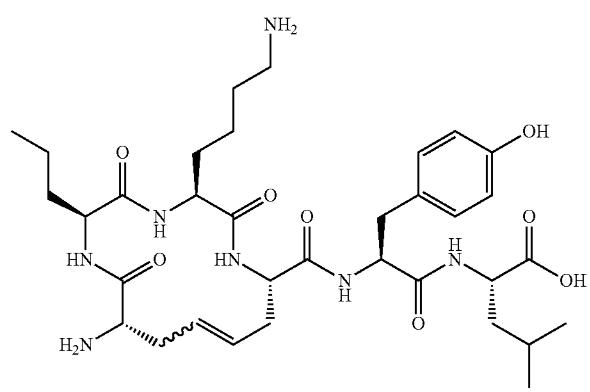 [SMILES: CCC[C@@H]1NC(=O)[C@@H](N)CC=CC[C@@H](C(=O)N[C@@H](Cc2ccc(O)cc2)C(=O)N[C@@H](CC(C)C)C(=O)O)NC(=O)[C@H](CCCCN)NC1=O] |

-continued

| Code | Structure |
|---|---|
| 87. (SEQ ID NO: 89) | 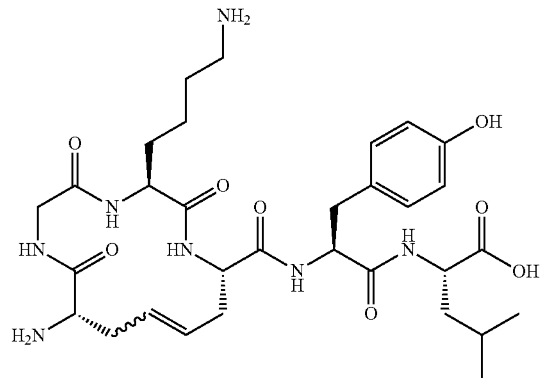 [SMILES: CC(C)C[C@H](NC(=O)[C@H](Cc1ccc(O)cc1)NC(=O)[C@@H]1CC=CC[C@H](N)C(=O)NCC(=O)N[C@@H](CCCCN)C(=O)N1)C(=O)O] |
| 88. (SEQ ID NO: 90) | 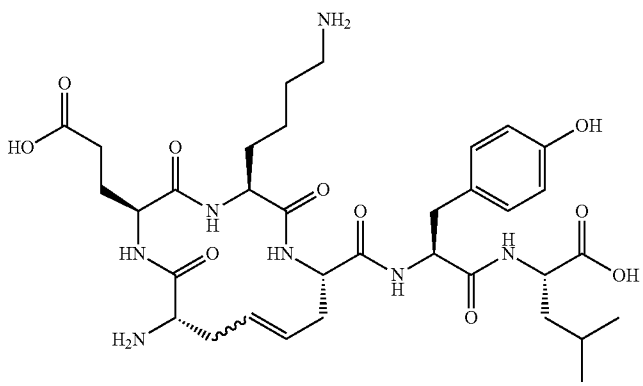 [SMILES: CC(C)C[C@H](NC(=O)[C@H](Cc1ccc(O)cc1)NC(=O)[C@@H]1CC=CC[C@H](N)C(=O)N[C@@H](CCC(=O)O)C(=O)N[C@@H](CCCCN)C(=O)N1)C(=O)O] |
| 89. (SEQ ID NO: 91) | 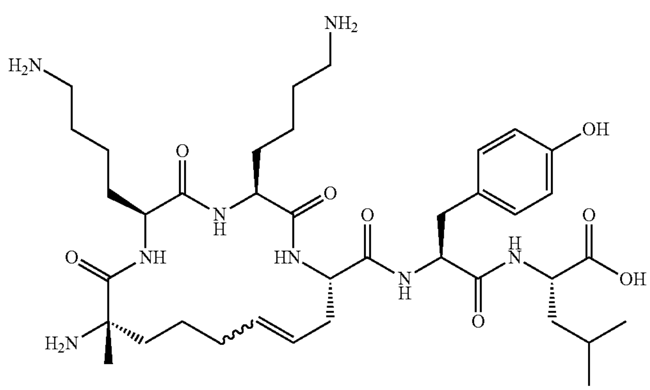 [SMILES: CC(C)C[C@H](NC(=O)[C@H](Cc1ccc(O)cc1)NC(=O)[C@@H]1CC=CCCC[C@](C)(N)C(=O)N[C@@H](CCCCN)C(=O)N[C@@H](CCCCN)C(=O)N1)C(=O)O] |
| 90. (SEQ ID NO: 92) | 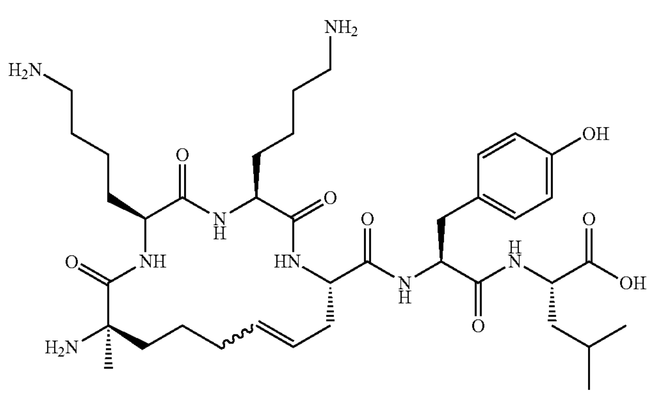 [SMILES: CC(C)C[C@H](NC(=O)[C@H](Cc1ccc(O)cc1)NC(=O)[C@@H]1CC=CCCC[C@@](C)(N)C(=O)N[C@@H](CCCCN)C(=O)N[C@@H](CCCCN)C(=O)N1)C(=O)O] |

| Code | Structure |
|---|---|
| 91. (SEQ ID NO: 93) | 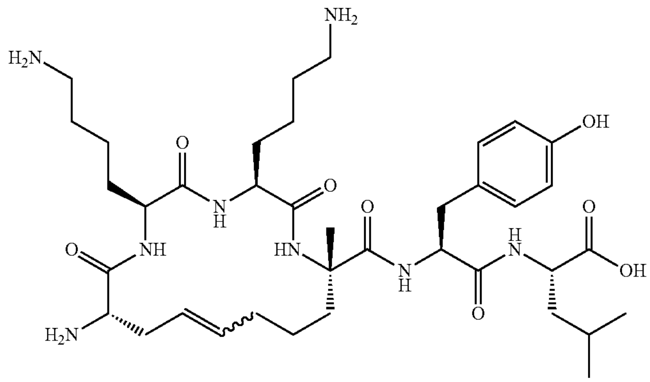 |
| 92. (SEQ ID NO: 94) | 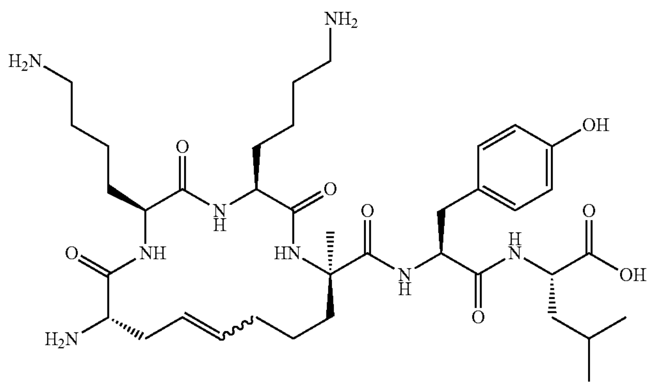 |
| 93. (SEQ ID NO: 95) | 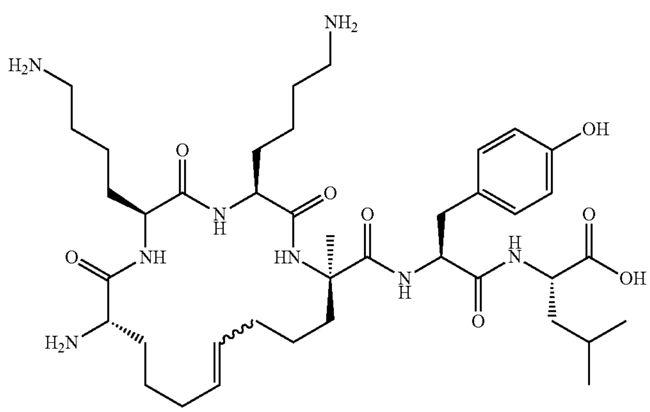 |
| 94. (SEQ ID NO: 96) | 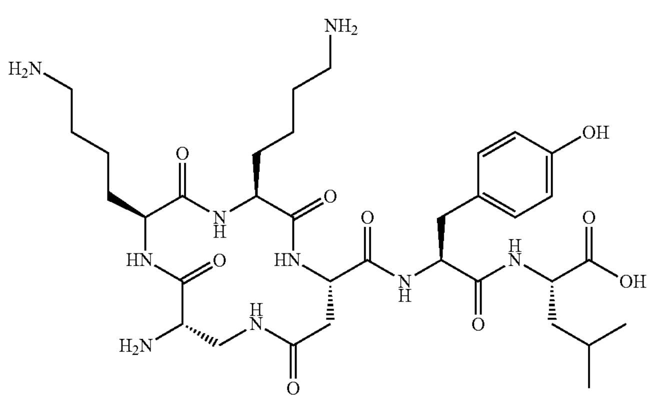 [SMILES: CC(C)C[C@H](NC(=O)[C@H](Cc1ccc(O)cc1)NC(=O)[C@@H]1CC(=O)NC[C@H](N)C(=O)N[C@@H](CCCCN)C(=O)N[C@@H](CCCCN)C(=O)N1)C(=O)O] |

| Code | Structure |
|---|---|
| 95. (SEQ ID NO: 97) | 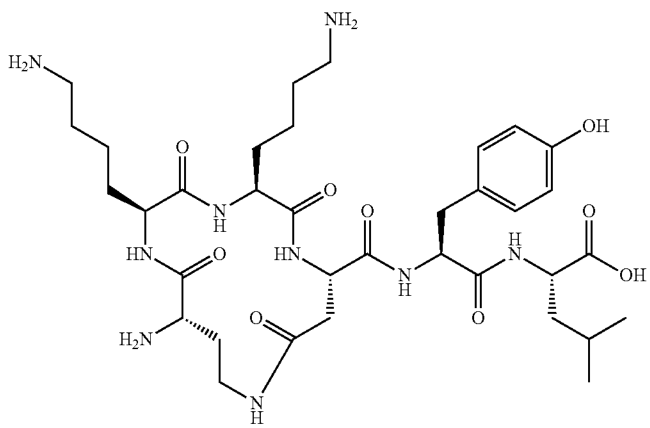 [SMILES: CC(C)C[C@H](NC(=O)[C@H](Cc1ccc(O)cc1)NC(=O)[C@@H]1CC(=O)NCC[C@H](N)C(=O)N[C@@H](CCCCN)C(=O)N[C@@H](CCCCN)C(=O)N1)C(=O)O] |
| 96. (SEQ ID NO: 98) | 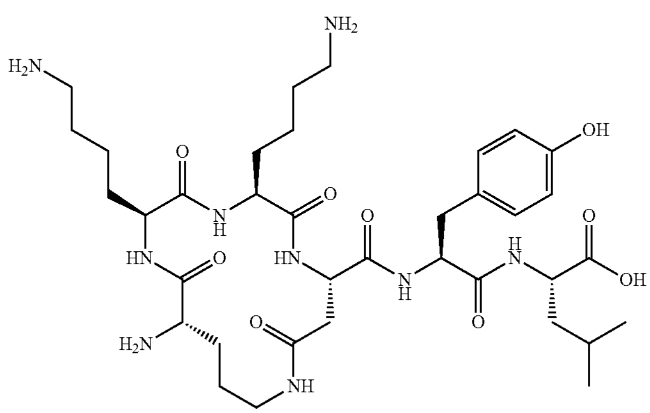 [SMILES: CC(C)C[C@H](NC(=O)[C@H](Cc1ccc(O)cc1)NC(=O)[C@@H]1CC(=O)NCCC[C@H](N)C(=O)N[C@@H](CCCCN)C(=O)N[C@@H](CCCCN)C(=O)N1)C(=O)O] |
| 97. (SEQ ID NO: 99) | 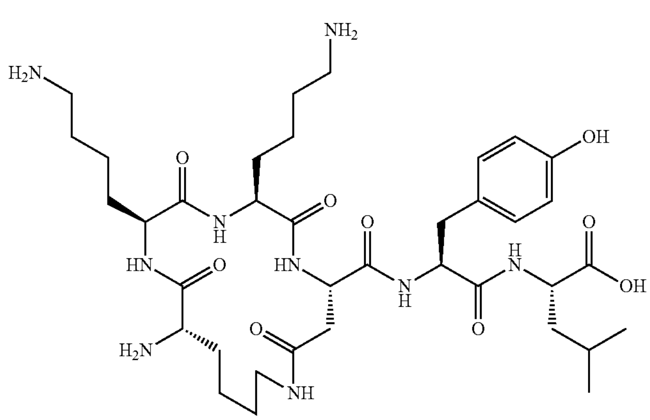 [SMILES: CC(C)C[C@H](NC(=O)[C@H](Cc1ccc(O)cc1)NC(=O)[C@@H]1CC(=O)NCCCC[C@H](N)C(=O)N[C@@H](CCCCN)C(=O)N[C@@H](CCCCN)C(=O)N1)C(=O)O] |

| Code | Structure |
|---|---|
| 98. (SEQ ID NO: 100) | 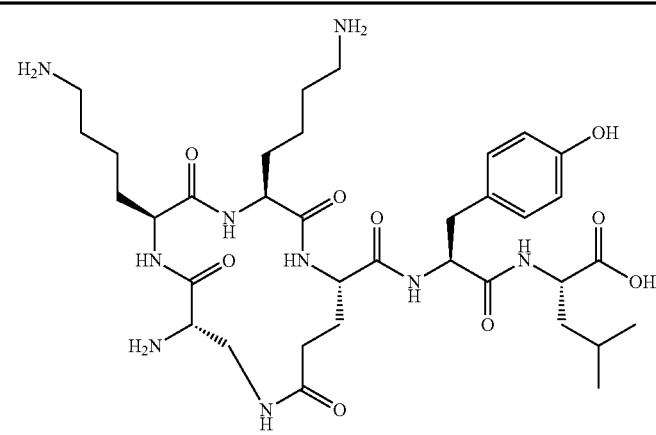 |
| 99. (SEQ ID NO: 101) | 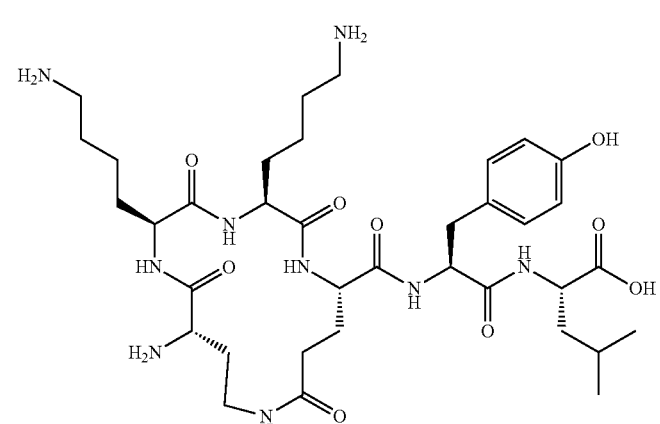 |
| 100. (SEQ ID NO: 102) | 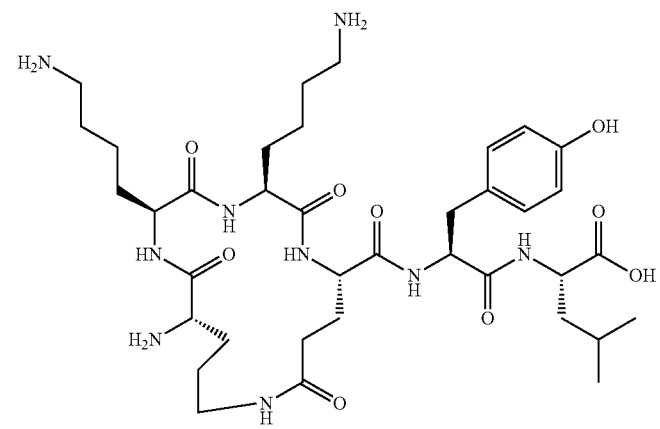 [SMILES: CC(C)C[C@H](NC(=O)[C@H](Cc1ccc(O)cc1)NC(=O)[C@@H]1CCC(=O)NCCC[C@H](N)C(=O)N[C@@H](CCCCN)C(=O)N[C@@H](CCCCN)C(=O)N1)C(=O)O] |

| Code | Structure |
|---|---|
| 101. (SEQ ID NO: 103) | 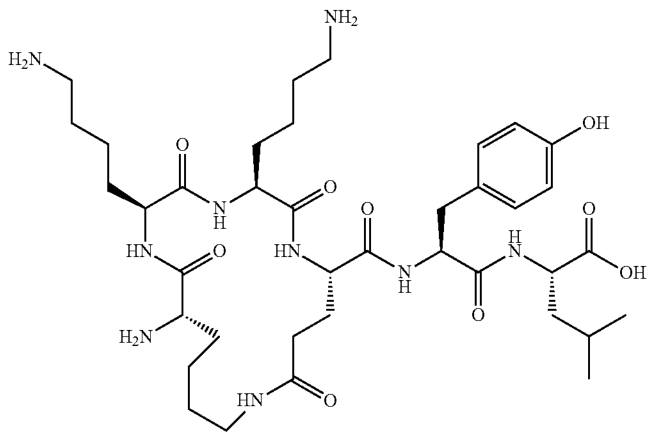 [SMILES: CC(C)C[C@H](NC(=O)[C@H](Cc1ccc(O)cc1)NC(=O)[C@@H]1CCC(=O)NCCCC[C@H](N)C(=O)N[C@@H](CCCCN)C(=O)N[C@@H](CCCCN)C(=O)N1)C(=O)O] |
| 102. (SEQ ID NO: 104) | 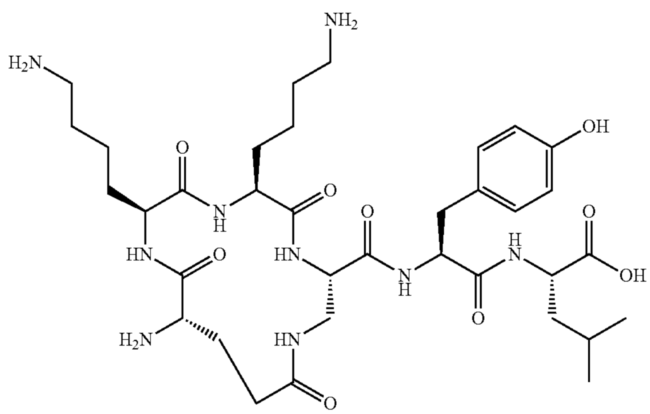 [SMILES: CC(C)C[C@H](NC(=O)[C@H](Cc1ccc(O)cc1)NC(=O)[C@@H]1CNC(=O)CC[C@H](N)C(=O)N[C@@H](CCCCN)C(=O)N[C@@H](CCCCN)C(=O)N1)C(=O)O] |
| 103. (SEQ ID NO: 105) | 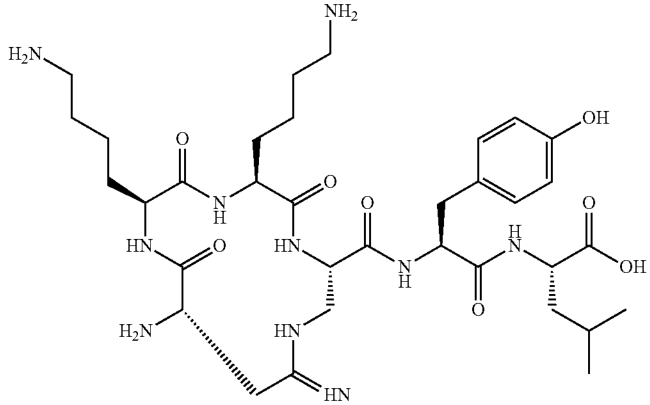 [SMILES: CC(C)C[C@H](NC(=O)[C@H](Cc1ccc(O)cc1)NC(=O)[C@@H]1CNC(=N)C[C@H](N)C(=O)N[C@@H](CCCCN)C(=O)N[C@@H](CCCCN)C(=O)N1)C(=O)O] |

| Code | Structure |
|---|---|
| 104. (SEQ ID NO: 106) | *chemical structure of cyclic peptide* |
| 105. (SEQ ID NO: 107) | *chemical structure of cyclic peptide* |
| 106. (SEQ ID NO: 108) | *chemical structure of cyclic peptide* |

| Code | Structure |
|---|---|
| 107. (SEQ ID NO: 109) | 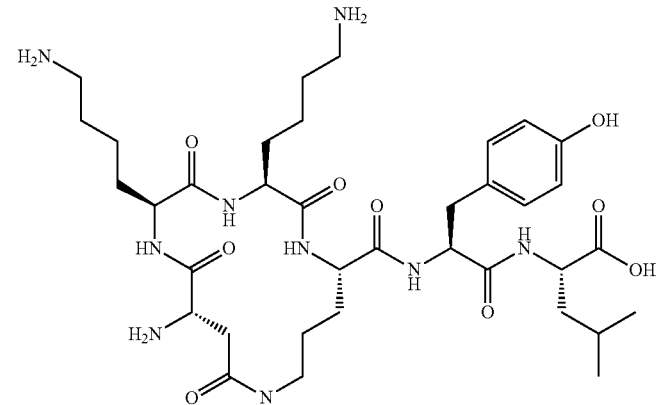 |
| 108. (SEQ ID NO: 110) | 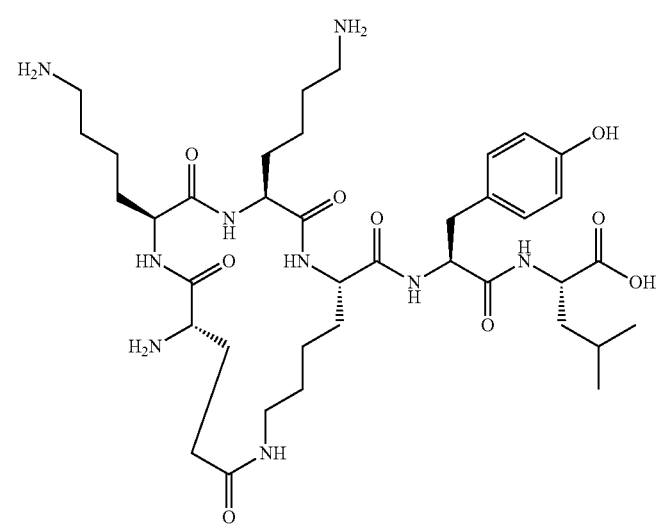 [SMILES: CC(C)C[C@H](NC(=O)[C@H](Cc1ccc(O)cc1)NC(=O)[C@@H]1CCCCNC(=O)CC[C@H](N)C(=O)N[C@@H](CCCCN)C(=O)N[C@@H](CCCCN)C(=O)N1)C(=O)O] |
| 109. (SEQ ID NO: 111) | 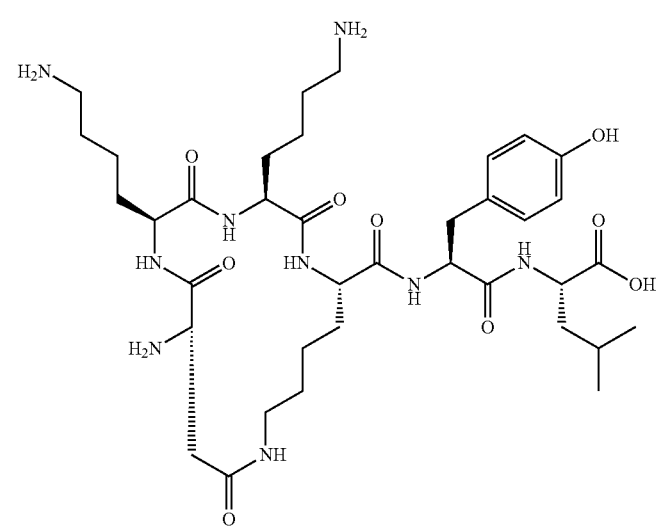 [SMILES: CC(C)C[C@H](NC(=O)[C@H](Cc1ccc(O)cc1)NC(=O)[C@@H]1CCCCNC(=O)C[C@H](N)C(=O)N[C@@H](CCCCN)C(=O)N[C@@H](CCCCN)C(=O)N1)C(=O)O] |

-continued
| Code | Structure |
|---|---|
| 110. (SEQ ID NO: 112) | 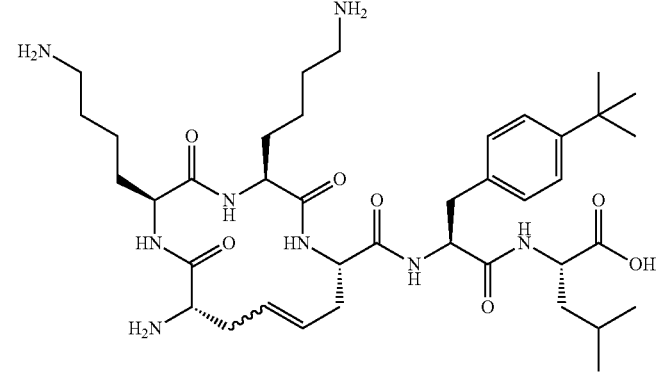 [SMILES: CC(C)C[C@H](NC(=O)[C@H](Cc1ccc(C(C)(C)C)cc1)NC(=O)[C@@H]1CC=CC[C@H](N)C(=O)N[C@@H](CCCCN)C(=O)N[C@@H](CCCCN)C(=O)N1)C(=O)O] |
| 111. (SEQ ID NO: 113) | 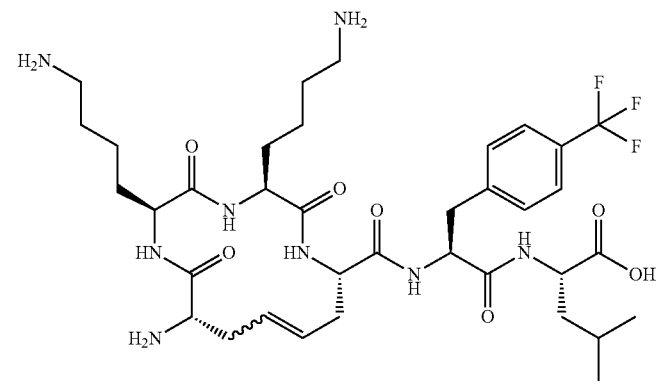 [SMILES: CC(C)C[C@H](NC(=O)[C@H](Cc1ccc(C(F)(F)F)cc1)NC(=O)[C@@H]1CC=CC[C@H](N)C(=O)N[C@@H](CCCCN)C(=O)N[C@@H](CCCCN)C(=O)N1)C(=O)O] |
| 112. (SEQ ID NO: 114) | 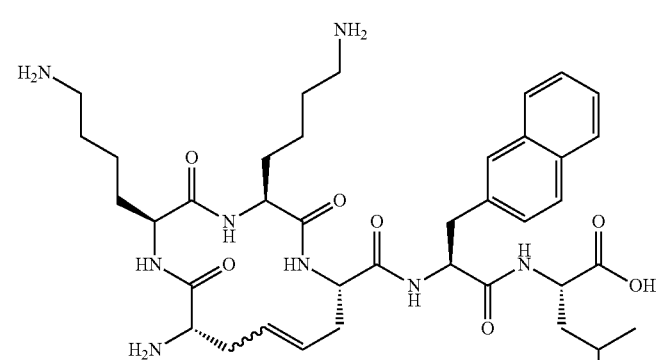 |
| 113. (SEQ ID NO: 115) | 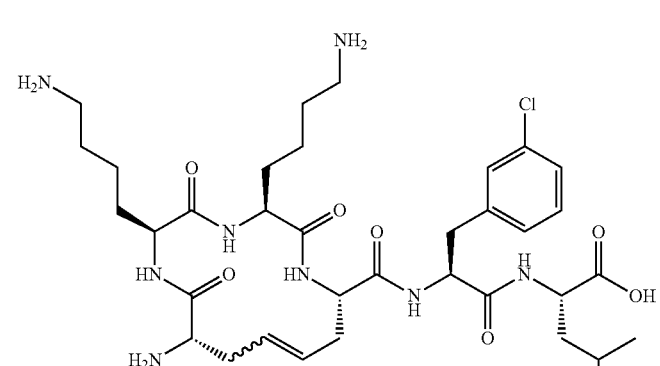 |

| Code | Structure |
|---|---|
| 114. (SEQ ID NO: 116) | 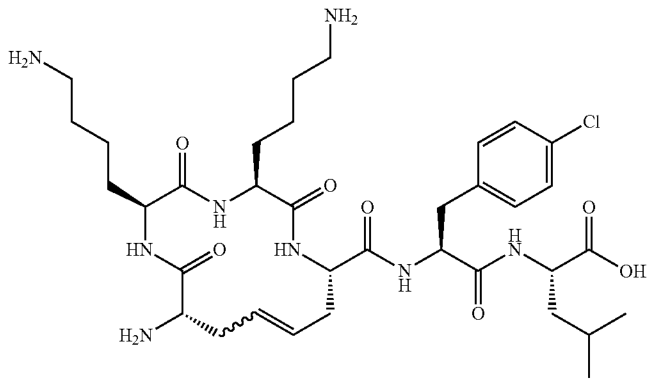 [SMILES: CC(C)C[C@H](NC(=O)[C@H](Cc1ccc(Cl)cc1)NC(=O)[C@@H]1CC=CC[C@H](N)C(=O)N[C@@H](CCCCN)C(=O)N[C@@H](CCCCN)C(=O)N1)C(=O)O] |
| 115. (SEQ ID NO: 117) | 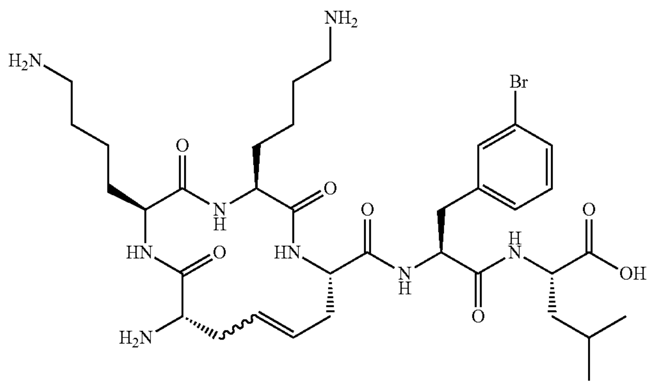 [SMILES: CC(C)C[C@H](NC(=O)[C@H](Cc1cccc(Br)c1)NC(=O)[C@@H]1CC=CC[C@H](N)C(=O)N[C@@H](CCCCN)C(=O)N[C@@H](CCCCN)C(=O)N1)C(=O)O] |
| 116. (SEQ ID NO: 118) | 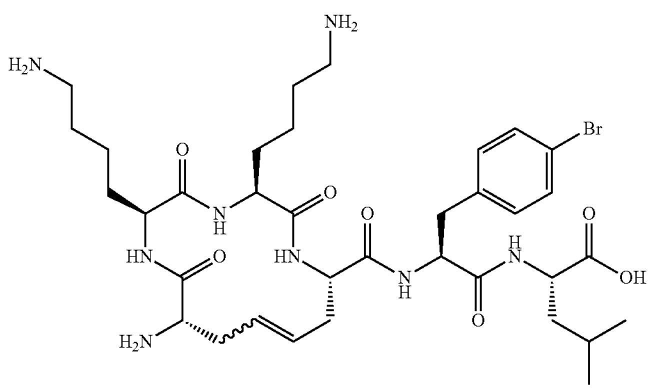 |
| 117. (SEQ ID NO: 119) | 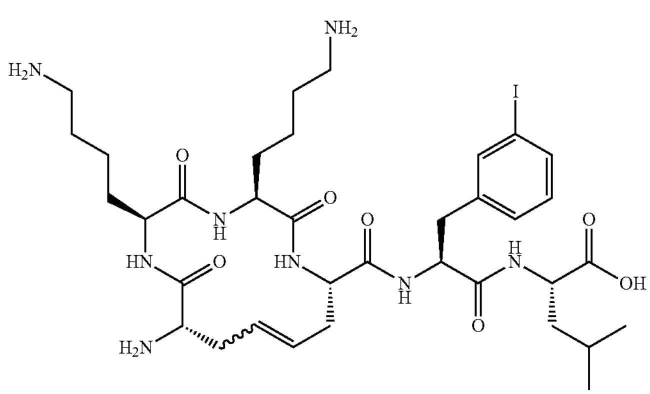 [SMILES: CC(C)C[C@H](NC(=O)[C@H](Cc1cccc(I)c1)NC(=O)[C@@H]1CC=CC[C@H](N)C(=O)N[C@@H](CCCCN)C(=O)N[C@@H](CCCCN)C(=O)N1)C(=O)O] |

| Code | Structure |
|---|---|
| 118. (SEQ ID NO: 120) | 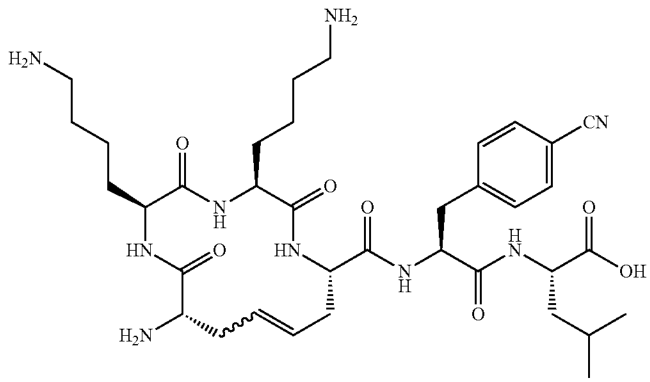 |
| 119. (SEQ ID NO: 121) | 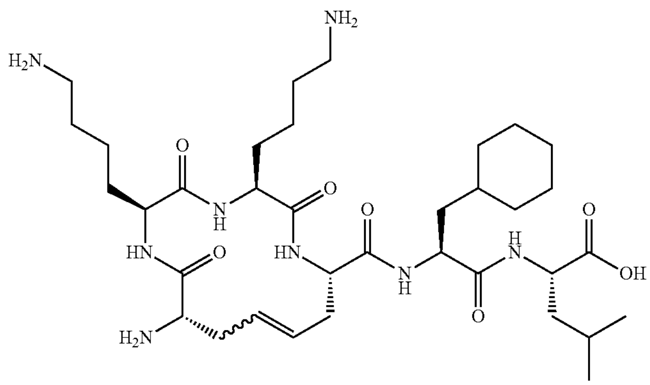 [SMILES: CC(C)C[C@H](NC(=O)[C@H](CC1CCCCC1)NC(=O)[C@@H]1CC=CC[C@H](N)C(=O)N[C@@H](CCCCN)C(=O)N[C@@H](CCCCN)C(=O)N1)C(=O)O] |
| 120. (SEQ ID NO: 122) | 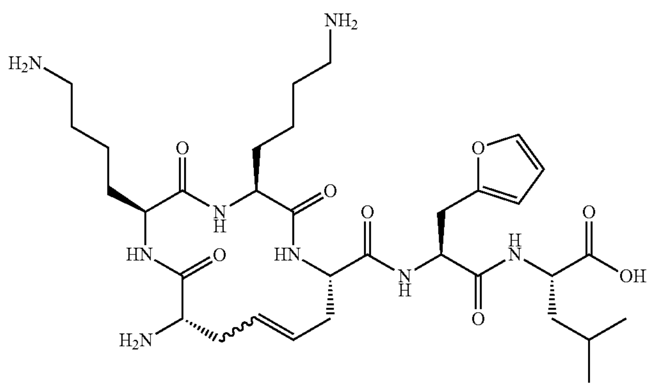 [SMILES: CC(C)C[C@H](NC(=O)[C@H](Cc1ccco1)NC(=O)[C@@H]1CC=CC[C@H](N)C(=O)N[C@@H](CCCCN)C(=O)N[C@@H](CCCCN)C(=O)N1)C(=O)O] |
| 121. (SEQ ID NO: 123) | 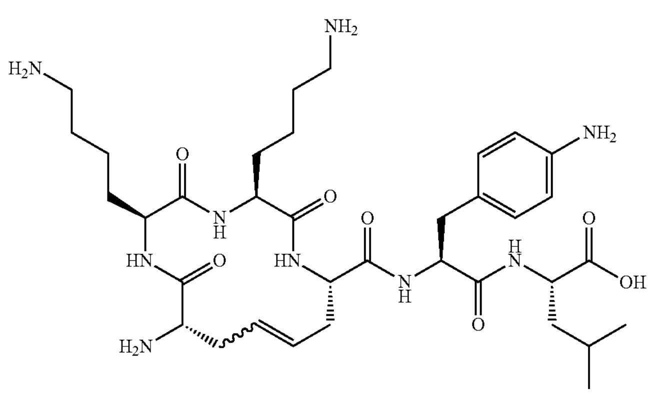 [SMILES: CC(C)C[C@H](NC(=O)[C@H](Cc1ccc(N)cc1)NC(=O)[C@@H]1CC=CC[C@H](N)C(=O)N[C@@H](CCCCN)C(=O)N[C@@H](CCCCN)C(=O)N1)C(=O)O] |

| Code | Structure |
|---|---|
| 122. (SEQ ID NO: 124) | 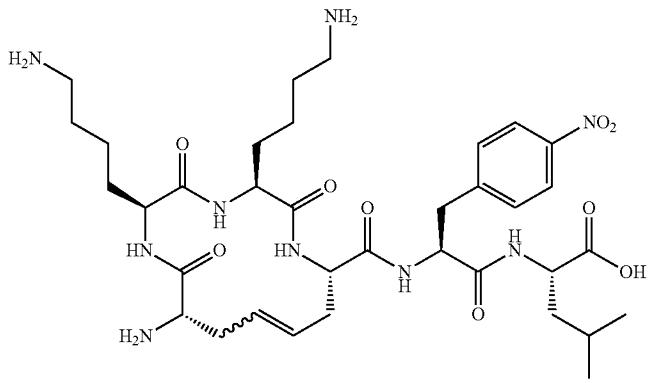 |
| 123. (SEQ ID NO: 125) | 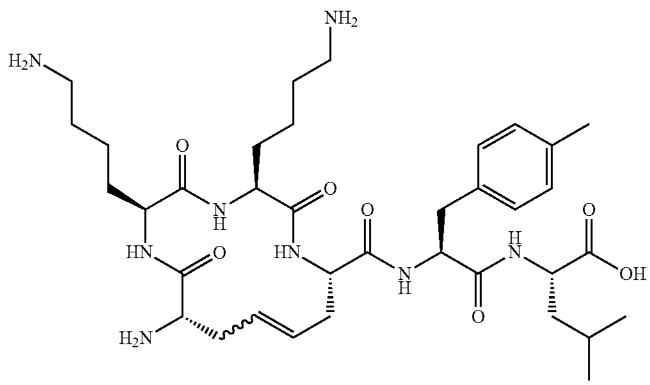 |
| 124. (SEQ ID NO: 126) | 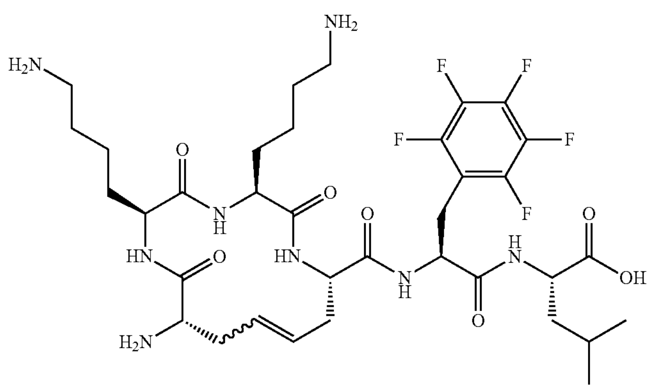 [SMILES: CC(C)C[C@H](NC(=O)[C@H](Cc1c(F)c(F)c(F)c(F)c1F)NC(=O)[C@@H]1CC=CC[C@H](N)C(=O)N[C@@H](CCCCN)C(=O)N[C@@H](CCCCN)C(=O)N1)C(=O)O] |
| 125. (SEQ ID NO: 127) | 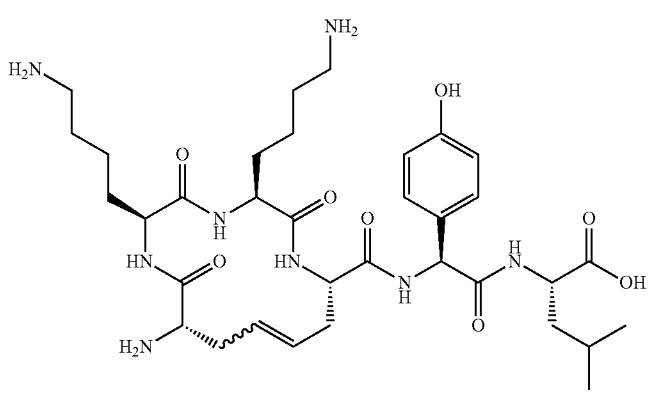 [SMILES: CC(C)C[C@H](NC(=O)[C@@H](NC(=O)[C@@H]1CC=CC[C@H](N)C(=O)N[C@@H](CCCCN)C(=O)N[C@@H](CCCCN)C(=O)N1)c1ccc(O)cc1)C(=O)O] |

| Code | Structure |
|---|---|
| 126. (SEQ ID NO: 128) | 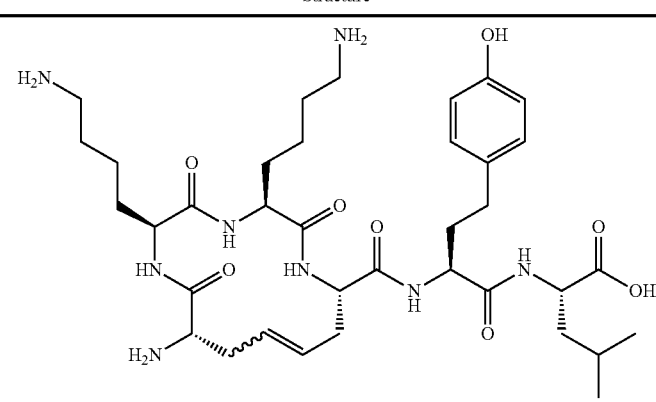 |
| 127. (SEQ ID NO: 129) | 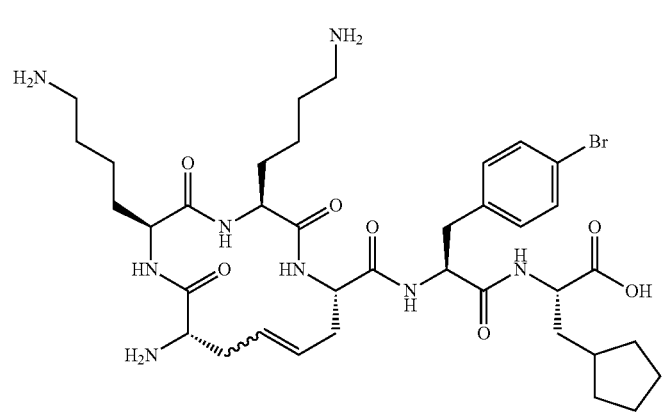 [SMILES: NCCCC[C@@H]1NC(=O)[C@H](CCCCN)NC(=O)[C@@H](N)CC=CC[C@@H](C(=O)N[C@@H](Cc2ccc(Br)cc2)C(=O)N[C@@H](CC2CCCC2)C(=O)O)NC1=O] |
| 128. (SEQ ID NO: 130) | 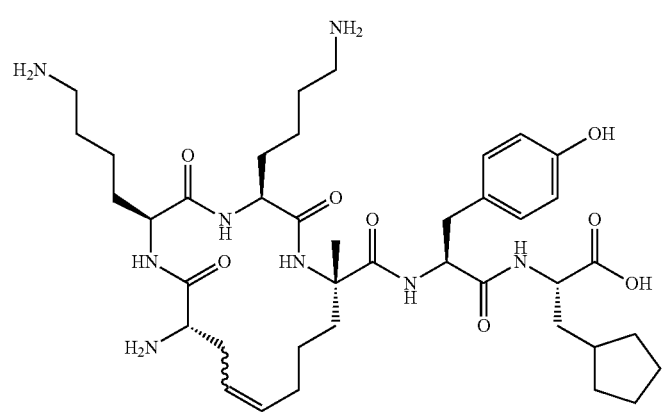 |
| 129. (SEQ ID NO: 131) | 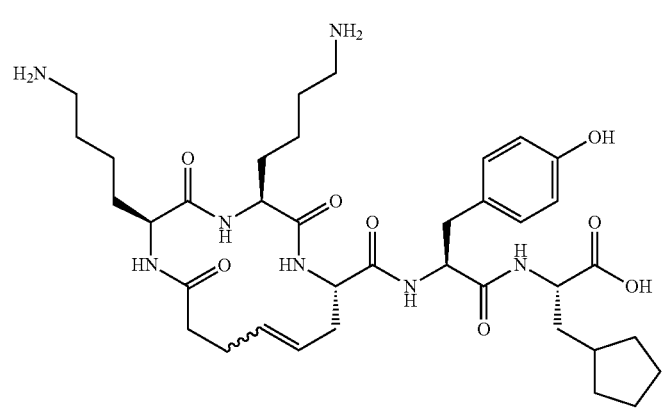 |

| Code | Structure |
|---|---|
| 130. (SEQ ID NO: 132) | 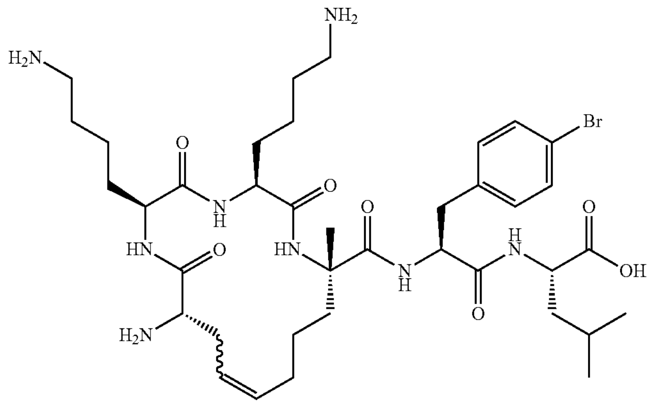 |
| 131. (SEQ ID NO: 133) | 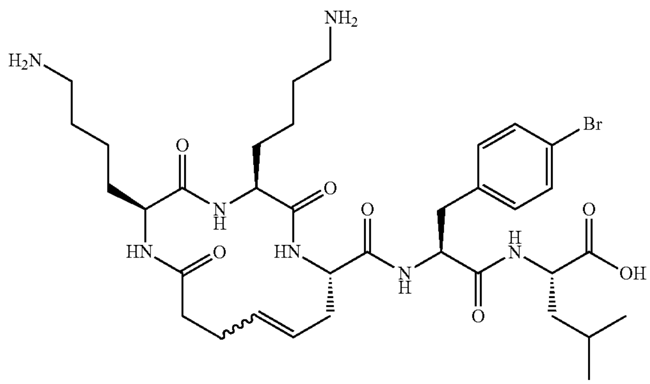 [SMILES: CC(C)C[C@H](NC(=O)[C@H](Cc1ccc(Br)cc1)NC(=O)[C@@H]1CC=CCCC(=O)N[C@@H](CCCCN)C(=O)N[C@@H](CCCCN)C(=O)N1)C(=O)O] |
| 132. (SEQ ID NO: 134) | 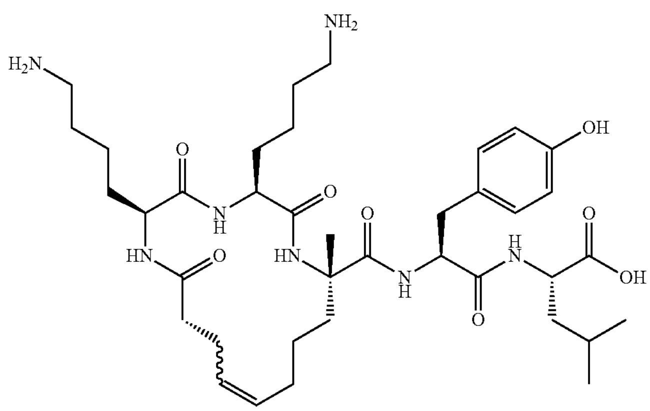 |
| 133. (SEQ ID NO: 135) | 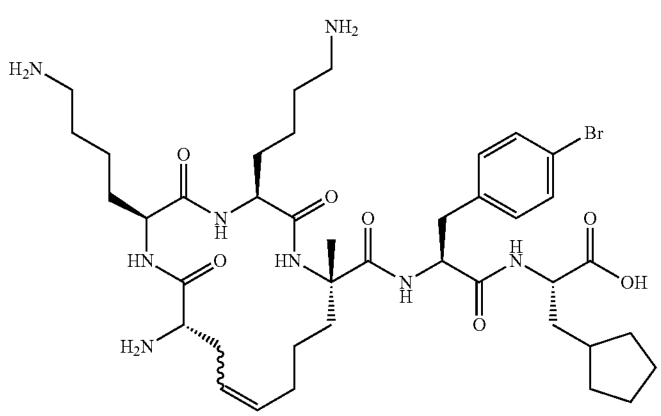 |

| Code | Structure |
|---|---|
| 134. (SEQ ID NO: 136) | 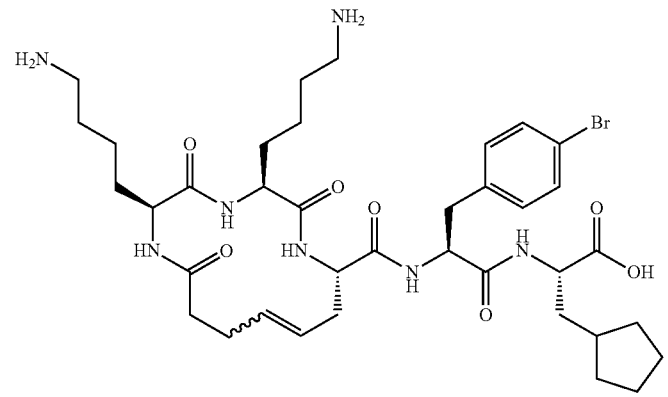 [SMILES: NCCCC[C@@H]1NC(=O)CCC=CC[C@@H](C(=O)N[C@@H](Cc2ccc(Br)cc2)C(=O)N[C@@H](CC2CCCC2)C(=O)O)NC(=O)[C@H](CCCCN)NC1=O] |
| 135. (SEQ ID NO: 137) | 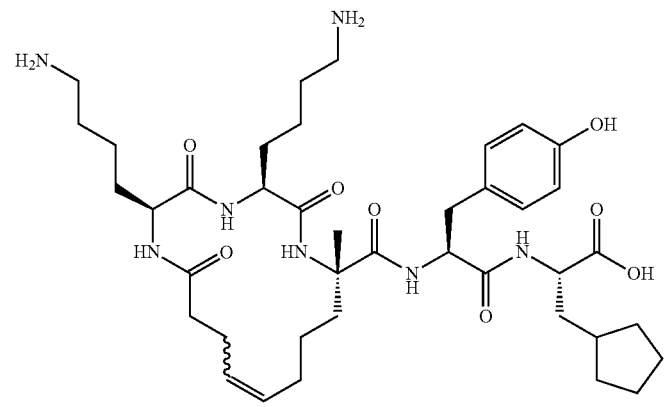 |
| 136. (SEQ ID NO: 138) | 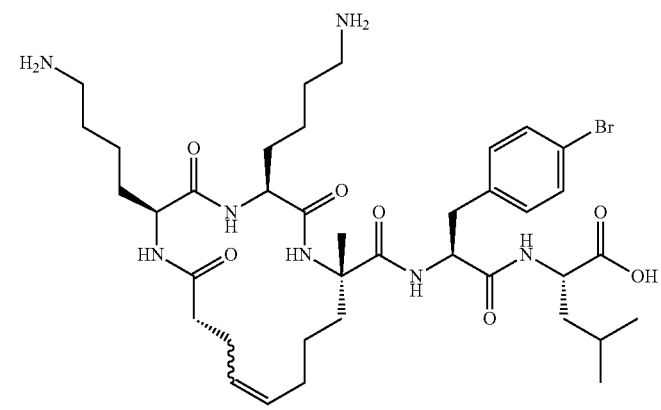 |

| Code | Structure |
|---|---|
| 137. (SEQ ID NO: 139) | 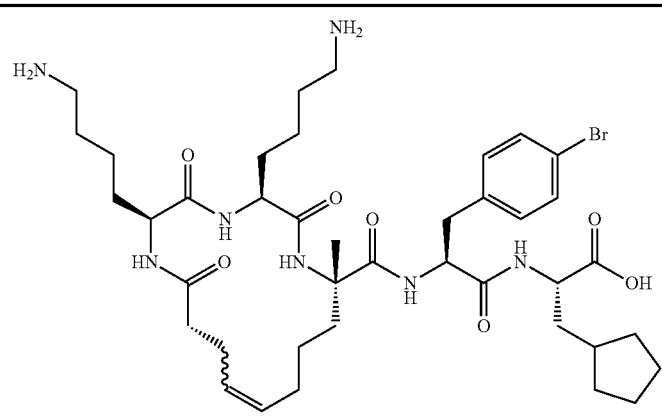 |
| 138. (SEQ ID NO: 140) | 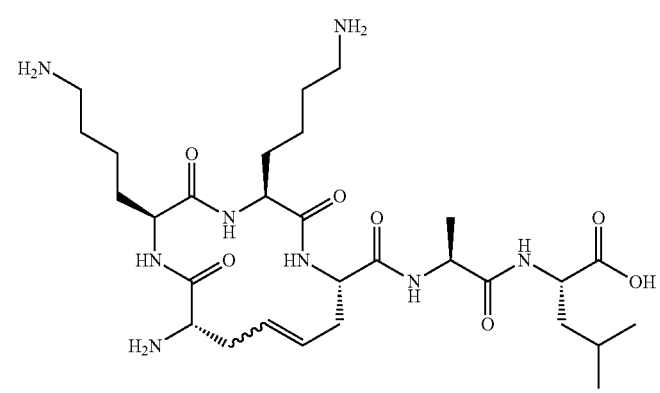 [SMILES: CC(C)C[C@H](NC(=O)[C@H](C)NC(=O)[C@@H]1CC=CC[C@H](N)C(=O)N[C@@H](CCCCN)C(=O)N[C@@H](CCCCN)C(=O)N1)C(=O)O] |
| 139. (SEQ ID NO: 141) | 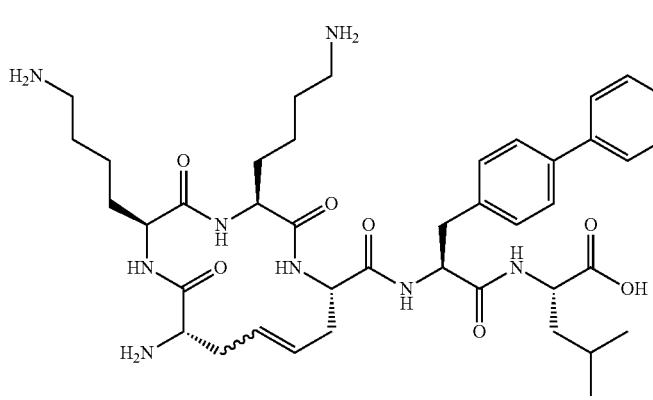 |
| 140. (SEQ ID NO: 142) | 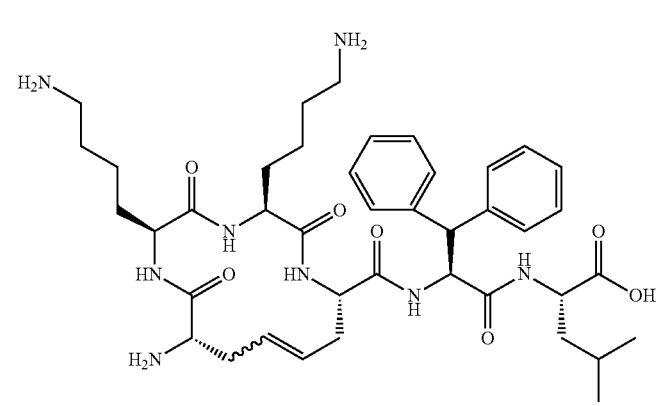 [SMILES: CC(C)C[C@H](NC(=O)[C@@H](NC(=O)[C@@H]1CC=CC[C@H](N)C(=O)N[C@@H](CCCCN)C(=O)N[C@@H](CCCCN)C(=O)N1)C(c1ccccc1)c1ccccc1)C(=O)O] |

| Code | Structure |
|---|---|
| 141. (SEQ ID NO: 143) | 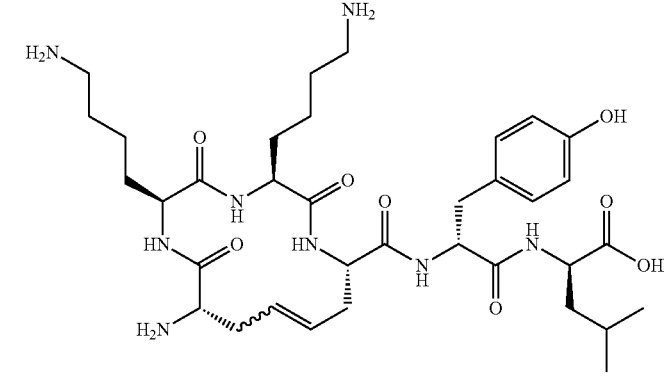 [SMILES: CC(C)C[C@@H](NC(=O)[C@@H](Cc1ccc(O)cc1)NC(=O)[C@@H]1CC=CC[C@H](N)C(=O)N[C@@H](CCCCN)C(=O)N[C@@H](CCCCN)C(=O)N1)C(=O)O] |
| 142. (SEQ ID NO: 144) | 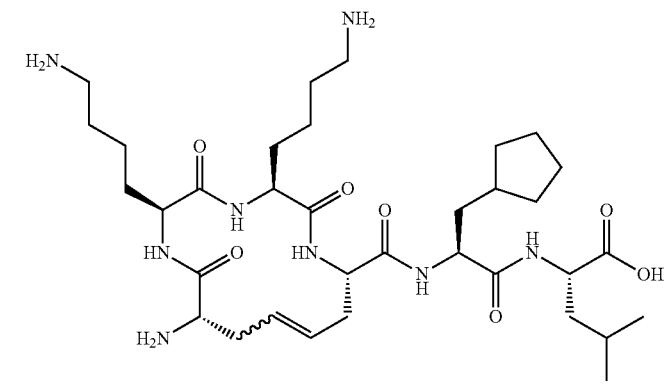 [SMILES: CC(C)C[C@H](NC(=O)[C@H](CC1CCCC1)NC(=O)[C@@H]1CC=CC[C@H](N)C(=O)N[C@@H](CCCCN)C(=O)N[C@@H](CCCCN)C(=O)N1)C(=O)O] |
| 143. (SEQ ID NO: 145) | 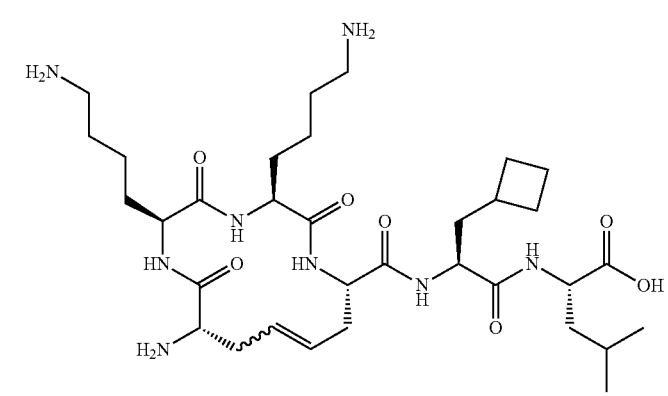 [SMILES: CC(C)C[C@H](NC(=O)[C@H](CC1CCC1)NC(=O)[C@@H]1CC=CC[C@H](N)C(=O)N[C@@H](CCCCN)C(=O)N[C@@H](CCCCN)C(=O)N1)C(=O)O] |
| 144. (SEQ ID NO: 146) | 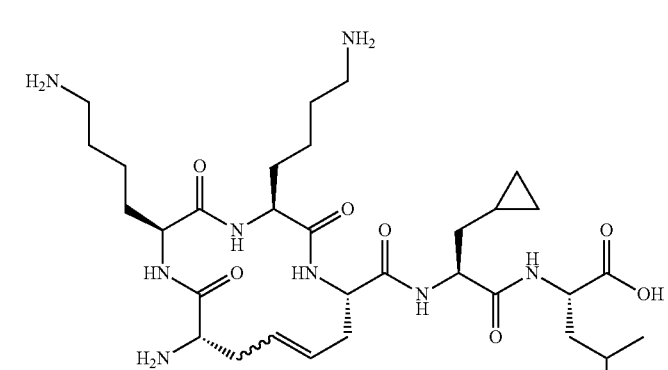 |

| Code | Structure |
|---|---|
| 145. (SEQ ID NO: 147) | 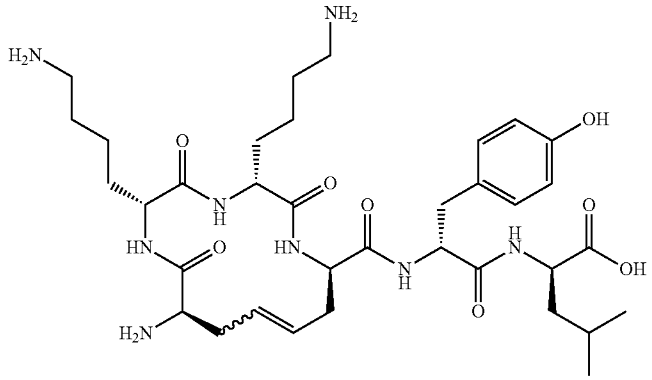 [SMILES: CC(C)C[C@@H](NC(=O)[C@@H](Cc1ccc(O)cc1)NC(=O)[C@H]1CC=CC[C@@H](N)C(=O)N[C@H](CCCCN)C(=O)N[C@H](CCCCN)C(=O)N1)C(=O)O] |
| 146. (SEQ ID NO: 148) | 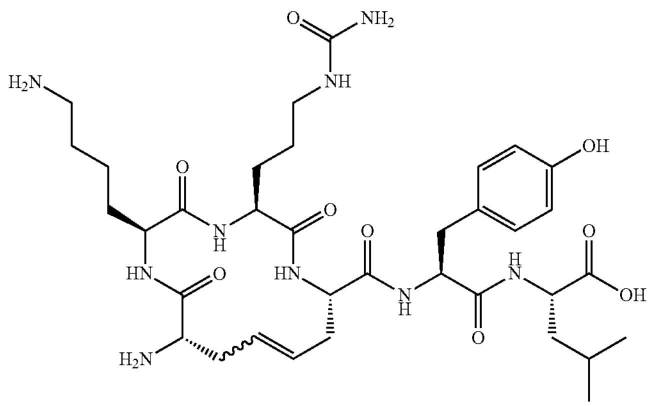 [SMILES: CC(C)C[C@H](NC(=O)[C@H](Cc1ccc(O)cc1)NC(=O)[C@@H]1CC=CC[C@H](N)C(=O)N[C@@H](CCCCN)C(=O)N[C@@H](CCCNC(N)=O)C(=O)N1)C(=O)O] |
| 147. (SEQ ID NO: 149) | 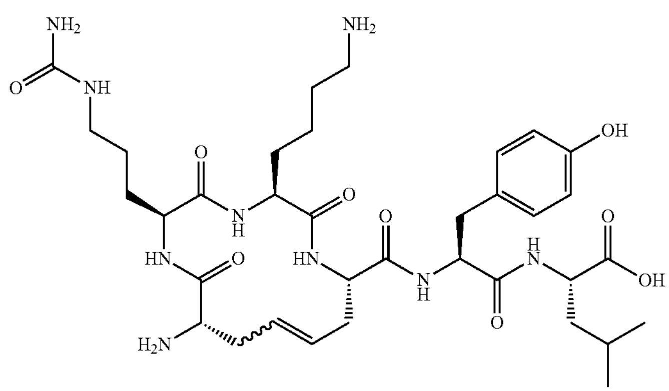 [SMILES: CC(C)C[C@H](NC(=O)[C@H](Cc1ccc(O)cc1)NC(=O)[C@@H]1CC=CC[C@H](N)C(=O)N[C@@H](CCCNC(N)=O)C(=O)N[C@@H](CCCCN)C(=O)N1)C(=O)O] |
| 148. (SEQ ID NO: 150) | 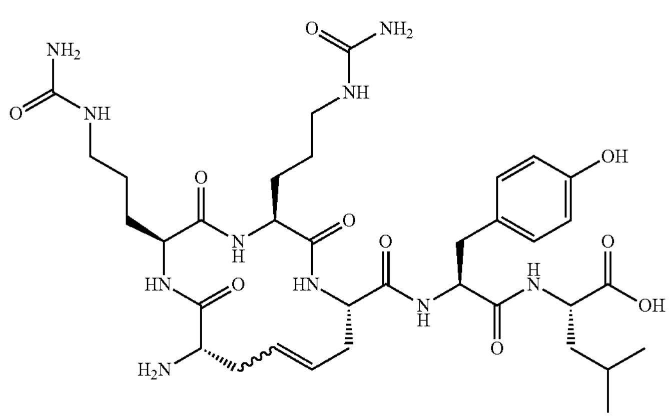 [SMILES: CC(C)C[C@H](NC(=O)[C@H](Cc1ccc(O)cc1)NC(=O)[C@@H]1CC=CC[C@H](N)C(=O)N[C@@H](CCCNC(N)=O)C(=O)N[C@@H](CCCNC(N)=O)C(=O)N1)C(=O)O] |

-continued

| Code | Structure |
|---|---|
| 149. (SEQ ID NO: 151) | 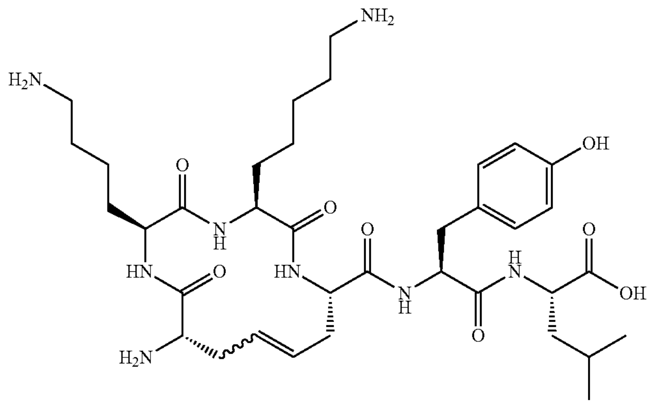 [SMILES: CC(C)C[C@H](NC(=O)[C@H](Cc1ccc(O)cc1)NC(=O)[C@@H]1CC=CC[C@H](N)C(=O)N[C@@H](CCCCN)C(=O)N[C@@H](CCCCCN)C(=O)N1)C(=O)O] |
| 150. (SEQ ID NO: 152) | 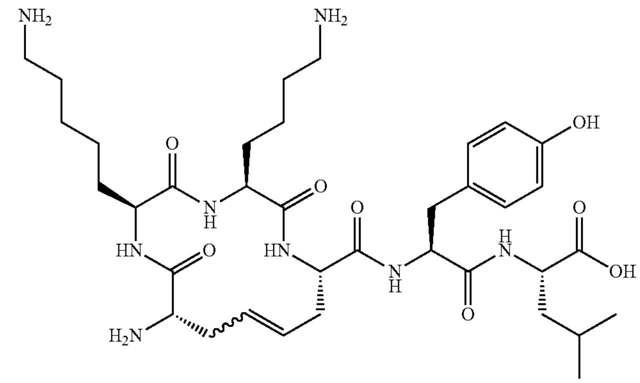 [SMILES: CC(C)C[C@H](NC(=O)[C@H](Cc1ccc(O)cc1)NC(=O)[C@@H]1CC=CC[C@H](N)C(=O)N[C@@H](CCCCCN)C(=O)N[C@@H](CCCCN)C(=O)N1)C(=O)O] |
| 151. (SEQ ID NO: 153) | 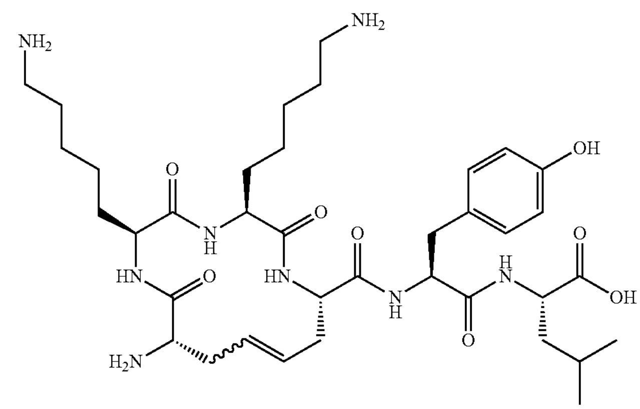 [SMILES: CC(C)C[C@H](NC(=O)[C@H](Cc1ccc(O)cc1)NC(=O)[C@@H]1CC=CC[C@H](N)C(=O)N[C@@H](CCCCCN)C(=O)N[C@@H](CCCCCN)C(=O)N1)C(=O)O] |
| 156. (SEQ ID NO: 158) | 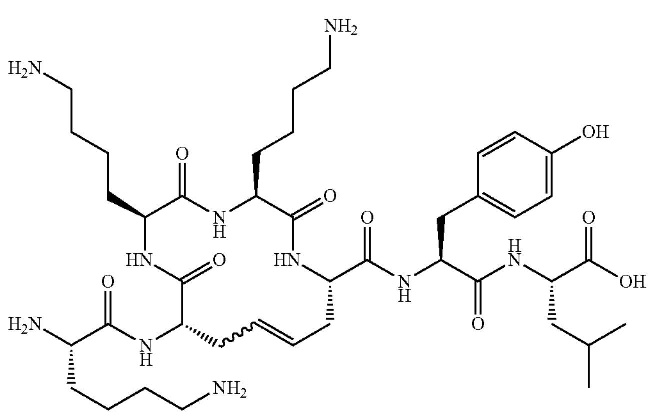 [SMILES: CC(C)C[C@H](NC(=O)[C@H](Cc1ccc(O)cc1)NC(=O)[C@@H]1CC=CC[C@H](NC(=O)[C@@H](N)CCCCN)C(=O)N[C@@H](CCCCN)C(=O)N[C@@H](CCCCN)C(=O)N1)C(=O)O] |

| Code | Structure |
|---|---|
| 159. (SEQ ID NO: 159) | *chemical structure of peptide with Lys, Lys, Lys, alkene-containing residue, thienyl-Ala, Leu* |
| 160. (SEQ ID NO: 160) | *chemical structure of peptide with Lys, Lys, Lys, alkene-containing residue, 4-benzoyl-Phe, Leu* |
| 161. (SEQ ID NO: 161) | *chemical structure of peptide with Lys, Lys, Lys, alkene-containing residue, styryl-Ala, Leu* |
| 162. (SEQ ID NO: 162) | *chemical structure of peptide with Lys, Lys, Lys, alkene-containing residue, 9-anthryl-Ala, Leu* |

-continued
| Code | Structure |
|---|---|
| 163. (SEQ ID NO: 163) | 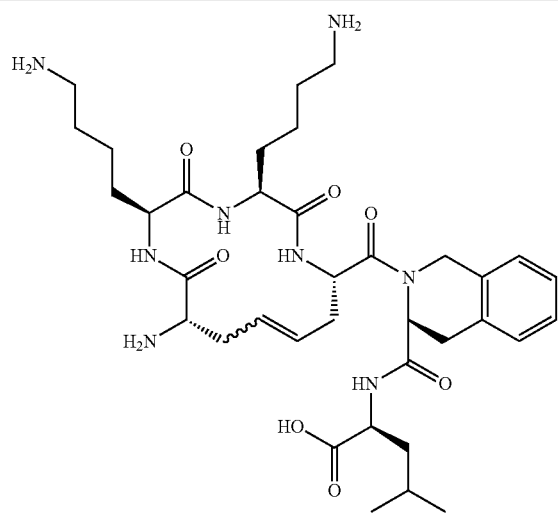 [SMILES: CC(C)C[C@H](NC(=O)[C@H]1Cc2ccccc2CN1C(=O)[C@@H]1CC=CC[C@H](N)C(=O)N[C@@H](CCCCN)C(=O)N[C@@H](CCCCN)C(=O)N1)C(=O)O] |
| 164. (SEQ ID NO: 164) | 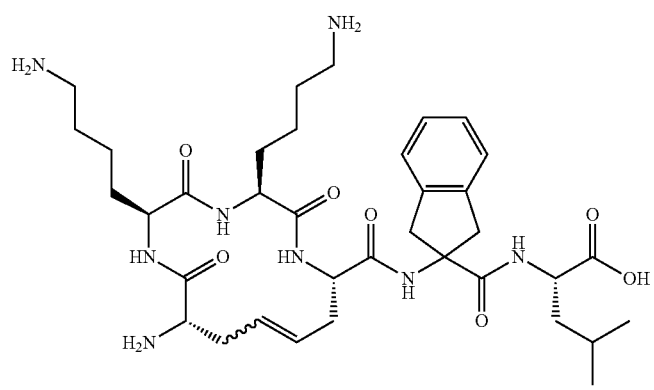 [SMILES: CC(C)C[C@H](NC(=O)C1(NC(=O)[C@@H]2CC=CC[C@H](N)C(=O)N[C@@H](CCCCN)C(=O)N[C@@H](CCCCN)C(=O)N2)Cc2ccccc2C1)C(=O)O] |
| 165. (SEQ ID NO: 165) | 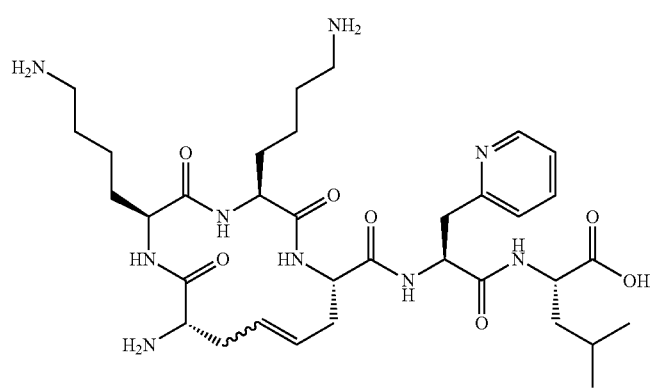 |

| Code | Structure |
| --- | --- |
| 166. (SEQ ID NO: 166) | 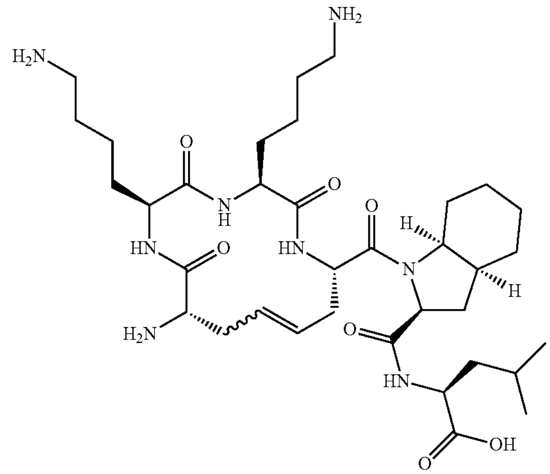 [SMILES: CC(C)C[C@H](NC(=O)[C@@H]1C[C@@H]2CCCC[C@@H]2N1C(=O)[C@@H]1CC=CC[C@H](N)C(=O)N[C@@H](CCCCN)C(=O)N[C@@H](CCCCN)C(=O)N1)C(=O)O] |
| 167. (SEQ ID NO: 167) | 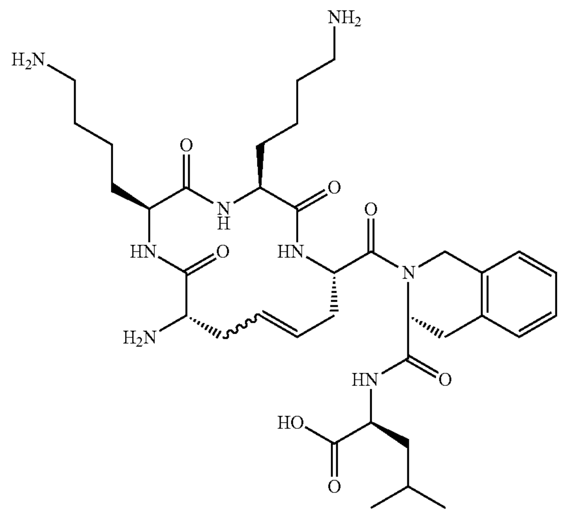 [SMILES: CC(C)C[C@H](NC(=O)[C@@H]1Cc2ccccc2CN1C(=O)[C@@H]1CC=CC[C@H](N)C(=O)N[C@@H](CCCCN)C(=O)N[C@@H](CCCCN)C(=O)N1)C(=O)O] |
| 168. (SEQ ID NO: 168) | 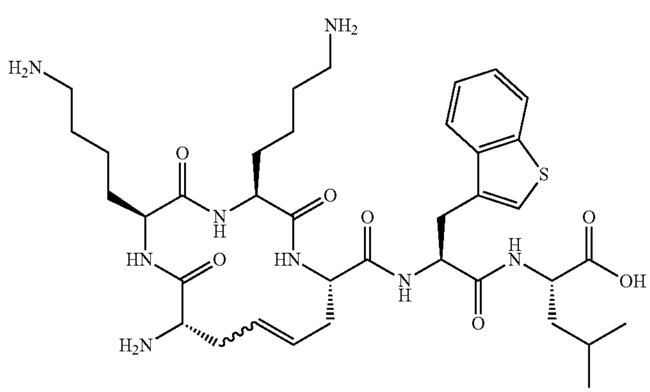 [SMILES: CC(C)C[C@H](NC(=O)[C@H](Cc1csc2ccccc12)NC(=O)[C@@H]1CC=CC[C@H](N)C(=O)N[C@@H](CCCCN)C(=O)N[C@@H](CCCCN)C(=O)N1)C(=O)O] |

| Code | Structure |
|---|---|
| 169. (SEQ ID NO: 169) | 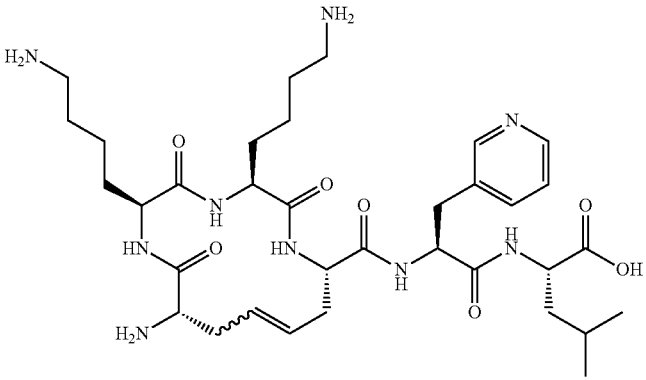 |
| | or |
| 170. (SEQ ID NO: 170) | 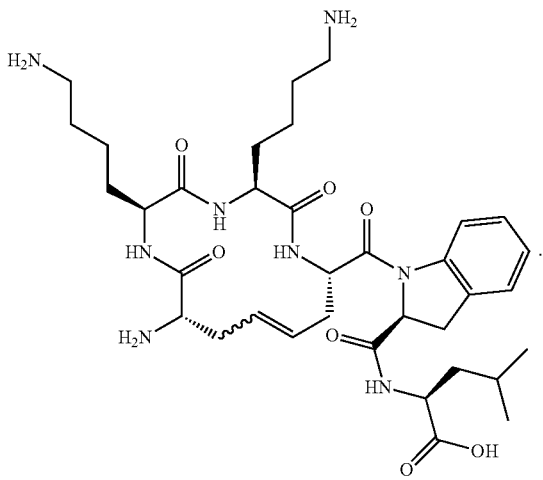 [SMILES: CC(C)C[C@H](NC(=O)[C@@H]1Cc2ccccc2N1C(=O)[C@@H]1CC=CC[C@H](N)C(=O)N[C@@H](CCCCN)C(=O)N[C@@H](CCCCN)C(=O)N1)C(=O)O] |

4. The compound, stereoisomer, mixture, pharmaceutically acceptable salt, ester or solvate thereof of claim 1, wherein:
  (i) $R_{10}$ or $R_{11}$ is the side chain of a phenylalanine, leucine, biphenylalanine, tryptophan, thienylalanine, homotyrosine, tyrosine, benzothienylalanine, furylalanine, styrylalanine, cyclopentylalanine, pyridylalanine, cyclobutylalanine, anthryl-alanine or diphenylalanine; a —CH$_2$-naphtyl; or a —CH$_2$-cycloalkyl, wherein the side chain, naphtyl and cycloalkyl is optionally substituted with one or more substituents, each substituent being independently an halogen, hydroxy, amino, trifluoromethyl, cyano, nitro, or a (C1-C5)alkyl; and the other one of $R_{10}$ and $R_{11}$ is H or $CH_3$; and/or
  (ii) $R_{13}$ or $R_{14}$ is a —(CH$_2$)s-(C3-C7)cycloalkyl or —(CH$_2$)s-(C4-C7)alkyl wherein s is 1-3; or the side chain of a leucine, tyrosine, phenylalanine, or norleucine, wherein the side chain is optionally substituted with one or more substituents, each substituent being independently an halogen, hydroxy, or alkoxy; and the other one of $R_{13}$ and $R_{14}$ is H or —CH$_3$.

5. The compound, stereoisomer, mixture, pharmaceutically acceptable salt, ester or solvate thereof of claim 3, wherein the compound is any one of compounds 43, 30, 101, 108, 86, 58, 57, 146, 84, 140, 72, 82,147, 138, 55, 87, 92, 32, 28, 63, 54, 65, 143, 52, 169,149,142, 53,150, 74, 81, 62, 80,132, 73,161, 41,120, 151, 168, 109, 167, 77, 47, 159, 31, 75, 76, 112, 126, 123, 79, 90, 51, 34, 118, 119, 122, 16, 139, 113, 111, 60, 135, 49, 114,110, 136,93,166, 117, 115,131, 66,162, 134, 116,78,129, 89,91, 130, 137, 128,64, 68, 156, 67, 133 and 127.

6. The compound, stereoisomer, mixture, pharmaceutically acceptable salt, ester or solvate thereof of claim 3, wherein the compound is any one of compounds 34, 67, 116, 127, 128 and 133.

7. A composition comprising (a) the compound, stereoisomer, mixture, pharmaceutically acceptable salt, ester or solvate thereof defined in claim 1; and (b) (i) at least another compound, stereoisomer, mixture, pharmaceutically acceptable salt, ester or solvate thereof defined in claim 1; (ii) an antalgic agent; (iii) an anxiolytic agent; (iv) an antidepressant agent; (v) a pharmaceutically acceptable carrier; or (vi) a combination of at least two of (i) to (v).

8. A kit for preventing or treating pain, comprising (a) the compound, stereoisomer, mixture, pharmaceutically acceptable salt, ester or solvate thereof defined in claim 1; and (b) (i) at least another compound, stereoisomer, mixture, pharmaceutically acceptable salt, ester or solvate thereof defined in claim 1; (ii) another antalgic agent; (iii) an anxiolytic agent; (iv) an antidepressant agent; (v) a pharmaceutically acceptable carrier; (vi) instructions to use the kit in the prevention or treatment of pain or of a symptom thereof; or (vii) a combination of at least two of (i) to (vi).

9. A method of preventing or treating pain in a subject in need thereof, comprising administering to the subject an effective amount of the compound, stereoisomer, mixture, pharmaceutically acceptable salt, ester or solvate thereof defined in claim 1; or of a composition comprising (a) the compound, stereoisomer, mixture, pharmaceutically acceptable salt, ester or solvate thereof (b) (i) at least another compound, stereoisomer, mixture, pharmaceutically acceptable salt, ester or solvate thereof defined in claim 1; (ii) an antalgic agent; (iii) an anxiolytic agent; (iv) an antidepressant agent; (v) a pharmaceutically acceptable carrier; or (vi) a combination of at least two of (i) to (v).

10. The compound, stereoisomer, mixture, pharmaceutically acceptable salt, ester or solvate thereof of claim 1, wherein:
  (a) $R_2$ is H or $CH_3$;
  (b) $R_5$ is H or $CH_3$;
  (c) $R_8$ is H;
  (d) $R_9$ is H;
  (e) $R_{12}$ is H, $CH_3$ or N-isobutyl;
  (f) Y is —$(CH_2)m$- or —CH=CH$(CH_2)m$-; or
  (g) any combination of at least two of (a) to (f).

11. The compound, stereoisomer, mixture, pharmaceutically acceptable salt, ester or solvate thereof of claim 1, wherein:
  $R_3$ is a —(C1-C5)aminoalkyl, wherein the aminoalkyl is optionally substituted with one or more substituents, wherein each substituent is independently an halogen, amine, hydroxy, oxo, or a (C1-C5)alkyl; and $R_4$ is H or —$CH_3$; or
  $R_4$ is a —(C1-C5)aminoalkyl, wherein the aminoalkyl is optionally substituted with one or more substituents, wherein each substituent is independently an halogen, amine, hydroxy, oxo, or a (C1-C5)alkyl; and $R_3$ is H or —$CH_3$; and/or
  $R_6$ is a —(C1-C5)aminoalkyl, wherein the aminoalkyl is optionally substituted with one or more substituents, wherein each substituent is independently an halogen, amine, hydroxy, oxo, or a (C1-C5)alkyl; and $R_7$ is H or —$CH_3$; or
  $R_7$ is a —(C1-C5)aminoalkyl, wherein aminoalkyl is optionally substituted with one or more substituents, wherein each substituent is independently an halogen, amine, hydroxy, oxo, or a (C1-C5)alkyl; and $R_6$ is H or —$CH_3$.

12. The compound, stereoisomer, mixture, pharmaceutically acceptable salt, ester or solvate thereof of claim 1, wherein:
  $R_3$ is the side chain of a lysine, ornithine, diaminobutyric acid (Dab), diaminopropionic acid (Dap), citrulline, or homolysine; and $R_4$ is H or —$CH_3$; or
  $R_4$ is the side chain of a lysine, ornithine, diaminobutyric acid (Dab), diaminopropionic acid (Dap), citrulline, or homolysine; and $R_3$ is H or —$CH_3$; and/or
  $R_6$ is the side chain of a lysine, ornithine, diaminobutyric acid (Dab), diaminopropionic acid (Dap), citrulline, or homolysine; and $R_7$ is H or —$CH_3$; or
  $R_7$ is the side chain of a lysine, ornithine, diaminobutyric acid (Dab), diaminopropionic acid (Dap), citrulline or homolysine; and $R_6$ is H or —$CH_3$.

* * * * *